US010957859B2

(12) United States Patent
Jatsch et al.

(10) Patent No.: US 10,957,859 B2
(45) Date of Patent: Mar. 23, 2021

(54) HETEROCYCLIC COMPOUNDS FOR USE IN ELECTRONIC DEVICES

(71) Applicant: Merck Patent GmbH, Darmstadt (DE)

(72) Inventors: Anja Jatsch, Frankfurt am Main (DE); Amir Hossain Parham, Frankfurt am Main (DE); Thomas Eberle, Landau (DE); Tobias Grossmann, Darmstadt (DE); Jonas Valentin Kroeber, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/528,310

(22) PCT Filed: Nov. 3, 2015

(86) PCT No.: PCT/EP2015/002199
§ 371 (c)(1),
(2) Date: May 19, 2017

(87) PCT Pub. No.: WO2016/078747
PCT Pub. Date: May 26, 2016

(65) Prior Publication Data
US 2017/0324038 A1 Nov. 9, 2017

(30) Foreign Application Priority Data

Nov. 21, 2014 (EP) .................................... 14003925

(51) Int. Cl.
*C07D 209/86* (2006.01)
*C07D 209/94* (2006.01)
*C07D 219/02* (2006.01)
*C07D 265/38* (2006.01)
*C07D 401/10* (2006.01)
*C07D 405/04* (2006.01)
*C07D 405/12* (2006.01)
*C07D 409/12* (2006.01)
*C07D 471/04* (2006.01)
*C07D 491/048* (2006.01)
*C07D 495/04* (2006.01)
*C09K 11/06* (2006.01)
*H01L 51/00* (2006.01)
*H01L 51/50* (2006.01)

(52) U.S. Cl.
CPC .......... *H01L 51/006* (2013.01); *C07D 209/86* (2013.01); *C07D 209/94* (2013.01); *C07D 219/02* (2013.01); *C07D 265/38* (2013.01); *C07D 401/10* (2013.01); *C07D 405/04* (2013.01); *C07D 405/12* (2013.01); *C07D 409/12* (2013.01); *C07D 471/04* (2013.01); *C07D 491/048* (2013.01); *C07D 495/04* (2013.01); *C09K 11/06* (2013.01); *H01L 51/004* (2013.01); *H01L 51/0037* (2013.01); *H01L 51/0061* (2013.01); *H01L 51/0072* (2013.01); *H01L 51/0085* (2013.01); *C09K 2211/1007* (2013.01); *C09K 2211/1029* (2013.01); *C09K 2211/185* (2013.01); *H01L 51/0052* (2013.01); *H01L 51/0056* (2013.01); *H01L 51/0058* (2013.01); *H01L 51/0067* (2013.01); *H01L 51/0071* (2013.01); *H01L 51/0073* (2013.01); *H01L 51/0074* (2013.01); *H01L 51/5016* (2013.01); *H01L 51/5056* (2013.01); *H01L 51/5088* (2013.01); *H01L 51/5096* (2013.01); *H01L 2251/308* (2013.01); *Y02E 10/549* (2013.01)

(58) Field of Classification Search
CPC .. C07D 209/94; C07D 219/02; C07D 265/38; C07D 401/10; C07D 405/04; C07D 405/12; C07D 409/12; C07D 471/04; C07D 491/048; C07D 495/04; C07D 209/86; C07D 403/12; C07D 487/04; C09K 11/06; C09K 2211/1029
See application file for complete search history.

(56) References Cited

U.S. PATENT DOCUMENTS

| | | | |
|---|---|---|---|
| 9,502,667 B2 | 11/2016 | Saito et al. | |
| 9,773,979 B2 | 9/2017 | Parham et al. | |
| 9,831,441 B2 * | 11/2017 | Parham | C07D 413/14 |
| 2014/0296519 A1 * | 10/2014 | Matsumoto | C07D 209/86 |
| | | | 544/212 |

FOREIGN PATENT DOCUMENTS

| | | | |
|---|---|---|---|
| EP | 2772483 A1 | 9/2014 | |
| JP | 2014101275 A | 6/2014 | |
| JP | 2014160813 A | 9/2014 | |
| KR | 20130136359 A | 12/2013 | |
| KR | 20140130297 A | 11/2014 | |
| WO | WO-2010108579 A1 * | 9/2010 | ............ H01L 51/008 |

(Continued)

OTHER PUBLICATIONS

Hyun et al. "Novel compound for organic electroluminescent device and organic electroluminescent device comprising same" WO-2013183851-A1 (Dec. 2013) English machine Translation. (Year: 2013).*
Hyun et al. WO 2013/183851 A1 English Machine Translation [online][accessed on Sep. 4, 2019 from <https://patentscope.wipo.int/search/en/detail.jsf?docId=WO2013183851&_cid=P12-K05S6X-18050-1>]. (Year: 2019).*
Kaiser et al. WO 2010/108579 A1 English Machine Translation [online][accessed on Sep. 5, 2019 from < https://patentscope.wipo.int/search/en/detail.jsf?docId=WO2010108579&tab=PCTDESCRIPTION&_cid=P11-K06ZWJ-43032-1>]. (Year: 2019).*

(Continued)

*Primary Examiner* — Amanda L. Aguirre
(74) *Attorney, Agent, or Firm* — Faegre Drinker Biddle & Reath

(57) ABSTRACT

The present invention relates to heterocyclic compounds and to electronic devices, especially organic electroluminescent devices, comprising these compounds.

15 Claims, No Drawings

(56) References Cited

FOREIGN PATENT DOCUMENTS

| WO | WO-2010110553 A2 * | 9/2010 | ......... H01L 51/0059 |
|---|---|---|---|
| WO | WO-2013017192 A1 | 2/2013 | |
| WO | WO-2013120577 A1 | 8/2013 | |
| WO | WO-2013183851 A1 * | 12/2013 | ............. H01L 51/50 |
| WO | WO-2014067614 A1 * | 5/2014 | ........... C07C 211/61 |
| WO | WO-2014163228 A1 * | 10/2014 | ........... H01L 51/006 |
| WO | WO-2015108377 A1 * | 7/2015 | ......... H01L 51/0059 |

OTHER PUBLICATIONS

International Search Report for PCT/EP2015/002199 dated Dec. 10, 2015.
Written Opinion of the International Searching Authority for PCT/EP2015/002199 dated Dec. 10, 2015.

* cited by examiner

HETEROCYCLIC COMPOUNDS FOR USE IN ELECTRONIC DEVICES

CROSS-REFERENCE TO RELATED APPLICATIONS

This application is a national stage application (under 35 U.S.C. § 371) of PCT/EP2015/002199, filed Nov. 3, 2015, which claims benefit of European Application No. 14003925.6, filed Nov. 21, 2014.

The present invention relates to heterocyclic compounds suitable for use in electronic devices. The present invention further relates to processes for preparation thereof and to electronic devices.

BACKGROUND OF THE INVENTION

Electronic devices containing organic, organometallic and/or polymeric semiconductors are becoming increasingly important, and are being used in many commercial products for reasons of cost and because of their performance. Examples here include organic-based charge transport materials (for example triarylamine-based hole transporters) in photocopiers, organic or polymeric light-emitting diodes (OLEDs or PLEDs) and in readout and display devices or organic photoreceptors in photocopiers. Organic solar cells (O-SCs), organic field-effect transistors (O-FETs), organic thin-film transistors (O-TFTs), organic integrated circuits (O-ICs), organic optical amplifiers and organic laser diodes (O-lasers) are at an advanced stage of development and may have great future significance.

Many of these electronic devices, irrespective of the respective end use, have the following general substrate structure which can be adjusted for the particular application:
(1) substrate,
(2) electrode, frequently metallic or inorganic, but also composed of organic or polymeric conductive materials,
(3) charge injection layer(s) or interlayer(s), for example to compensate for unevenness in the electrode ("planarization layer"), frequently composed of a conductive doped polymer,
(4) organic semiconductor,
(5) possibly further charge transport, charge injection or charge blocker layers,
(6) counterelectrode, materials as specified in (2),
(7) encapsulation.

The above arrangement is the general structure of an organic electronic device, it being possible to combine various layers, such that the result in the simplest case is an arrangement composed of two electrodes with an organic layer in between. In this case, the organic layer fulfils all functions including the emission of light in the case of OLEDs. A system of this kind is described, for example, in WO 90/13148 A1, based on poly(p-phenylenes).

Electronic devices comprising heterocyclic compounds are known inter alia from publications WO 2014/088047 A1, WO 2013/120577 A1, WO 2013/183851 A1, EP 2 468 725 A1, KR 2013 0134426 A1 and KR 101395080 B1.

Known electronic devices have a useful profile of properties. However, there is a constant need to improve the properties of these devices.

These properties especially include the energy efficiency with which an electronic device solves the problem defined. In the case of organic light-emitting diodes, which may be based either on low molecular weight compounds or on polymeric materials, the light yield in particular should be sufficiently high that a minimum amount of electrical power has to be applied to achieve a particular luminous flux. In addition, a minimum voltage should also be necessary to achieve a defined luminance. A further particular problem is the lifetime of the electronic devices.

BRIEF SUMMARY OF THE INVENTION IDC

It is therefore an object of the present invention to provide novel compounds which lead to electronic devices having improved properties. It is a particular object to provide electron blocker materials, hole transport materials, hole injection materials and/or matrix materials which exhibit improved properties in relation to efficiency, operating voltage and/or lifetime. Moreover, the compounds should be processible in a very simple manner, and especially exhibit good solubility and film formation.

A further object can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, these objects and others which are not specified explicitly but can be inferred or discerned directly from the connections discussed herein by way of introduction are achieved by compounds having all the features of Claim 1. Appropriate modifications to the compounds of the invention are protected in the dependent claims that refer back to Claim 1.

DETAILED DESCRIPTION OF THE INVENTION

The invention thus provides a compound comprising at least one structure of the formula (I)

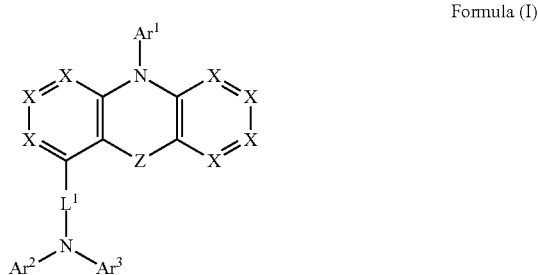

Formula (I)

where the symbols used are as follows:
X is the same or different at each instance and is N or $CR^1$, preferably $CR^1$, with the proviso that not more than two of the X groups in one cycle are N;
Z is a bond, $C(R^1)_2$, O or S;
$L^1$ is a bond, an aromatic ring system having 6 to 60, preferably 6 to 40 and more preferably 6 to 20 carbon atoms or a heteroaromatic ring system having 3 to 60, preferably 3 to 40 and more preferably 3 to 20 carbon atoms, each of which may be substituted by one or more $R^1$ radicals, preferably a bond, an aryl group having 6 to 60, preferably 6 to 40 and more preferably 6 to 20 carbon atoms or a heteroaryl group having 3 to 60, preferably 6 to 40 and more preferably 6 to 20 carbon atoms, each of which may be substituted by one or more $R^1$ radicals;

Ar$^1$, Ar$^2$, Ar$^3$ is an aryl group having 6 to 40 and preferably 6 to 20 carbon atoms or a heteroaryl group having 3 to 40 and preferably 3 to 20 carbon atoms, each of which may be substituted by one or more R$^1$ radicals;

R$^1$ is the same or different at each instance and is H, D, F, Cl, Br, I, B(OR$^2$)$_2$, CHO, C(=O)R$^2$, CR$^2$=C(R$^2$)$_2$, CN, C(=O)OR$^2$, C(=O)N(R$^2$)$_2$, Si(R$^2$)$_3$, N(R$^2$)$_2$, NO$_2$, P(=O)(R$^2$)$_2$, OSO$_2$R$^2$, OR$^2$, S(=O)R$^2$, S(=O)$_2$R$^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^2$ radicals, where one or more nonadjacent CH$_2$ groups may be replaced by —R$^2$C=CR$^2$—, —C≡C—, Si(R$^2$)$_2$, C=O, C=S, C=NR$^2$, —C(=O)O—, —C(=O)NR$^2$—, NR$^2$, P(=O)(R$^2$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^2$ radicals, or an aryloxy or heteroaryloxy group which has 5 to 40 aromatic ring atoms and may be substituted by one or more R$^2$ radicals, or a combination of these systems; at the same time, two or more adjacent R$^1$ substituents together may also form a mono- or polycyclic, aliphatic or aromatic ring system;

R$^2$ is the same or different at each instance and is H, D, F, Cl, Br, I, B(OR$^3$)$_2$, CHO, C(=O)R$^3$, CR$^3$=C(R$^3$)$_2$, CN, C(=O)OR$^3$, C(=O)N(R$^3$)$_2$, Si(R$^3$)$_3$, N(R$^3$)$_2$, NO$_2$, P(=O)(R$^3$)$_2$, OSO$_2$R$^3$, OR$^3$, S(=O)R$^3$, S(=O)$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^3$ radicals, where one or more nonadjacent CH$_2$ groups may be replaced by —R$^3$C=CR$^3$—, —C≡C—, Si(R$^3$)$_2$, C=O, C=S, C=NR$^3$, —C(=O)O—, —C(=O)NR$^3$—, NR$^3$, P(=O)(R$^3$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^3$ radicals, or an aryloxy or heteroaryloxy group which has 5 to 40 aromatic ring atoms and may be substituted by one or more R$^3$ radicals, or a combination of these systems; at the same time, two or more adjacent R$^2$ substituents together may also form a mono- or polycyclic, aliphatic or aromatic ring system;

R$^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more adjacent R$^3$ substituents together may also form a mono- or polycyclic, aliphatic or aromatic ring system;

with the proviso that at least one of the Ar$^2$ and/or Ar$^3$ radicals is a group of the formula (IIa) or (IIb)

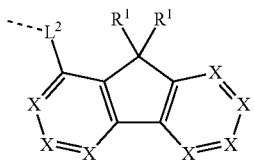

Formula (IIa)

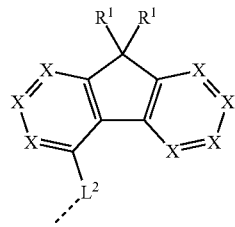

Formula (IIb)

in which

X is the same or different at each instance and is N or CR$^1$, preferably CR$^1$, with the proviso that not more than two of the X groups in one cycle are N;

L$^2$ is a bond, an aromatic ring system having 6 to 60, preferably 6 to 40 and more preferably 6 to 20 carbon atoms or a heteroaromatic ring system having 3 to 60, preferably 3 to 40 and more preferably 3 to 20 carbon atoms, each of which may be substituted by one or more R$^1$ radicals, preferably a bond, an aryl group having 6 to 60, preferably 6 to 40 and more preferably 6 to 20 carbon atoms or a heteroaryl group having 3 to 60, preferably 3 to 40 and more preferably 3 to 20 carbon atoms, each of which may be substituted by one or more R$^1$ radicals;

R$^1$ is as defined above and the dotted line represents the bonding site, such that L$^2$ binds to the same nitrogen atom as L$^1$.

In this context, "adjacent carbon atoms" means that the carbon atoms are bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 60 carbon atoms in the ring system. A heteroaromatic ring system in the context of this invention contains 3 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention is understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9'-diarylfluorene, triarylamine, diaryl ethers, stilbene, etc. are also to be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl or terphenyl, shall likewise be regarded as an aromatic or heteroaromatic ring system.

A cyclic alkyl, alkoxy or thio alkoxy group in the context of this invention is understood to mean a monocyclic, bicyclic or polycyclic group.

In the context of the present invention, a $C_1$- to $C_{40}$-alkyl group in which individual hydrogen atoms or $CH_2$ groups may be replaced by the abovementioned groups are understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexy)cyclohex-1-yl, 1-(n-octyl)cyclohex-1-yl- and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$ to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 3-60 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred configuration, it may be the case that a structure of formula (Ia) is formed

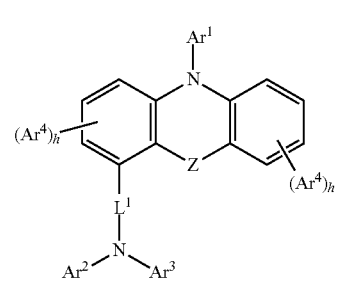

Formula (Ia)

in which h independently at each instance is 0, 1, 2, 3 or 4, preferably 0, 1 or 2 and more preferably 0 or 1;

$Ar^4$ is an aryl group having 6 to 40 carbon atoms or a heteroaryl group having 3 to 40 carbon atoms, each of which may be substituted by one or more $R^1$ radicals, and the symbols $Ar^1$, $Ar^2$, $Ar^3$, $L^1$ and Z may be as defined above.

In addition, it may be the case that the Z group in formula (I) is a bond, such that a structure of the formula (Ib) or (Ic) is formed

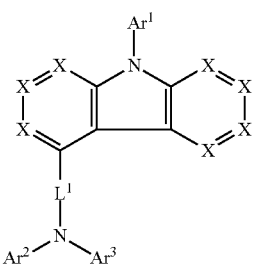

Formula (Ib)

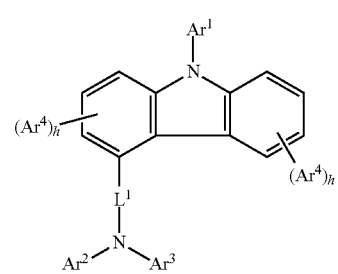

Formula (Ic)

in which the symbols may assume the definitions set out above.

For illustration of the remarks which follow, the structural formula of fluorene is depicted below, together with the numbering of the positions. In spirobifluorene derivatives, the numbering is analogous, with the sole difference that the 9 position cannot be substituted.

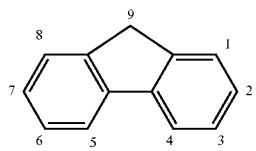

In structures of the formulae (IIa) or (IIb), it may be the case that the two $R^1$ radicals bonded to the carbon atom in position 9 in the fluorene structure are identical. In this way, symmetric substitution at this position may be obtained.

In addition, it may be the case that the two $R^1$ radicals bonded to the carbon atom in position 9 in the fluorene structure of formula (IIa) or (IIb) are different. In this case, the difference may be that one of the two R radicals is an aromatic or heteroaromatic ring system which has 5 to 30 aromatic ring atoms and may be substituted by one or more $R^2$ radicals, whereas the other $R^1$ radical is a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $C=O$, $C=S$, $C=NR^2$, $-C(=O)O-$, $-C(=O)NR^2-$, $NR^2$, $P(=O)(R^2)$, $-O-$, $-S-$, $SO$ or $SO_2$ and where one or more hydrogen atoms may be replaced by D, F, Cl, Br, I, CN or $NO_2$. In addition, the difference may be that the two $R^1$ radicals bonded to the carbon atom in position 9 in the fluorene structure of formula (IIa) or (IIb) are different aromatic or heteroaromatic ring systems which have 5 to 30 ring atoms and may be substituted by one or more $R^2$ radicals. Furthermore, the two $R^1$ radicals bonded to the carbon atom in position 9 in the fluorene structure of formula (IIa) or (IIb) may be different straight-chain alkyl, alkoxy or thioalkoxy groups having 1 to 40 carbon atoms or branched or cyclic alkyl, alkoxy or thioalkoxy groups having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $C=O$, $C=S$, $C=NR^2$, $-C(=O)O-$, $-C(=O)NR^2-$, $NR^2$, $P(=O)(R^2)$, $-O-$, $-S-$, $SO$ or $SO_2$ and where one or more hydrogen atoms may be replaced by D, F, Cl, Br, I, CN or $NO_2$.

More preferably, the two $R^1$ radicals bonded to the carbon atom in position 9 in the fluorene structure of formula (IIa) or (IIb) are the same.

Preferably, the two $R^1$ radicals bonded to the carbon atom in position 9 in the fluorene structure of formula (IIa) or (IIb) may each be an aromatic or heteroaromatic ring system which has 5 to 30 aromatic ring atoms and may be substituted by one or more $R^1$ radicals, where the two ring systems are joined to one another.

In addition, surprising advantages are exhibited by compounds of formula (I) in which the two $R^1$ radicals bonded to the carbon atom in position 9 in the fluorene structure of formula (IIa) or (IIb) may each be an aromatic or heteroaromatic ring system which has 5 to 30 aromatic ring atoms and may be substituted by one or more $R^1$ radicals, where the two ring systems are joined to one another.

Particular preference is given here to compounds of formula (I) in which at least one of the $Ar^2$ and/or $Ar^3$ radicals comprises a group of the formula (IIc) or (IId)

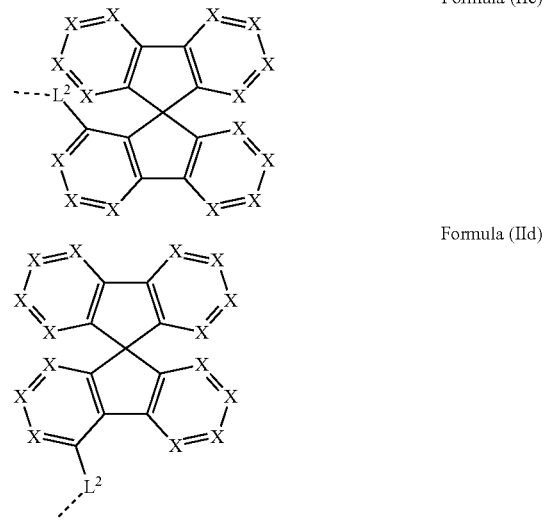

in which the symbols may assume the definitions set out above.

In addition, preference is given to compounds which are characterized in that the two $R^1$ radicals bonded to the carbon atom in position 9 in the fluorene structure of formula (IIa) or (IIb) are each an aromatic or heteroaromatic ring system which has 5 to 30 aromatic ring atoms and may be substituted by one or more $R^1$ radicals, where the two ring systems are not joined to one another, or a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $C=O$, $C=S$, $C=NR^2$, $-C(=O)O-$, $-C(=)NR^2-$, $NR^2$, $P(=O)(R^2)$, $-O-$, $-S-$, $SO$ or $SO_2$ and where one or more hydrogen atoms may be replaced by D, F, Cl, Br, I, CN or $NO_2$.

Particular preference is given here to compounds of formula (I) in which at least one of the $Ar^2$ and/or $Ar^3$ radicals comprises a group of the formula (IIe) or (IIf)

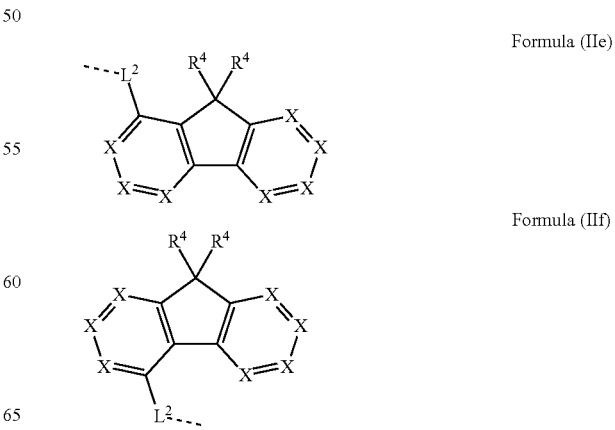

in which the symbols X and $L^2$ may be as defined above and $R^4$ is H, an aromatic ring system having 6 to 30 aromatic ring atoms, preferably an aryl group having 6 to 20 carbon atoms, more preferably phenyl, biphenyl or naphthyl, or an alkyl group having 1 to 20 carbon atoms, preferably methyl, ethyl, propyl or butyl, more preferably methyl.

In structures of the formulae (IIe) or (IIf), it may be the case that the two $R^4$ radicals bonded to the carbon atom in position 9 in the fluorene structure are identical. In addition, it may be the case that the two $R^4$ radicals bonded to the carbon atom in position 9 in the fluorene structure of formula (IIe) or (IIf) are different. Preferably, the two $R^4$ radicals bonded to the carbon atom in position 9 in the fluorene structure in structures of the formulae (IIe) or (IIf) are identical.

In addition, surprising advantages are exhibited by compounds of formulae (I), (Ib), (IIa), (IIb), (IIc), (IId), (IIe) and formula (IIf) in which not more than two and preferably not more than one X group is N, and preferably all X are $CR^1$, where preferably at most 4, more preferably at most 3 and especially preferably at most 2 of the $CR^1$ groups that X represents are not the CH group.

In the structures of formulae (I), (Ia), (Ib), (Ic), (IIa), (IIb), (IIc), (IId), (IIe) and formula (IIf), it may preferably be the case that the $L^1$ and/or $L^2$ radical, if it is not a bond, is bonded via an aryl group or heteroaryl group to the nitrogen atom, the fluorene group (formulae (IIa), (IIb), (IIc), (IId), (IIe) and (IIf)) and/or the heterocyclic radical shown in formulae (I), (Ia), (Ib), (Ic), preferably a carbazole group. If the $L^1$ and $L^2$ radicals are not a bond, these $L^1$ and $L^2$ radicals are preferably bonded to the nitrogen atom and the fluorene group (formulae (IIa), (IIb), (IIc), (IId), (IIe) and (IIf)) and the heterocyclic radical shown in formulae (I), (Ia), (Ib), (Ic), preferably a carbazole group, via an aryl group or heteroaryl group.

Preference is given to compounds comprising structures of the formula (I) in which at least one $L^1$ and/or $L^2$ group of formula (I), (Ia) and/or (IIb) is a group selected from the formulae (L-1) to (L-78)

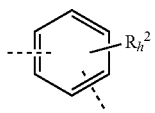

Formula (L-1)

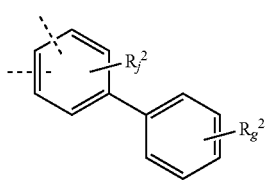

Formula (L-2)

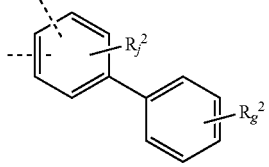

Formula (L-3)

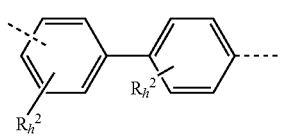

Formula (L-4)

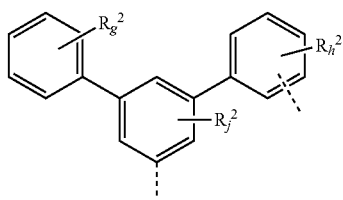

Formula (L-5)

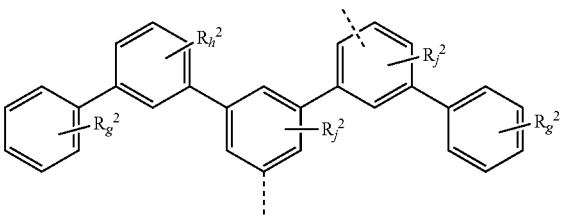

Formula (L-6)

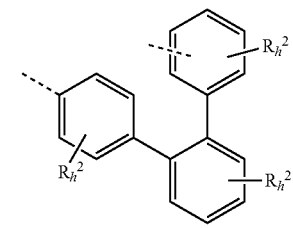

Formula (L-7)

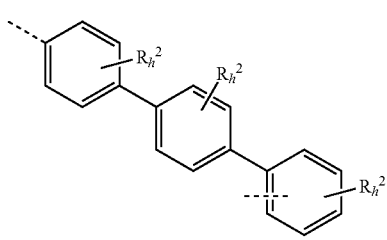

Formula (L-8)

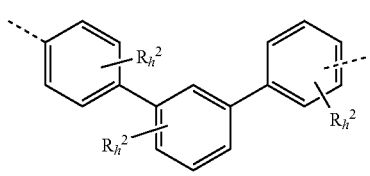

Formula (L-9)

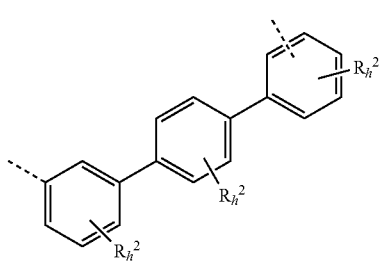

Formula (L-10)

Formula (L-11)
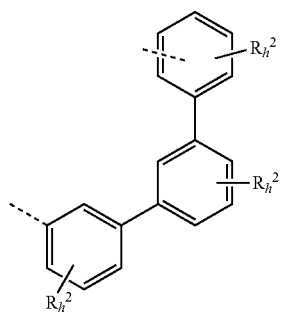
Formula (L-12)
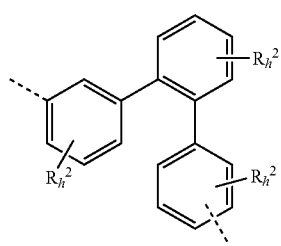
Formula (L-13)
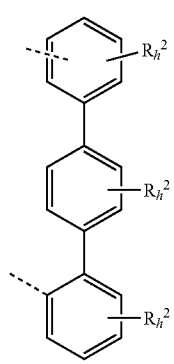
Formula (L-14)
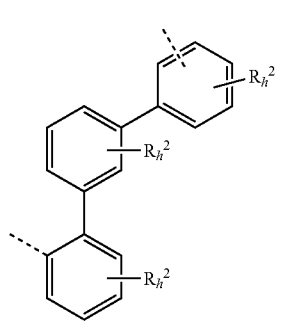
Formula (L-15)
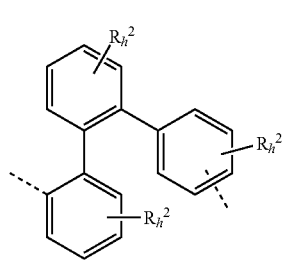
Formula (L-16)
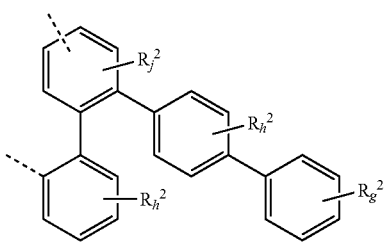
Formula (L-17)
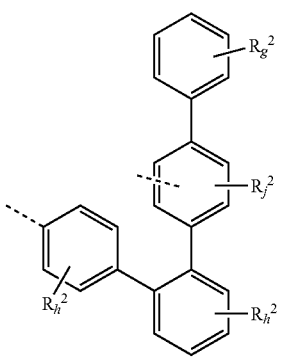
Formula (L-18)
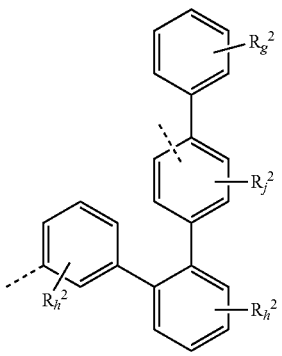
Formula (L-19)
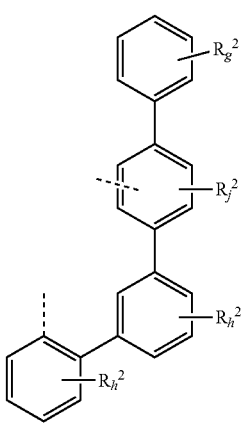

Formula (L-20)
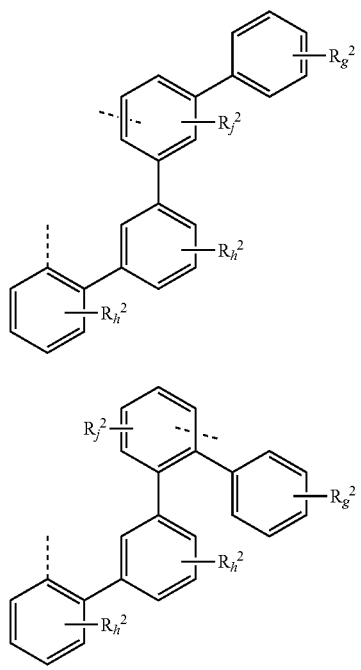
Formula (L-21)
Formula (L-22)
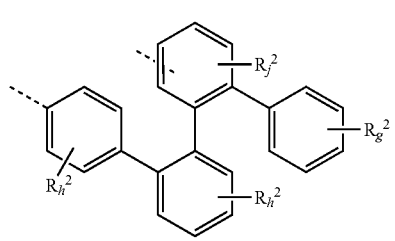
Formula (L-23)
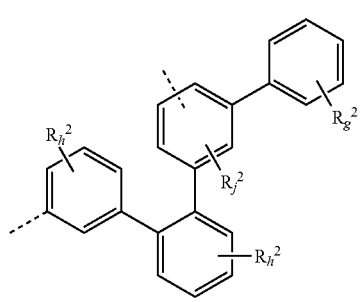
Formula (L-24)
Formula (L-25)
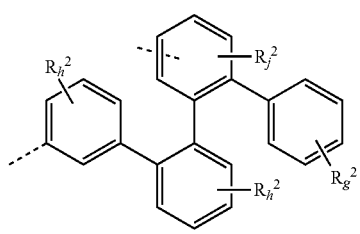
Formula (L-26)
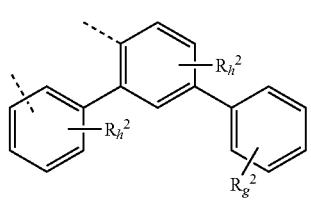
Formula (L-27)
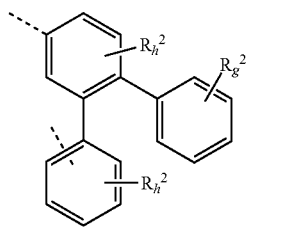
Formula (L-28)
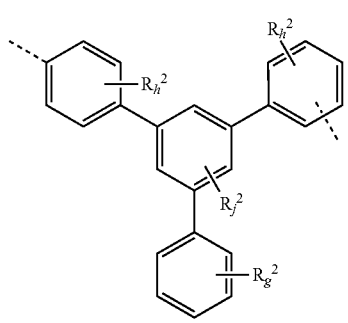
Formula (L-29)
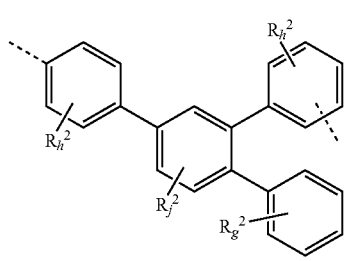
Formula (L-30)
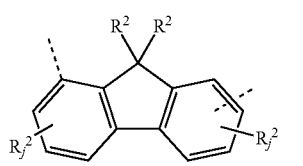
Formula (L-31)
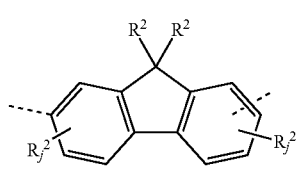

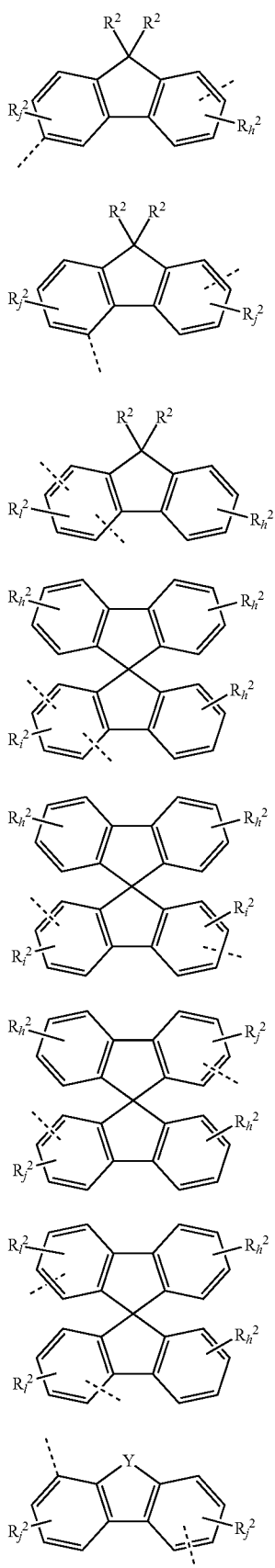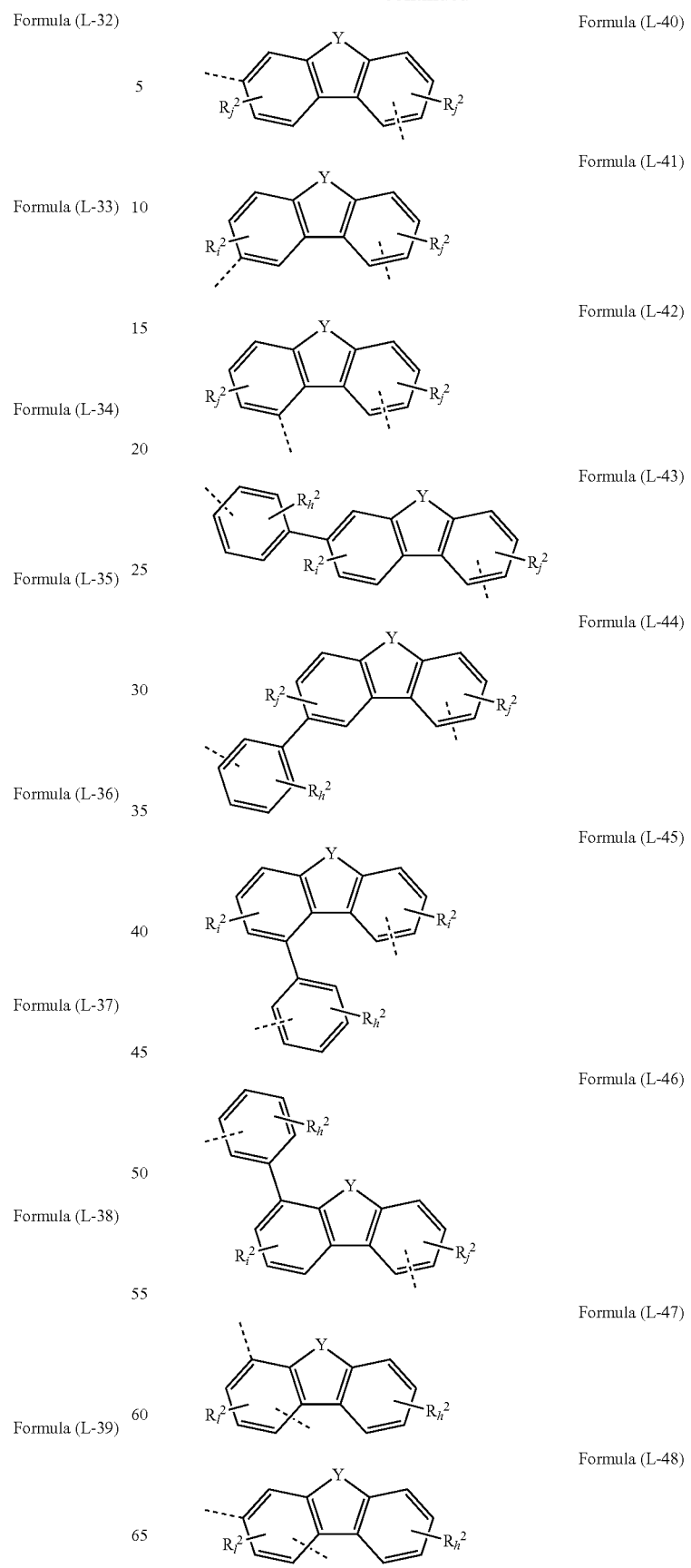

Formula (L-49)
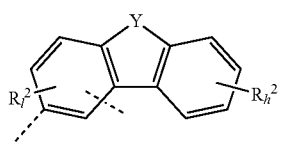
Formula (L-50)
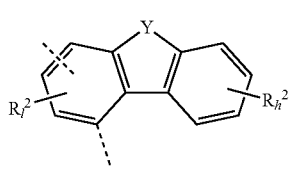
Formula (L-51)
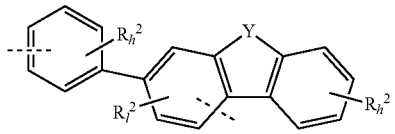
Formula (L-52)
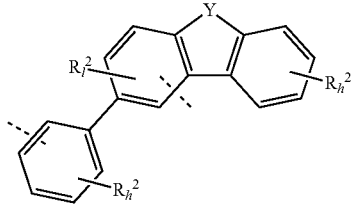
Formula (L-53)
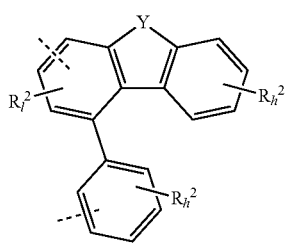
Formula (L-54)
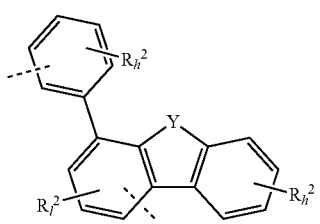
Formula (L-55)
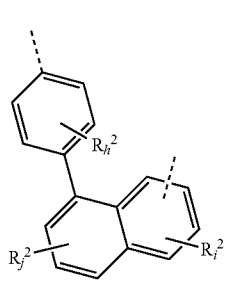
Formula (L-56)
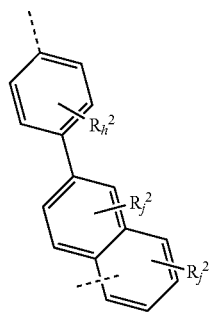
Formula (L-57)
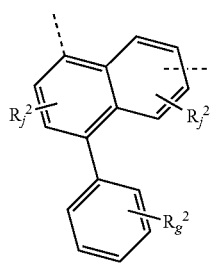
Formula (L-58)
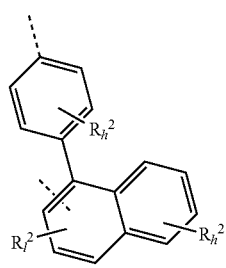
Formula (L-59)
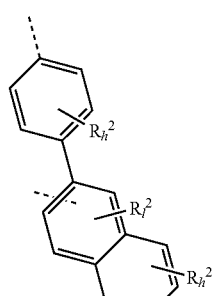
Formula (L-60)
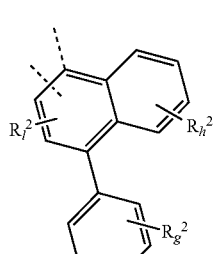
Formula (L-61)
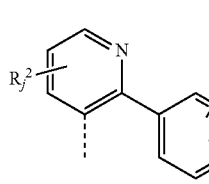

Formula (L-62)
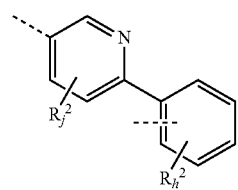
Formula (L-63)
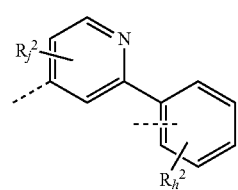
Formula (L-64)
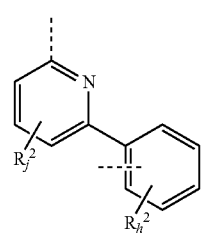
Formula (L-65)
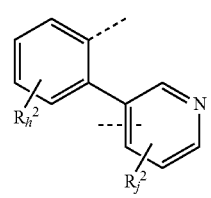
Formula (L-66)
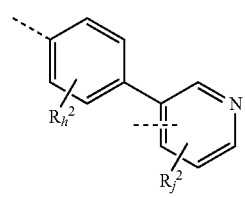
Formula (L-67)
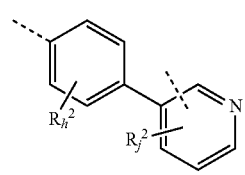
Formula (L-68)
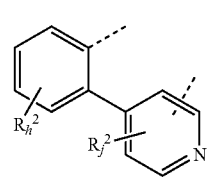
Formula (L-69)
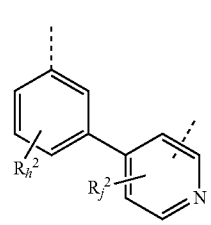
Formula (L-70)
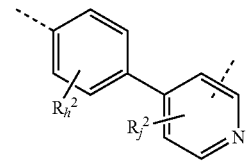
Formula (L-71)
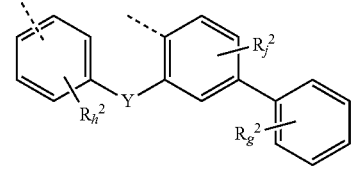
Formula (L-72)
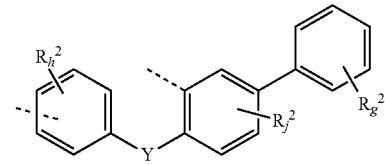
Formula (L-73)
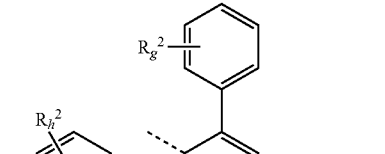
Formula (L-74)
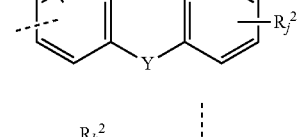
Formula (L-75)
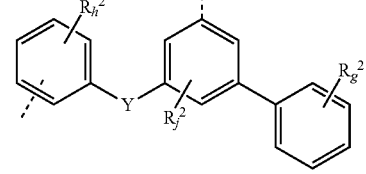
Formula (L-76)
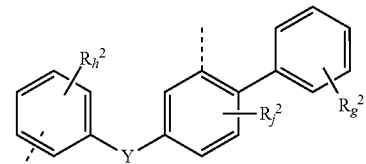
Formula (L-77)
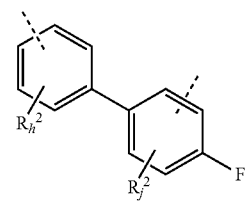
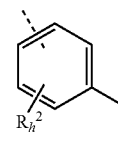

Formula (L-78)

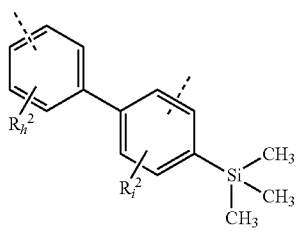

in which the dotted bonds in each case mark the attachment positions, the index l is 0, 1 or 2, the index g is 0, 1, 2, 3, 4 or 5, j independently at each instance is 0, 1, 2 or 3; h independently at each instance is 0, 1, 2, 3 or 4; Y is O, S or $NR^2$, preferably O or S; and $R^2$ may be as defined above.

It may preferably be the case that the sum total of the indices l, g, h and j in the structures of the formula (L-1) to (L-78) is at most 3 in each case, preferably at most 2 and more preferably at most 1.

More preferably, the $L^1$ and/or $L^2$ group of formula (I), (IIa) and/or (IIb) is an aromatic radical having 6 to 18 and preferably 6 to 12 carbon atoms, preference being given to structures of the formula (L-1) to (L-15) and particular preference to structures of the formula (L-1) to (L-4).

Preferably, the compound having structures of formula (I) may comprise $R^1$ radicals in which these $R^1$ radicals are the same or different at each instance and are preferably selected from the group consisting of H, D, F, Br, I, CN, $Si(R^2)_3$, $B(OR^2)_2$, $C(=O)Ar^1$, a straight-chain alkyl group having 1 to 10 carbon atoms or a straight-chain alkoxy group having 1 to 10 carbon atoms or an alkenyl group having 2 to 10 carbon atoms or a branched or cyclic alkoxy group having 3 to 10 carbon atoms or a branched or cyclic alkyl group having 3 to 10 carbon atoms, each of which may be substituted by one or more $R^2$ radicals, where one or more hydrogen atoms may be replaced by D or F, or an aromatic or heteroaromatic ring system which has 5 to 30 aromatic ring atoms and may be substituted in each case by one or more $R^2$ radicals; at the same time, two adjacent R or $R^1$ radicals together or R or $R^1$ radicals together with $R^2$ radicals may also form a mono- or polycyclic, aliphatic or aromatic ring system. More preferably, these $R^1$ radicals are the same or different at each instance and are preferably selected from the group consisting of H, D, F, a straight-alkoxy group having 1 to 6 carbon atoms or a branched or cyclic alkoxy group having 3 to 10 carbon atoms, a straight-chain alkyl group having 1 to 6 carbon atoms or a branched or cyclic alkyl group having 3 to 10 carbon atoms, where one or more hydrogen atoms may be replaced by D or F, or an aromatic or heteroaromatic ring system which has 5 to 24 aromatic ring atoms and may be substituted in each case by one or more $R^2$ radicals; at the same time, two adjacent R or $R^1$ radicals together or R or $R^1$ radicals together with $R^2$ radicals may also form a mono- or polycyclic, aliphatic or aromatic ring system. More preferably, at least one of the R or $R^1$ radicals in formula (I) may be an aryl group or a heteroaryl group which has 6 to 18 carbon atoms and may be substituted by up to three $R^2$ radicals.

Preferably, the compound having structures of formula (I) may comprise $R^2$ radicals in which these $R^2$ radicals are the same or different at each instance and are preferably selected from the group consisting of H, D, F, Cl, Br, I, CHO, $C(=O)Ar^1$, $P(=O)(Ar^1)_2$, $S(=O)Ar^1$, $S(=O)_2Ar^1$, CN, $NO_2$, $Si(R^3)_3$, $B(OR^3)_2$, $OSO_2R^3$, a straight-chain alkyl, alkoxy or thioalkoxy group having 1 to 10 carbon atoms or a branched or cyclic alkyl, alkoxy or thioalkoxy group having 3 to 10 carbon atoms, each of which may be substituted by one or more $R^3$ radicals, where one or more nonadjacent $CH_2$ groups may be replaced by C≡C, $Si(R)_2$, $Ge(R^3)_2$, $Sn(R^3)_2$, C=O, C=S, C=Se, $P(=O)(R^3)$, SO, $SO_2$, O, S or $CONR^3$ and where one or more hydrogen atoms may be replaced by D, F, Cl, Br, I, CN or $NO_2$, or an aromatic or heteroaromatic ring system which has 5 to 24 aromatic ring atoms and may be substituted in each case by one or more $R^3$ radicals, or an aryloxy or heteroaryloxy group which has 5 to 24 aromatic ring atoms and may be substituted by one or more $R^3$ radicals, or a combination of these systems; at the same time, two or more adjacent $R^2$ substituents together may form a mono- or polycyclic, aliphatic or aromatic ring system. More preferably, at least one of the $R^2$ radicals in formula (I) may be an aryl group or a heteroaryl group which has 6 to 18 carbon atoms and may be substituted by up to three $R^3$ radicals.

Preference is given to compounds comprising structures of the formula (I) in which at least one $R^1$, $Ar^2$, $Ar^3$ or $Ar^4$ radical in the structures of formulae (I), (Ib), (IIa), (IIb), (IIc), (IId), (IIe) or formula (IIf) is a group selected from the formulae ($R^1$-1) to ($R^1$-72)

(Formula $R^1$-1)

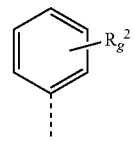

(Formula $R^1$-2)

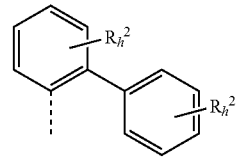

(Formula $R^1$-3)

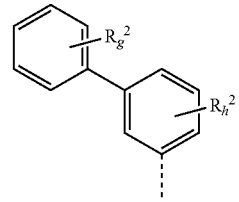

(Formula $R^1$-4)

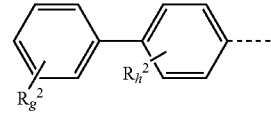

(Formula $R^1$-5)

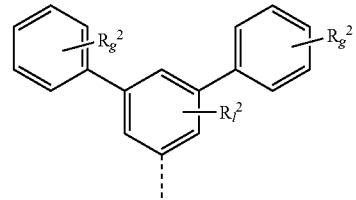

-continued
(Formula R¹-6)
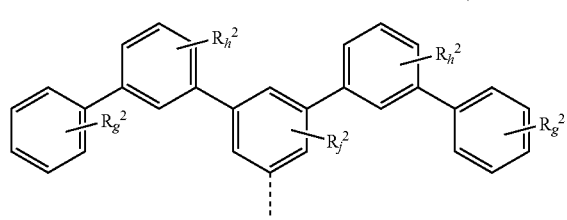
Formula (R¹-7)
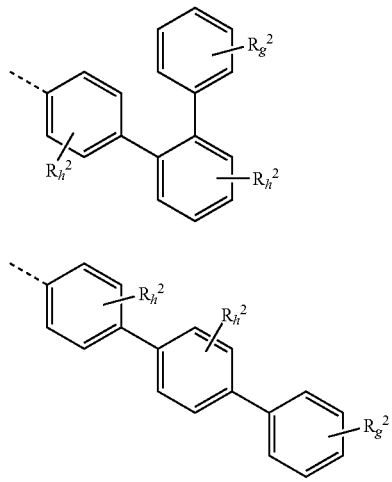
Formula (R¹-8)
Formula (R¹-9)
Formula (R¹-10)
Formula (R¹-11)
(Formula R¹-12)
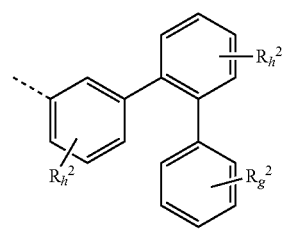
(Formula R¹-13)
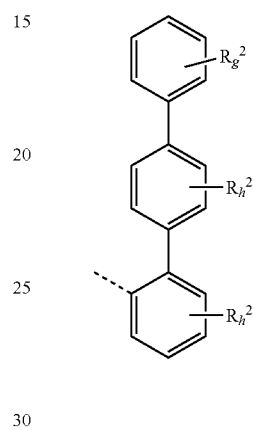
(Formula R¹-14)
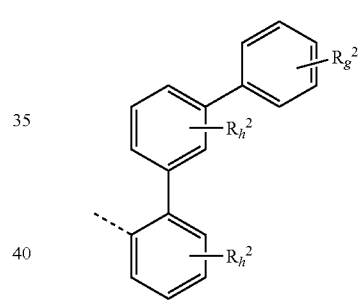
(Formula R¹-15)
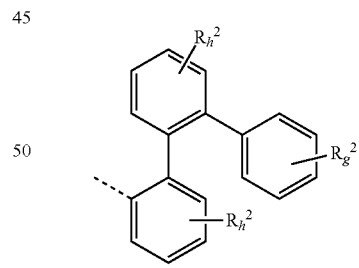
(Formula R¹-16)
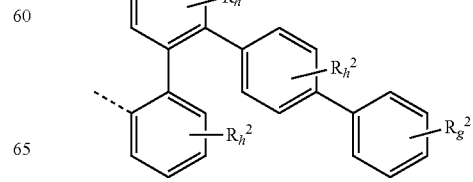

(Formula R¹-17)
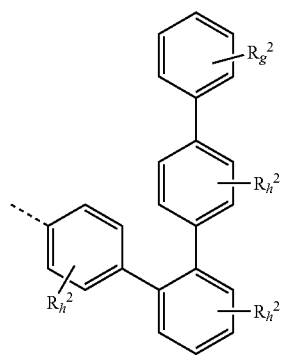
(Formula R¹-18)
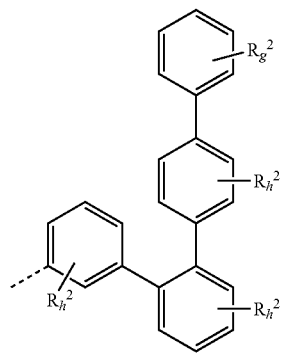
(Formula R¹-19)
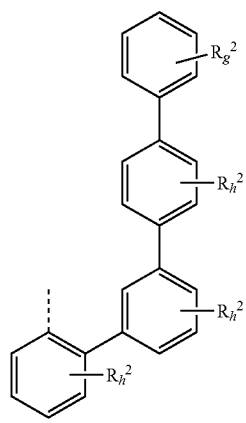
(Formula R¹-20)
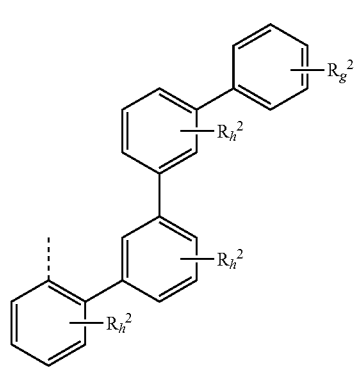
(Formula R¹-21)
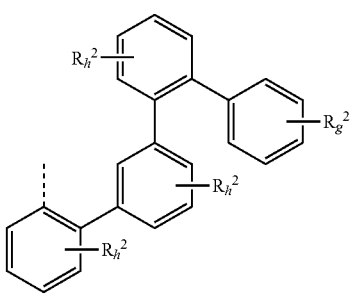
(Formula R¹-22)
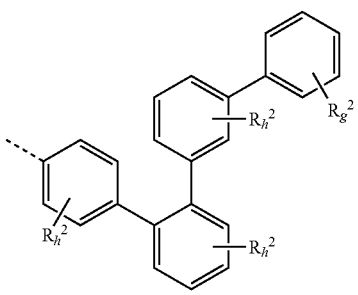
(Formula R¹-23)
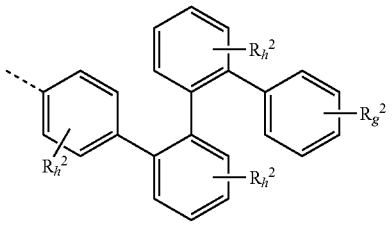
(Formula R¹-24)
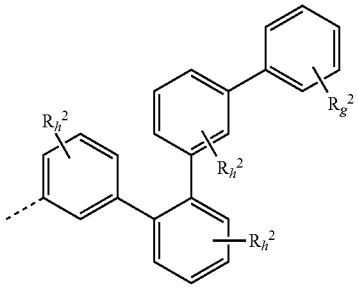
(Formula R¹-25)
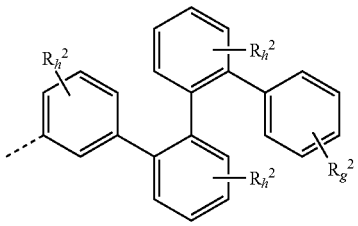
(Formula R¹-26)
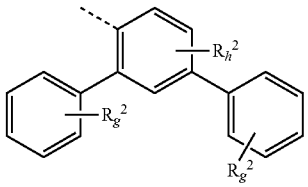

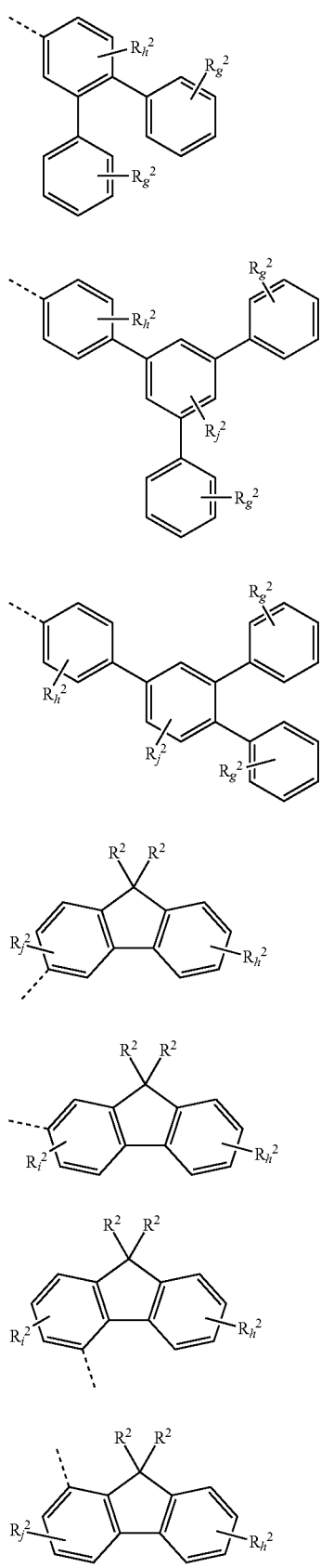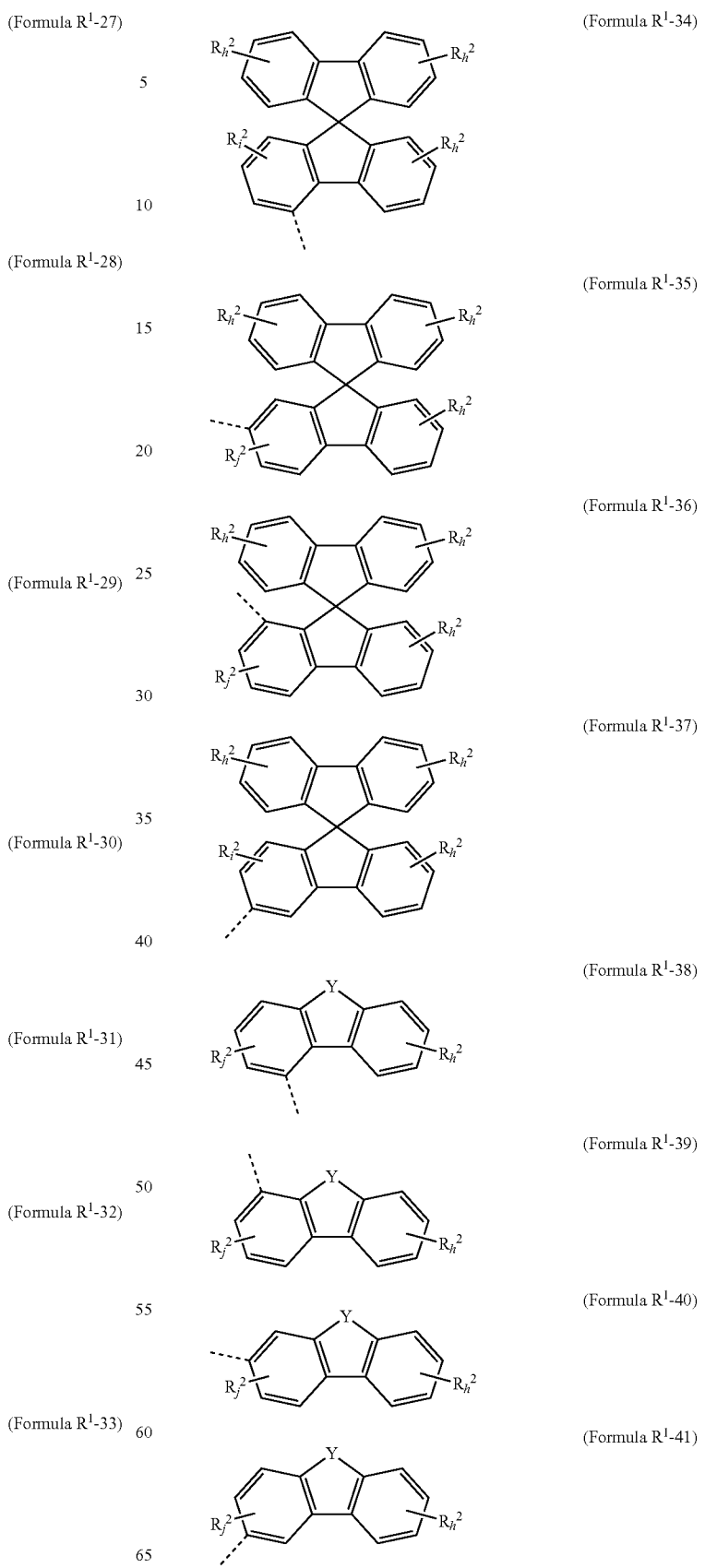

(Formula R¹-42)
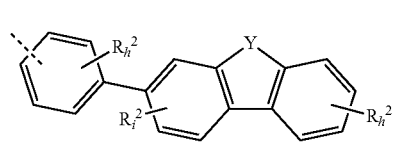
(Formula R¹-43)
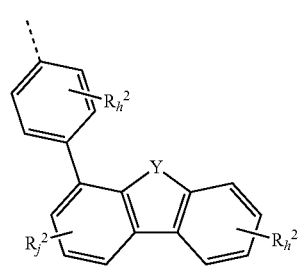
(Formula R¹-44)
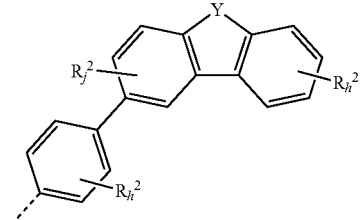
(Formula R¹-45)
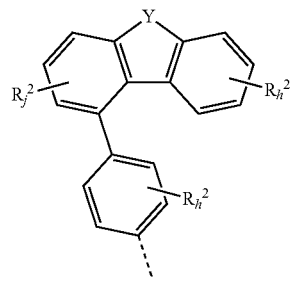
(Formula R¹-46)
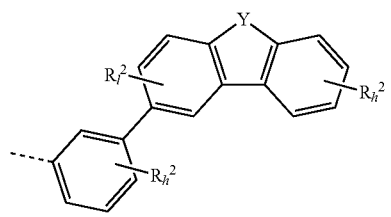
(Formula R¹-47)
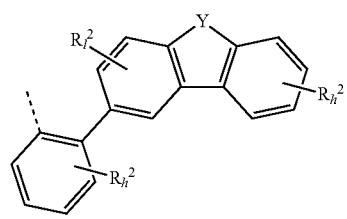
(Formula R¹-48)
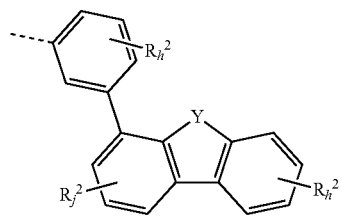
(Formula R¹-49)
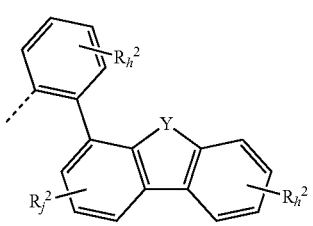
(Formula R¹-50)
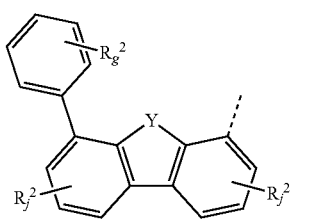
(Formula R¹-51)
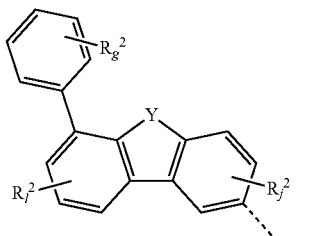
(Formula R¹-52)
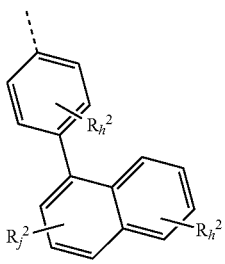
(Formula R¹-53)
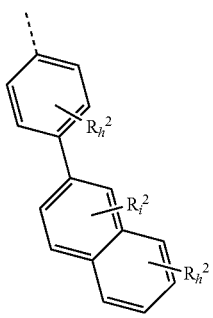
(Formula R¹-54)
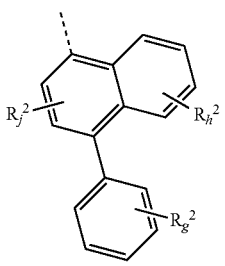

(Formula R¹-55)
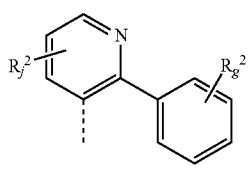
(Formula R¹-56)
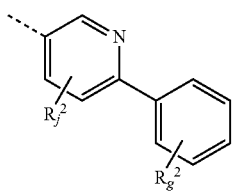
(Formula R¹-57)
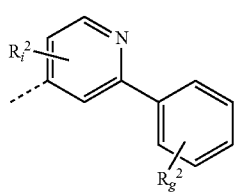
(Formula R¹-58)
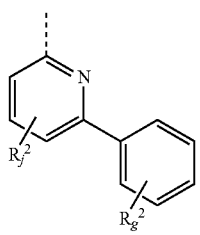
(Formula R¹-59)
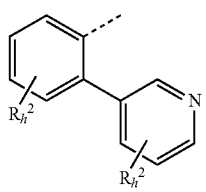
(Formula R¹-60)
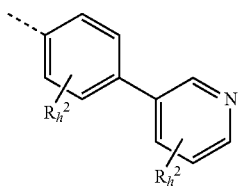
(Formula R¹-61)
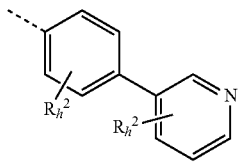
(Formula R¹-62)
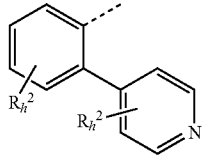
(Formula R¹-63)
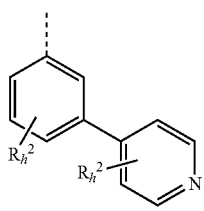
(Formula R¹-64)
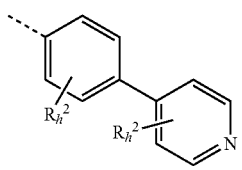
(Formula R¹-65)
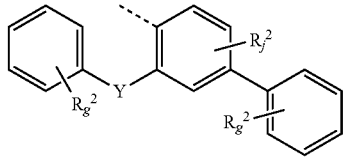
(Formula R1-66)
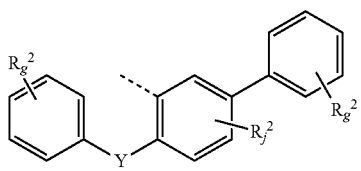
(Formula R1-67)
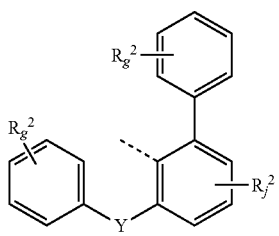
(Formula R¹-68)
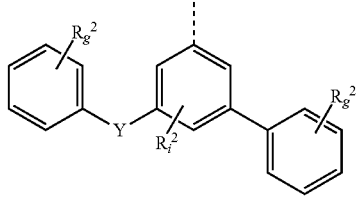
(Formula R¹-69)
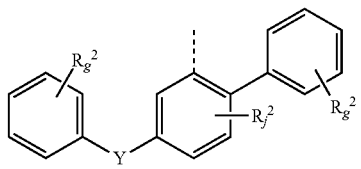
(Formula R¹-70)
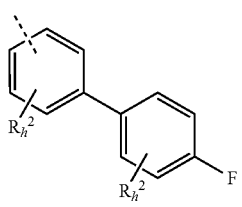

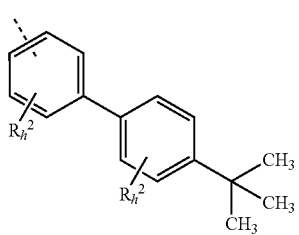

(Formula R¹-71)

(Formula R¹-72)

where the symbols used are as follows:
Y is O, S or $NR^2$, preferably O or S;
j independently at each instance is 0, 1, 2 or 3;
h independently at each instance is 0, 1, 2, 3 or 4;
g independently at each instance is 0, 1, 2, 3, 4 or 5;
the dotted bond marks the attachment position; and
$R^2$ may be as defined above.

It may preferably be the case that the sum total of the indices g, h and j in the structures of the formula (R¹-1) to (R¹-72) is at most 3 in each case, preferably at most 2 and more preferably at most 1.

More preferably, the $R^1$, $Ar^2$, $Ar^3$ or $Ar^4$ group of formula (I), (IIa) and/or (Ib) may be an aromatic radical having 6 to 18 and preferably 6 to 12 carbon atoms, preference being given to structures of the formula (R¹-1) to (R¹-15) and particular preference to structures of the formula (R¹-1) to (R¹-4). However, one of the $Ar^2$ and $Ar^3$ radicals must be a group of the formula (IIa) or (IIb).

It may additionally be the case that, in the structure of formula (I), the $L^1$ group is a bond and, in formula (IIa) and/or (IIb), the $L^2$ group is a group selected from the formulae (L-1) to (L-78), preferably from the formulae (L-1) to (L-15), more preferably from the formulae (L-1) to (L-5), as described above.

It may additionally be the case that, in the structure of formula (IIa) and/or (IIb), the $L^2$ group is a bond and, in formula (I), the $L^1$ group is a group selected from the formulae (L-1) to (L-78), preferably from the formulae (L-1) to (L-15), more preferably from the formulae (L-1) to (L-5), as described above.

It may additionally be the case that, in the structure of formula (I), (IIa) and/or (IIb), the $L^1$ and $L^2$ groups are a bond.

It may additionally be the case that, in the structure of formula (I), (IIa) and/or (IIb), the $L^1$ and $L^2$ groups are a group selected from the formulae (L-1) to (L-78), preferably from the formulae (L-1) to (L-15), more preferably from the formulae (L-1) to (L-5), as described above.

Preferably, the $Ar^1$ and/or $Ar^3$ radical in structures of the formula (I) may be an aromatic ring system which has 6 to 18 and preferably 6 to 12 aromatic ring atoms and may be substituted by one or more $R^1$ radicals, where preferably both $Ar^1$ and $Ar^3$ radicals in structures of the formula (I) are an aromatic ring system having 6 to 12 aromatic ring atoms.

Particularly preferred compounds include structures according to the following formulae 1 to 244:

Formula 1

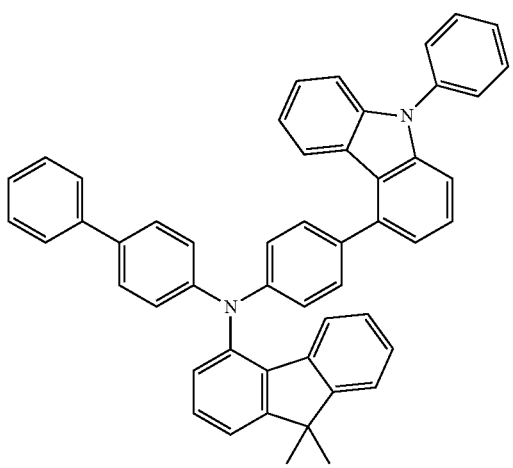

Formula 2

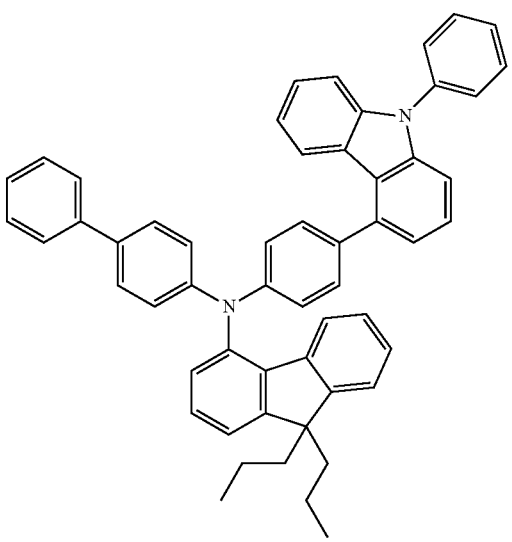

-continued
Formula 3
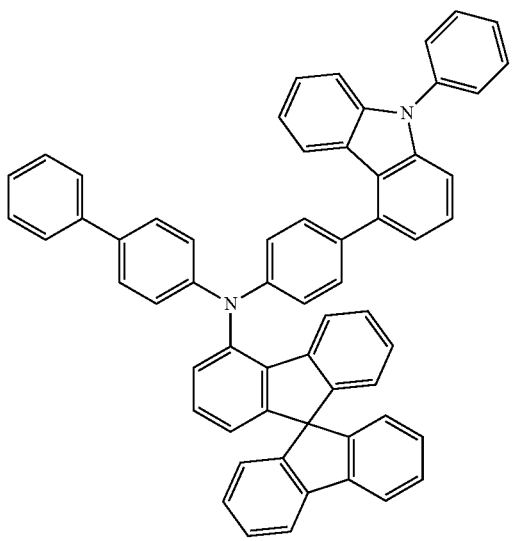
Formula 4
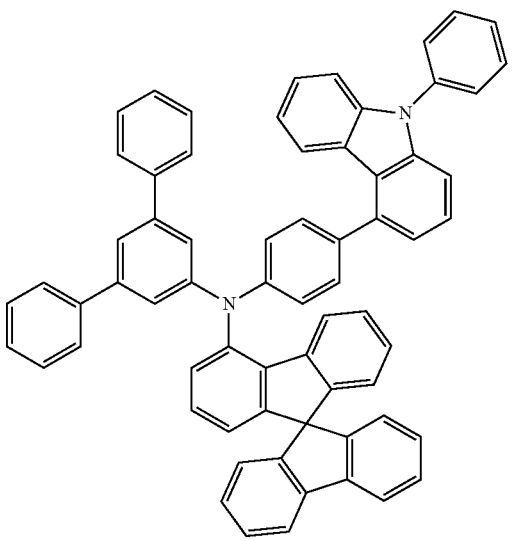
Formula 5
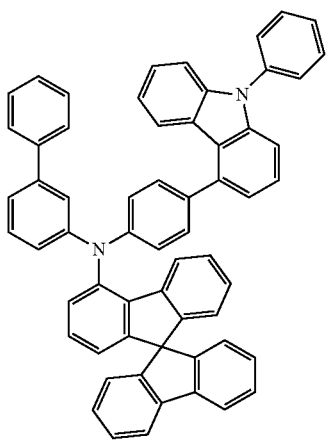
Formula 6
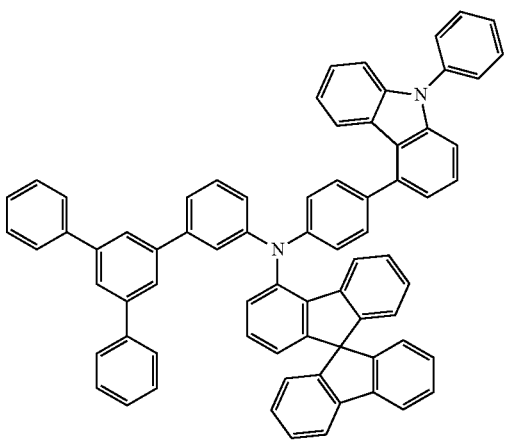
Formula 7
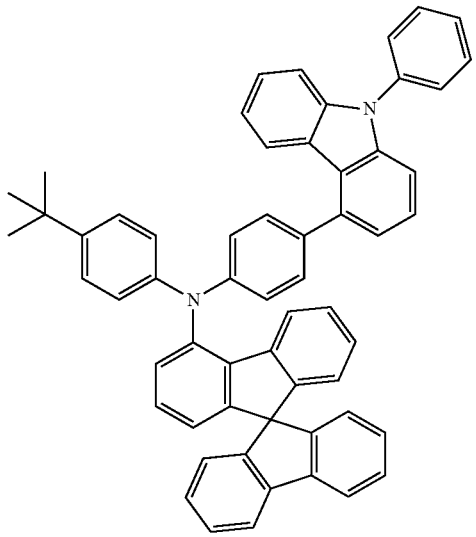
Formula 8
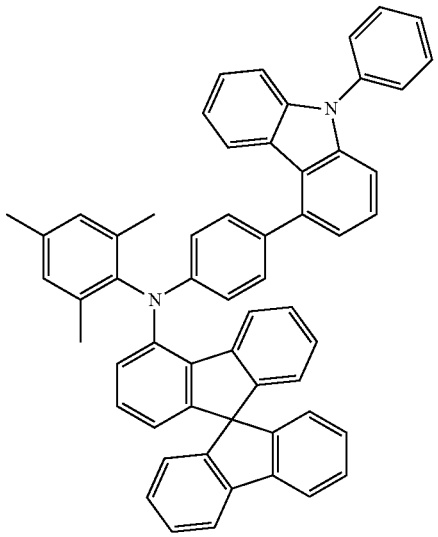

-continued
Formula 9
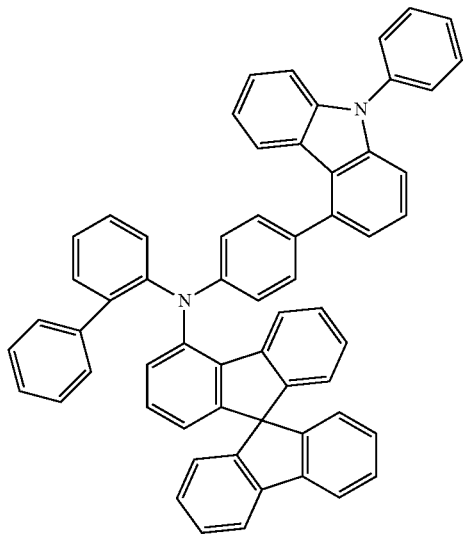
Formula 10
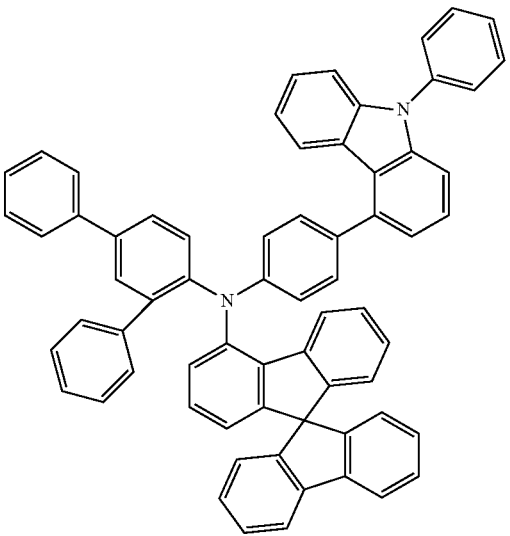
Formula 11
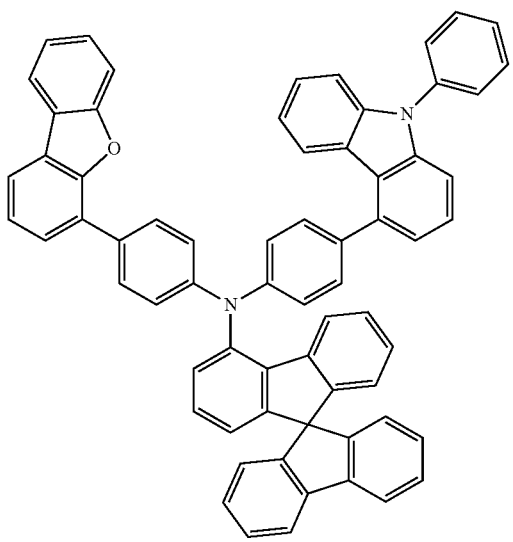
Formula 12
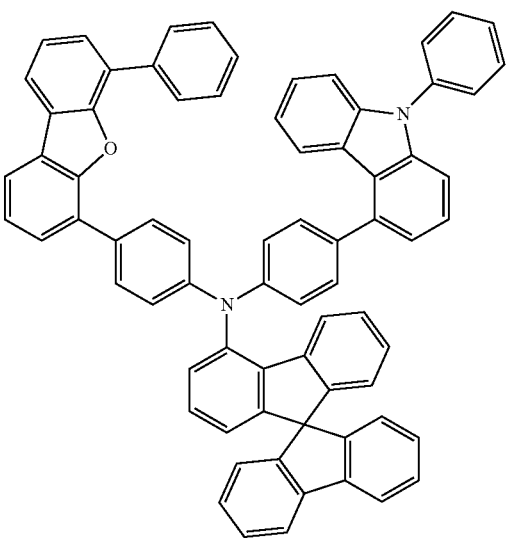
Formula 13
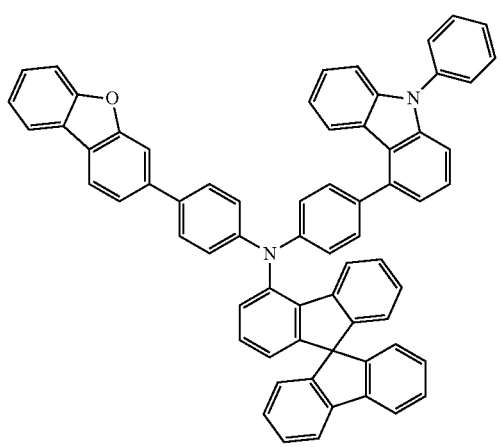
Formula 14
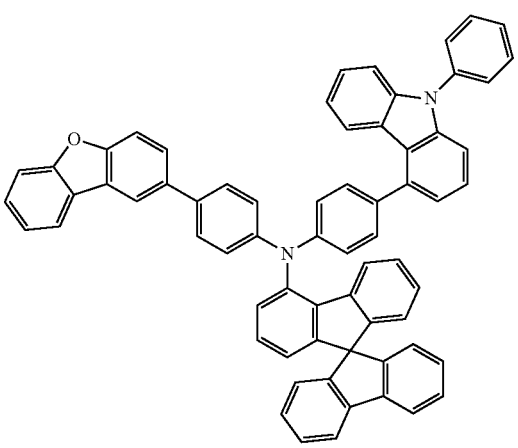

-continued
Formula 15
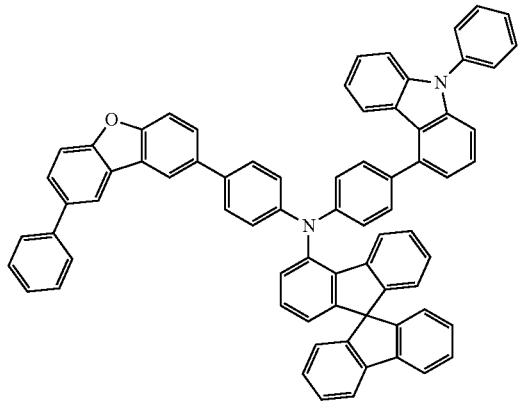
Formula 16
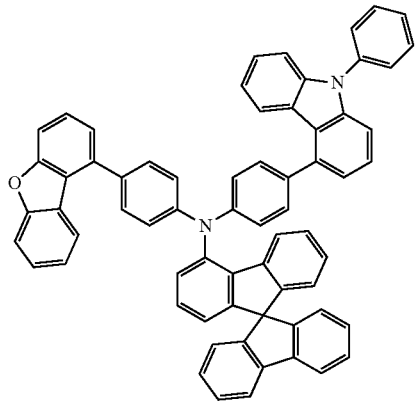
Formula 17
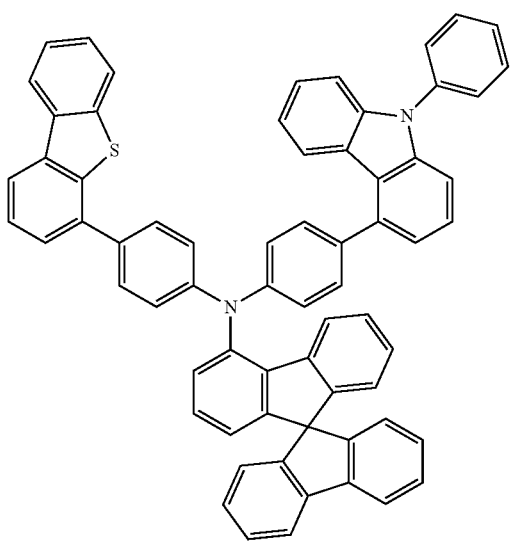
Formula 18
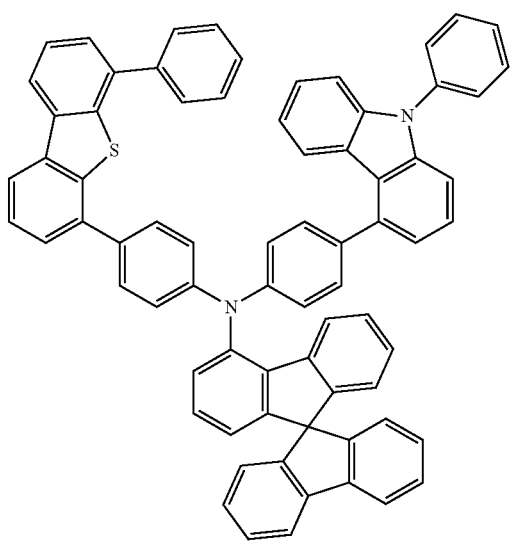
Formula 19
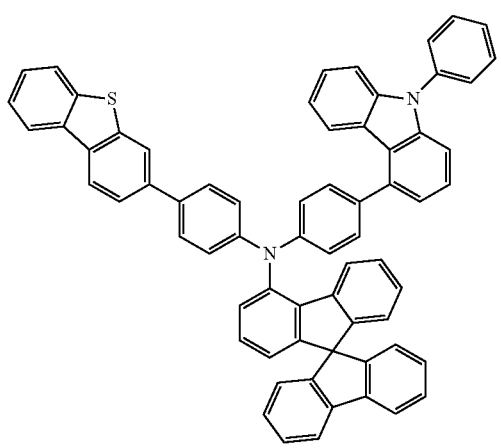
Formula 20
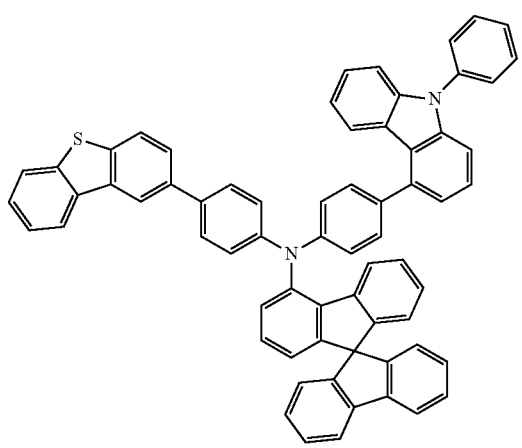

-continued
Formula 21
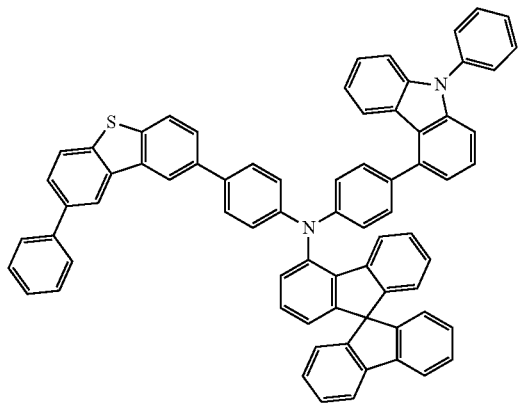
Formula 22
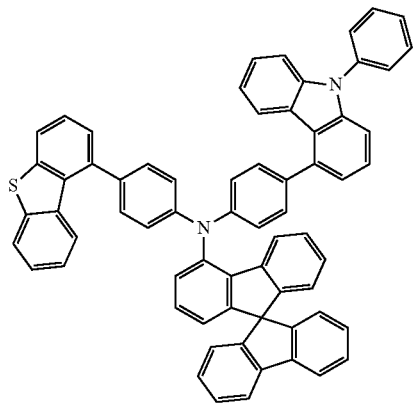
Formula 23
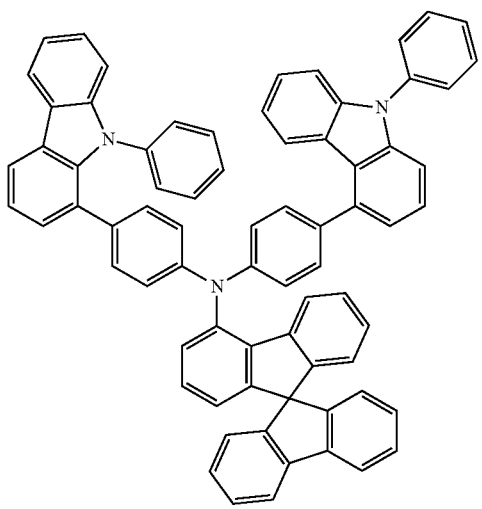
Formula 24
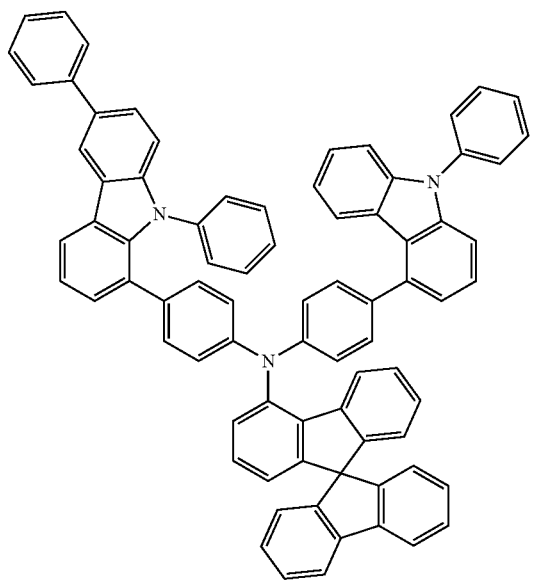
Formula 25
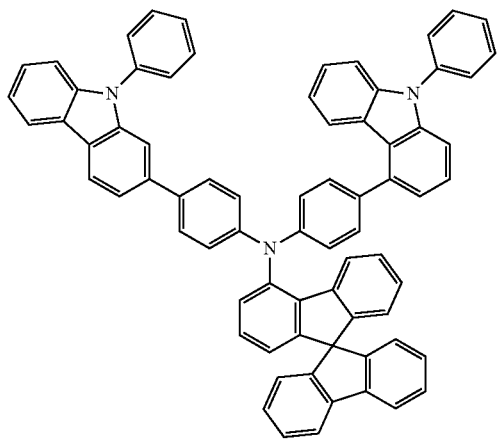
Formula 26
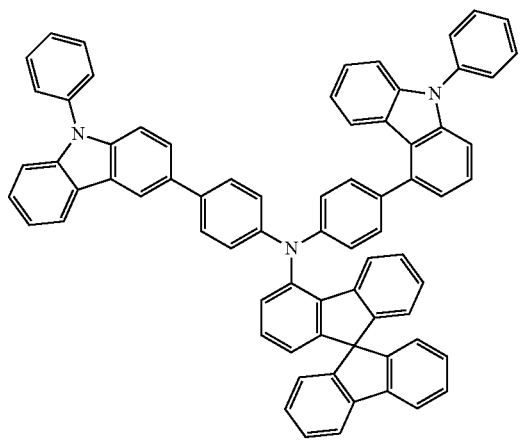

Formula 27
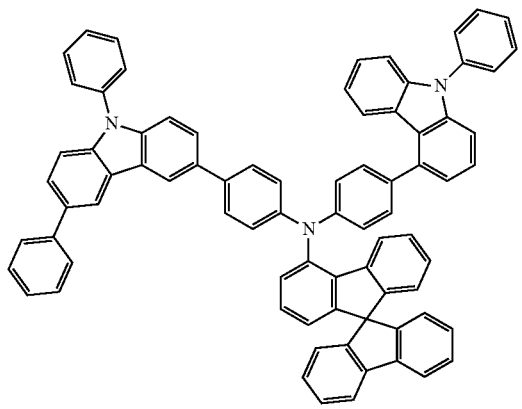
Formula 28
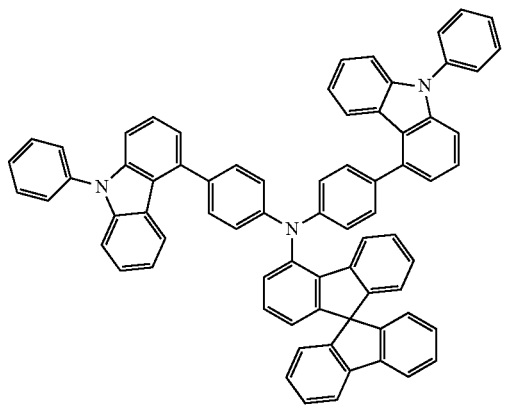
Formula 29
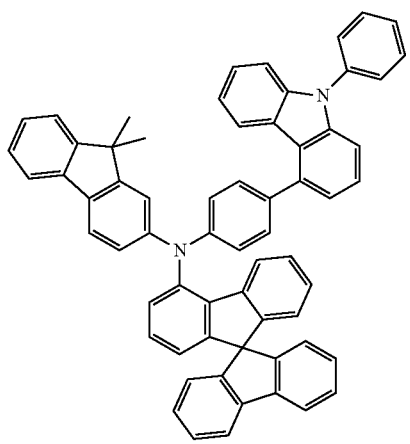
Formula 30
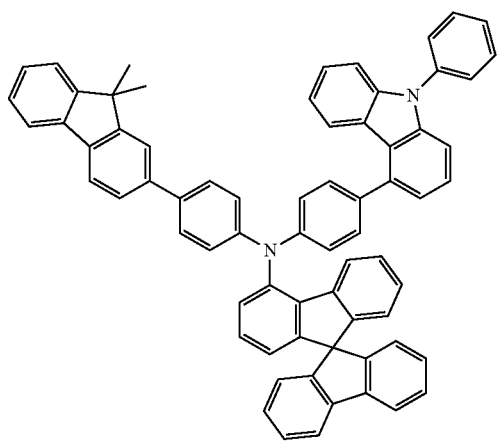
Formula 31
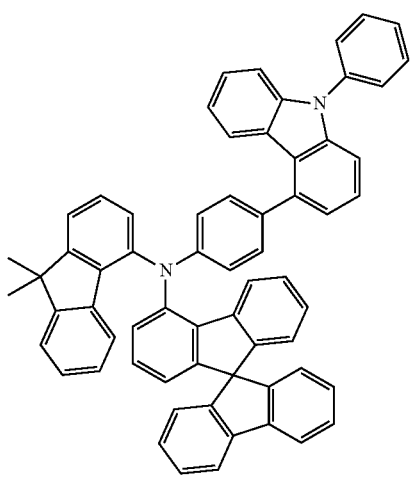
Formula 32
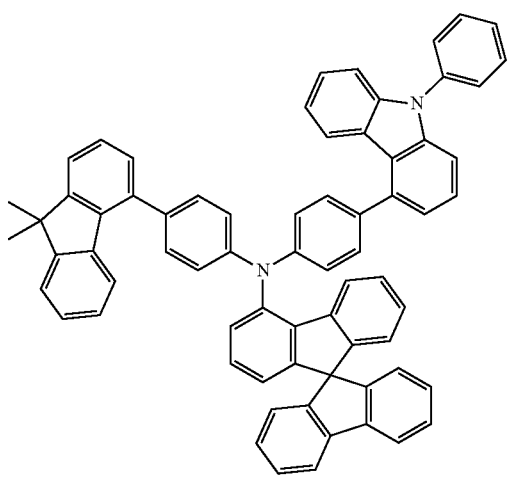

-continued
Formula 33
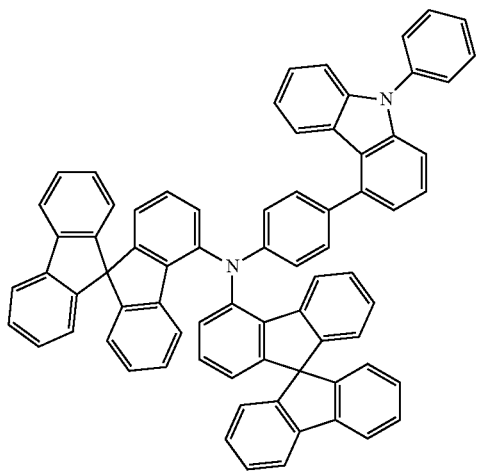
Formula 34
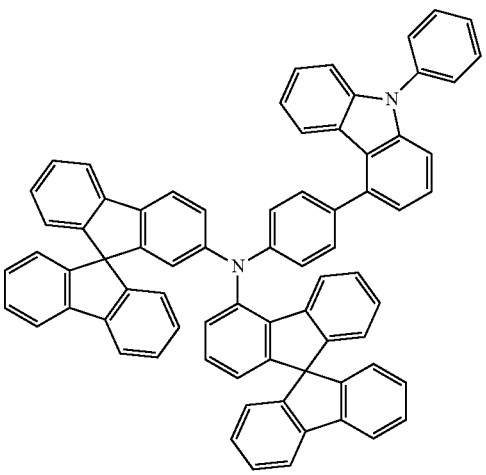
Formula 35
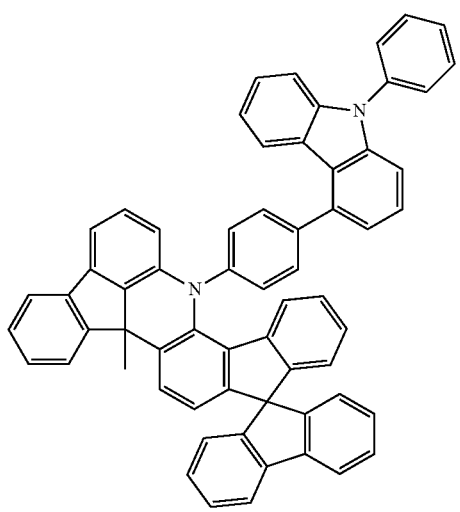
Formula 36
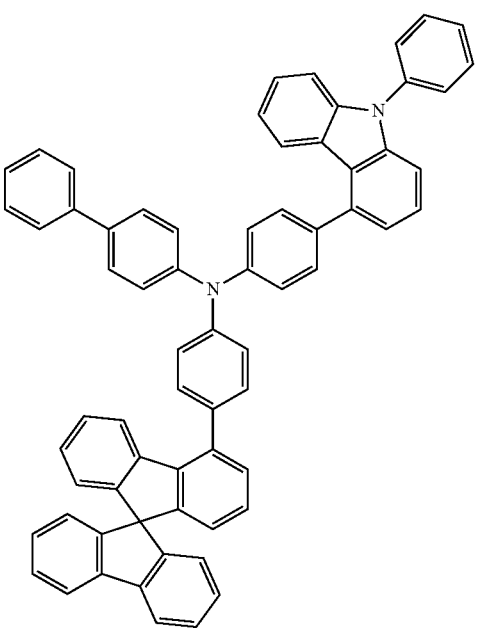
Formula 37
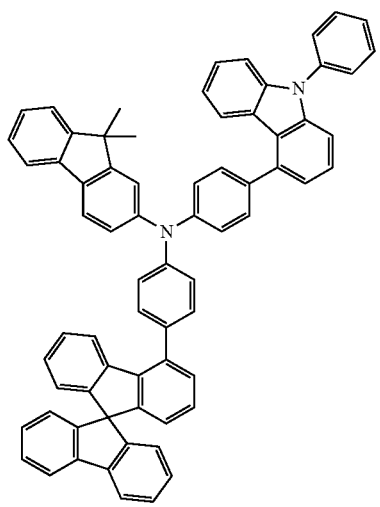
Formula 38
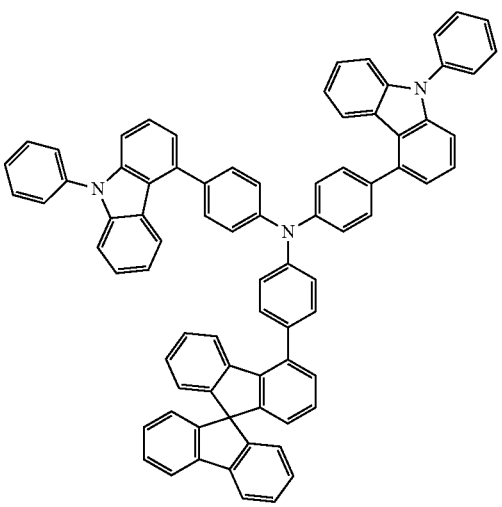

Formula 39
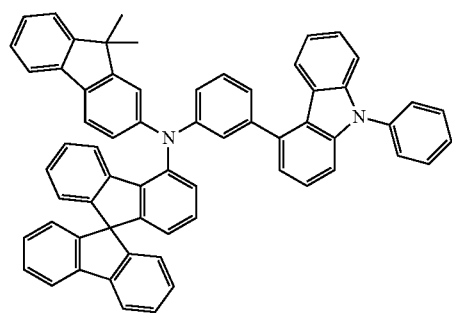
Formula 40
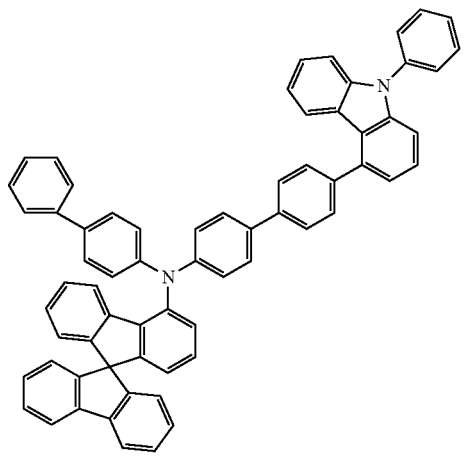
Formula 41
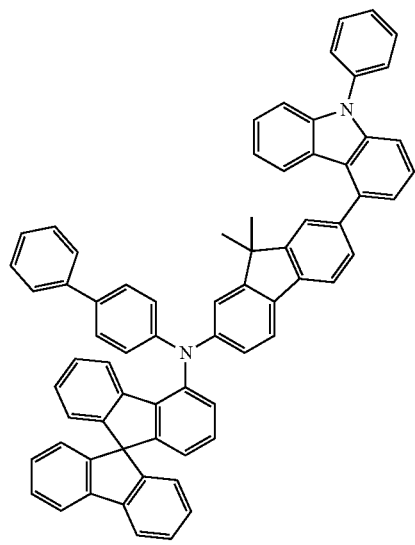
Formula 42
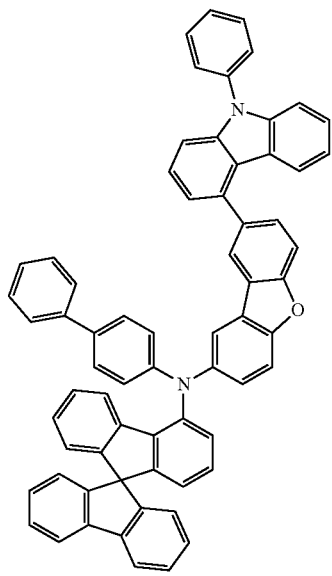

-continued
Formula 43
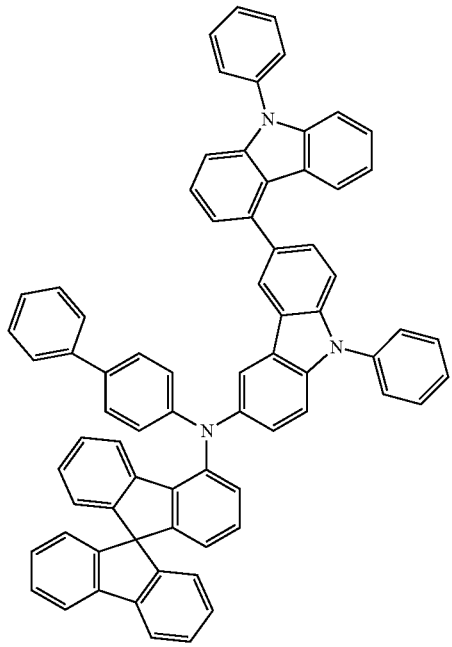
Formula 44
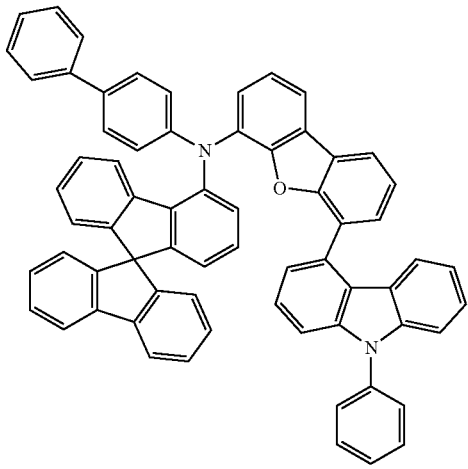
Formula 45
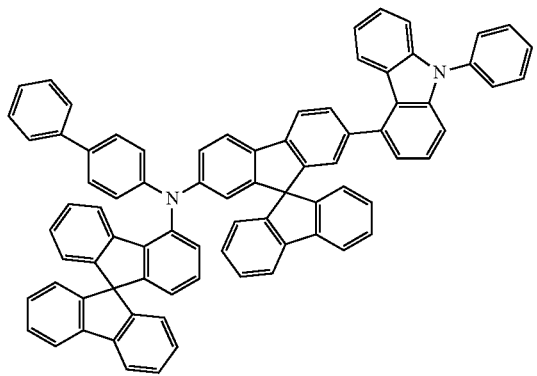
Formula 46
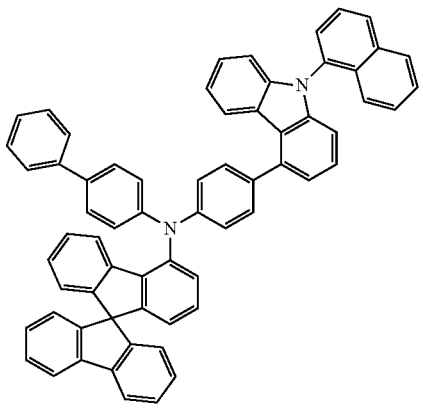
Formula 47
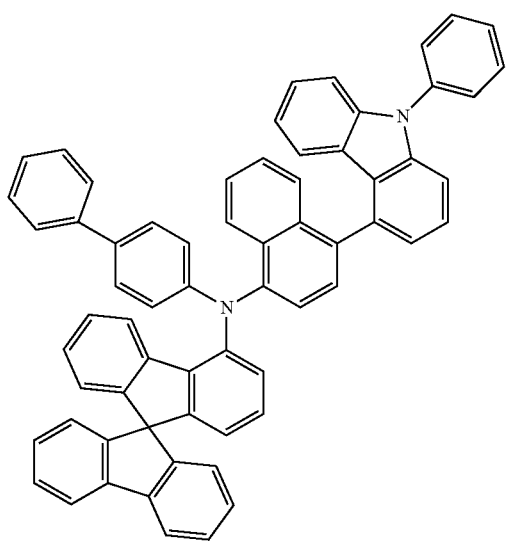
Formula 48
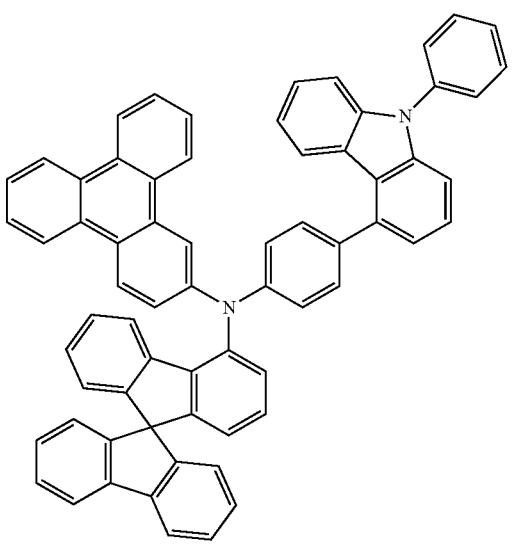

-continued
Formula 49
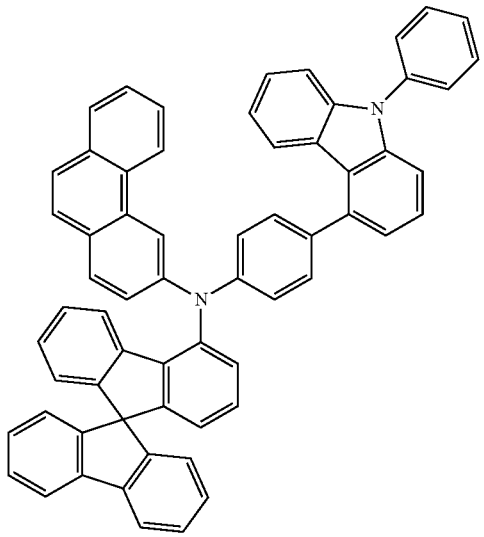
Formula 50
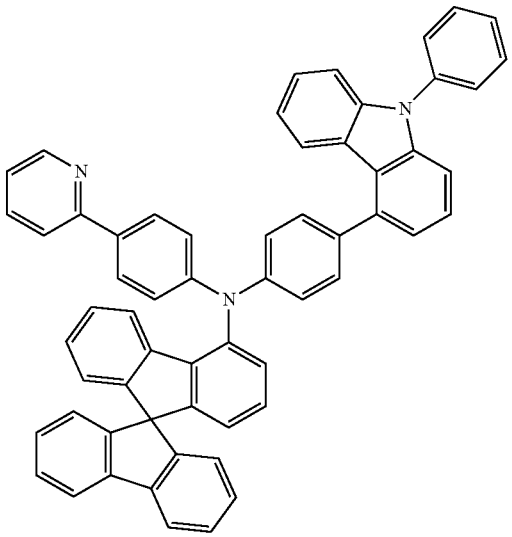
Formula 51
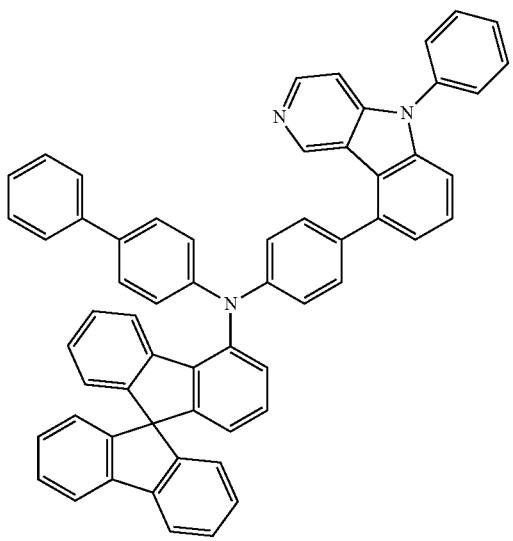
Formula 52
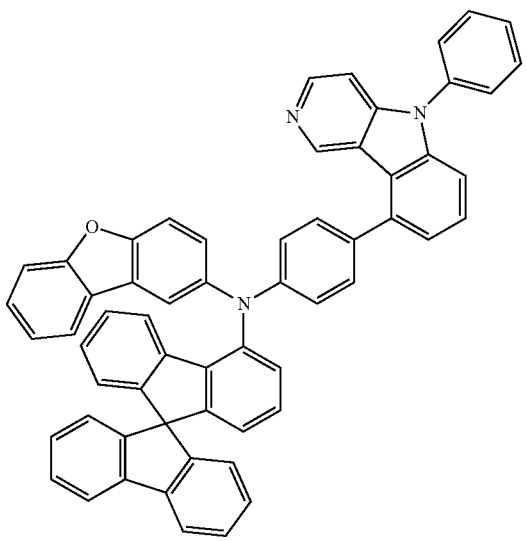
Formula 53
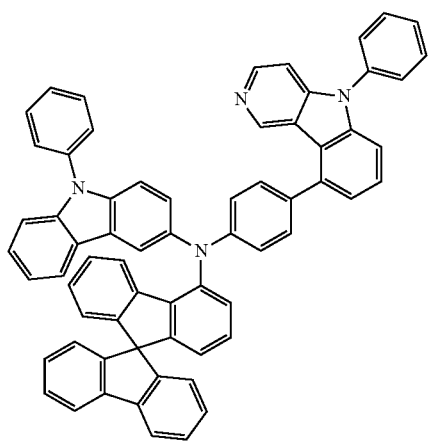
Formula 54
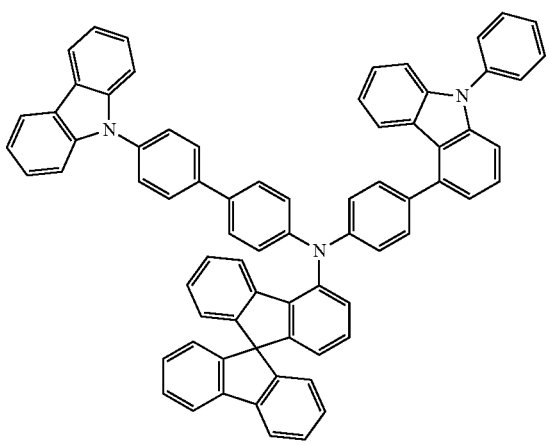

Formula 55
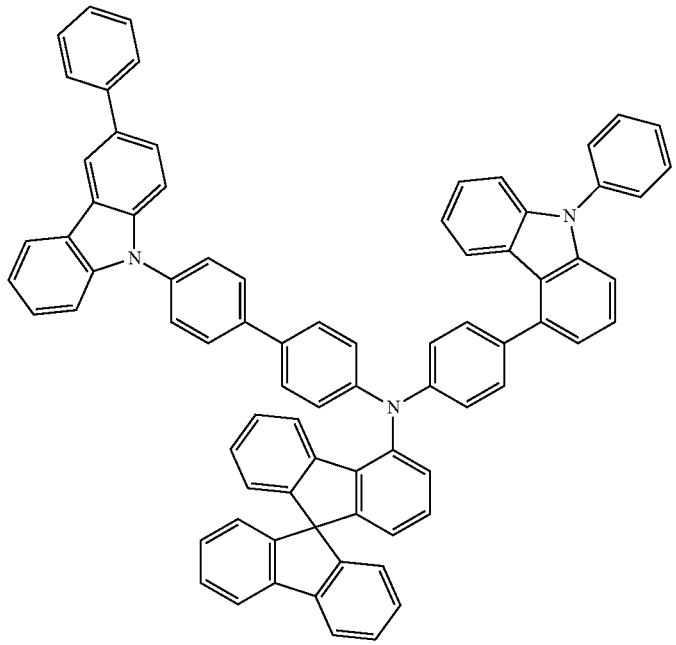
Formula 56
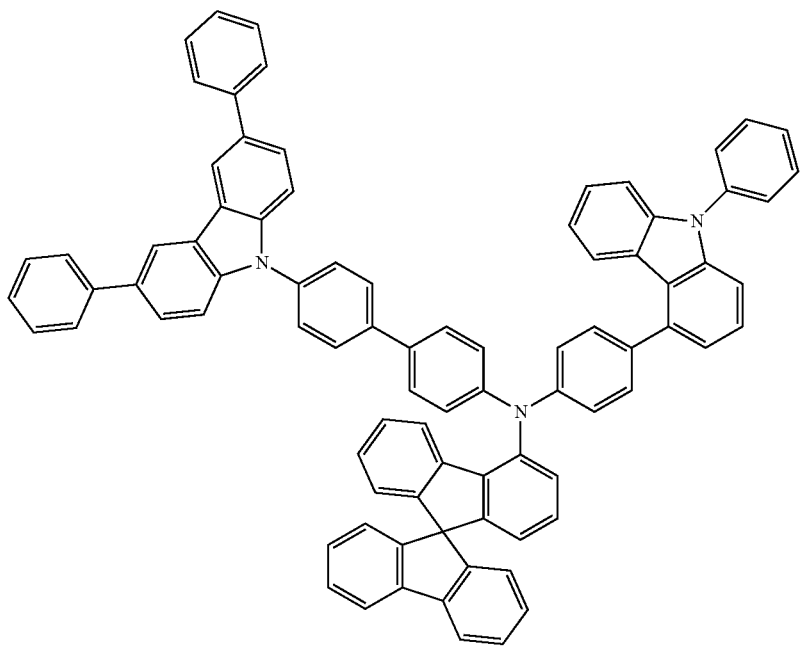
Formula 57
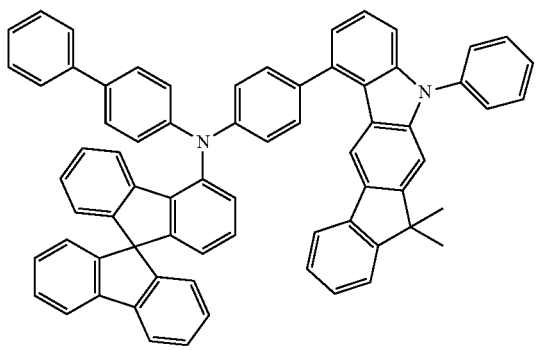
Formula 58
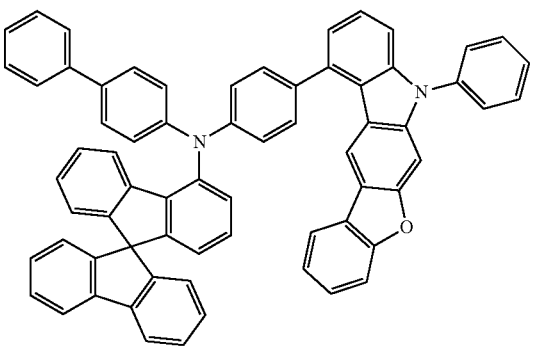

-continued
Formula 59
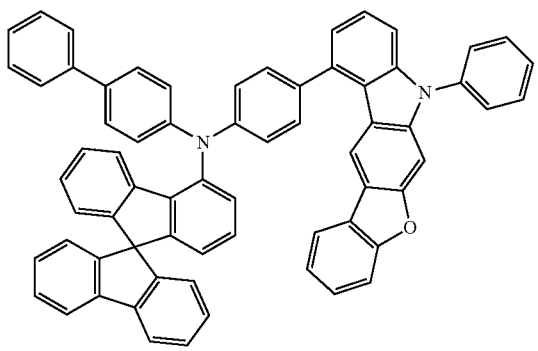
Formula 60
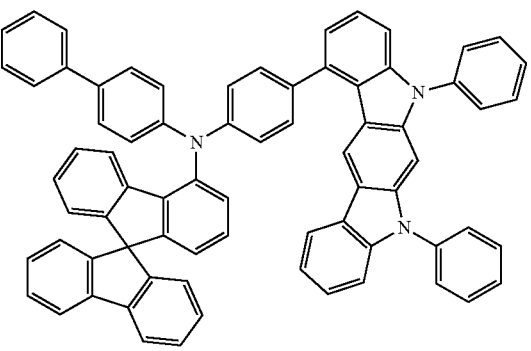
Formula 61
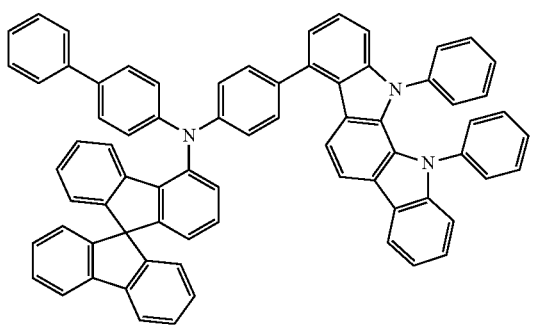
Formula 62
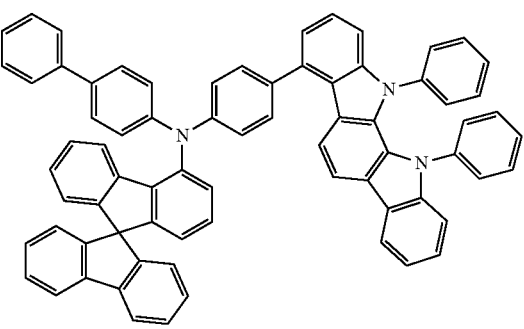
Formula 63
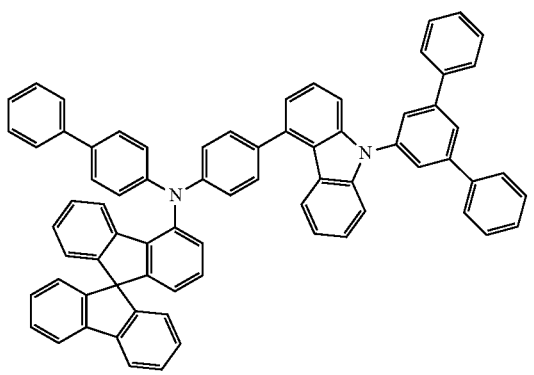
Formula 64
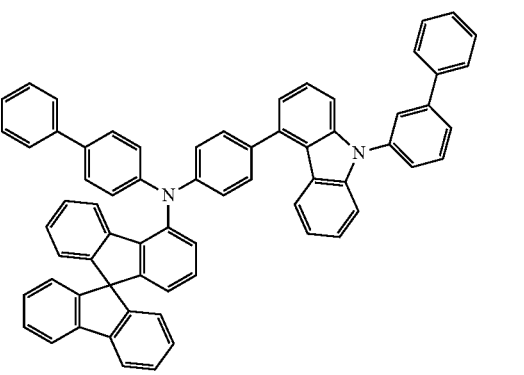
Formula 65
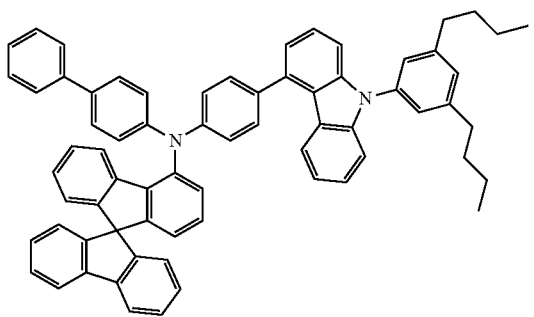
Formula 66
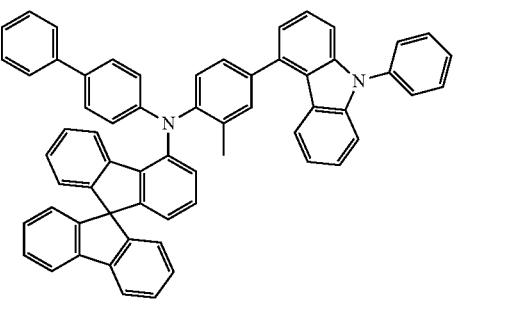

-continued
Formula 67
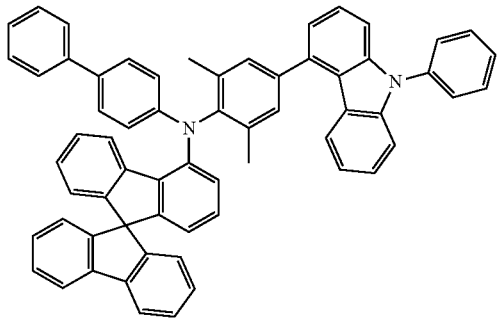
Formula 68
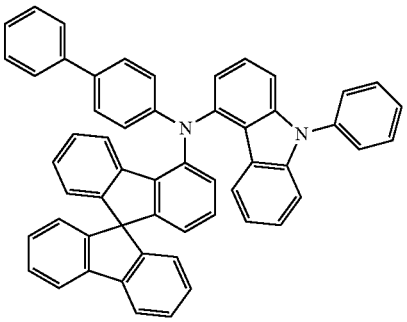
Formula 69
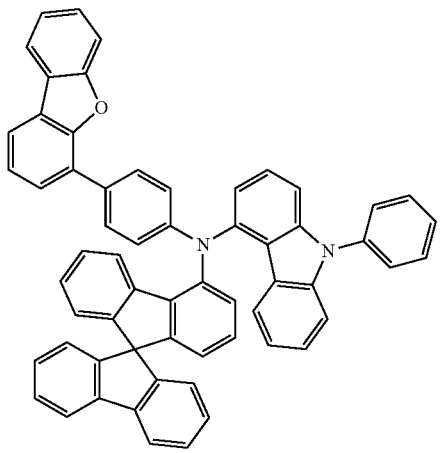
Formula 70
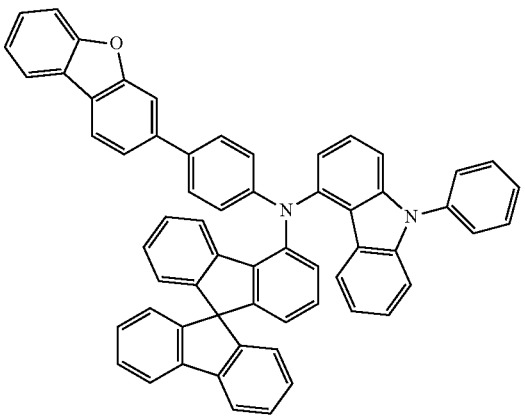
Formula 71
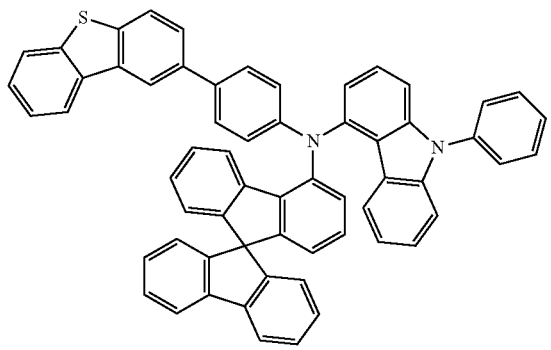
Formula 72
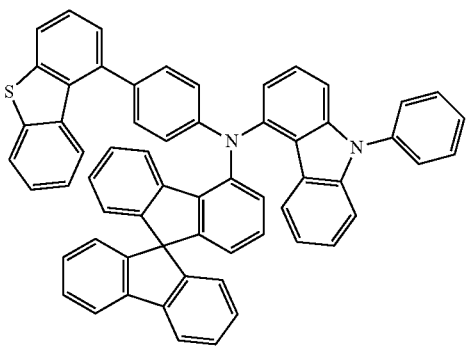
Formula 73
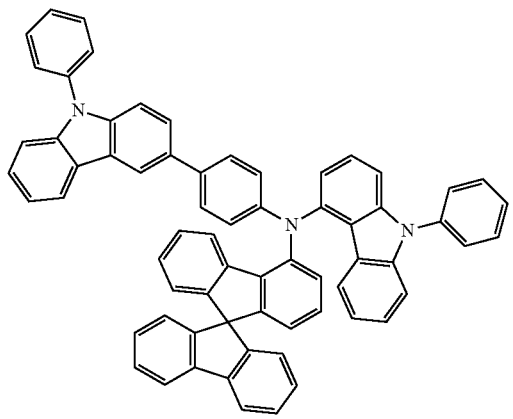
Formula 74
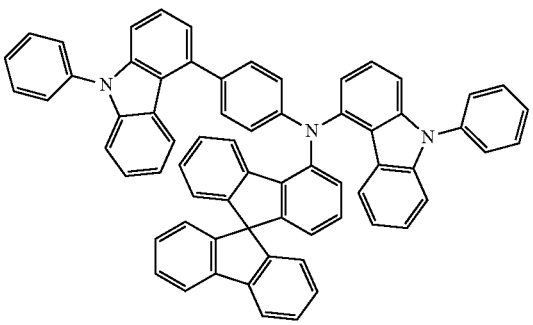

-continued
Formula 75
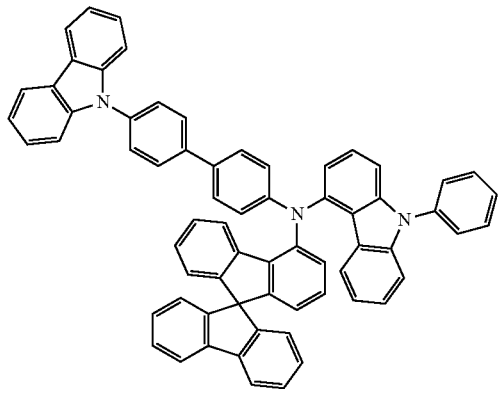
Formula 76
Formula 77
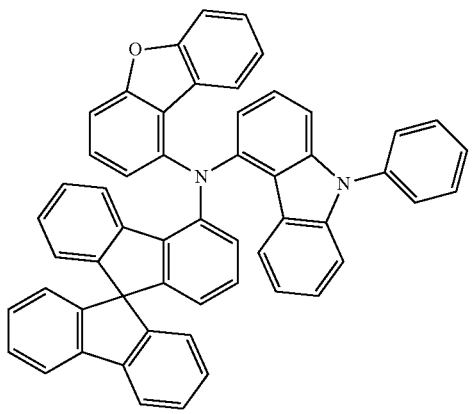
Formula 78
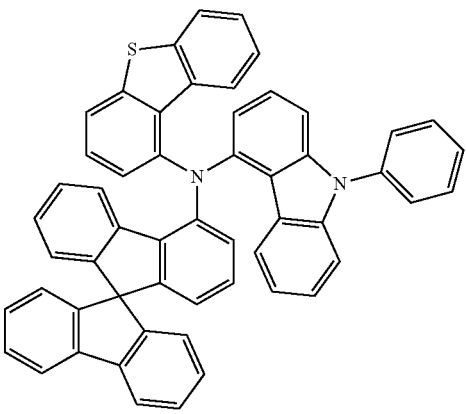
Formula 79
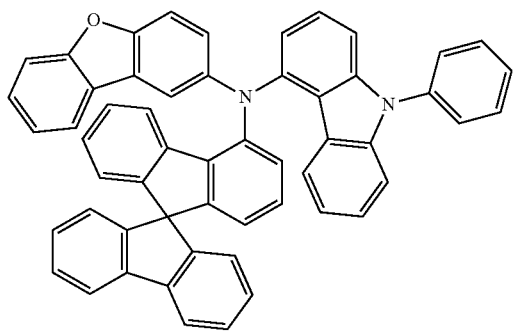
Formula 80
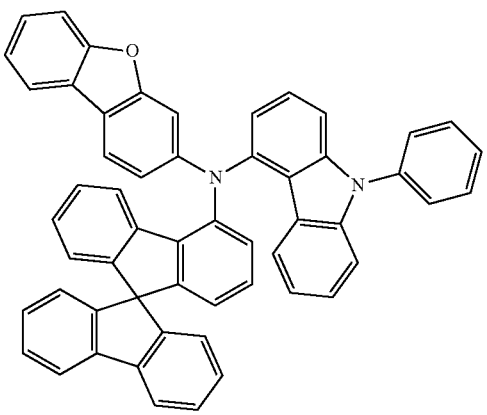

-continued
Formula 81
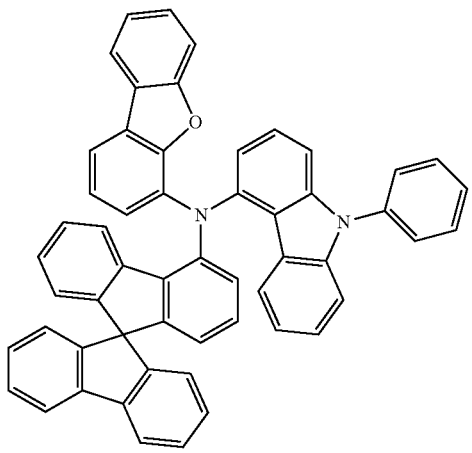
Formula 82
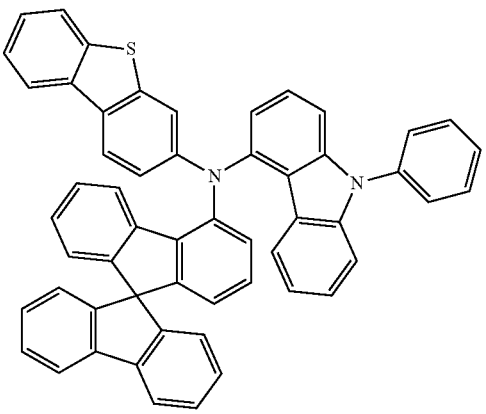
Formula 83
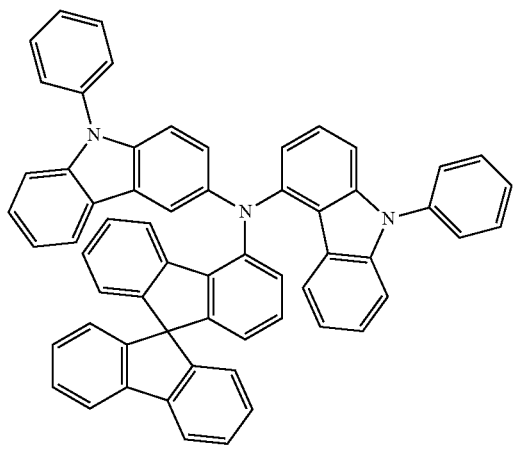
Formula 84
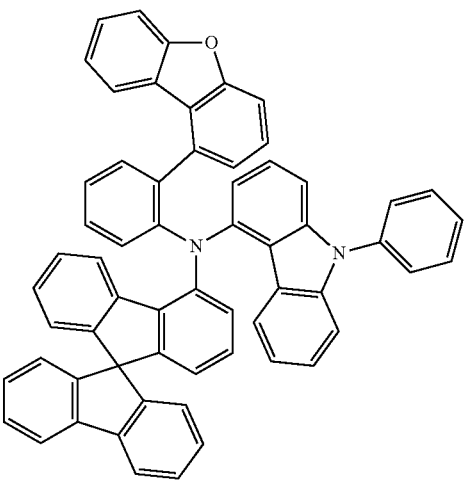
Formula 85
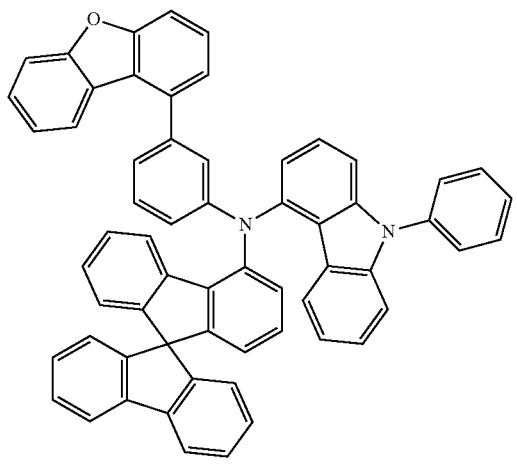
Formula 86
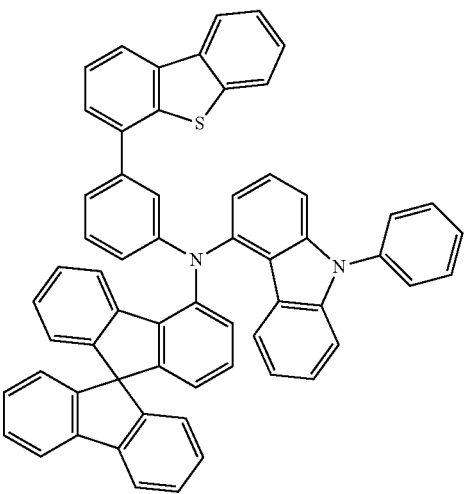

Formula 87
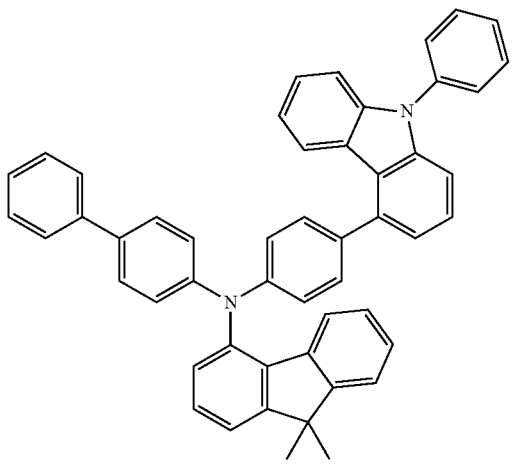
Formula 88
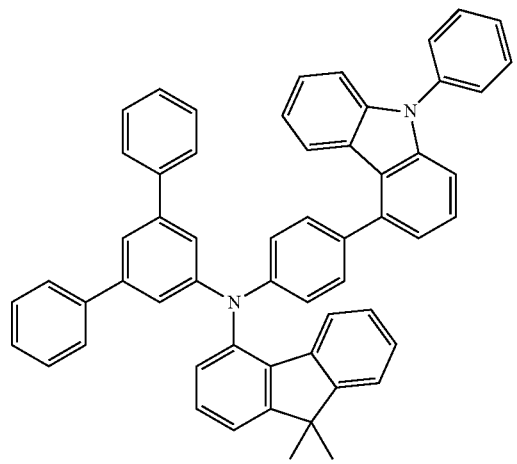
Formula 89
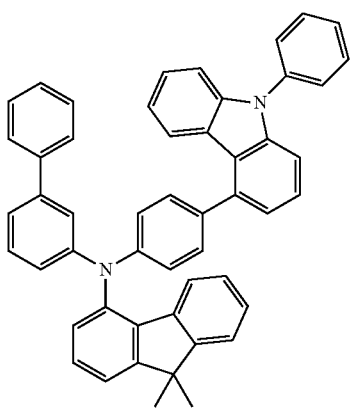
Formula 90
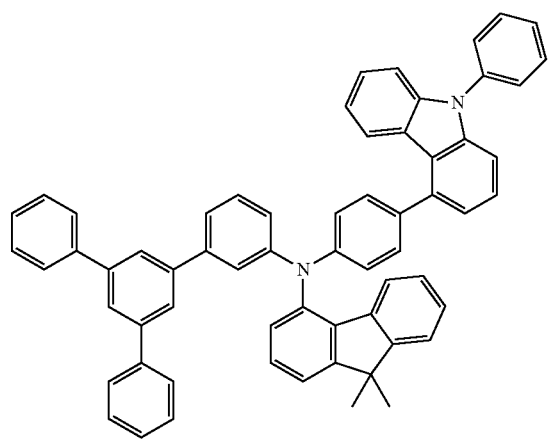
Formula 91
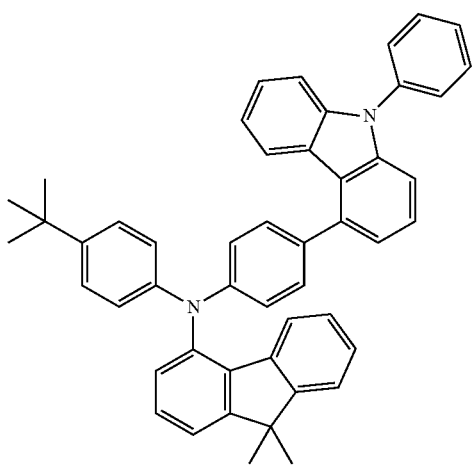
Formula 92
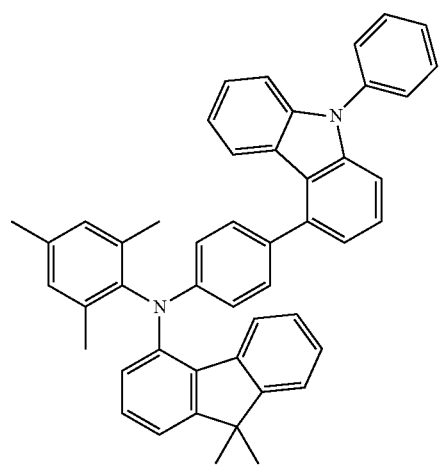

Formula 93
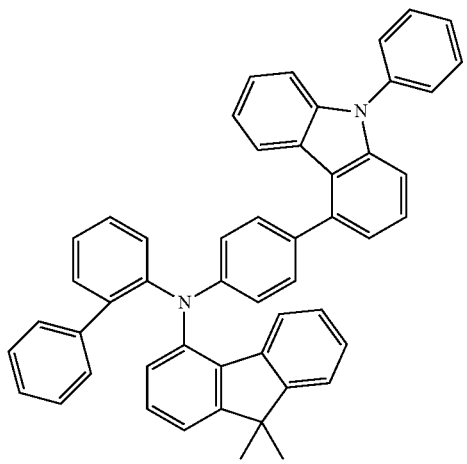
Formula 94
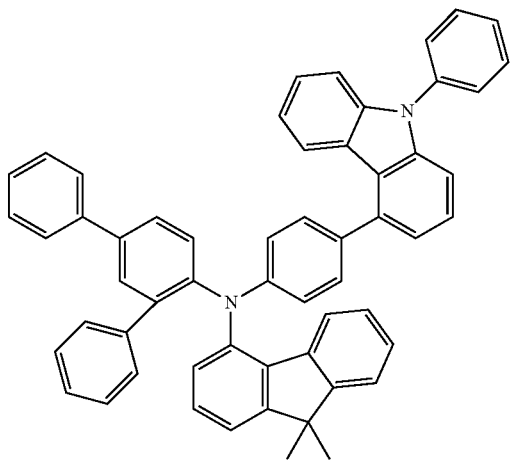
Formula 95
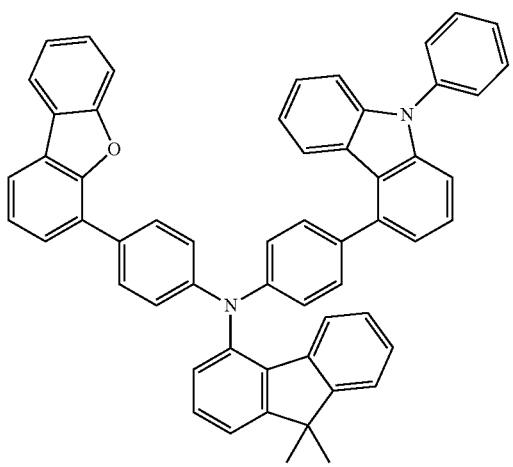
Formula 96
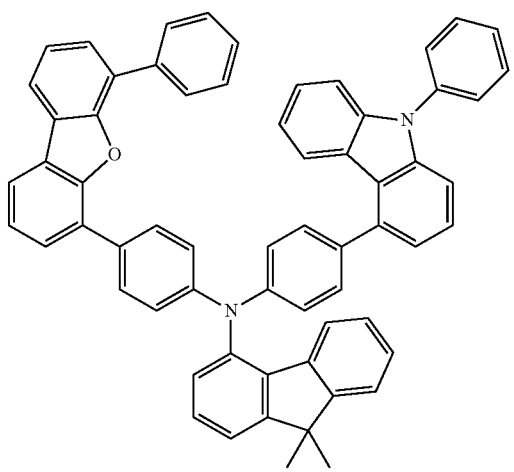
Formula 97
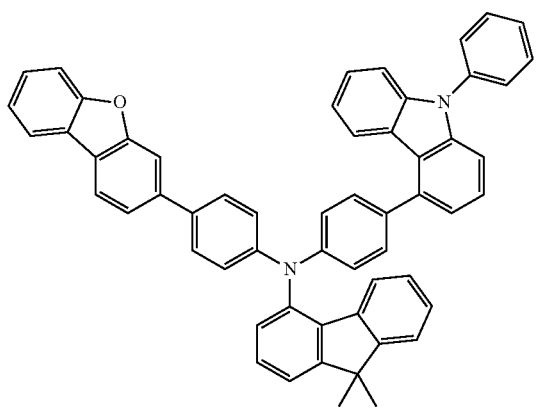
Formula 98
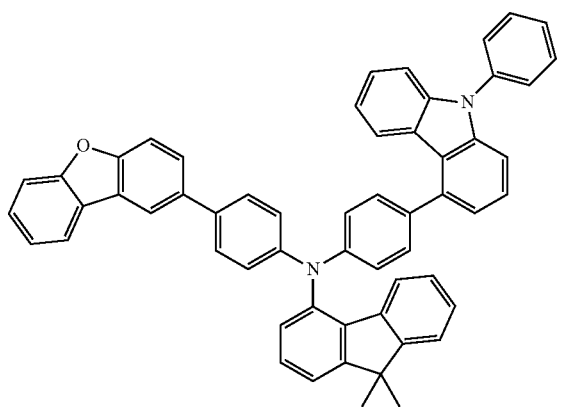

-continued
Formula 99
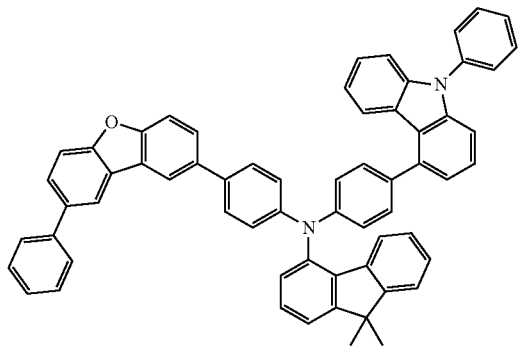
Formula 100
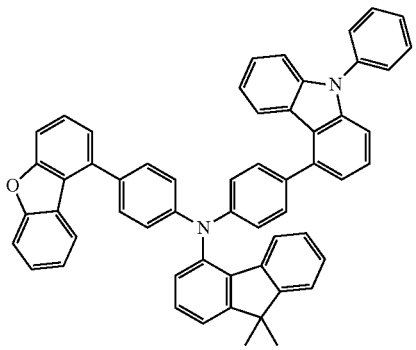
Formula 101
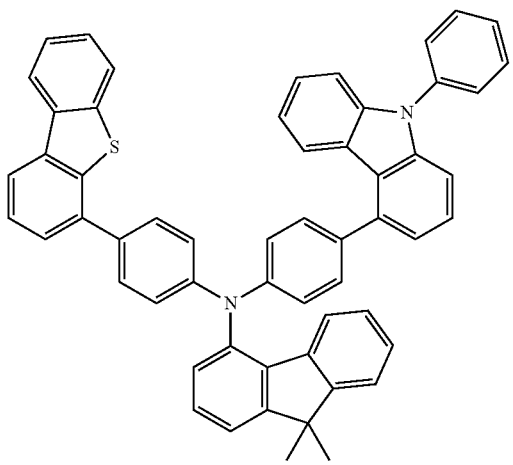
Formula 102
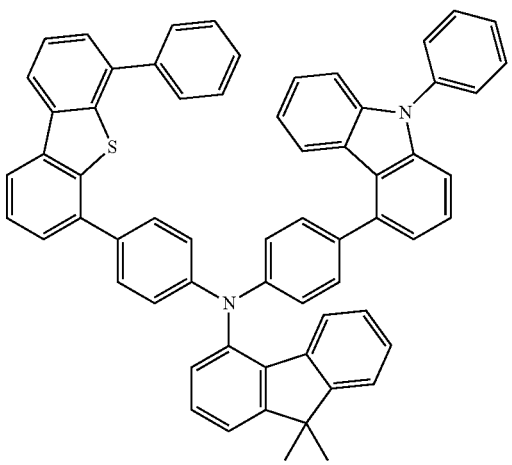
Formula 103
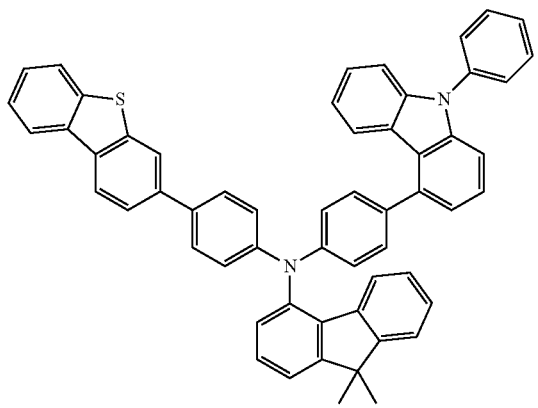
Formula 104
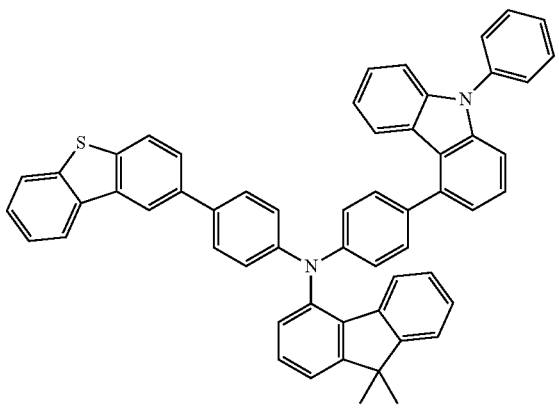
Formula 105
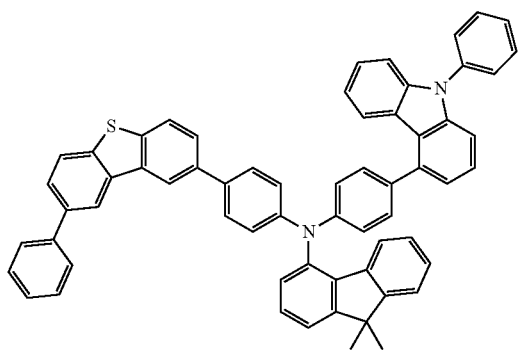
Formula 106
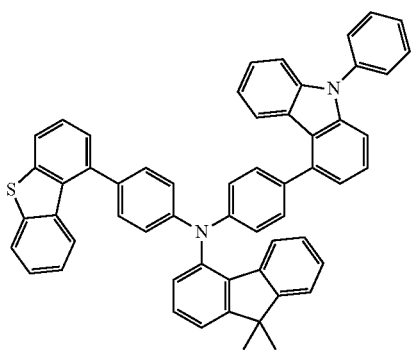

-continued
Formula 107
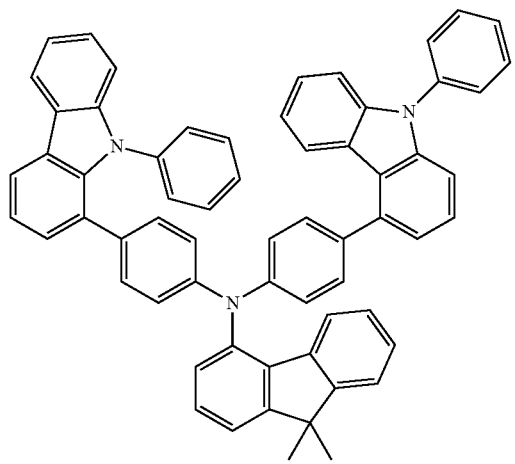
Formula 108
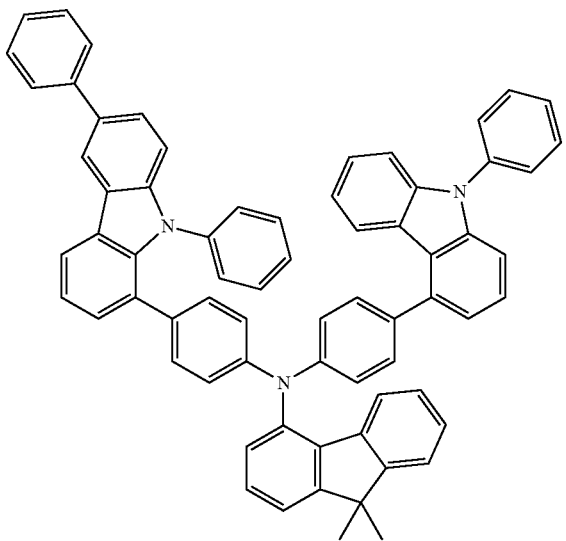
Formula 109
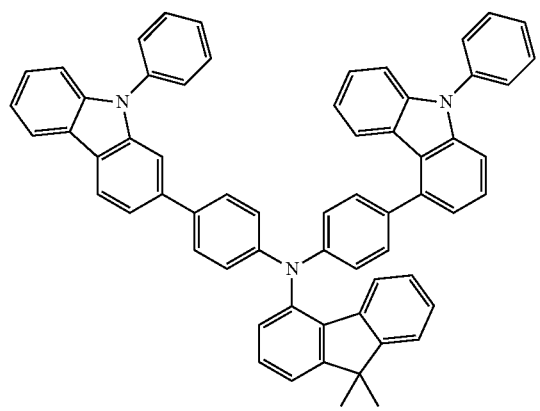
Formula 110
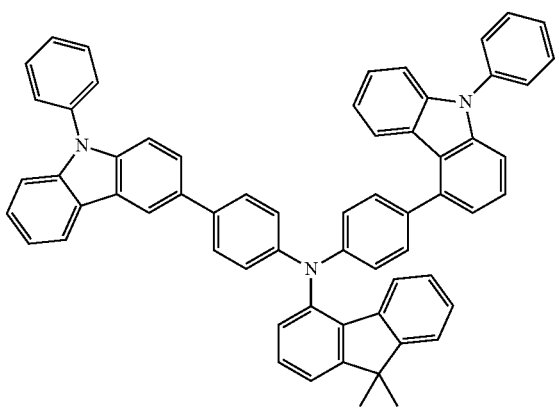
Formula 111
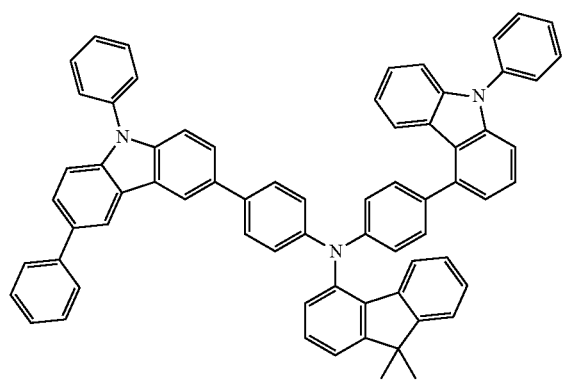
Formula 112
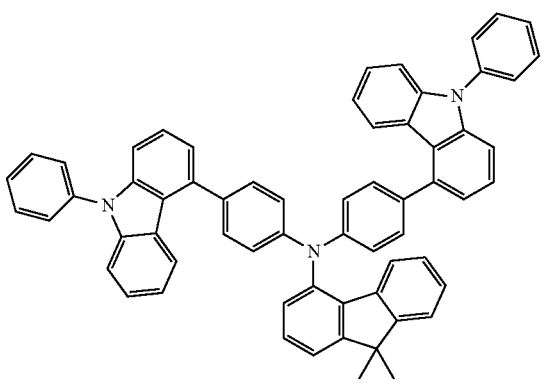

Formula 113
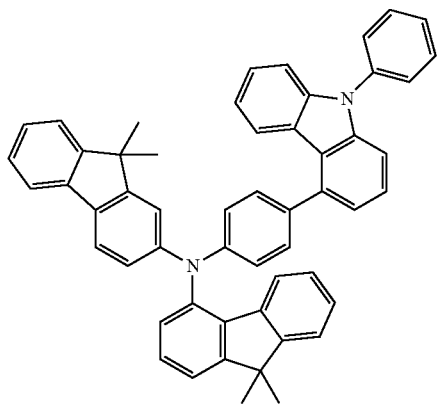
Formula 114
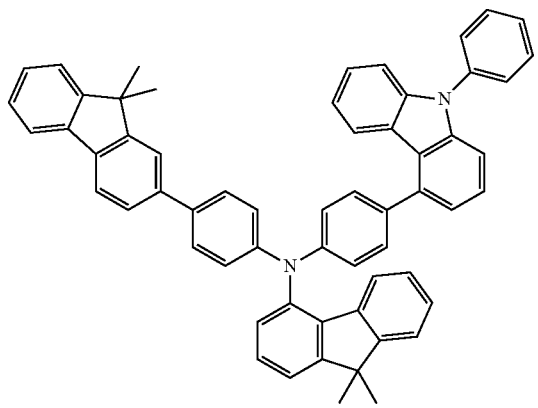
Formula 115
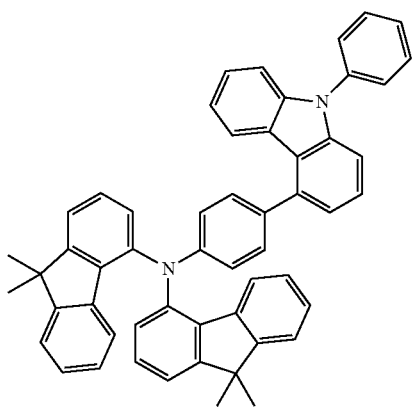
Formula 116
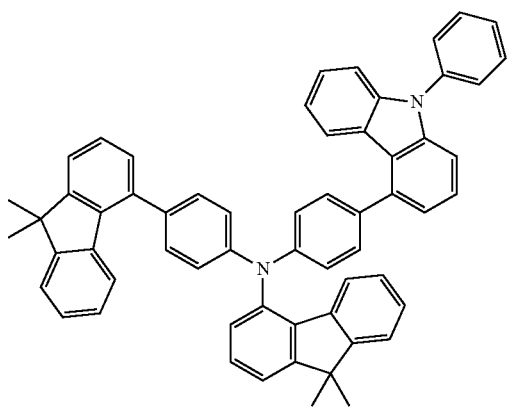
Formula 117
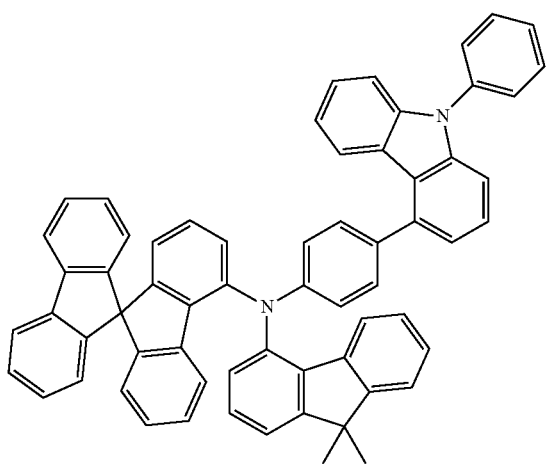
Formula 118
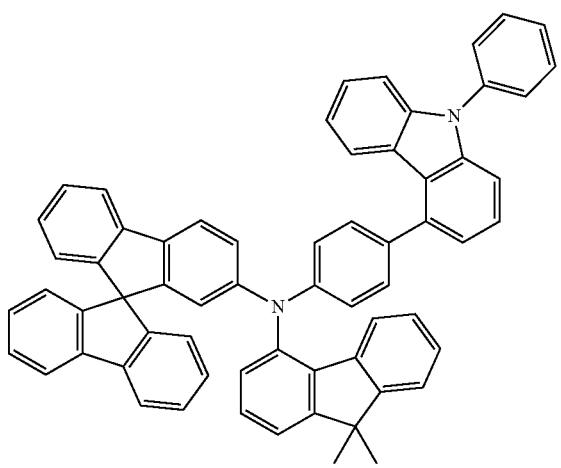

-continued
Formula 119
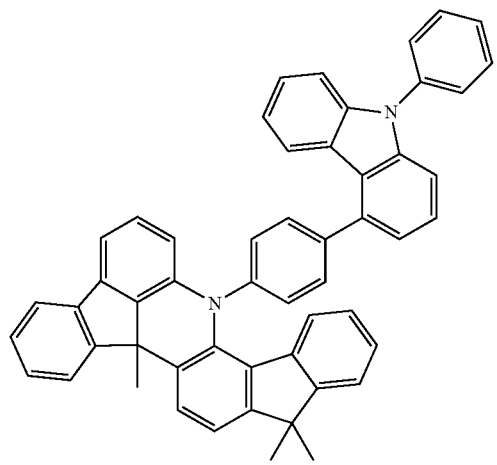
Formula 120
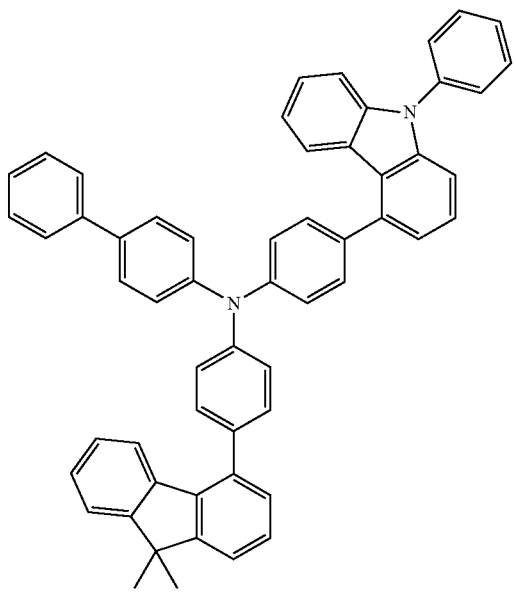
Formula 121
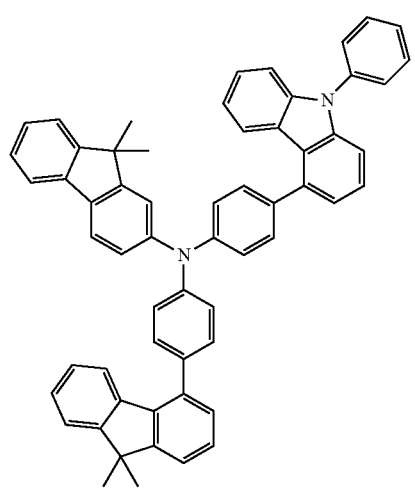
Formula 122
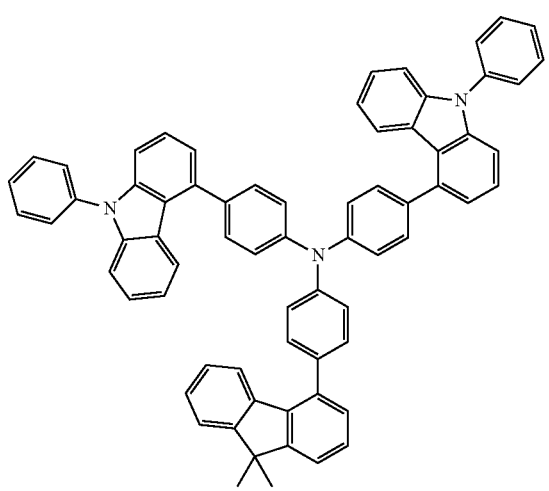
Formula 123
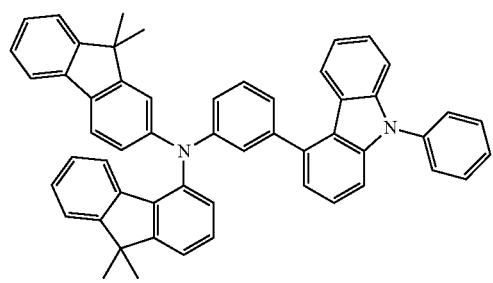
Formula 124
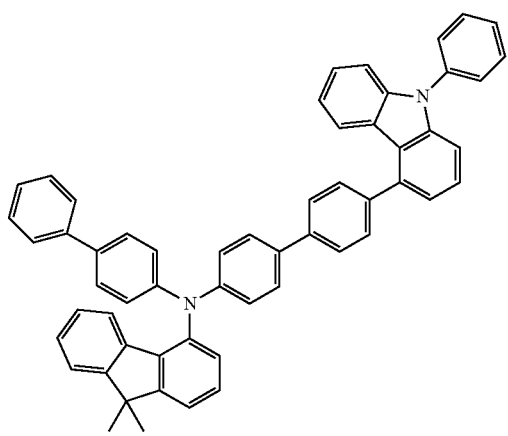

Formula 125
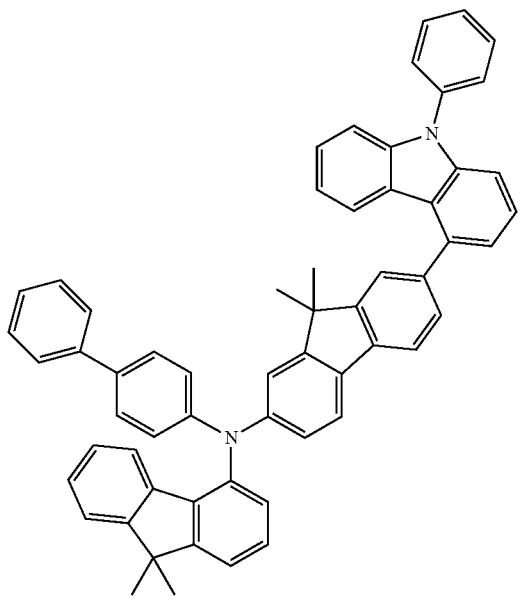
Formula 126
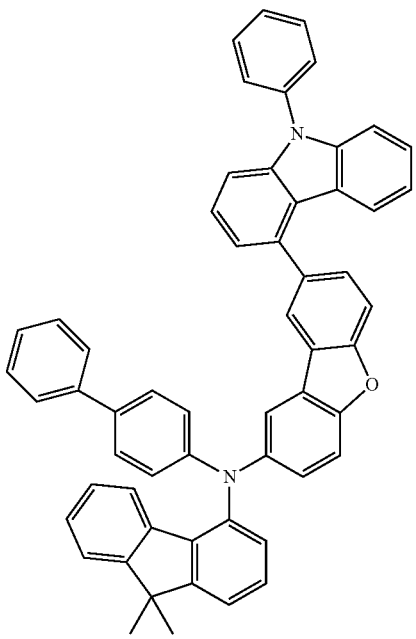
Formula 127
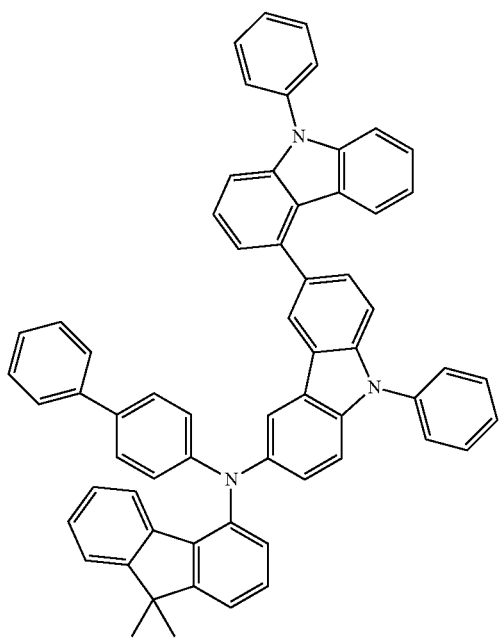
Formula 128
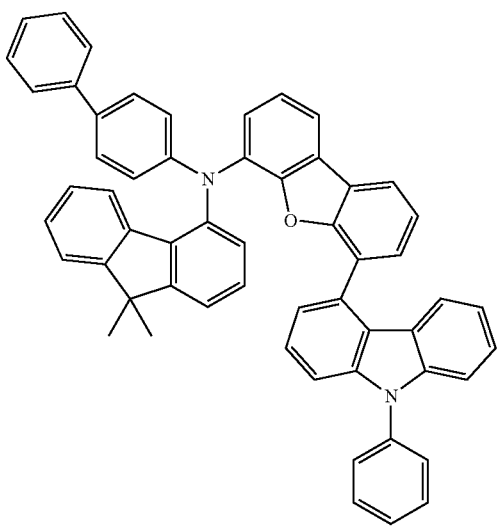

-continued
Formula 129
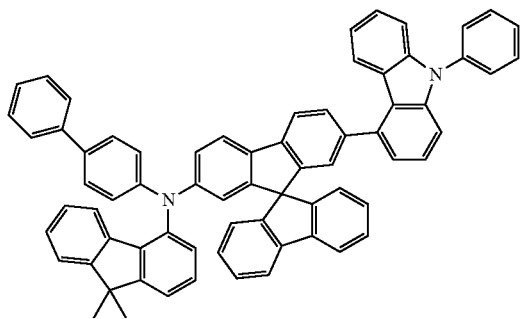
Formula 130
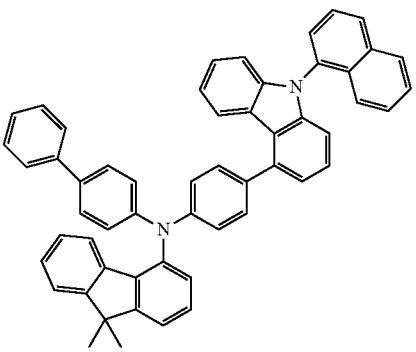
Formula 131
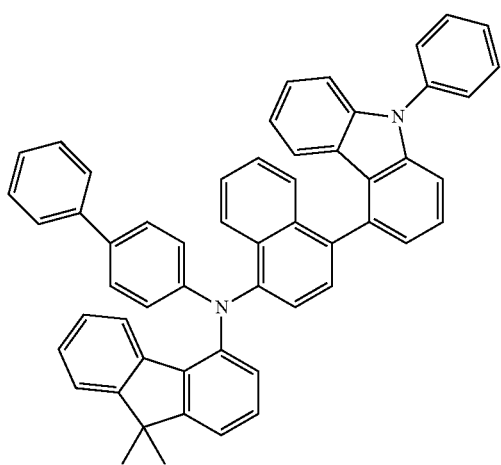
Formula 132
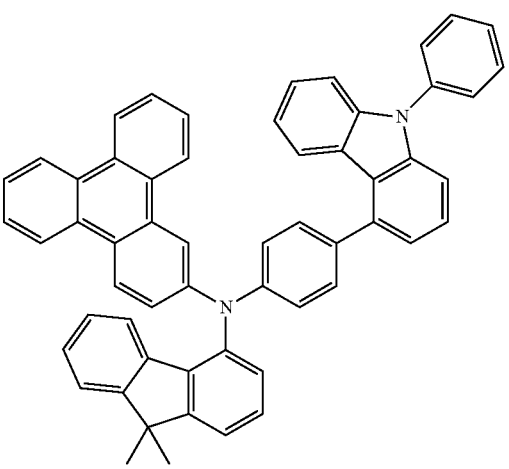
Formula 133
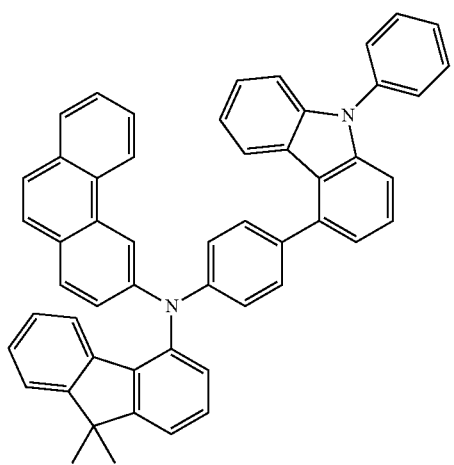
Formula 134
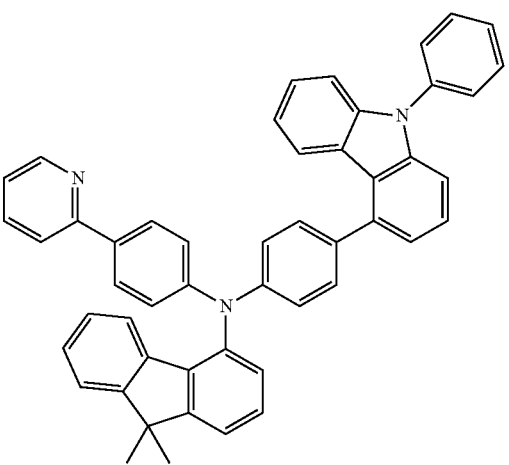

-continued
Formula 135
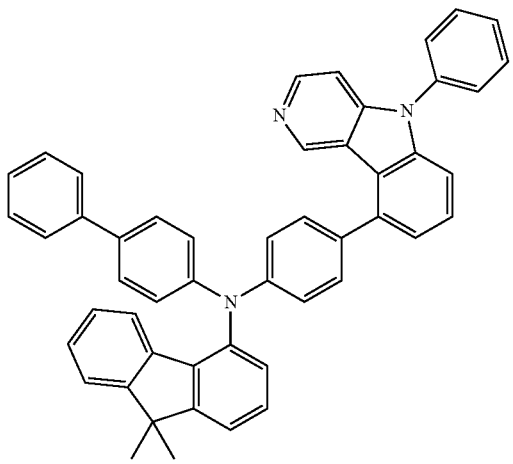
Formula 136
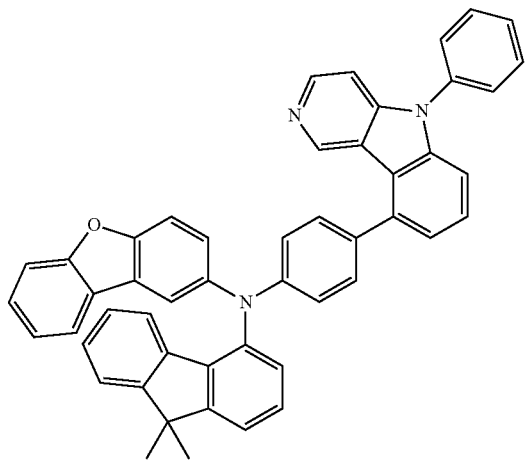
Formula 137
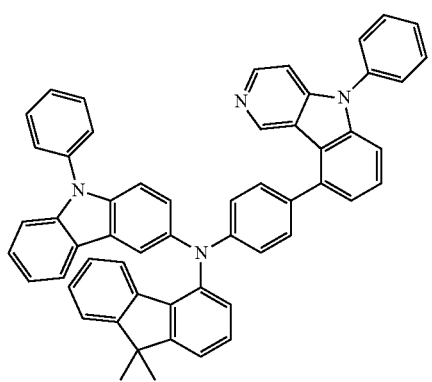
Formula 138
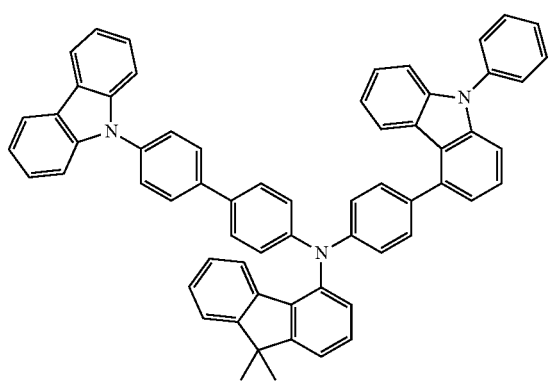
Formula 139
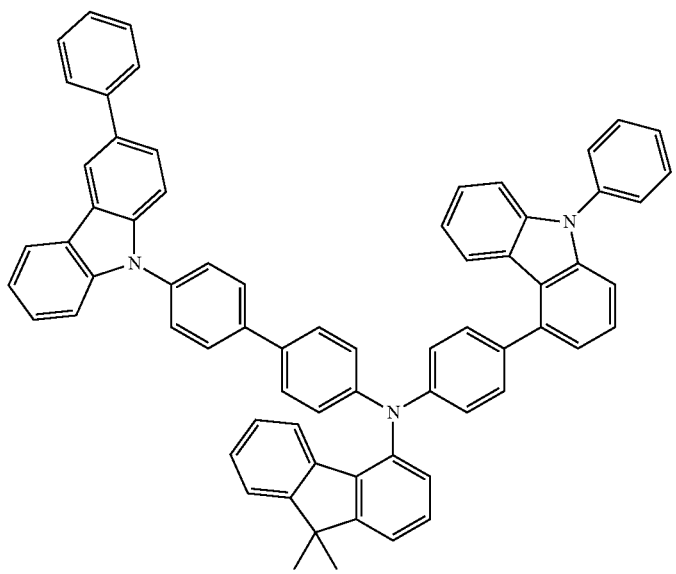

Formula 140
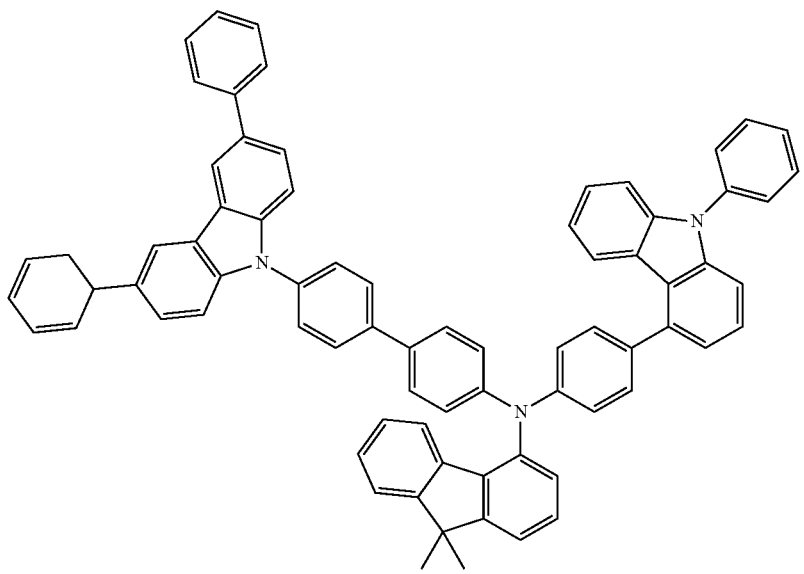
Formula 141 Formula 142
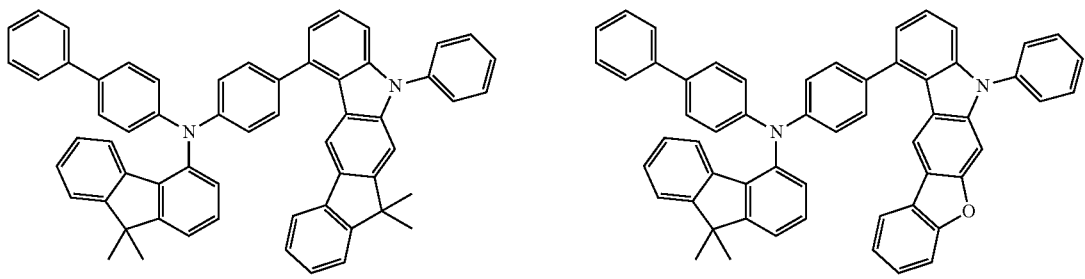
Formula 143 Formula 144
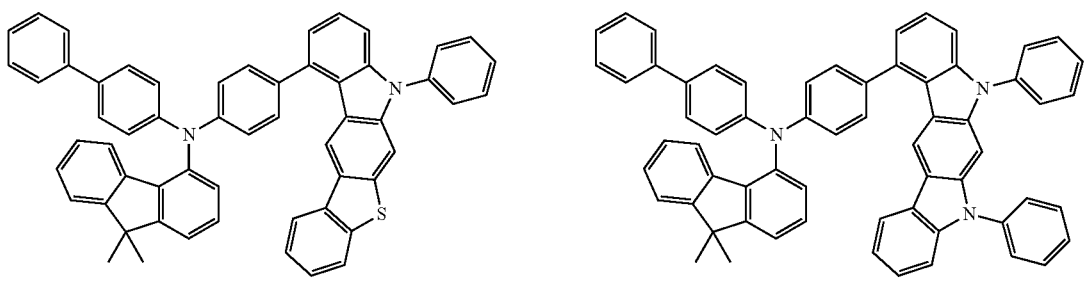
Formula 145 Formula 146
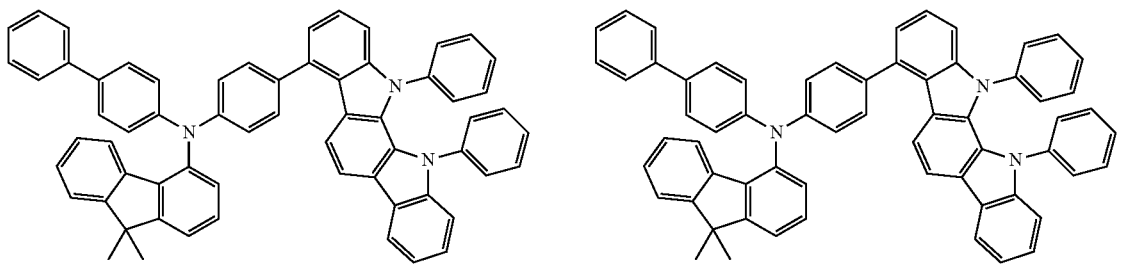

-continued
Formula 147
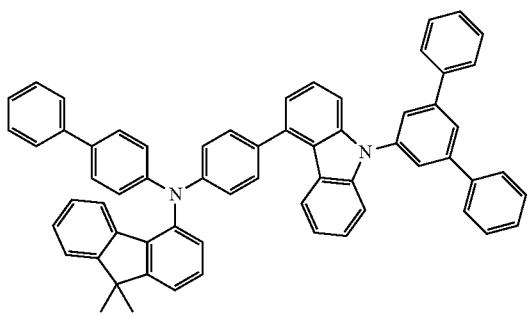
Formula 148
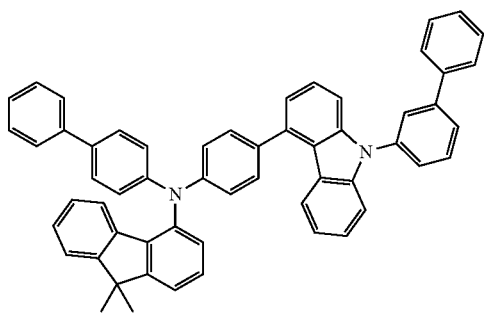
Formula 149
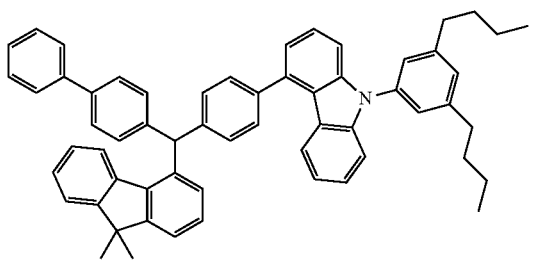
Formula 150
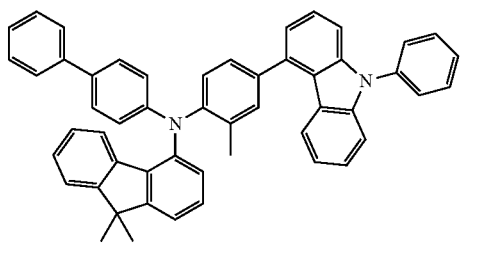
Formula 151
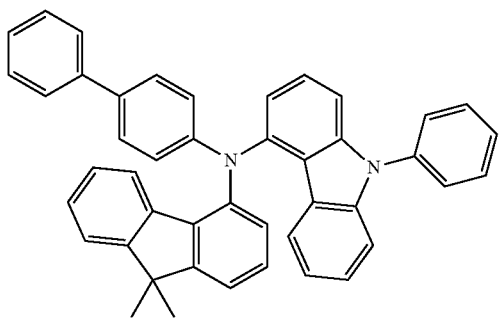
Formula 152
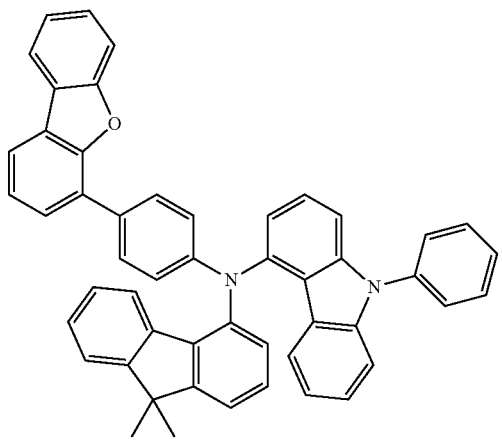
Formula 153
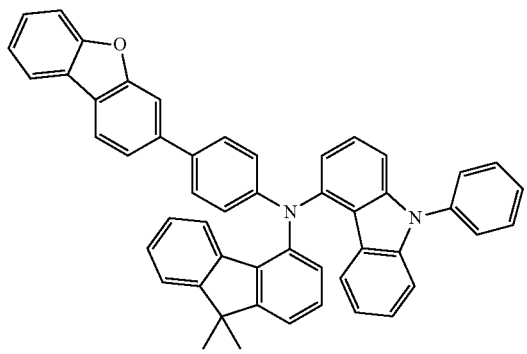
Formula 154
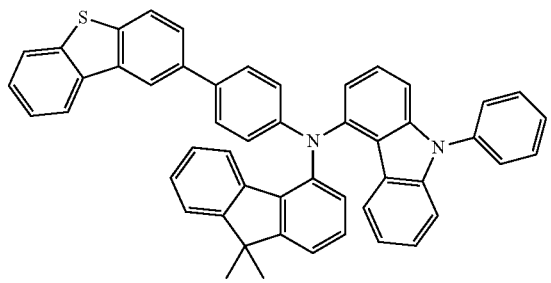

-continued
Formula 155
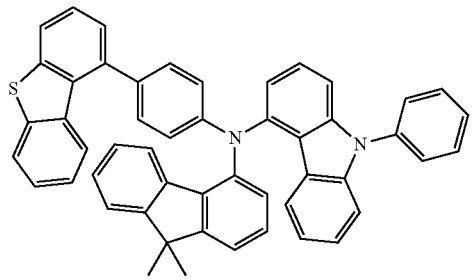
Formula 156
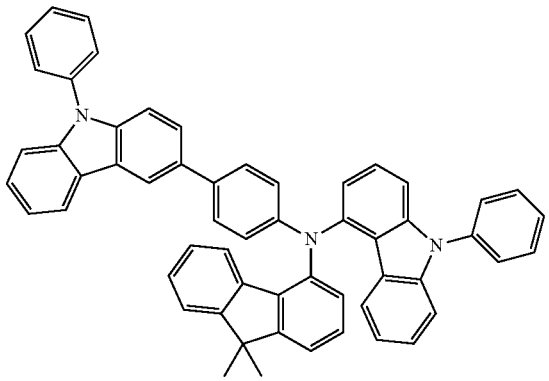
Formula 157
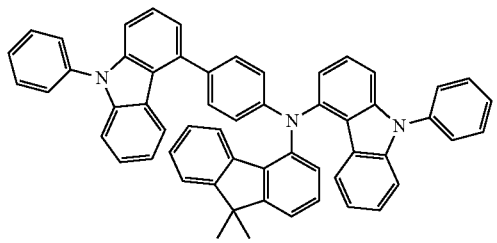
Formula 158
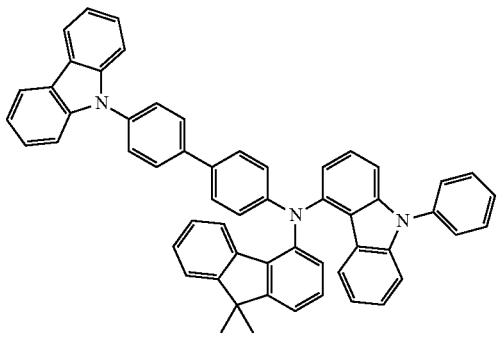
Formula 159
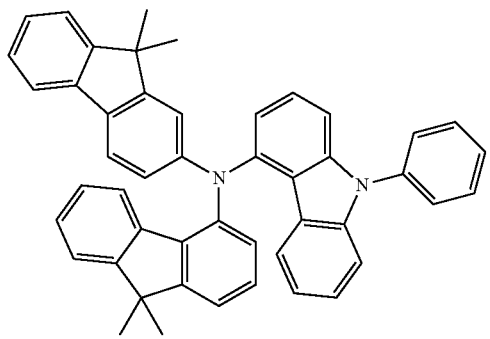
Formula 160
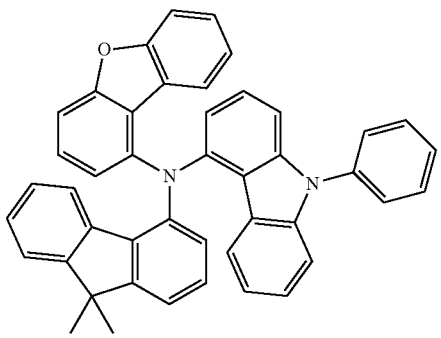
Formula 161
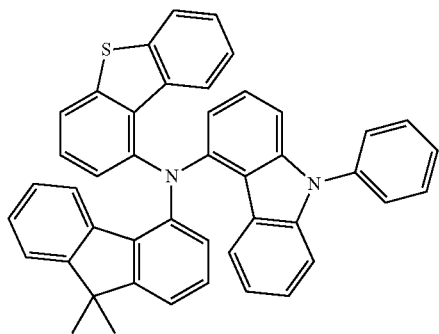
Formula 162
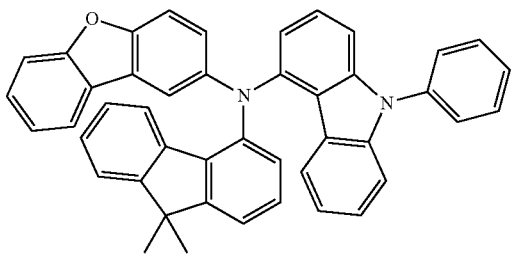

-continued
Formula 163
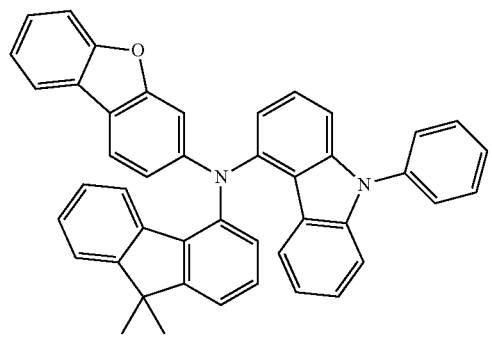
Formula 164
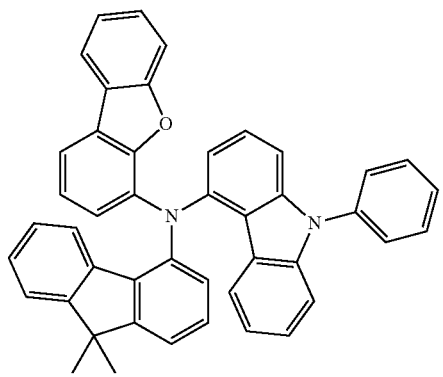
Formula 165
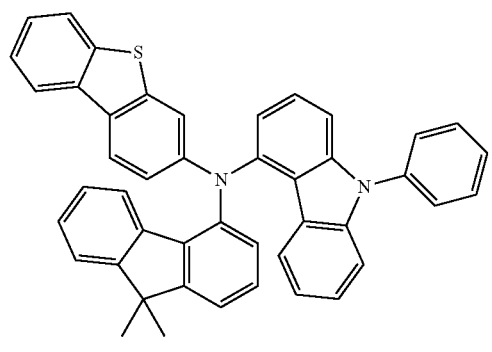
Formula 166
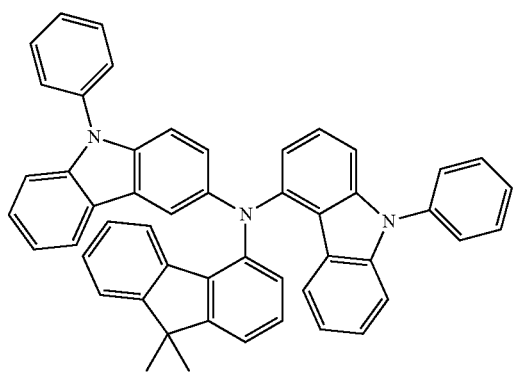
Formula 167
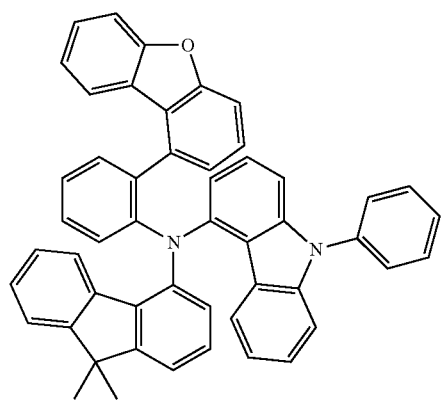
Formula 168
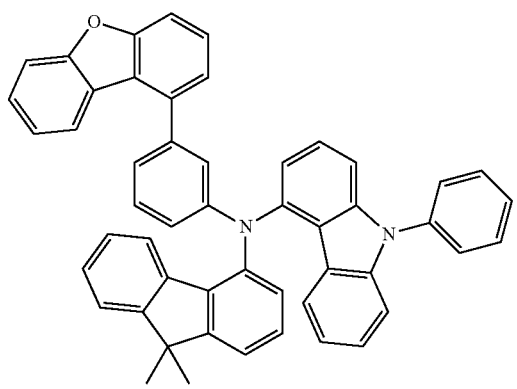

-continued
Formula 169
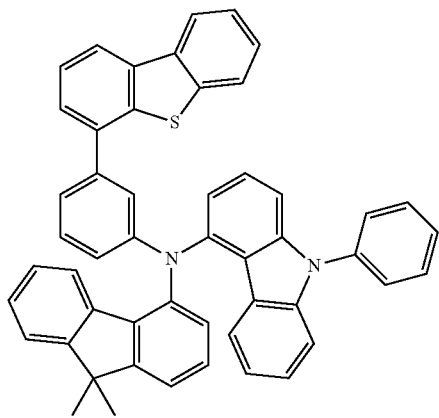
Formula 170
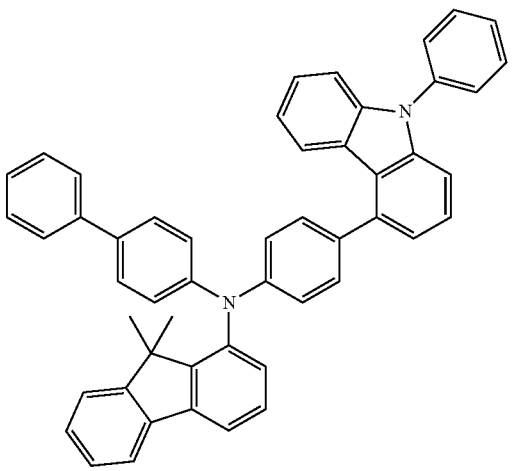
Formula 171
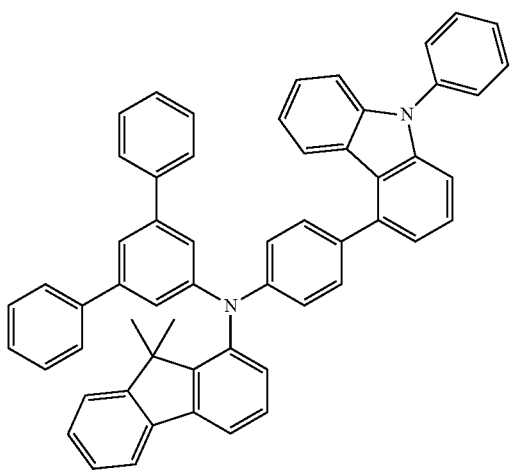
Formula 172
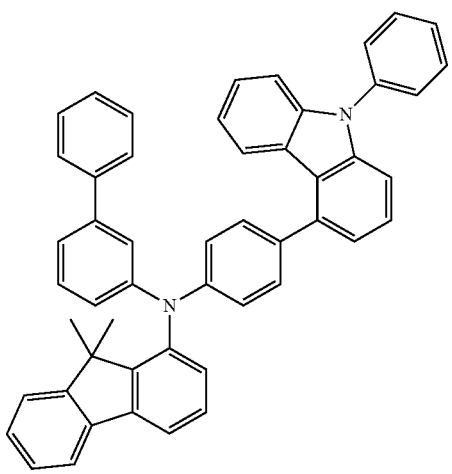
Formula 173
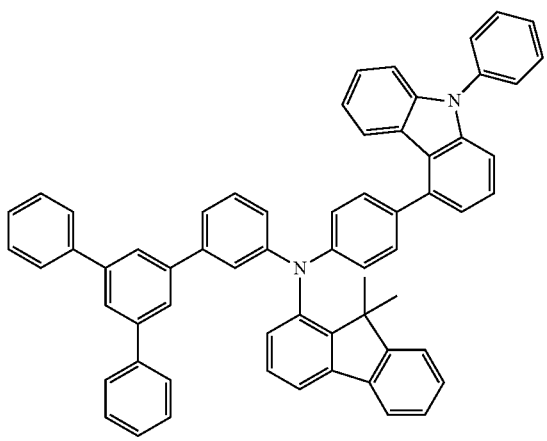
Formula 174
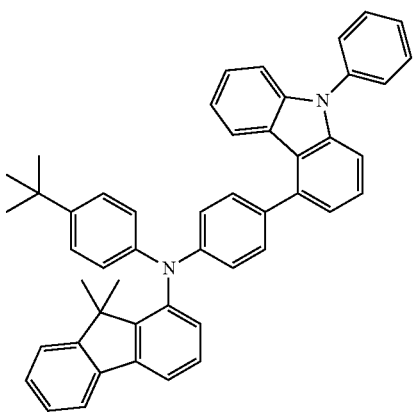

-continued
Formula 175
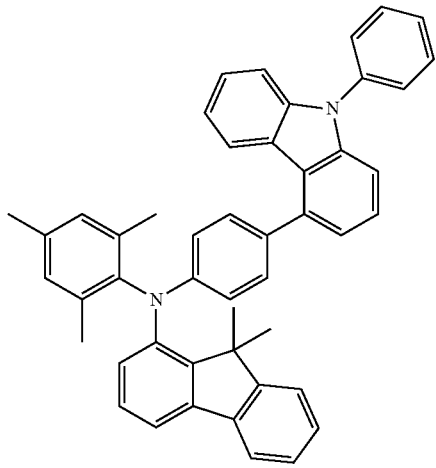
Formula 176
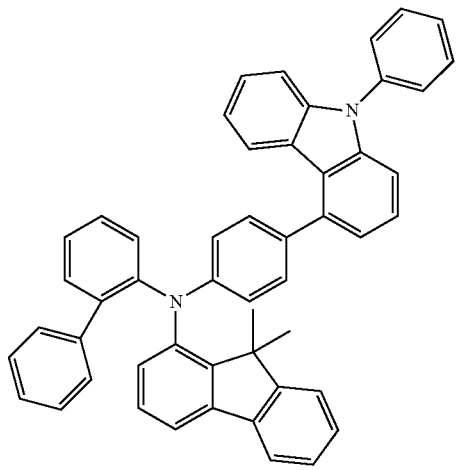
Formula 177
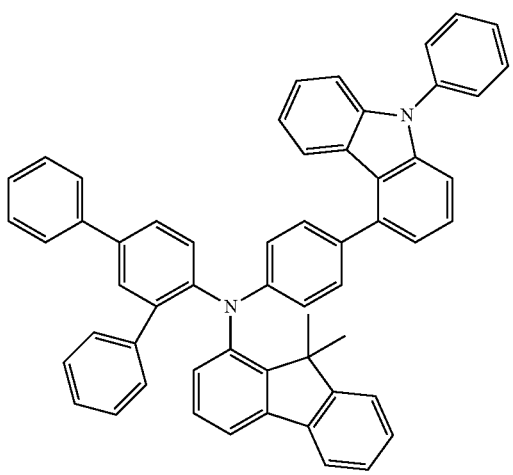
Formula 178
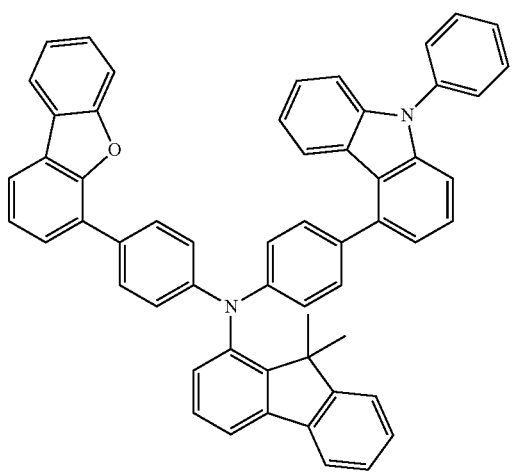
Formula 179
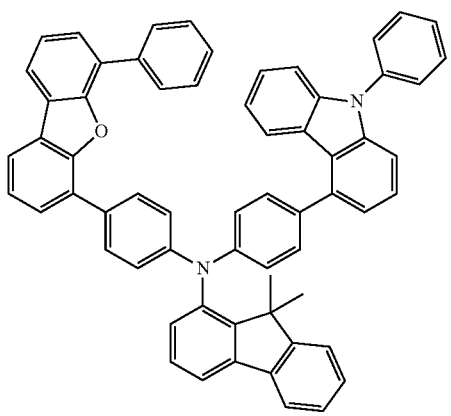
Formula 180
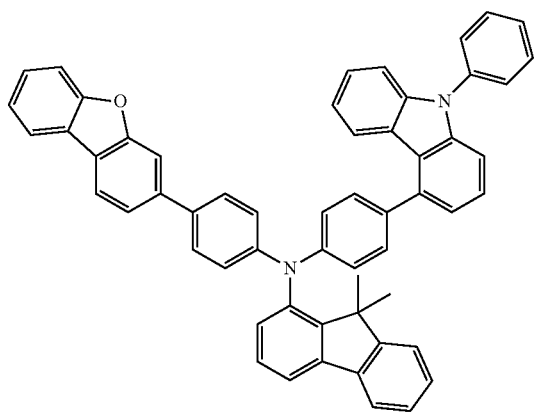

Formula 181
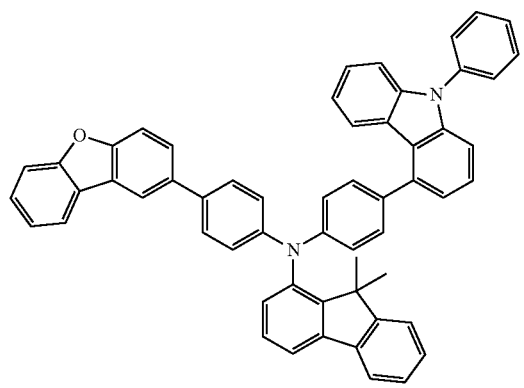
Formula 182
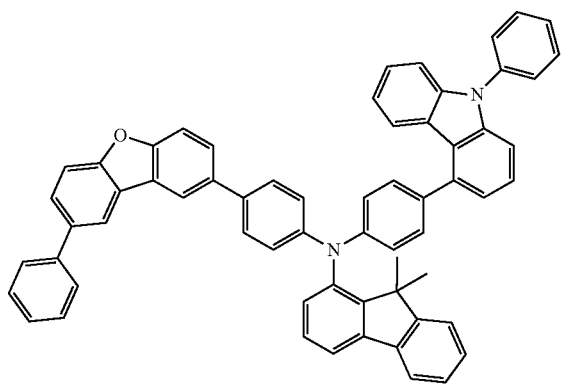
Formula 183
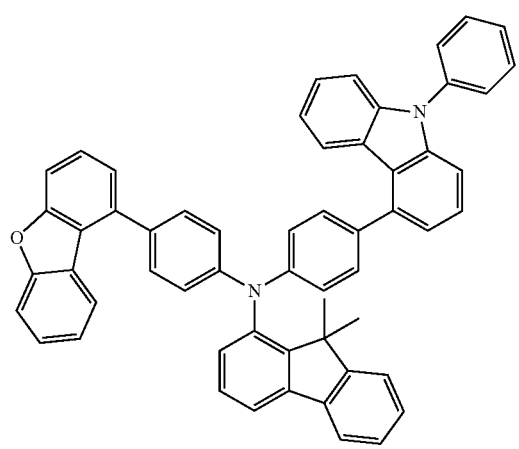
Formula 184
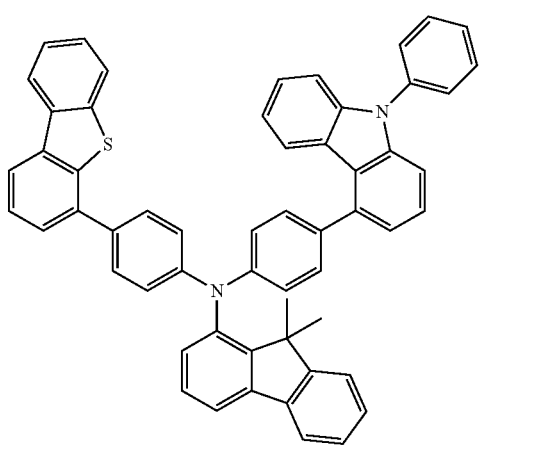
Formula 185
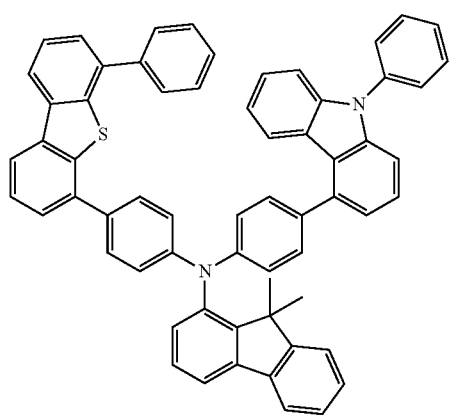
Formula 186
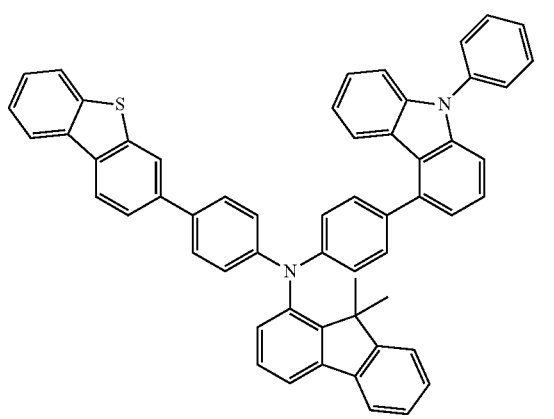

-continued
Formula 187
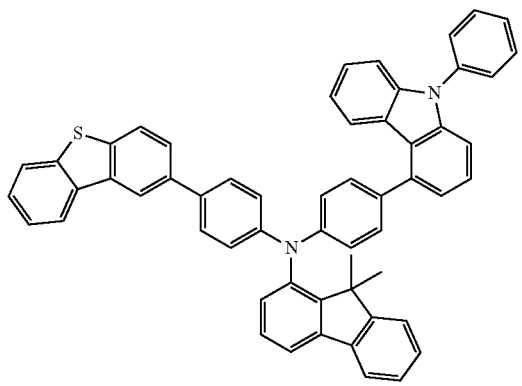
Formula 188
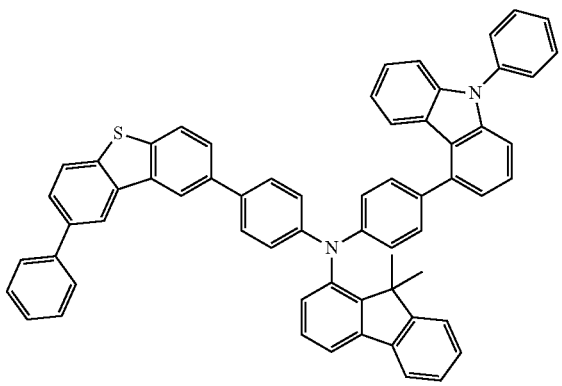
Formula 189
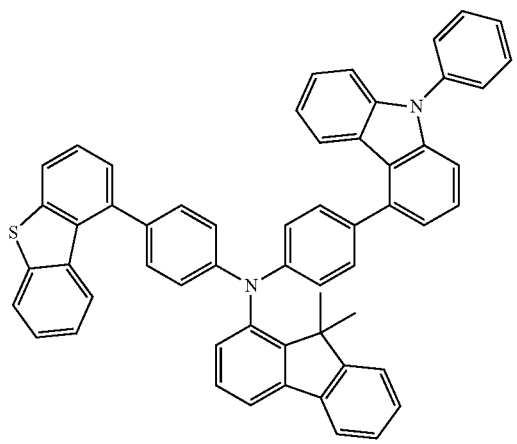
Formula 190
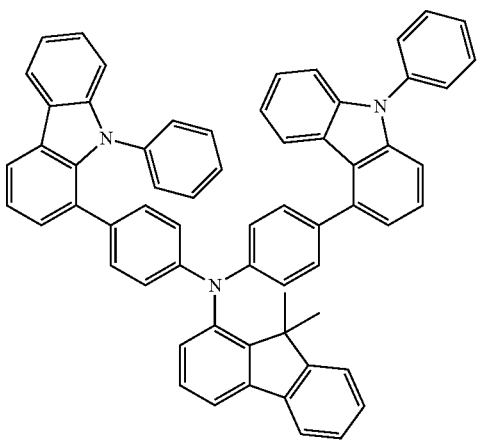
Formula 191
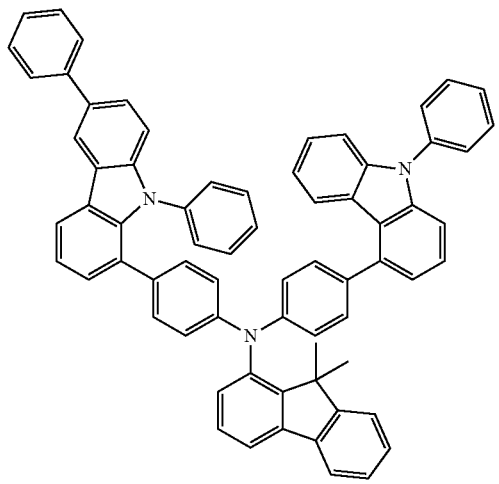
Formula 192
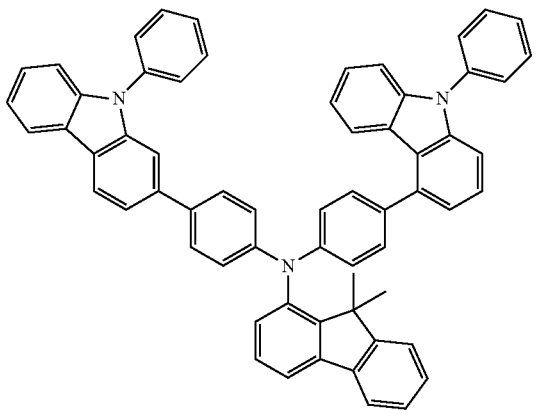

-continued
Formula 193
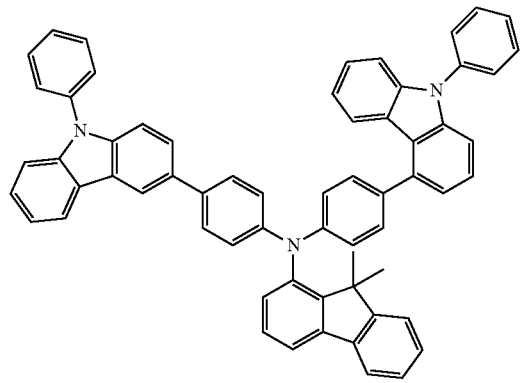
Formula 194
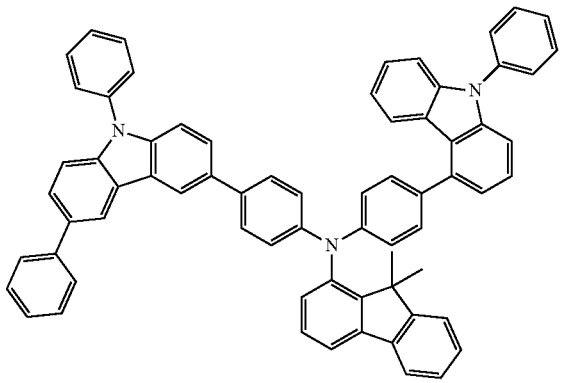
Formula 195
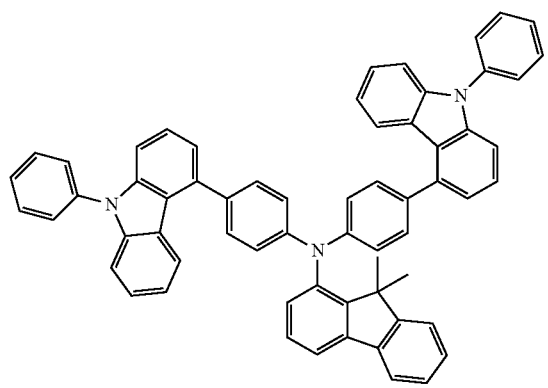
Formula 196
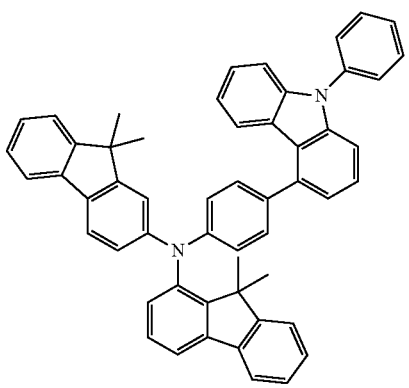
Formula 197
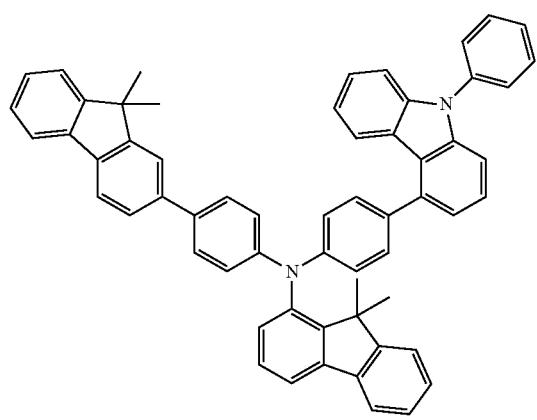
Formula 198
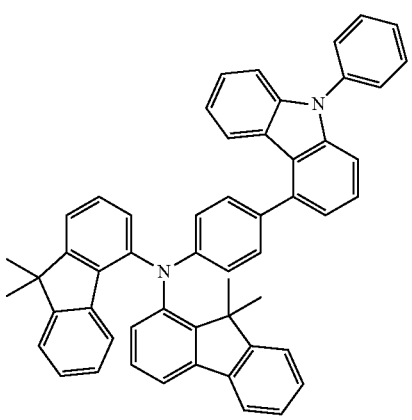

Formula 199
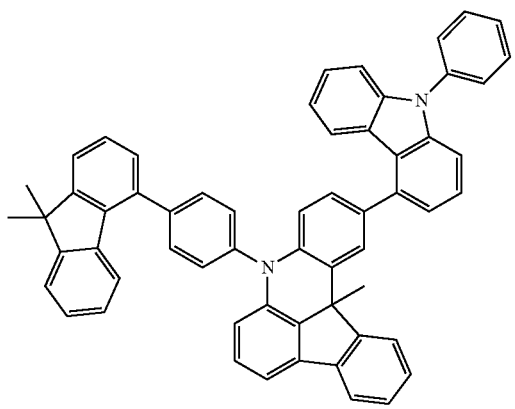
Formula 200
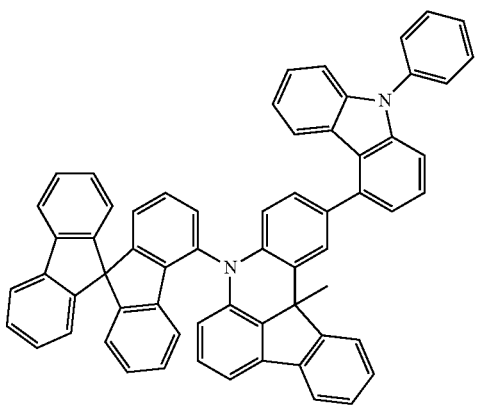
Formula 201
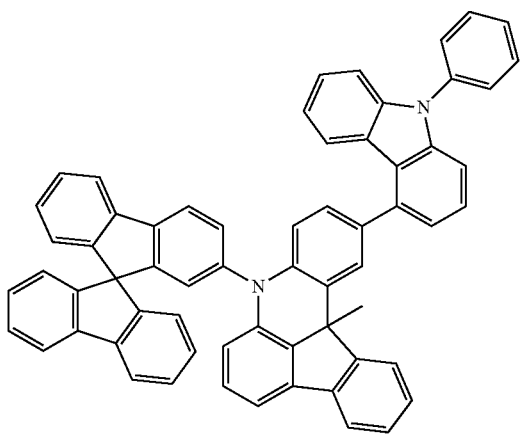
Formula 202
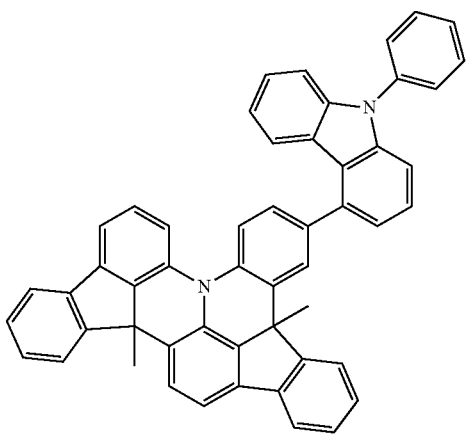
Formula 203
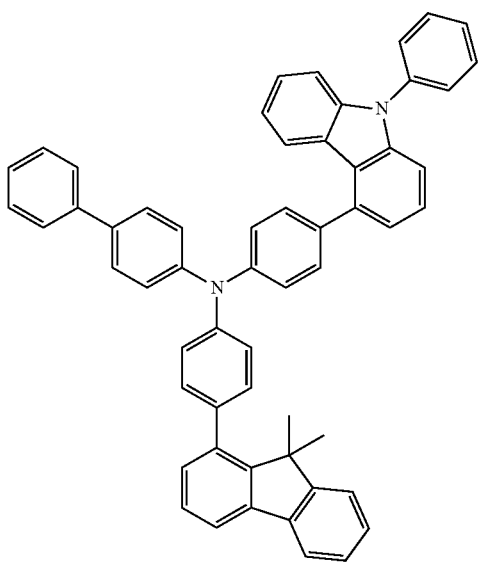
Formula 204
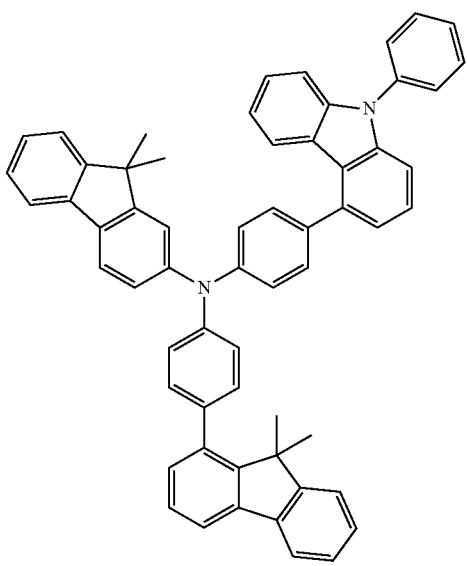

-continued
Formula 205
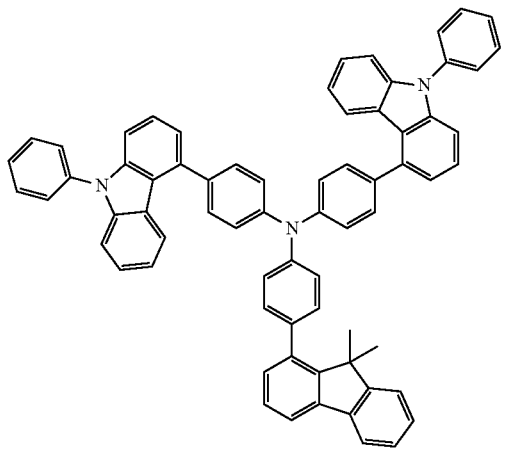
Formula 206
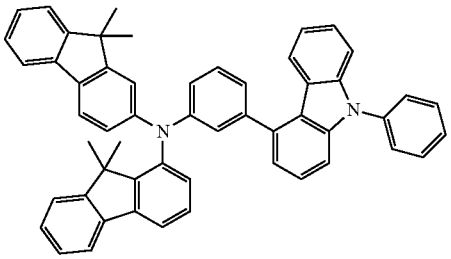
Formula 207
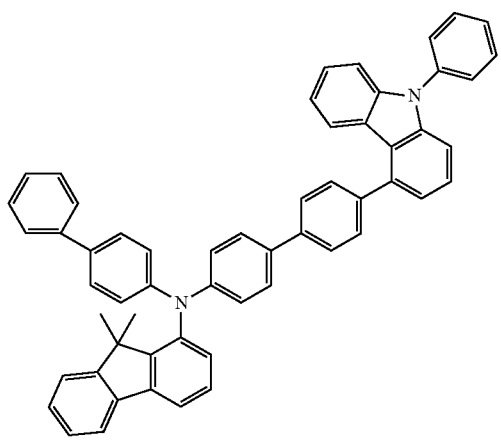
Formula 208
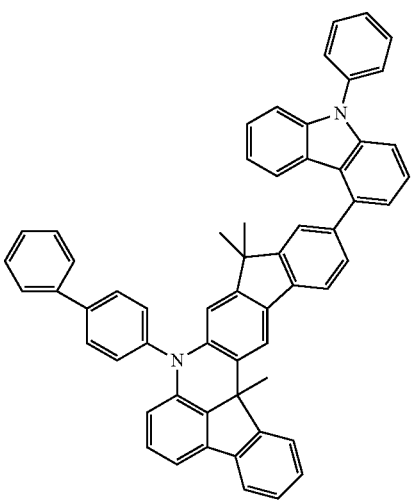
Formula 209
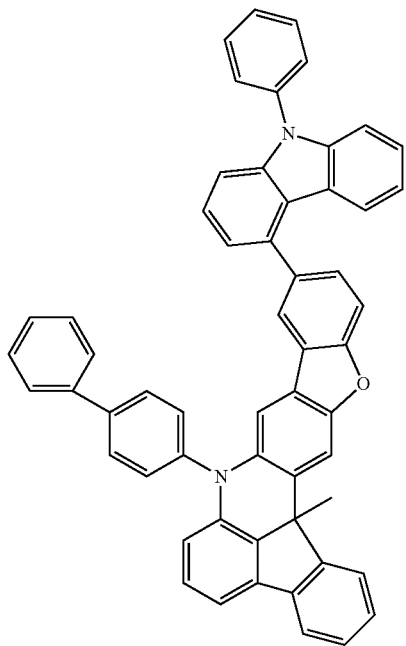
Formula 210
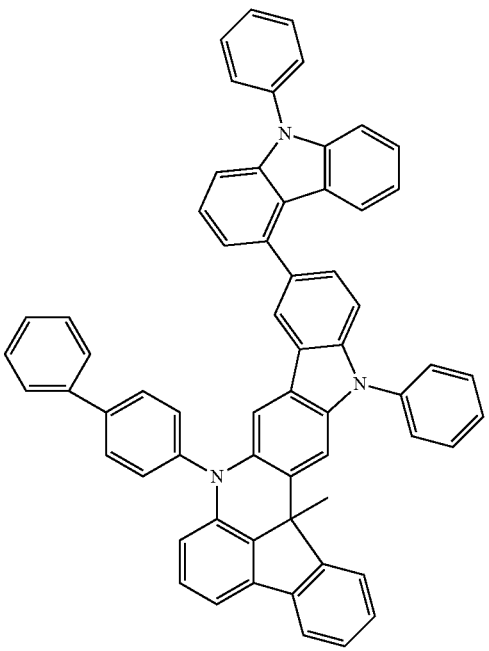

-continued
Formula 211
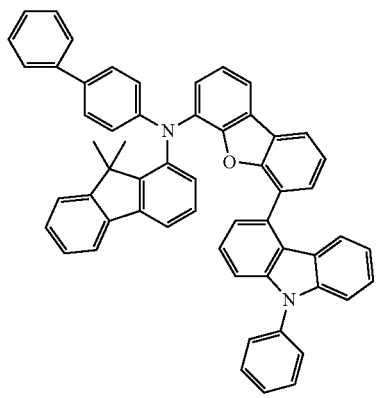
Formula 212
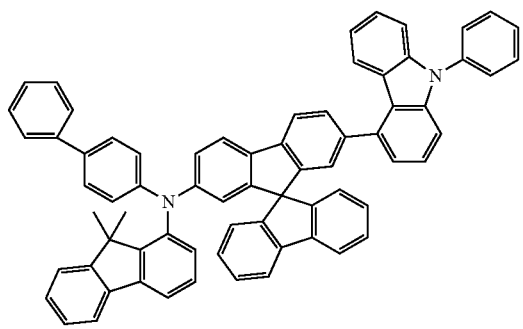
Formula 213
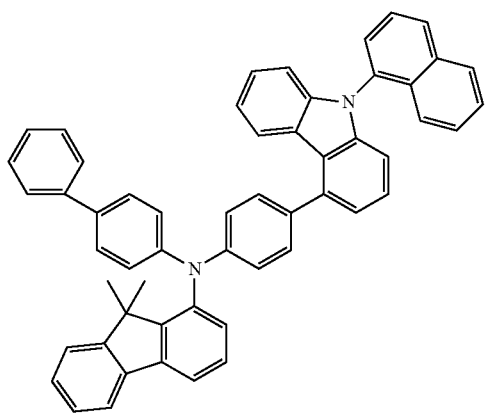
Formula 214
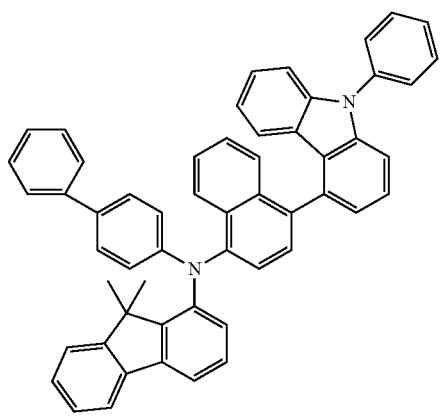
Formula 215
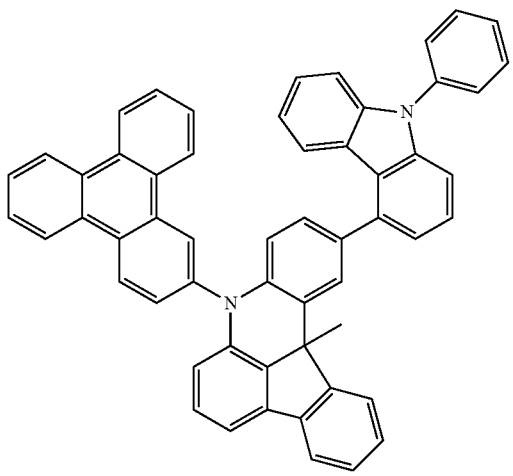
Formula 216
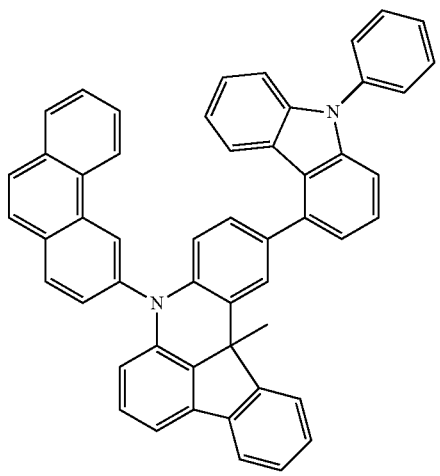

-continued
Formula 217
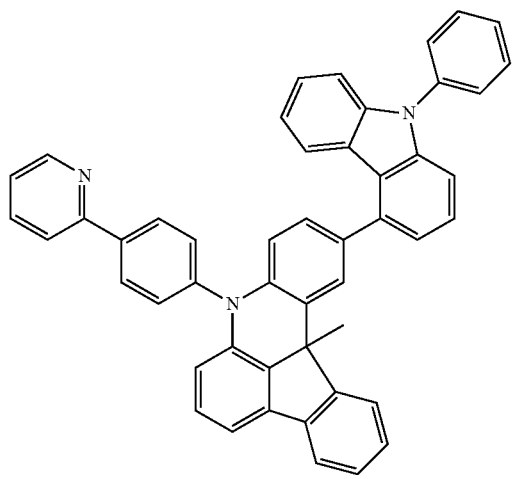
Formula 218
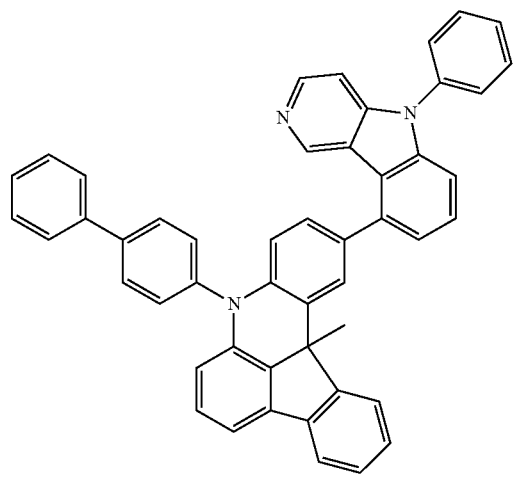
Formula 219
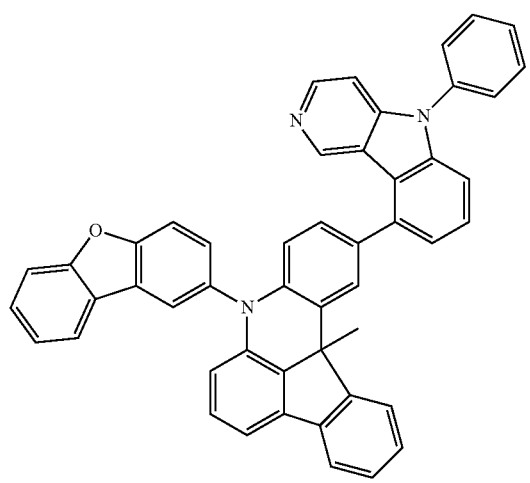
Formula 220
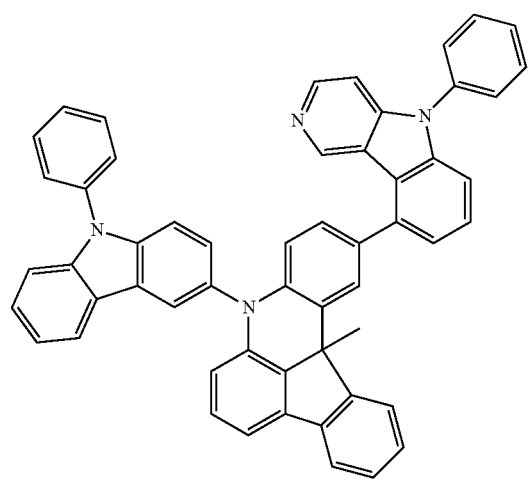
Formula 221
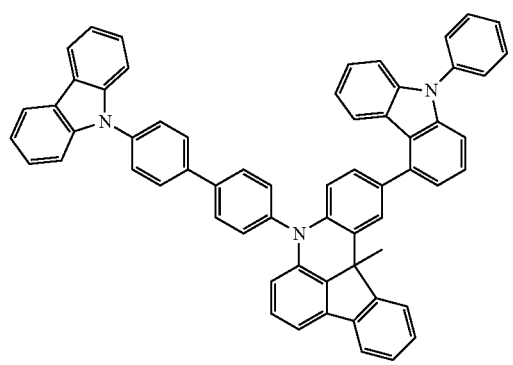
Formula 222
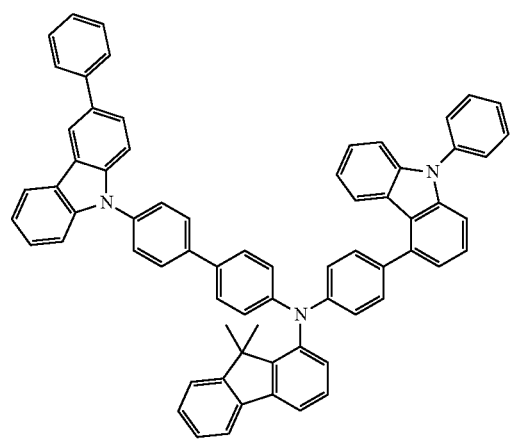

Formula 223
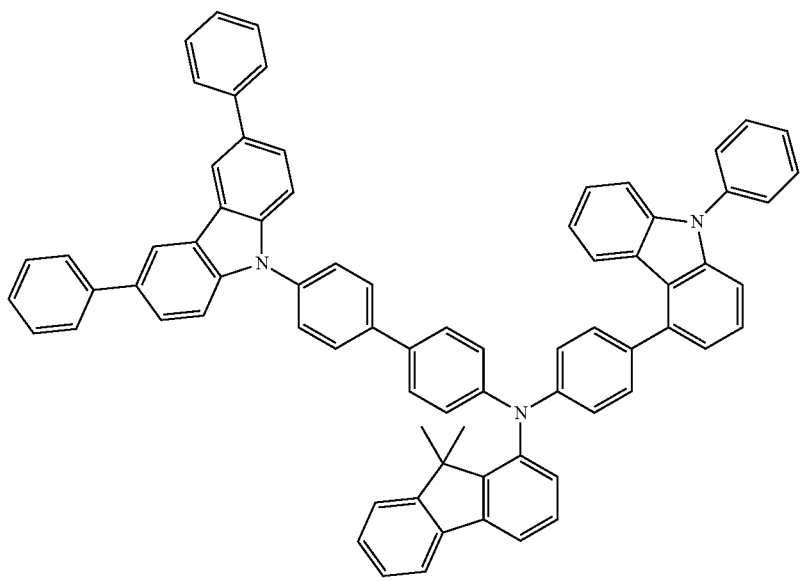
Formula 224
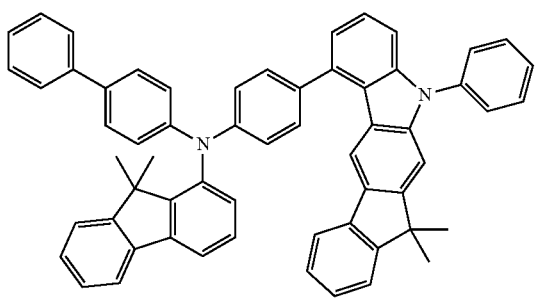
Formula 225
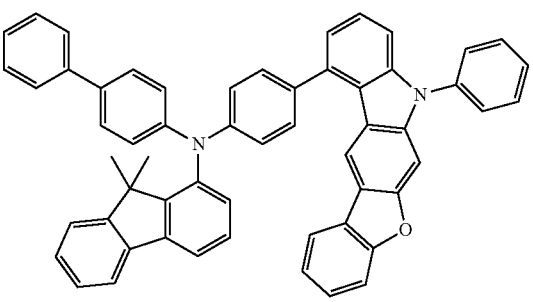
Formula 226
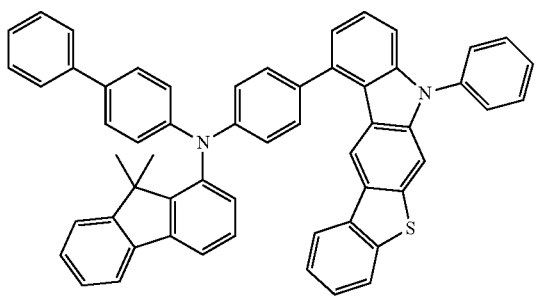
Formula 227
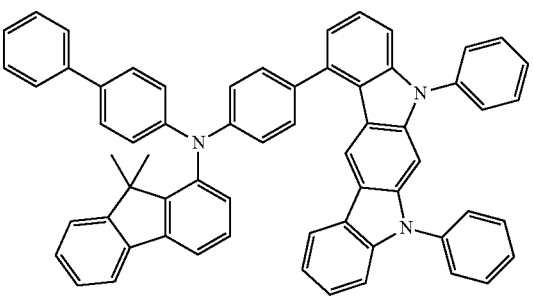
Formula 228
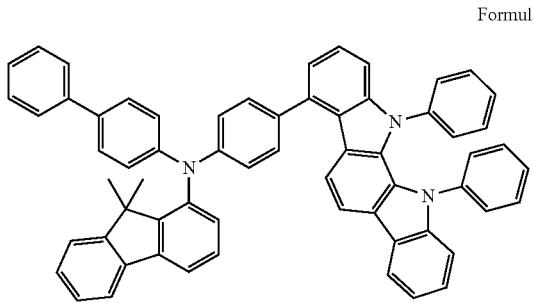
Formula 229
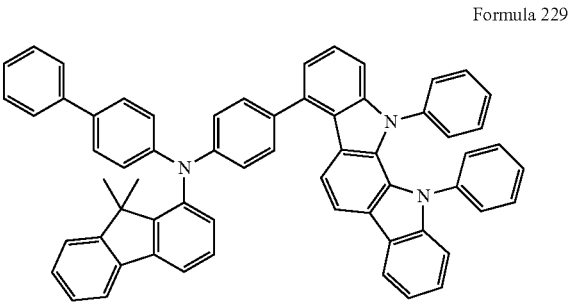

-continued
Formula 230
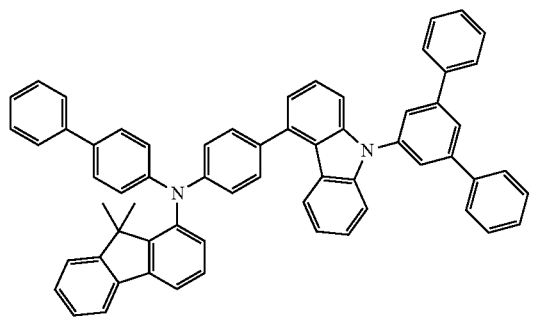
Formula 231
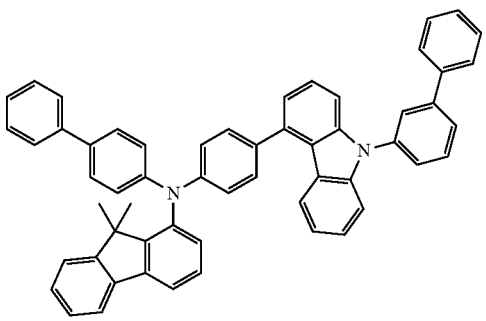
Formula 232
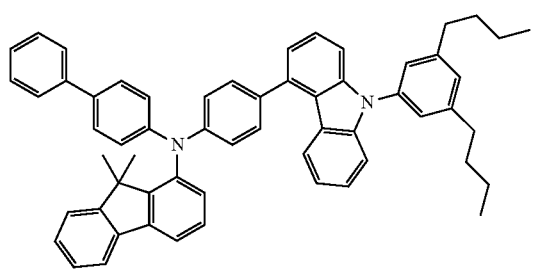
Formula 233
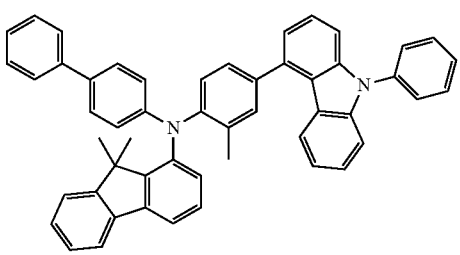
Formula 234
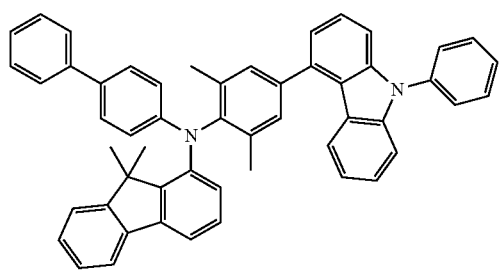
Formula 235
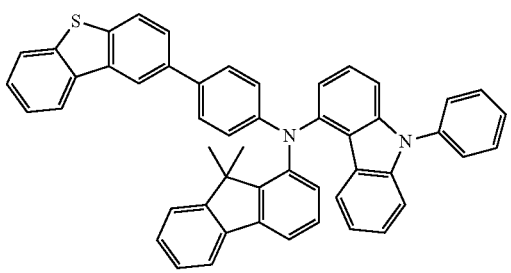
Formula 236
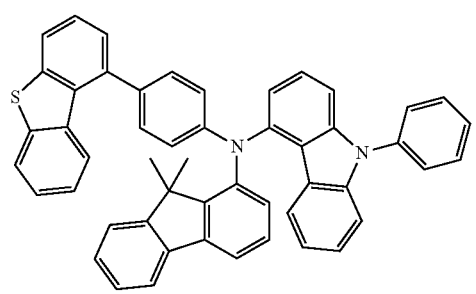
Formula 237
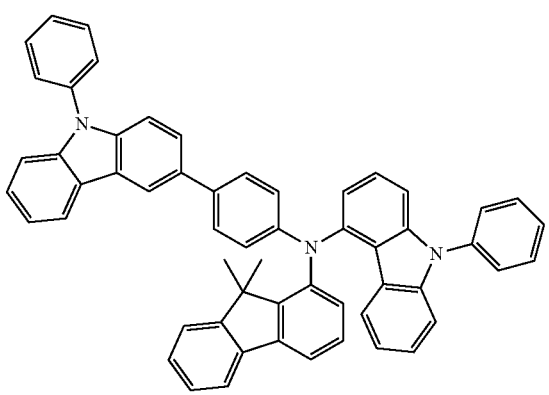

-continued
Formula 238
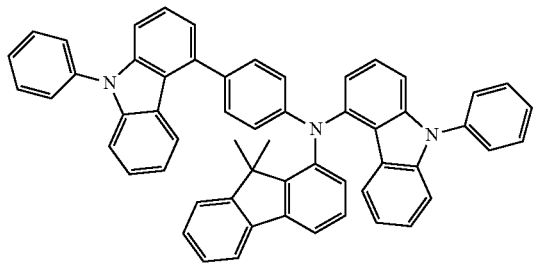
Formula 239
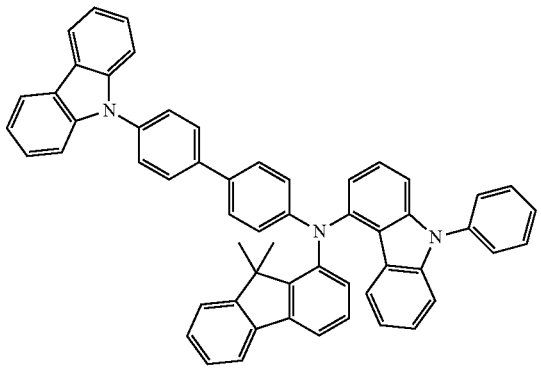
Formula 240
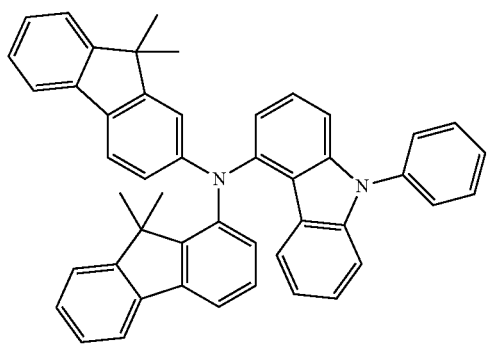
Formula 241
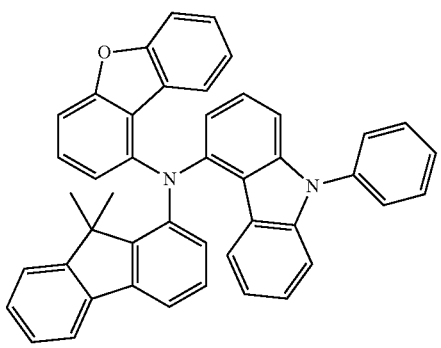
Formula 242
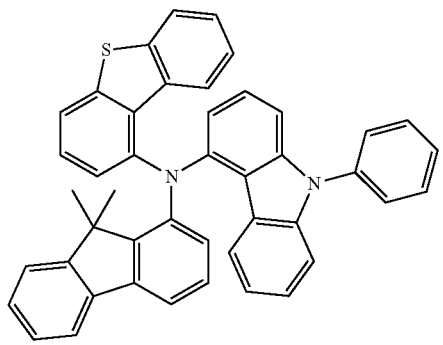
Formula 243
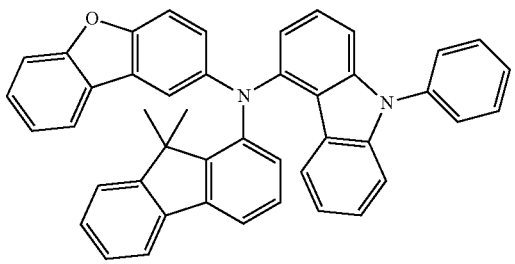
Formula 244
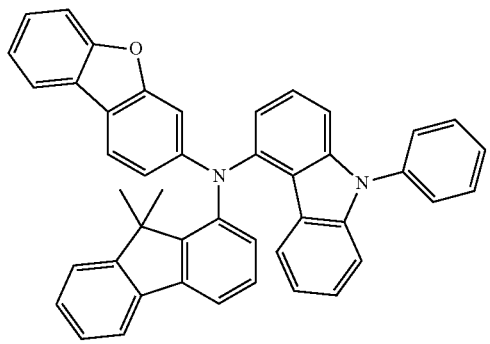
Formula 245
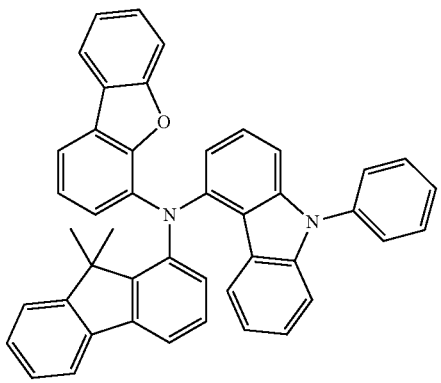

-continued
Formula 246
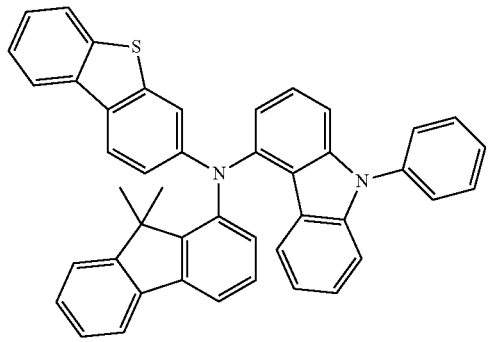
Formula 247
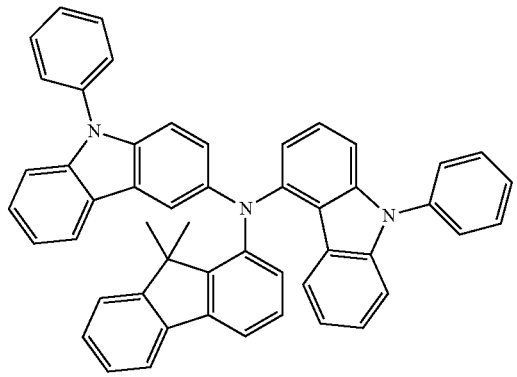
Formula 248
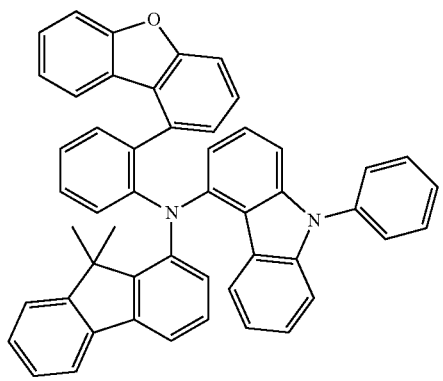
Formula 249
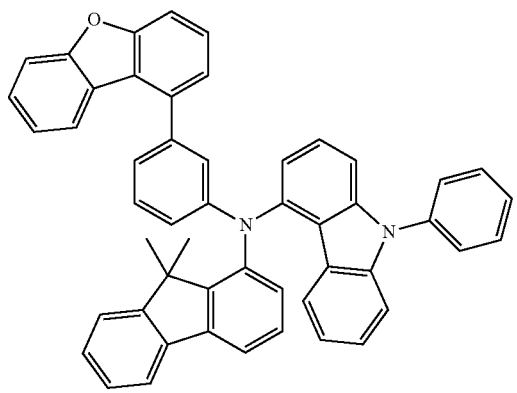
Formula 250
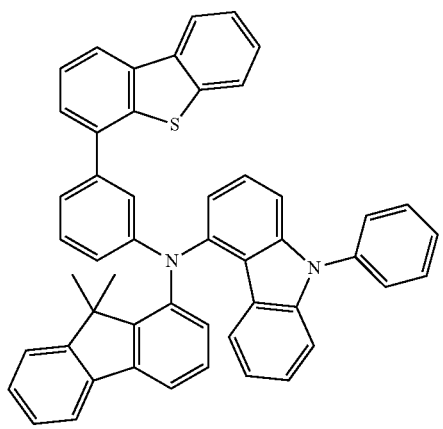
Formula 251
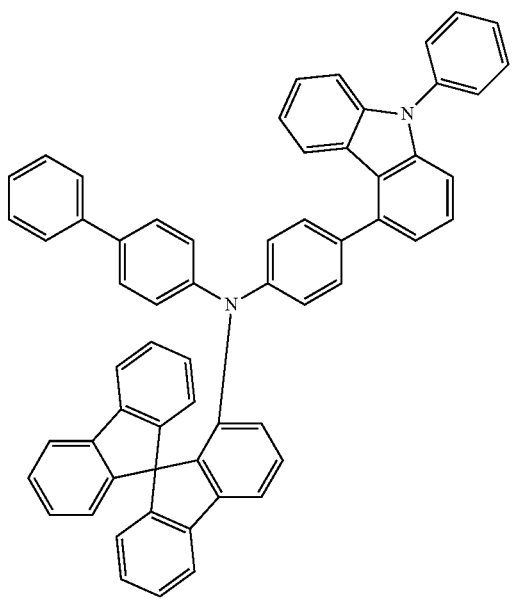

Formula 252
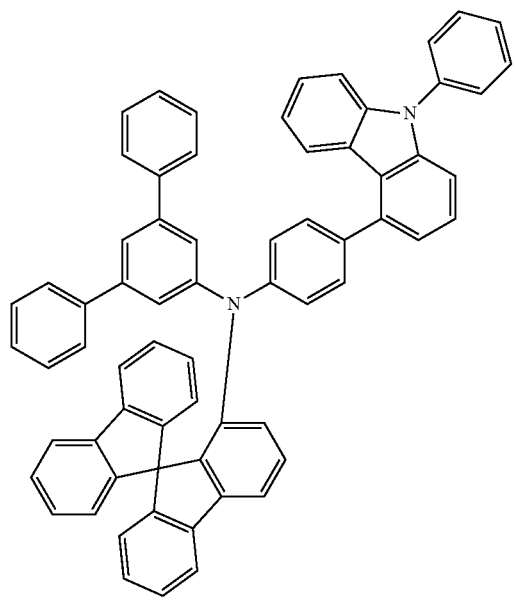
Formula 253
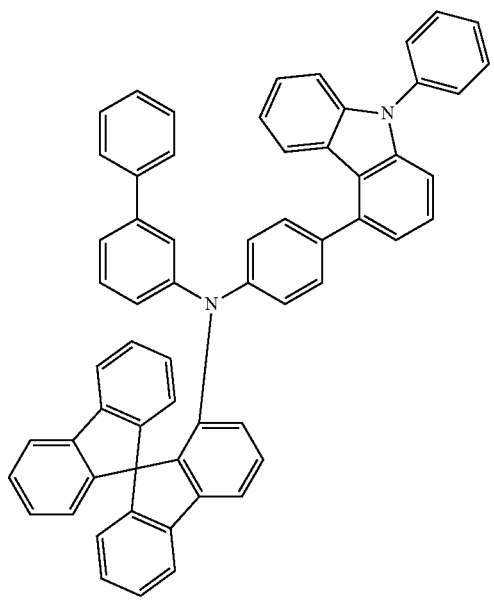
Formula 254
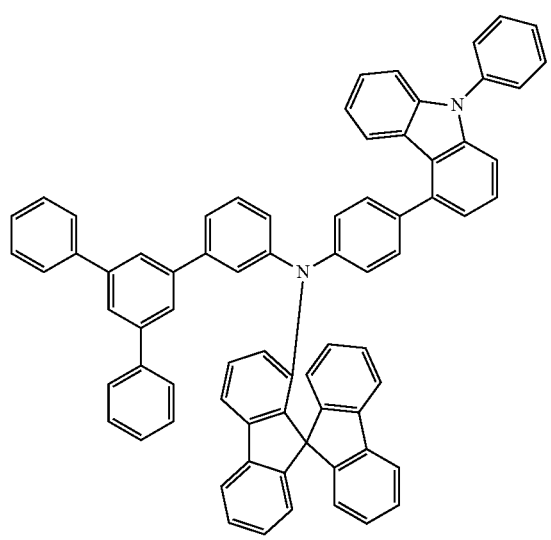
Formula 255
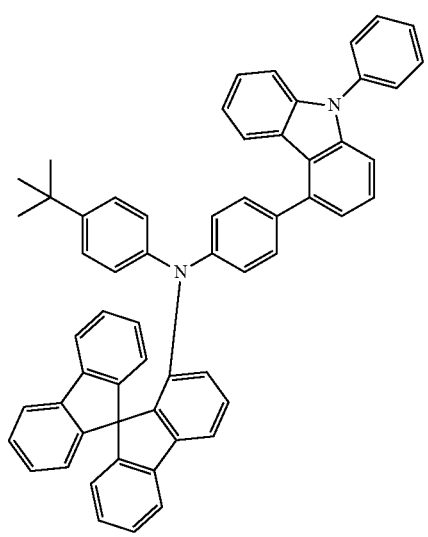

-continued
Formula 256
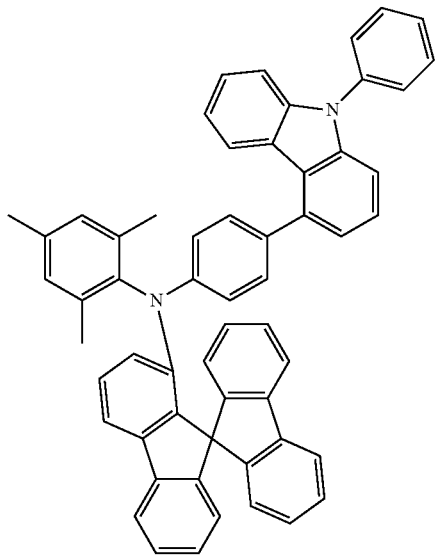
Formula 257
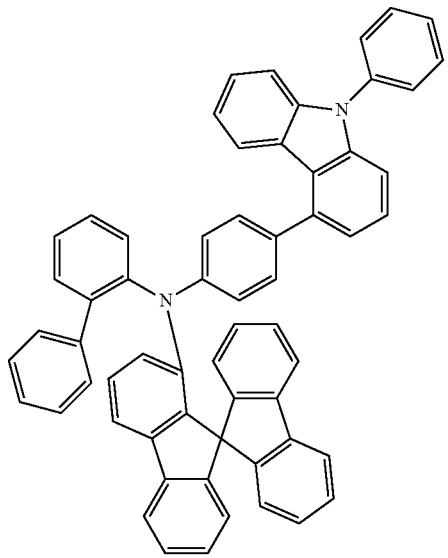
Formula 258
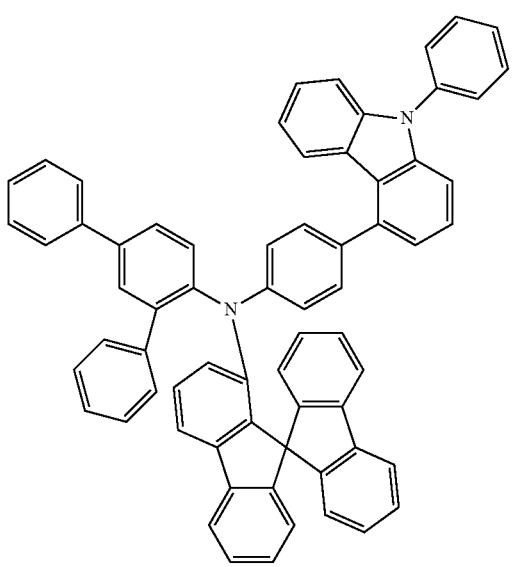
Formula 259
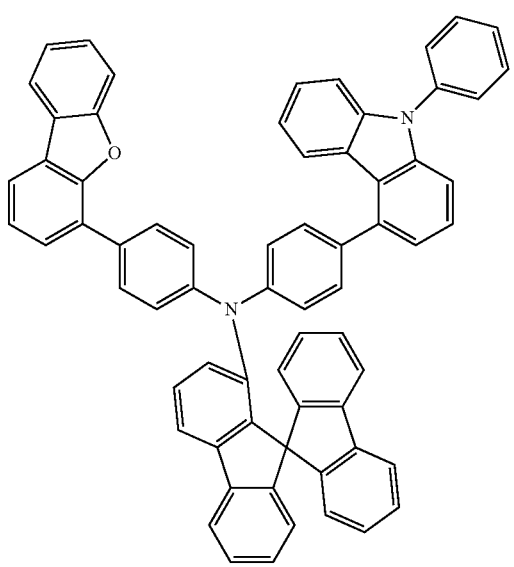
Formula 260
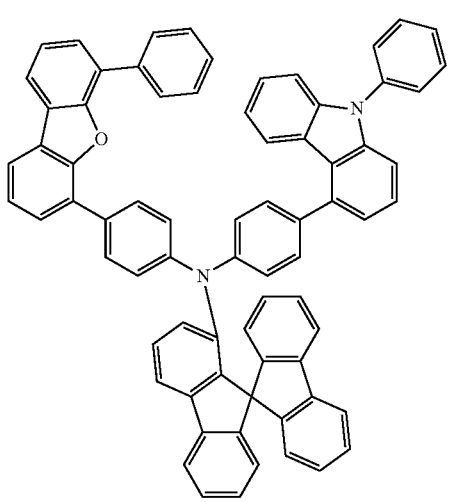
Formula 261
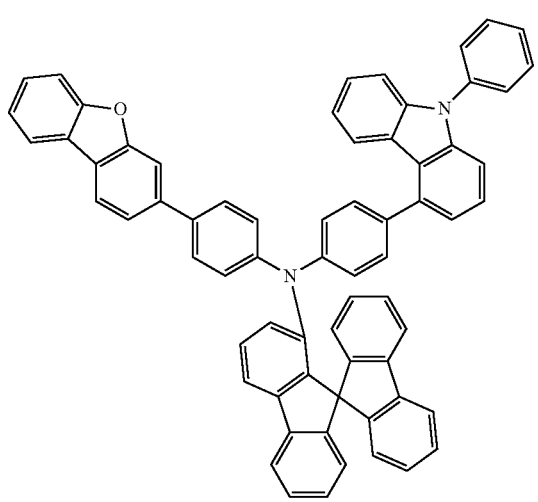

-continued
Formula 262
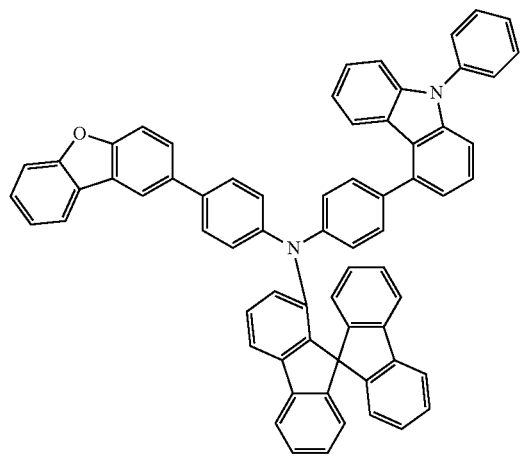
Formula 263
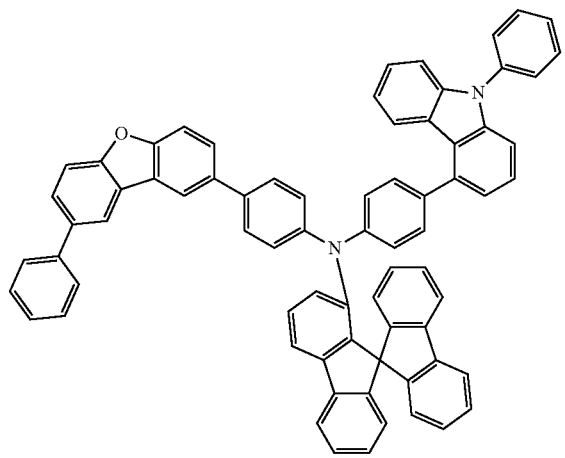
Formula 264
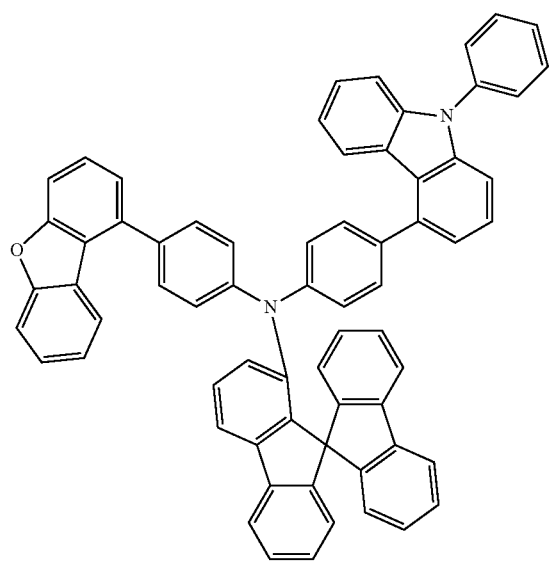
Formula 265
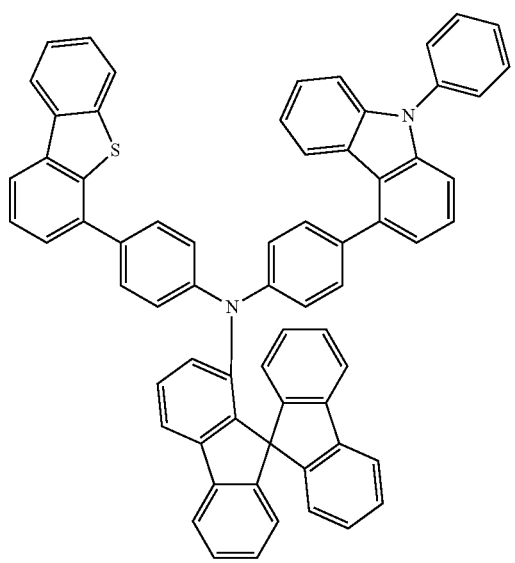
Formula 266
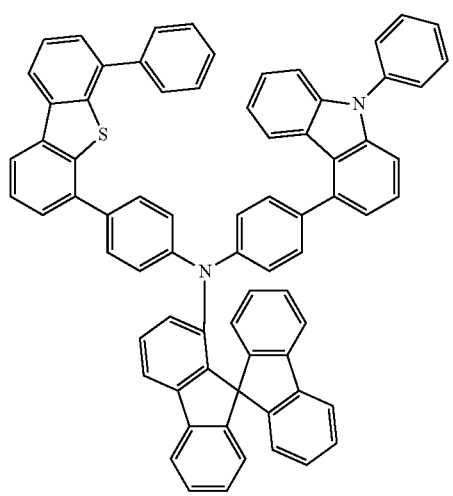
Formula 267
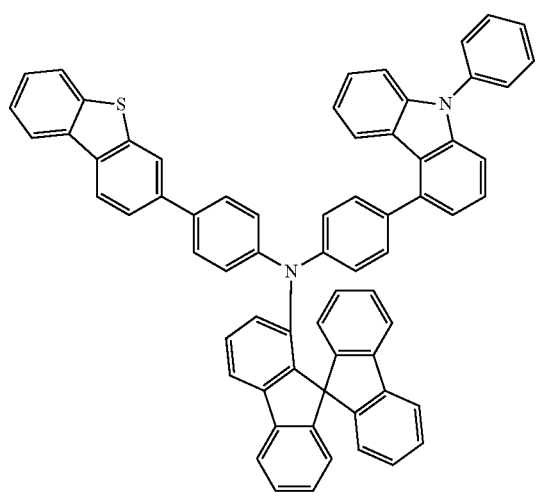

-continued
Formula 268
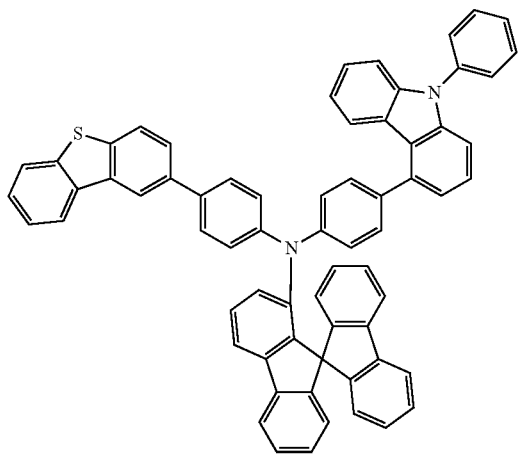
Formula 269
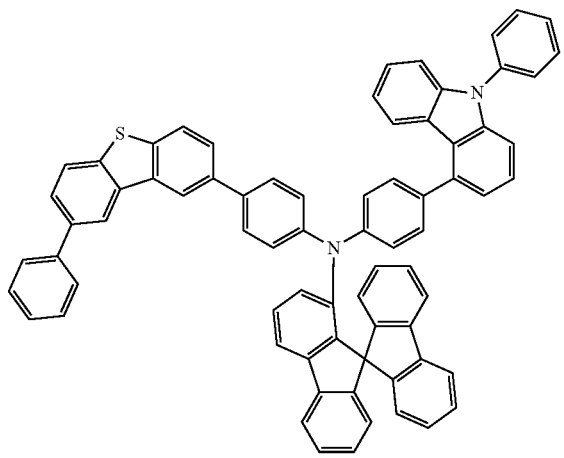
Formula 270
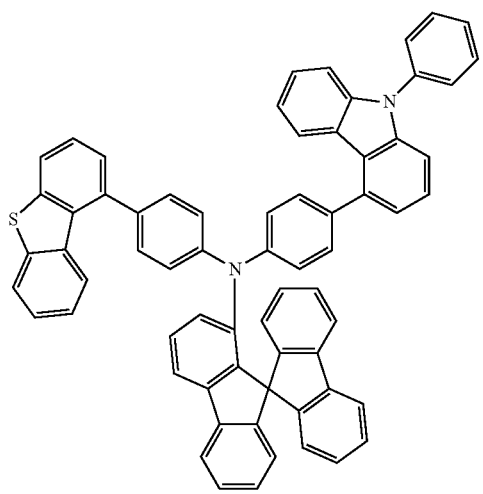
Formula 271
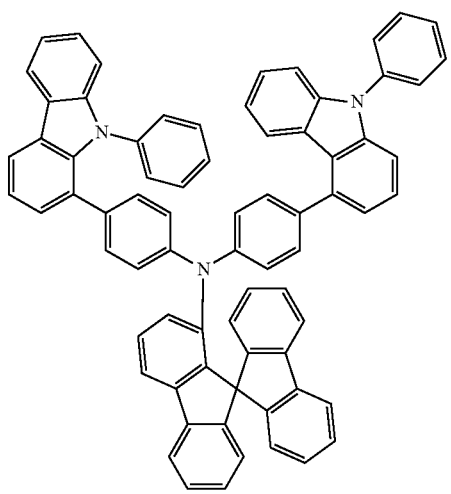
Formula 272
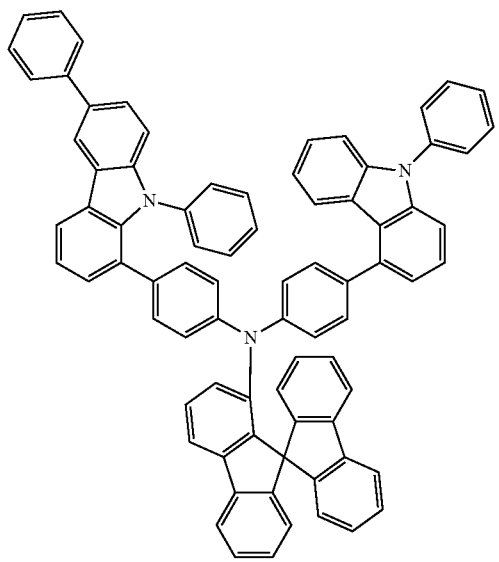
Formula 273
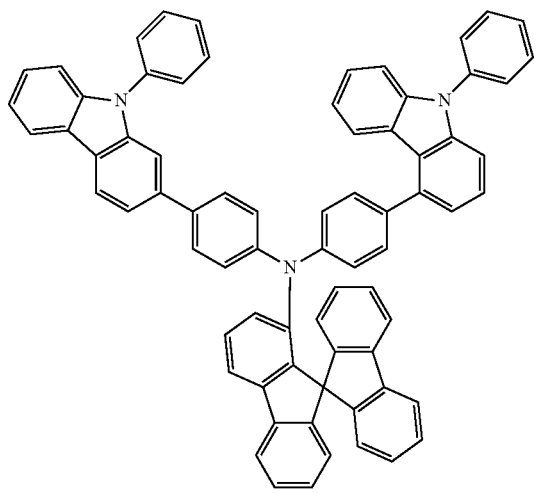

Formula 274
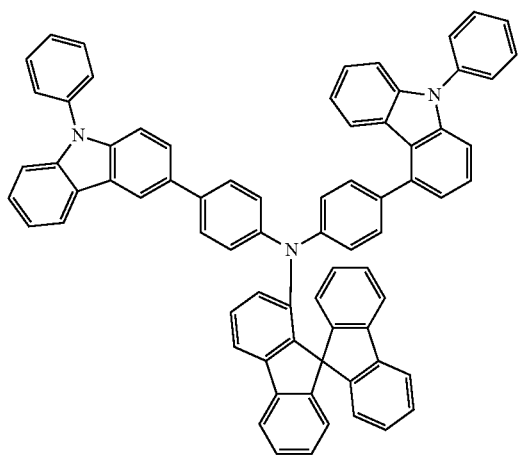
Formula 275
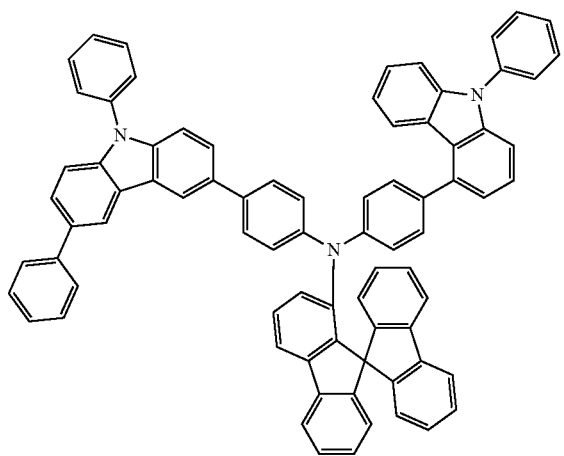
Formula 276
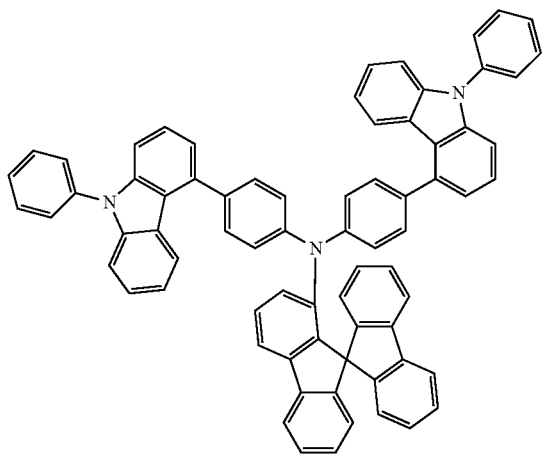
Formula 277
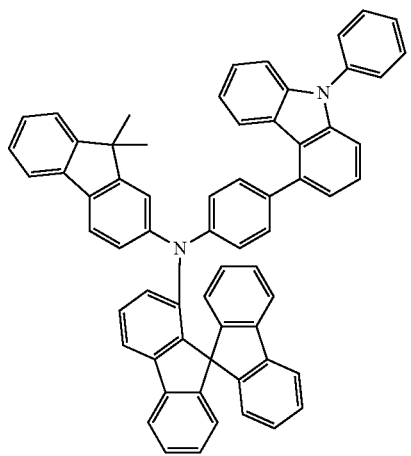
Formula 278
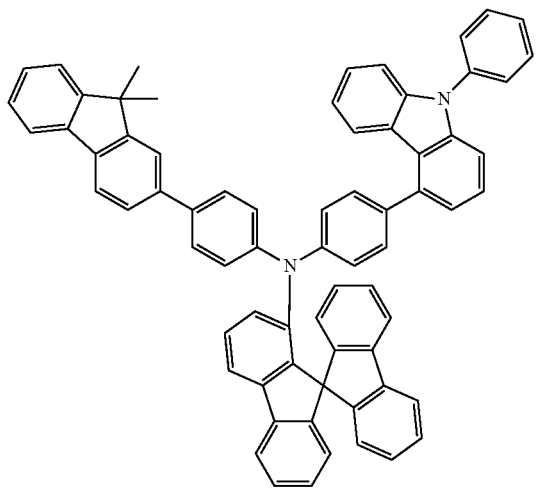
Formula 279
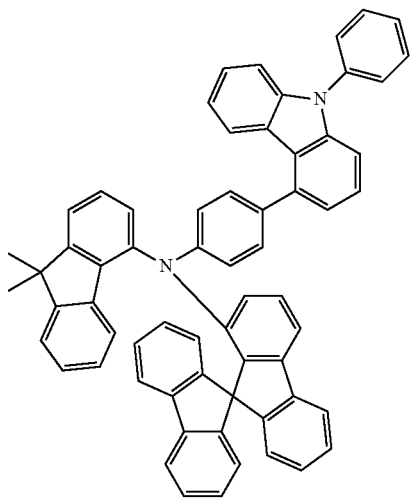

-continued
Formula 280
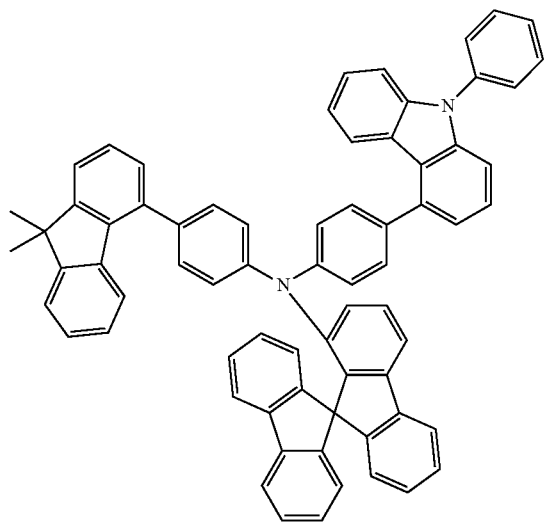
Formula 281
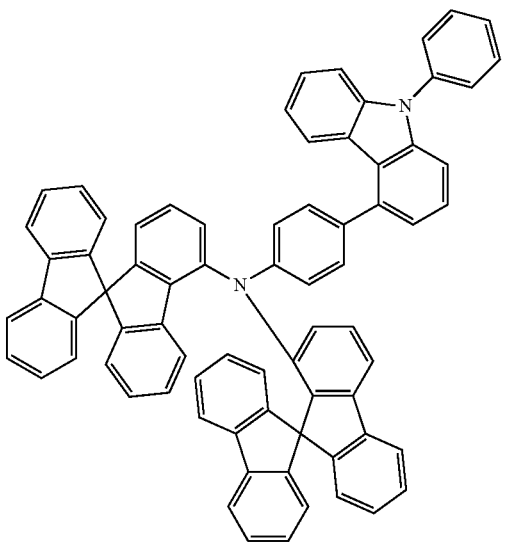
Formula 282
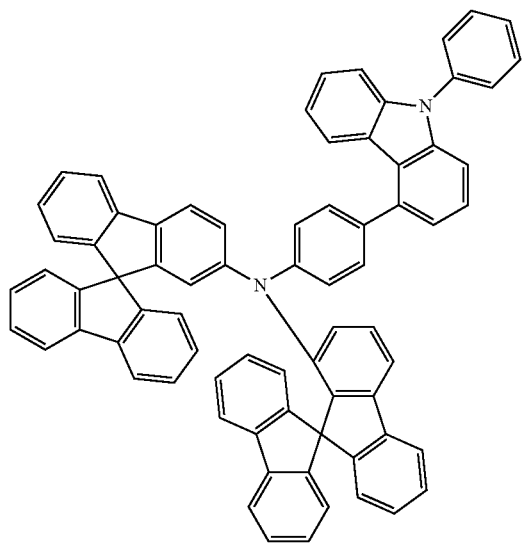
Formula 283
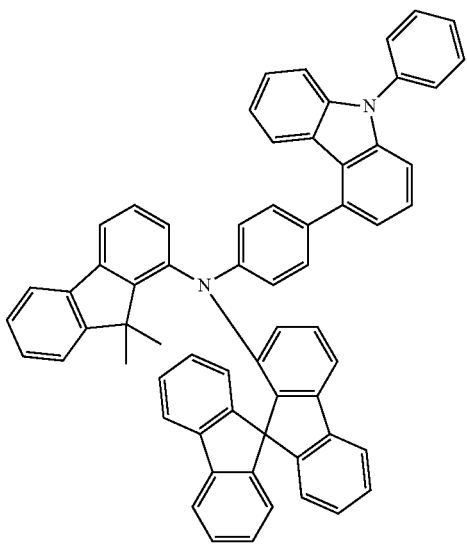

Formula 284
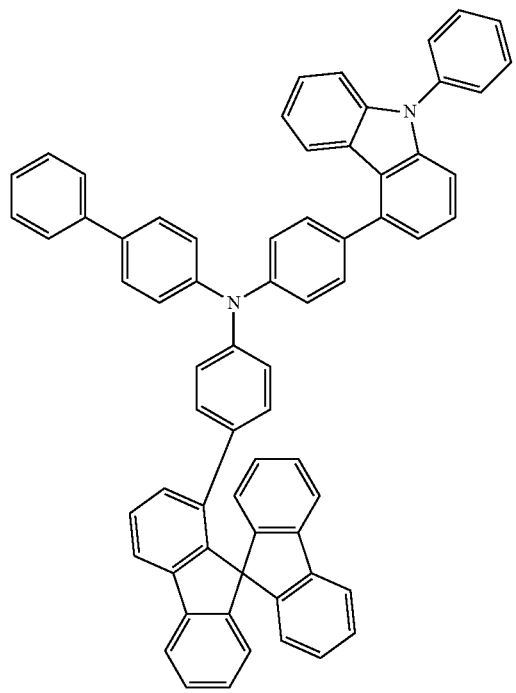
Formula 285
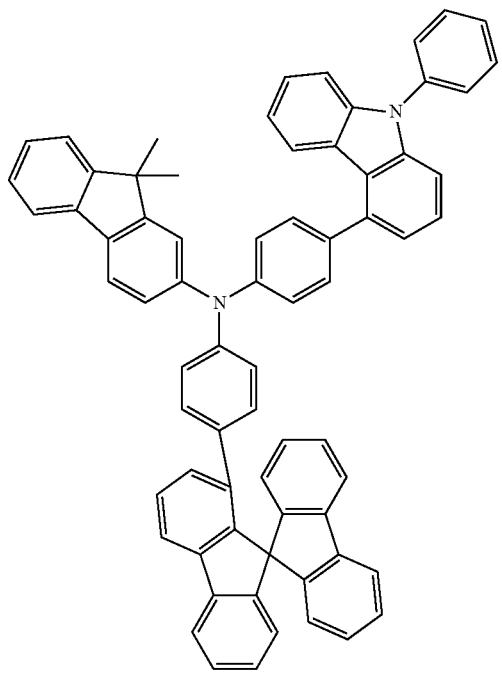
Formula 286
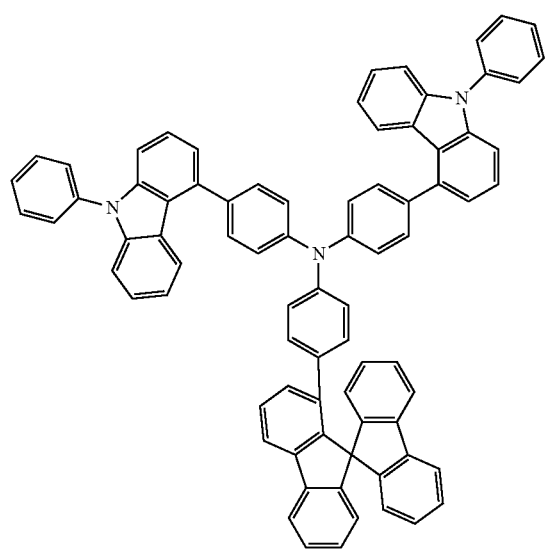
Formula 287
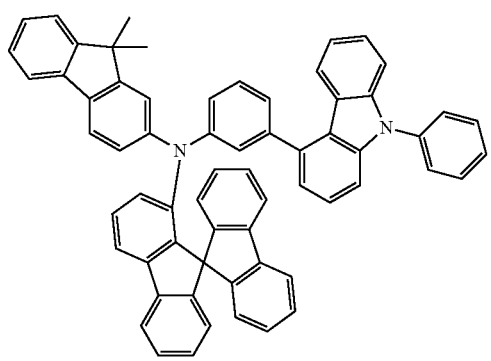

Formula 288
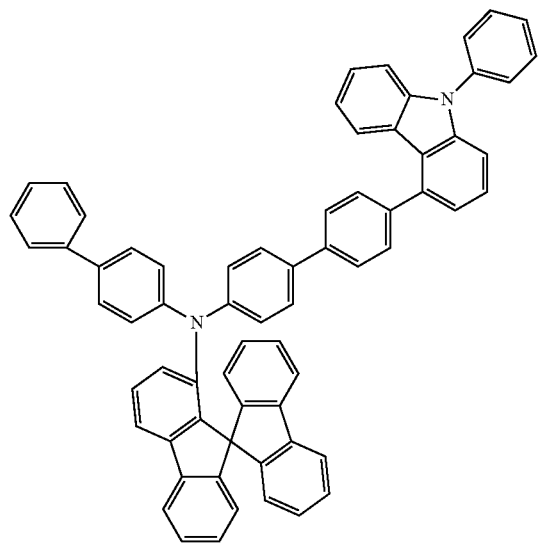
Formula 289
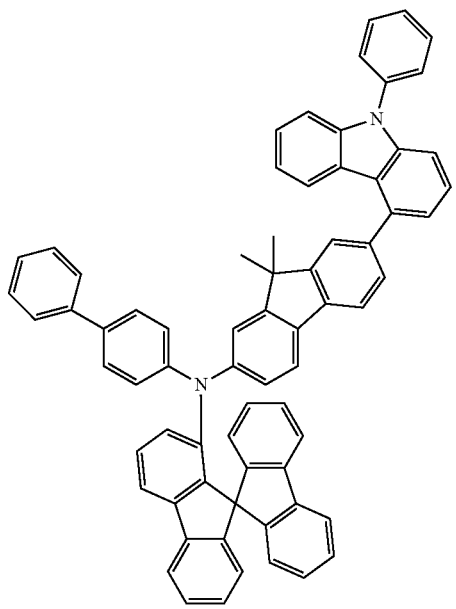
Formula 290
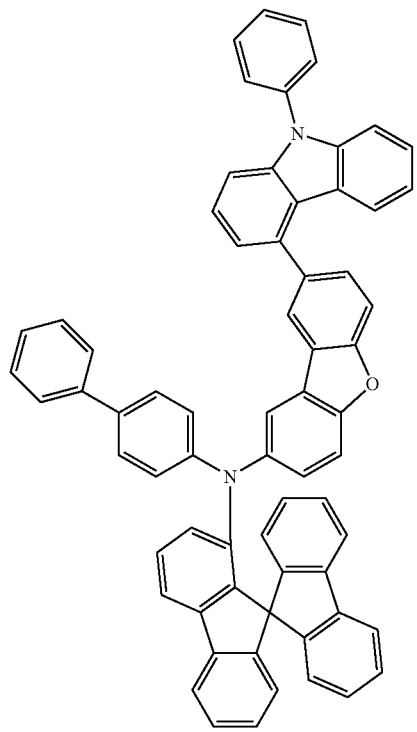
Formula 291
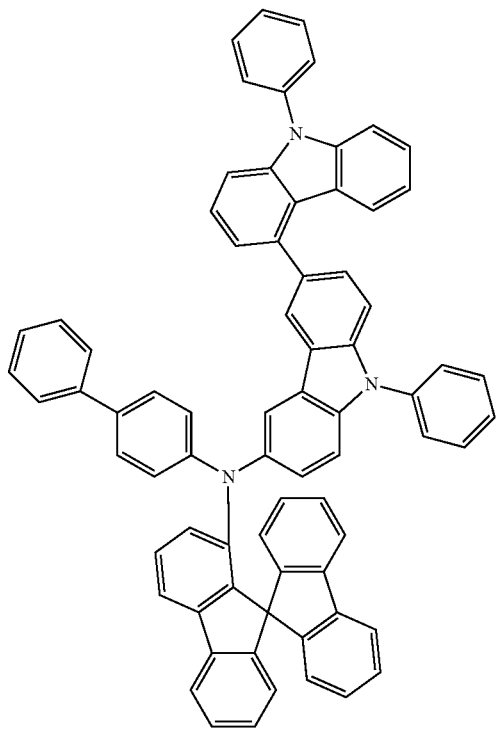

Formula 292
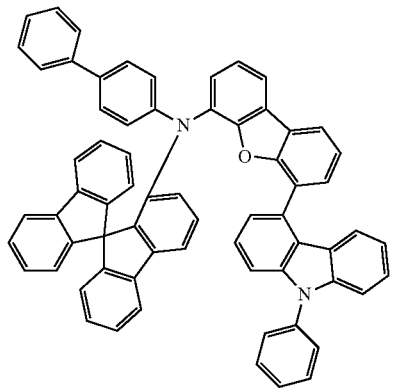
Formula 293
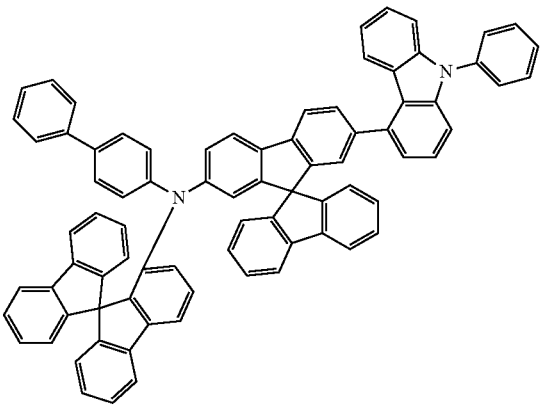
Formula 294
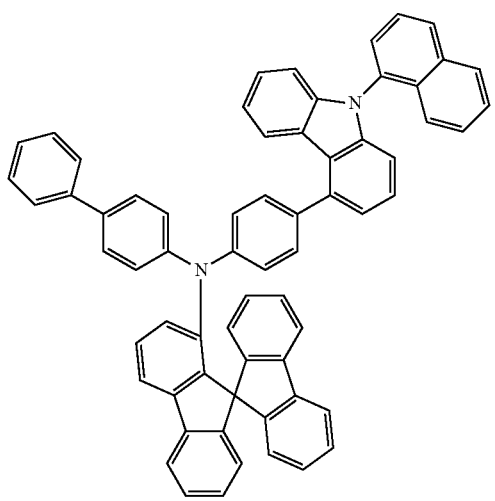
Formula 295
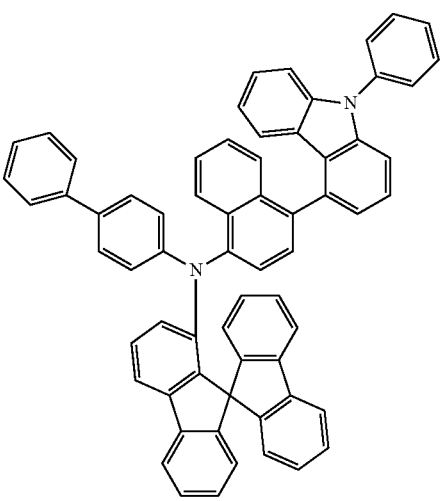
Formula 296
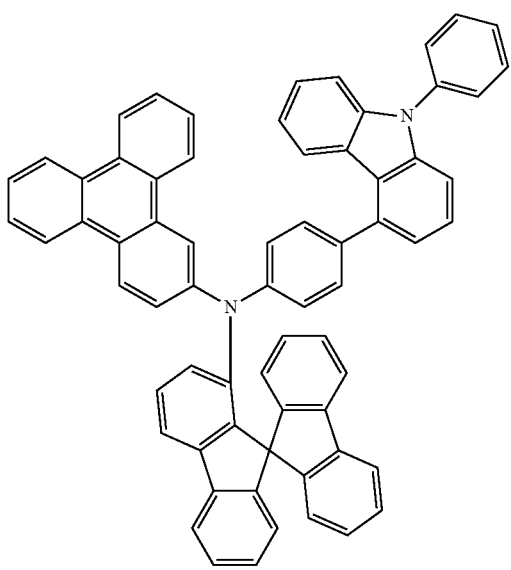
Formula 297
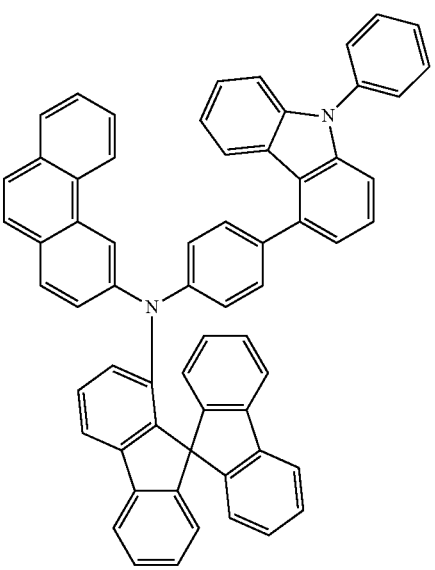

-continued
Formula 298
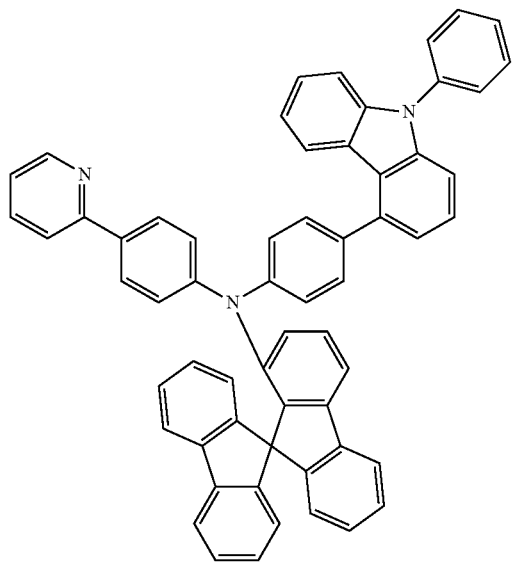
Formula 299
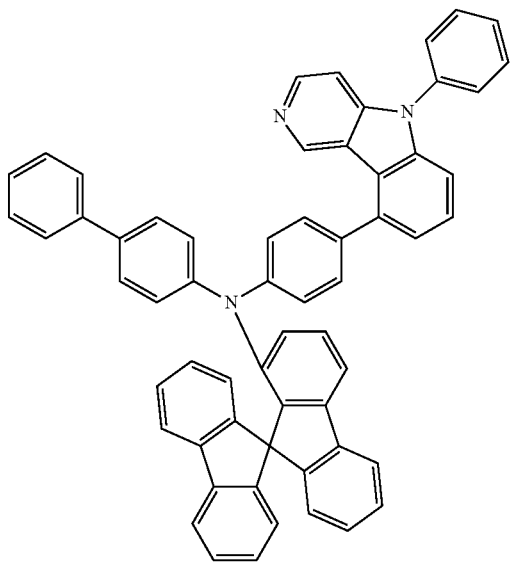
Formula 300
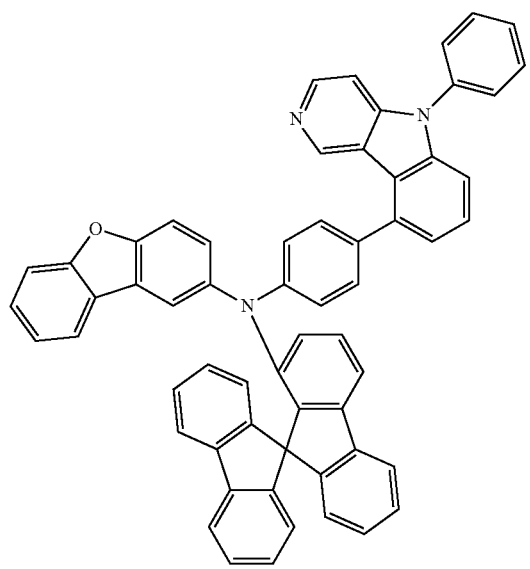
Formula 301
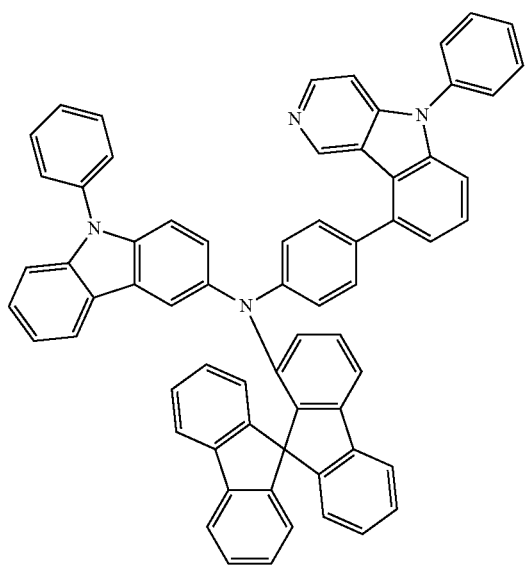

-continued
Formula 302
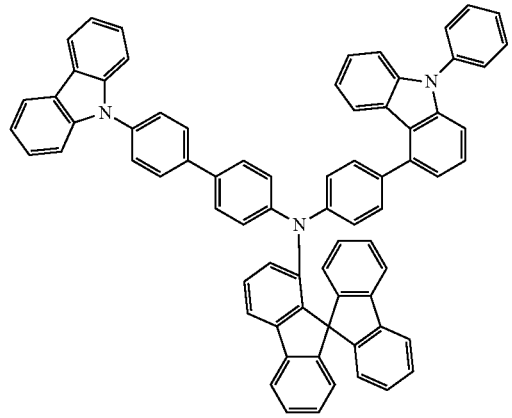
Formula 303
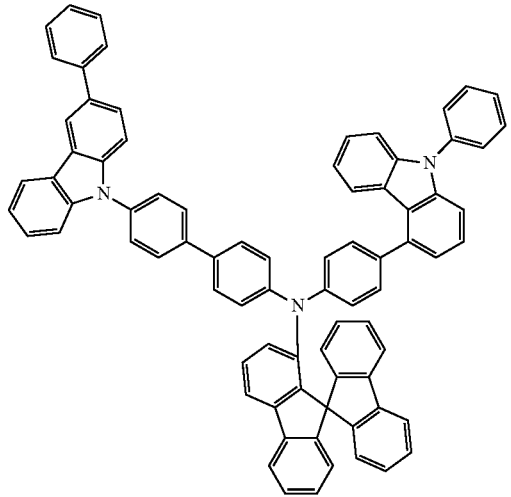
Formula 304
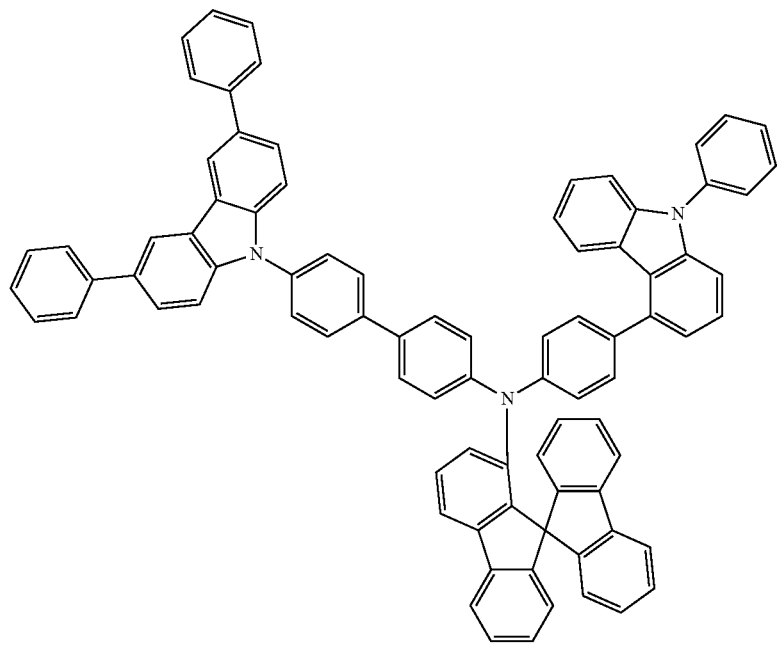
Formula 305
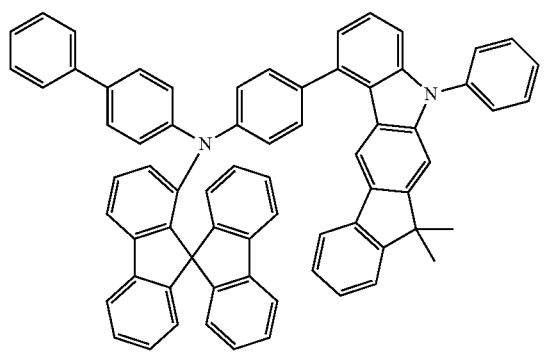
Formula 306
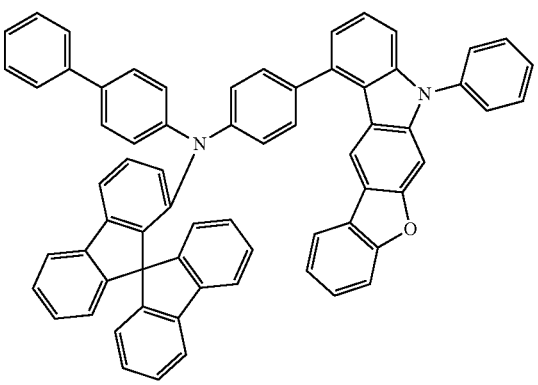

Formula 307
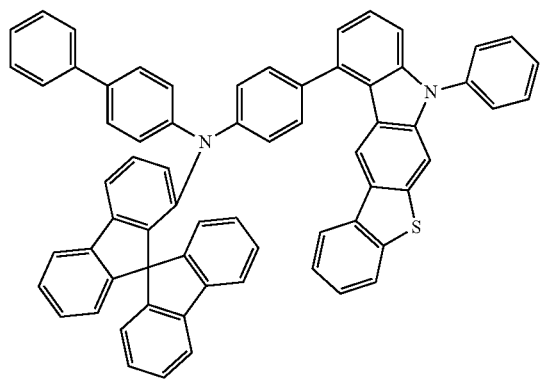
Formula 308
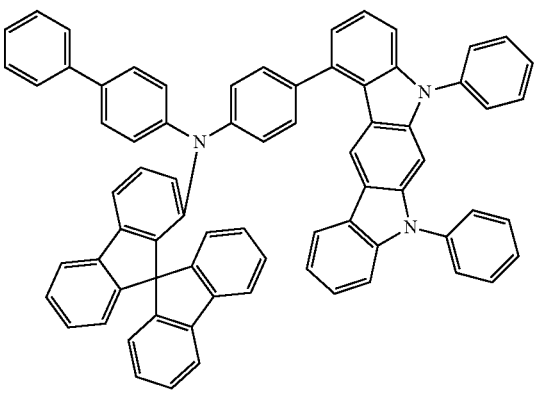
Formula 309
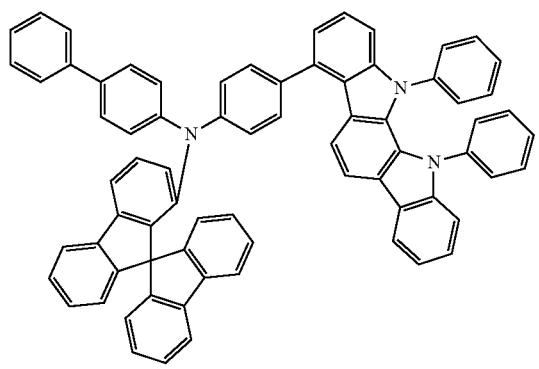
Formula 310
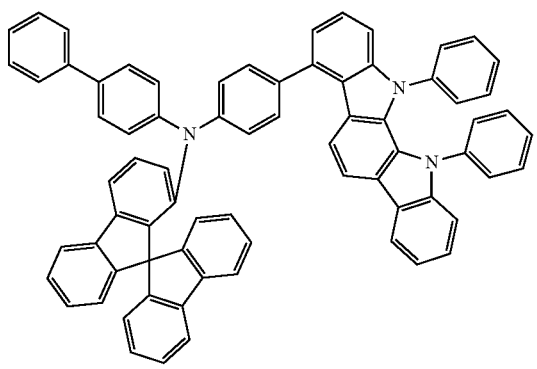
Formula 311
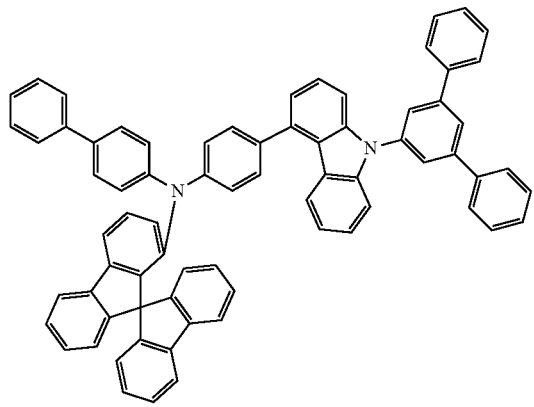
Formula 312
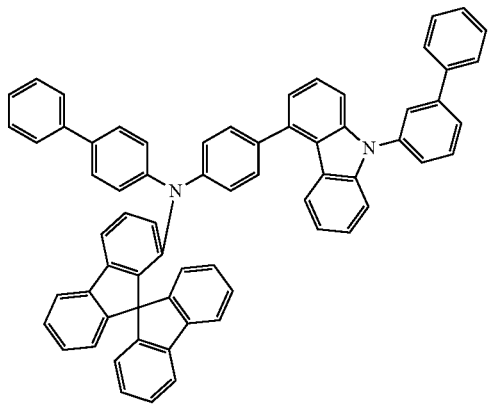
Formula 313
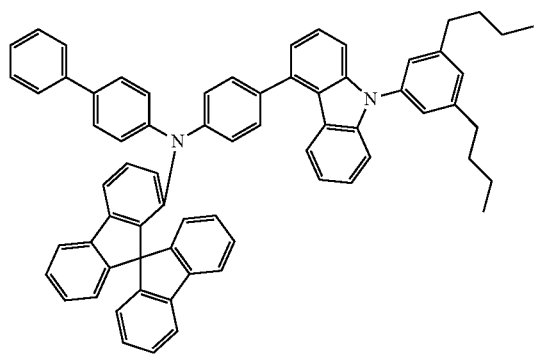
Formula 314
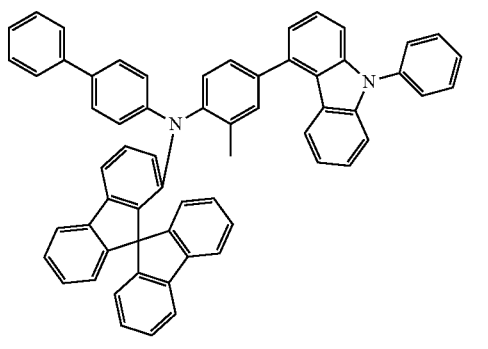

-continued
Formula 315
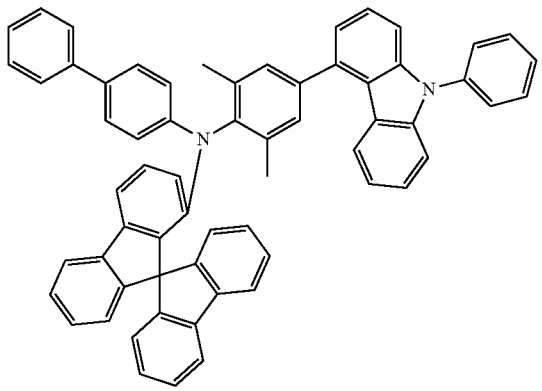
Formula 316
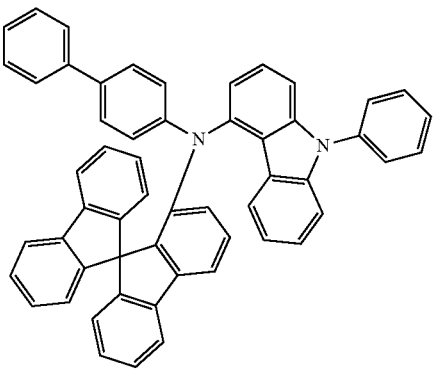
Formula 317
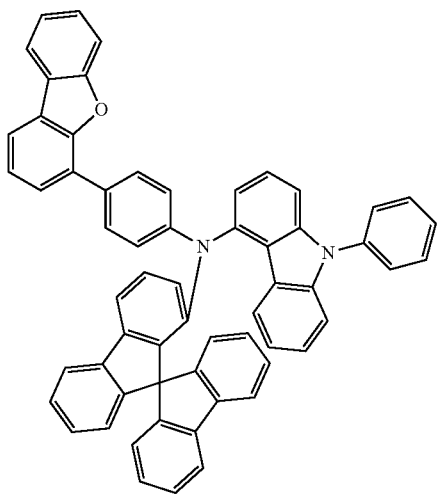
Formula 318
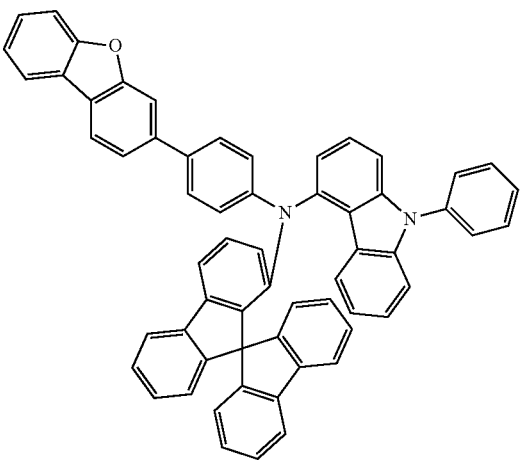
Formula 319
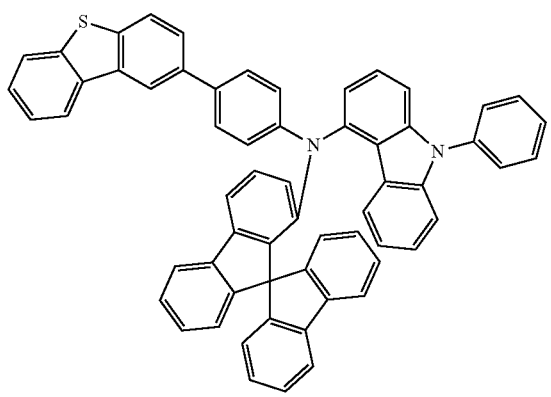
Formula 320
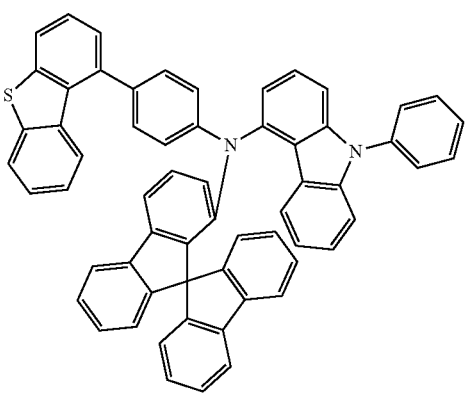

-continued
Formula 321
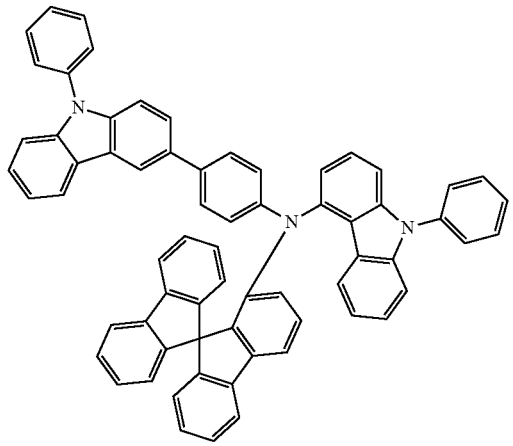
Formula 322
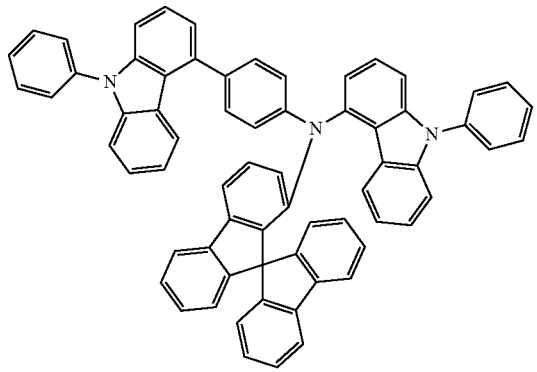
Formula 323
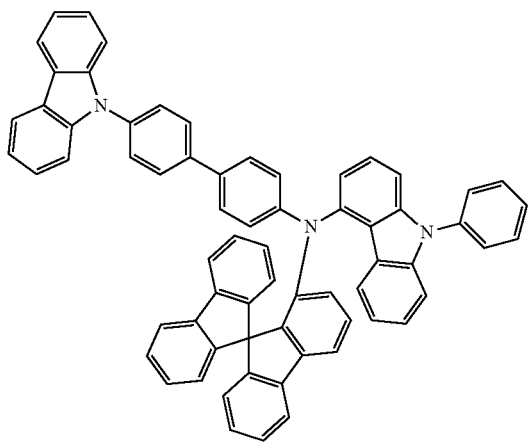
Formula 324
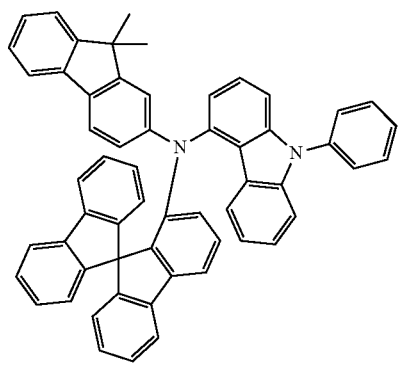
Formula 325
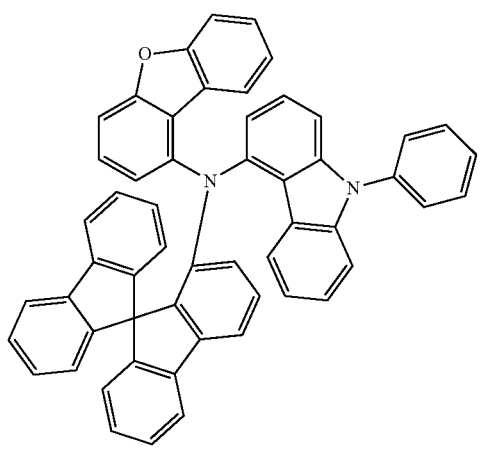
Formula 326
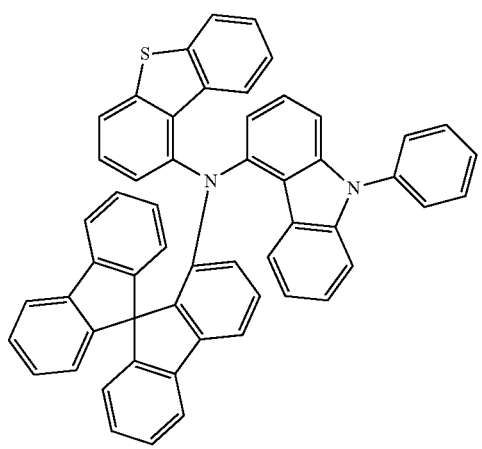

-continued
Formula 327
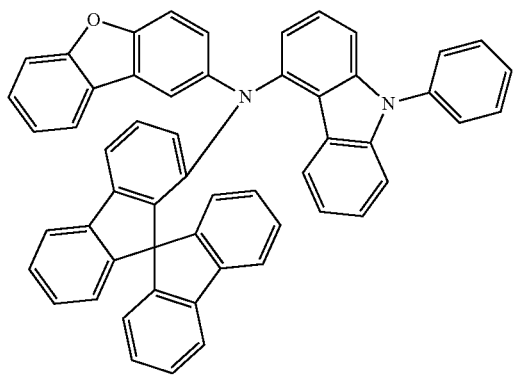
Formula 328
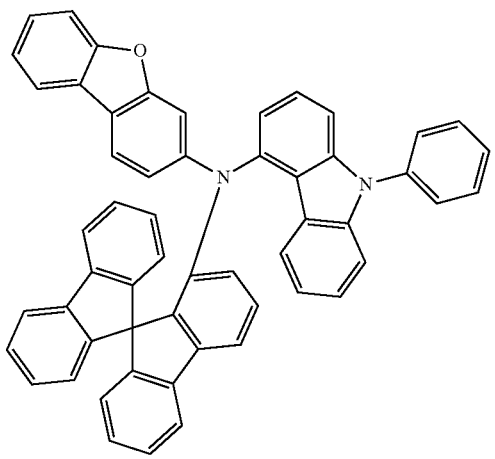
Formula 329
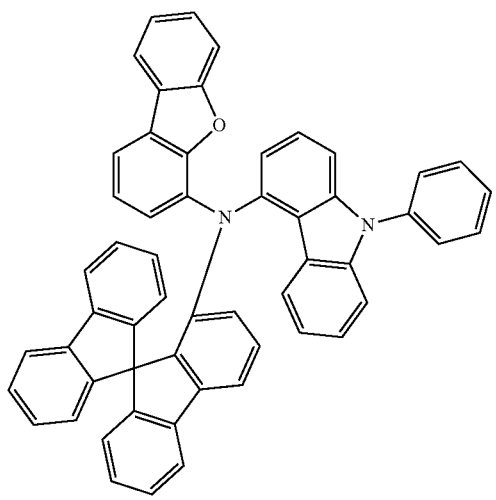
Formula 330
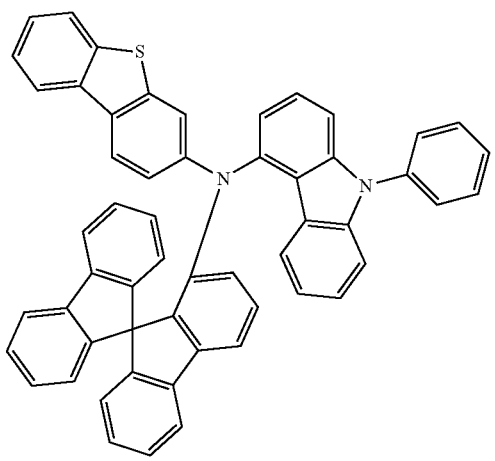
Formula 331
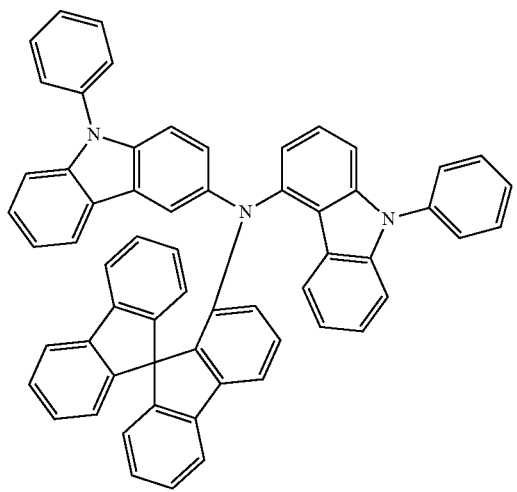
Formula 332
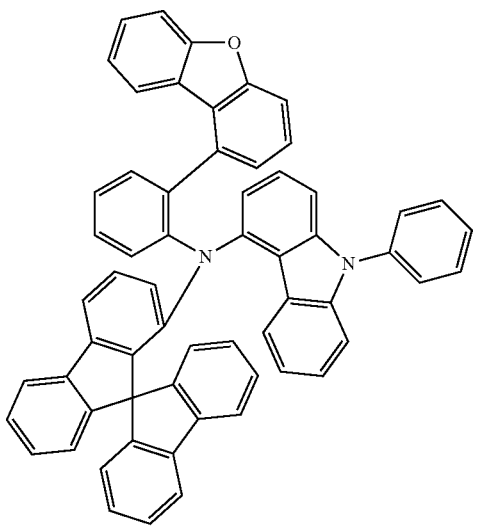

-continued
Formula 333
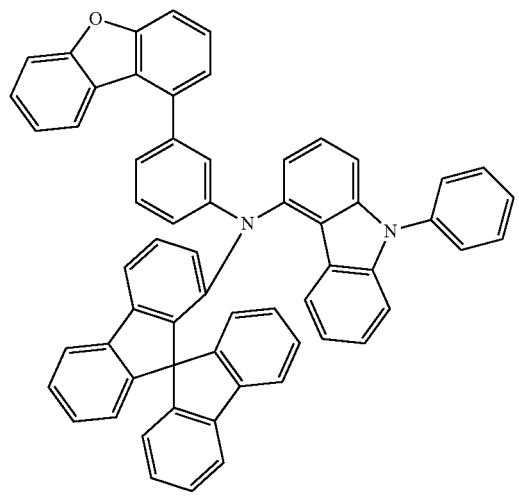
Formula 334
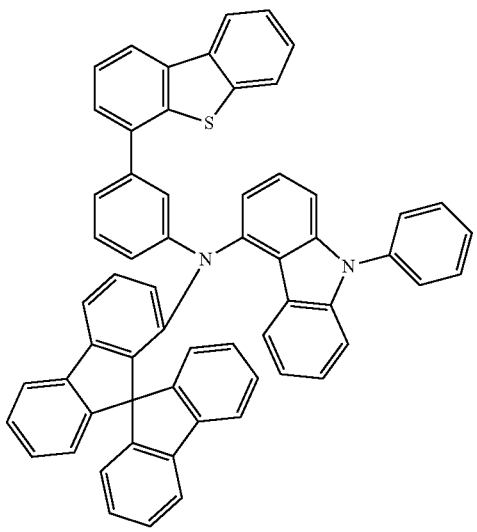
Formula 335
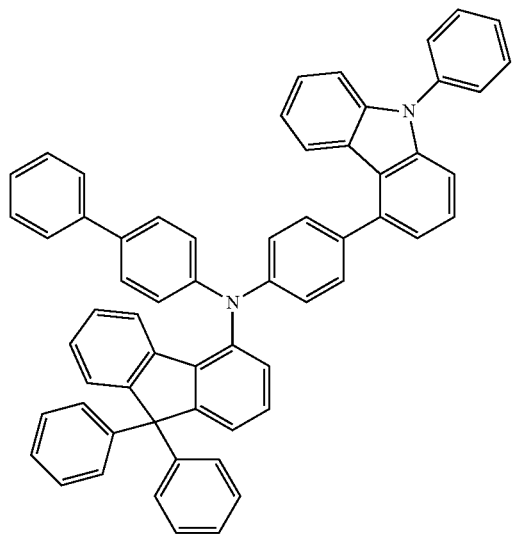
Formula 336
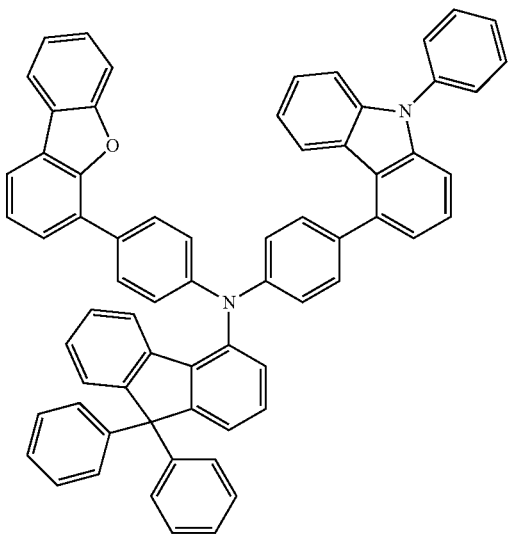
Formula 337
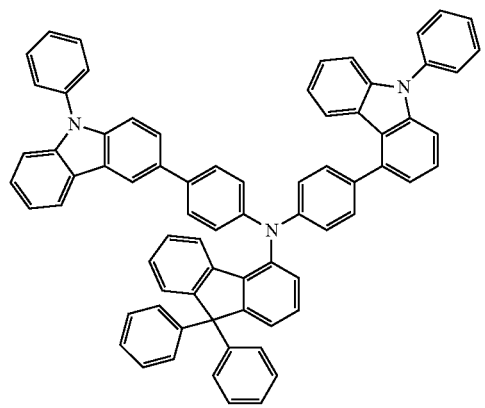
Formula 338
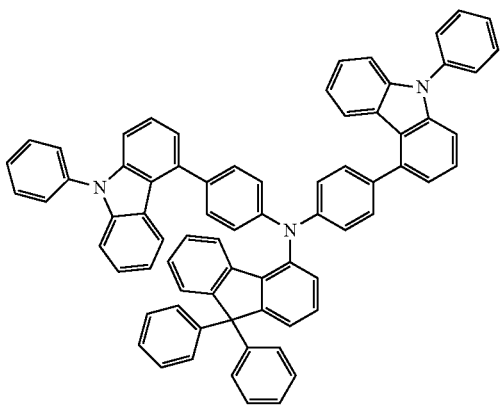

-continued
Formula 339
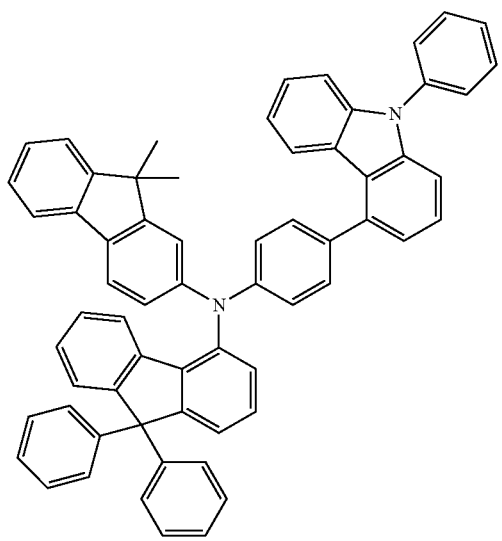
Formula 340
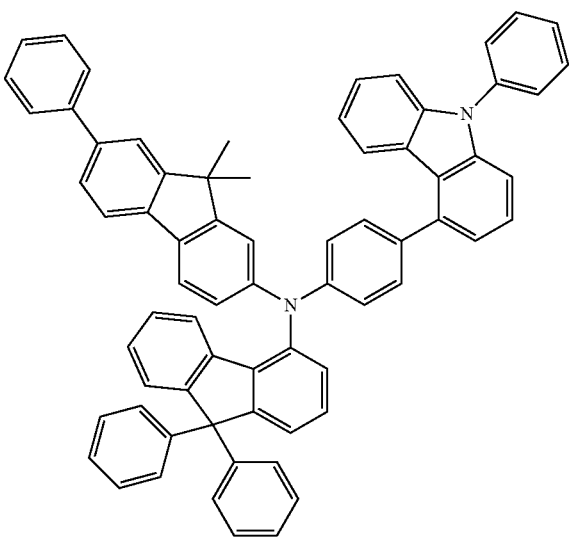
Formula 341
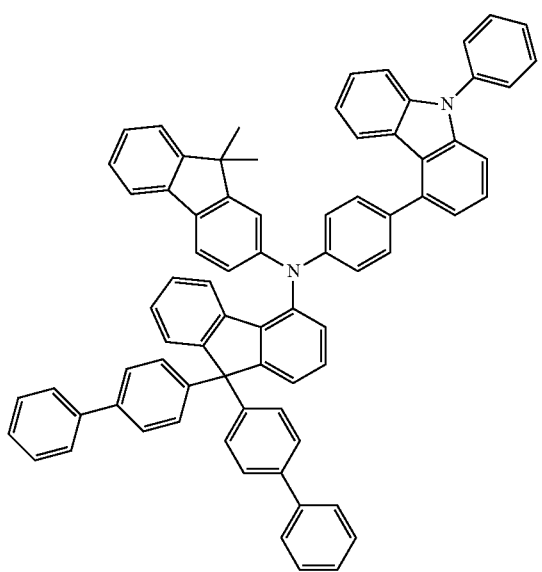
Formula 342
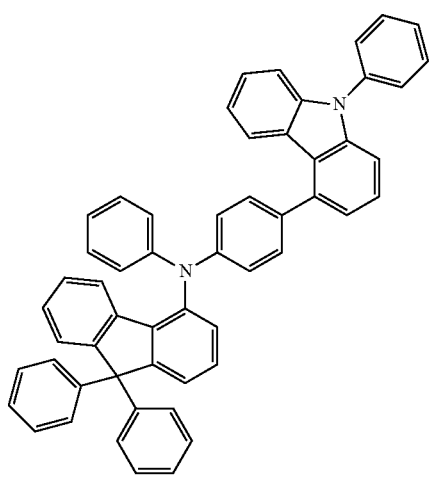

-continued
Formula 343
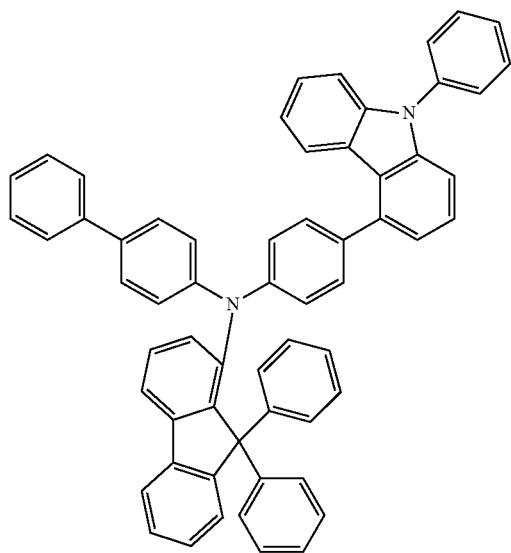
Formula 344
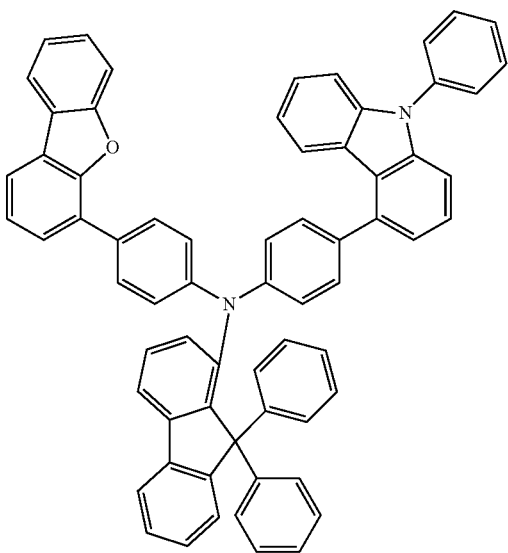
Formula 345
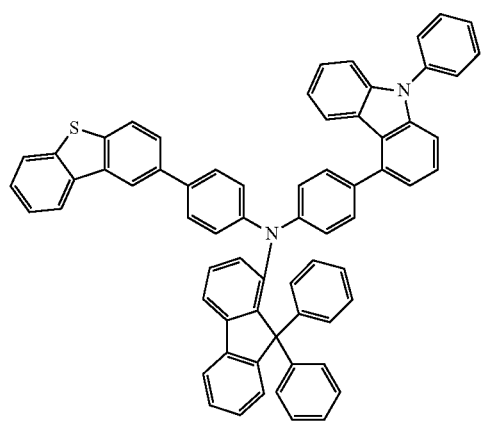
Formula 346
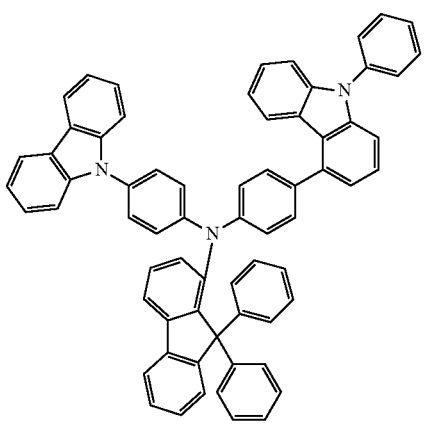
Formula 347
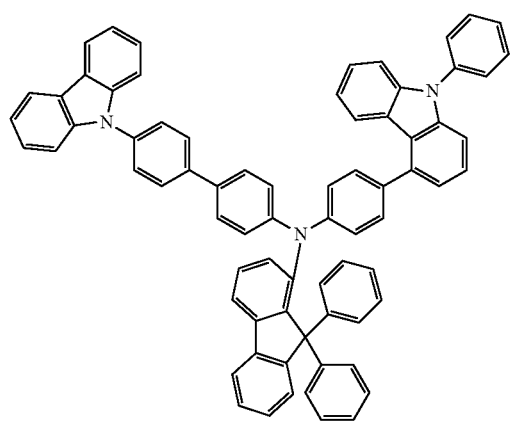
Formula 348
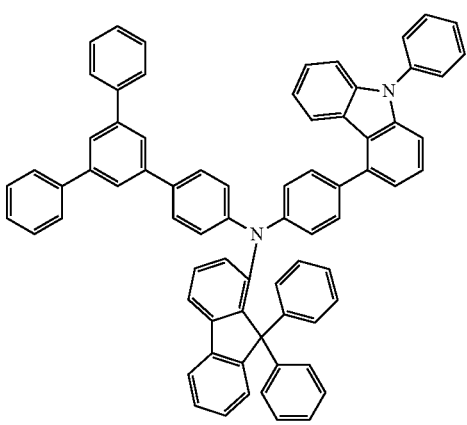

-continued
Formula 349
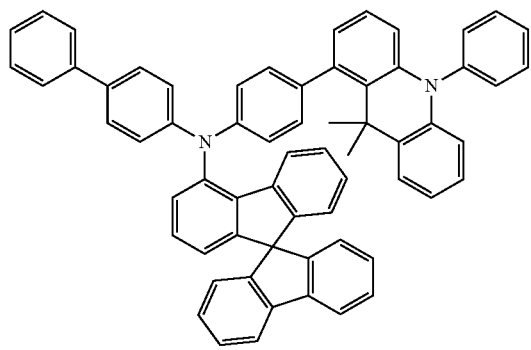
Formula 350
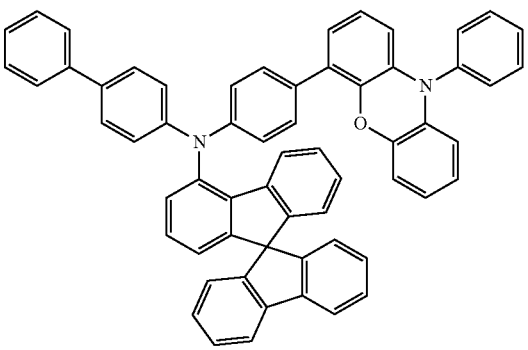
Formula 351
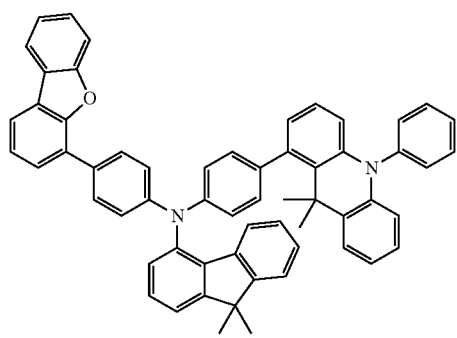
Formula 352
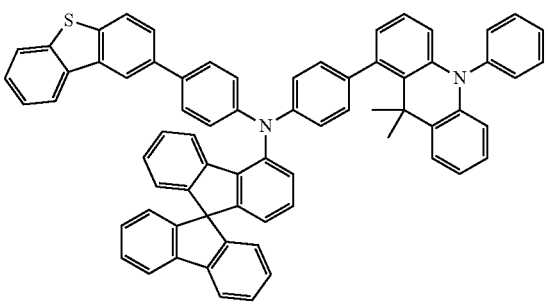
Formula 353
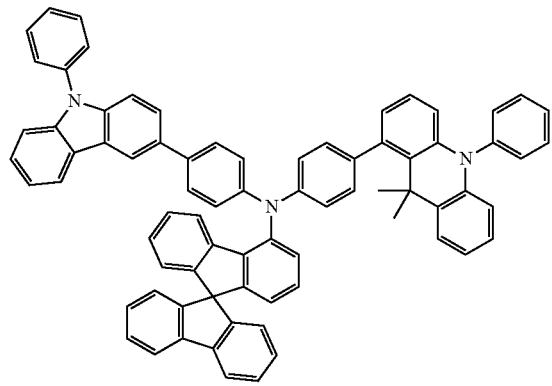
Formula 354
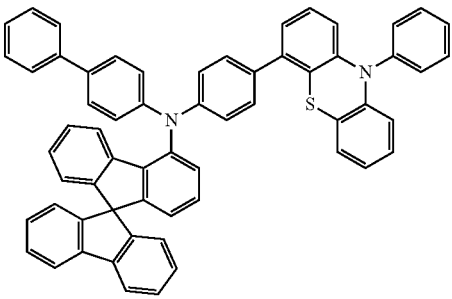
Formula 355
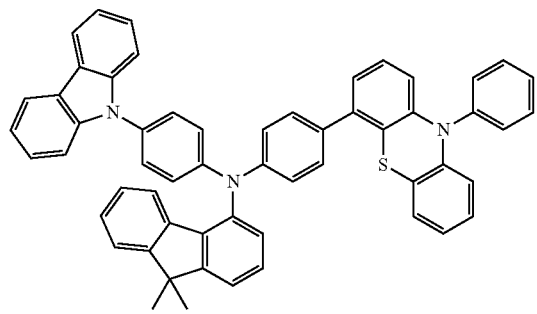
Formula 356
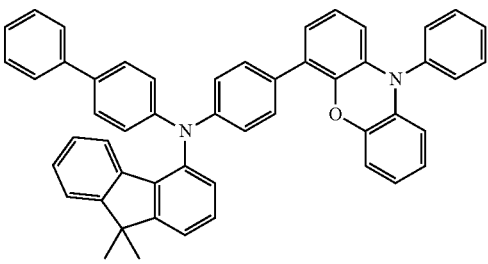

-continued
Formula 357
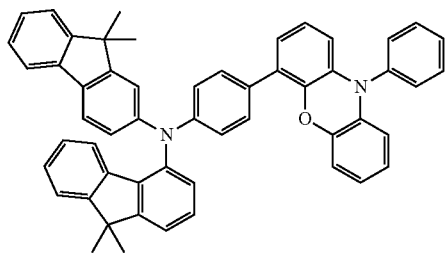
Formula 358
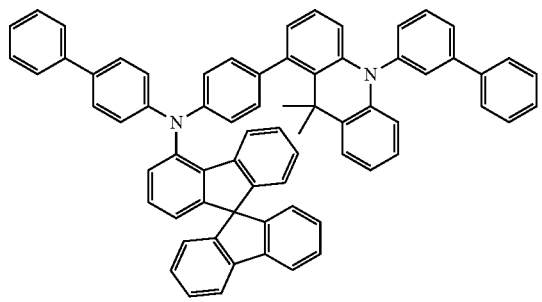
Formula 359
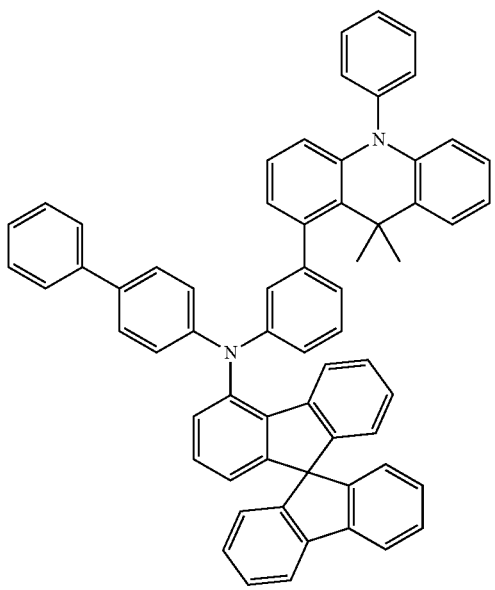
Formula 360
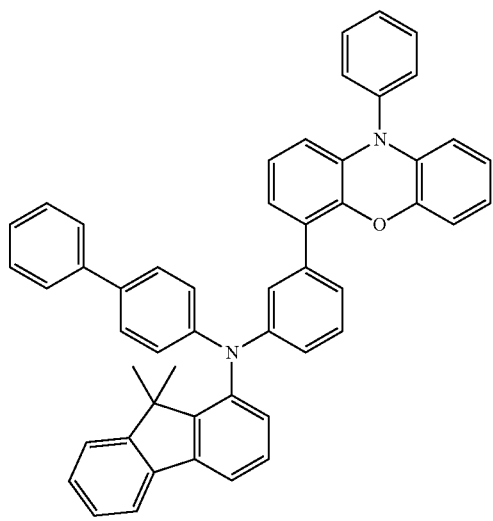
Formula 361
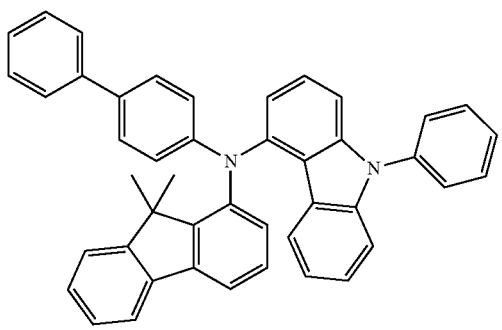
Formula 362
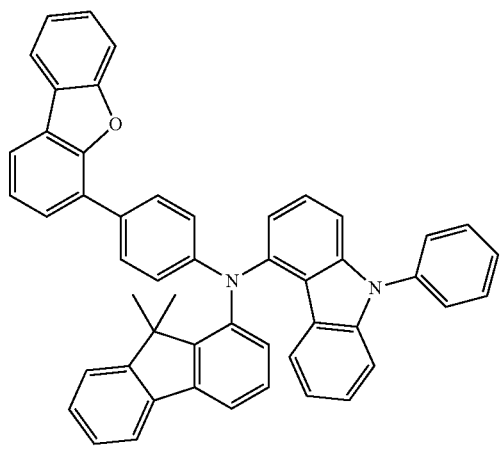

-continued
Formula 363
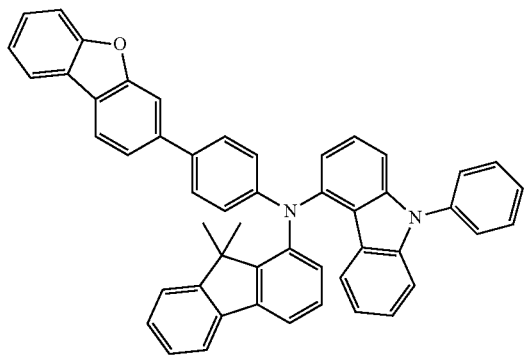
Formula 364
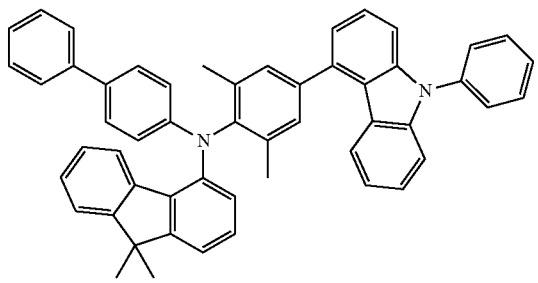
Formula 365
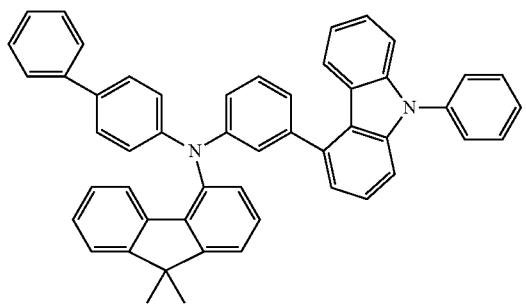
Formula 366
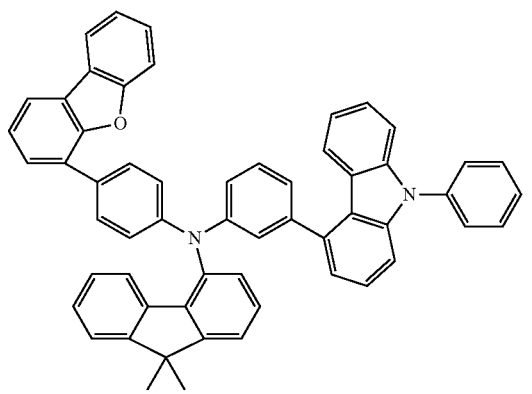
Formula 367
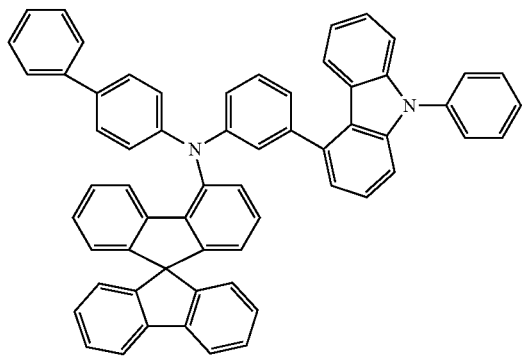
Formula 368
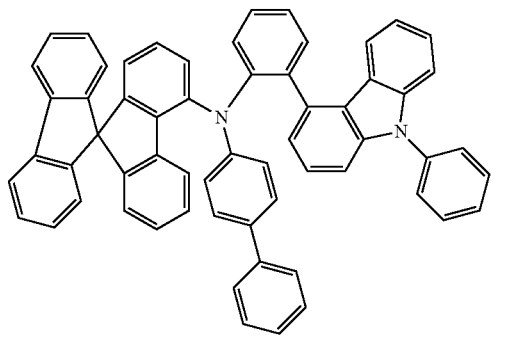
Formula 369
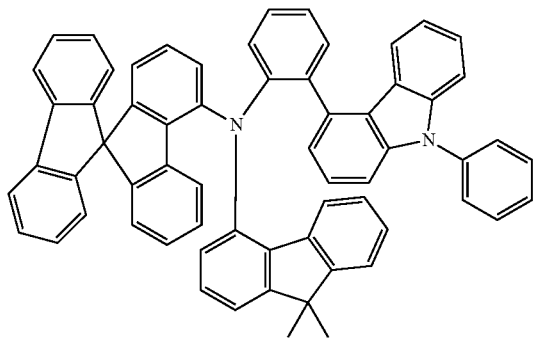
Formula 370
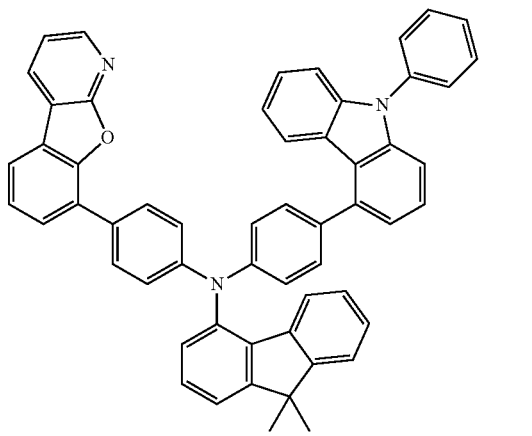

Formula 371

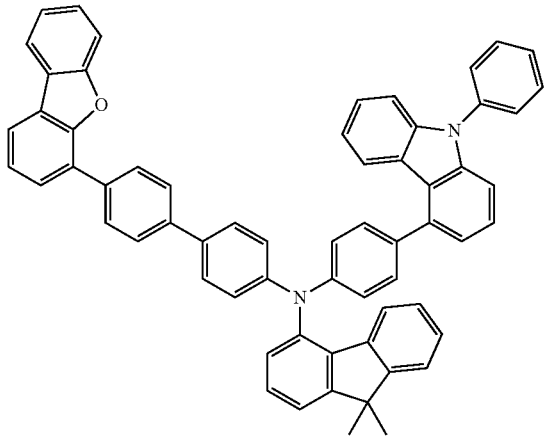

Formula 372

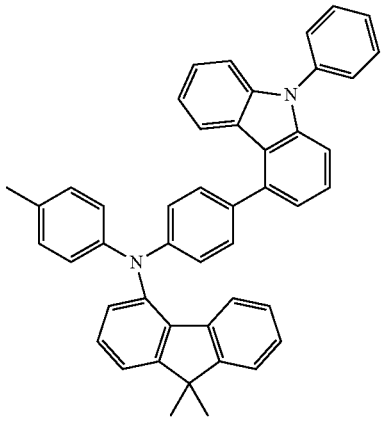

Preferred embodiments of compounds of the invention are detailed specifically in the examples, these compounds being usable alone or in combination with further compounds for all purposes of the invention.

Provided that the conditions specified in Claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds comprising structures of formula (I) in which, in a coupling reaction, a group comprising at least one nitrogen-comprising heterocyclic radical, preferably a carbazole radical, is joined to a group comprising at least one fluorene radical. In this case, a nitrogen-comprising heterocyclic compound, preferably a carbazole compound, comprising an amino group, preferably a secondary amino group, can be joined to a group comprising at least one fluorene radical. In addition, a compound having an amino group, preferably a secondary amino group, comprising at least one fluorene group, can be joined to a nitrogen-comprising heterocyclic radical, preferably a carbazole radical.

The necessary conditions for this are known to those skilled in the art, and the specific details given in the examples will support the person skilled in the art in conducting these reactions.

Particularly suitable and preferred coupling reactions which all lead to C—C bond formation and/or C—N bond formation are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

The above-described compounds of the invention, especially compounds substituted by reactive leaving groups, such as bromine, iodine, chlorine, boronic acid or boronic ester, may find use as monomers for production of corresponding oligomers, dendrimers or polymers. The oligomerization or polymerization is preferably effected via the halogen functionality or the boronic acid functionality.

In all the synthesis schemes which follow, the compounds are shown with a small number of substituents to simplify the structures. This does not rule out the presence of any desired further substituents in the processes.

An illustrative implementation is given by the schemes which follow, without any intention that these should impose a restriction. The component steps of the individual schemes may be combined with one another as desired.

A preferred synthesis route for preparation of the compounds of the invention is shown below. The synthesis route comprises two coupling reactions: first, the fluorene or spirobifluorene derivative is reacted in a first Buchwald coupling with an amine of the formula $Ar^3$—$NH_2$ (cf. formulae (I), (Ia), (Ib) or (Ic) of the compounds of the invention). Finally, a second Buchwald coupling is effected, in order to introduce the molecular moiety containing the heterocyclic nitrogen-comprising group, preferably the carbazole group.

The synthesis route is illustrated by way of example hereinafter using a compound of the formula (I) (Scheme 1). However, it should be emphasized that inventive compounds of the formula (Ia), (Ib) or (Ic) can likewise also be prepared by this synthesis route. Analogously to the fluorenyl starting compounds shown, it is also possible to use spirobifluorenyl compounds, so as to obtain compounds of the invention containing fluorene units.

Scheme 1:

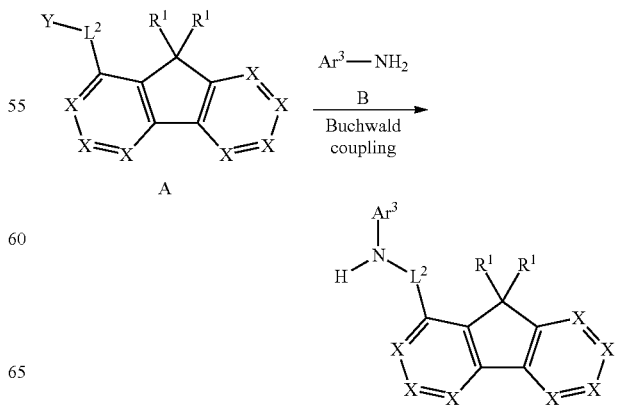

-continued

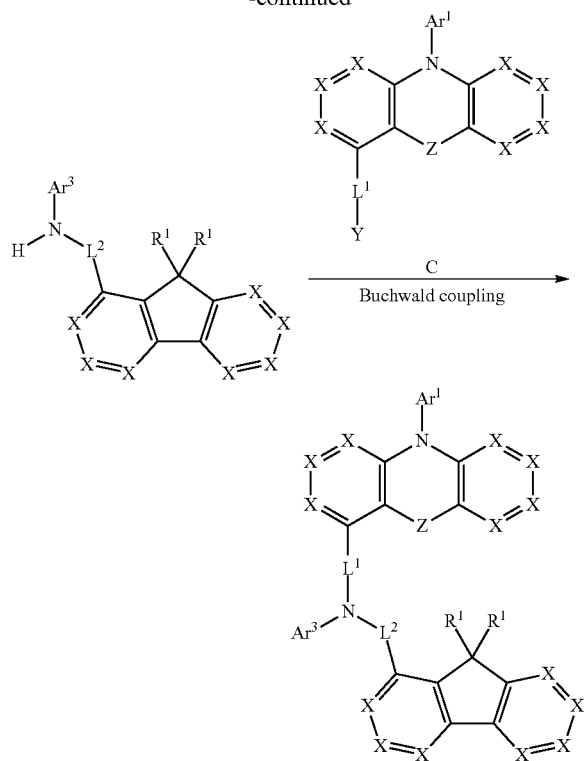

Y = leaving group, for example halogen

Synthesis routes for the starting compounds A, B and C which are used in the synthesis of the compounds of the invention (cf. Scheme 1) are known to those skilled in the art. In addition, in the working examples, some explicit synthesis methods are illustrated in detail.

The present invention thus provides a process for preparing a compound of formula (I), (Ia), (Ib) or (Ic), characterized in that a fluorenyl or spirobifluorenyl derivative is reacted in a first coupling reaction with an arylamino compound, and the product obtained is reacted in a second coupling reaction with an aromatic heterocyclic nitrogen compound, preferably a carbazole compound.

The coupling reactions are preferably Buchwald couplings.

The processes shown for synthesis of the compounds of the invention should be understood by way of example. The person skilled in the art will be able to develop alternative synthesis routes within the scope of his common knowledge in the art.

The principles of the preparation processes detailed above are known in principle from the literature for similar compounds and can be adapted easily by the person skilled in the art to the preparation of the compounds of the invention. Further information can be found in the examples.

It is possible by these processes, if necessary followed by purification, for example recrystallization or sublimation, to obtain the compounds of the invention comprising structures of formula (I) in high purity, preferably more than 99% (determined by means of $^1$H NMR and/or HPLC).

The compounds of the invention may also have suitable substituents, for example by relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, for example toluene or xylene, at room temperature in sufficient concentrations soluble, in order to be able to process the complexes from solution. These soluble compounds are of particularly good suitability for processing from solution, for example by printing methods. In addition, it should be emphasized that the compounds of the invention comprising at least one structure of the formula (I) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds of the invention and polymers may be used in the form of a crosslinked or uncrosslinked layer.

The invention therefore further provides oligomers, polymers or dendrimers containing one or more of the above-detailed structures of the formula (I) or compounds of the invention, wherein one or more bonds of compounds of the invention or of the structures of the formula (I) to the polymer, oligomer or dendrimer are present. According to the linkage of the structures of the formula (I) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I) or the above-recited preferred embodiments are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

In addition, the present compounds may have a relatively low molecular weight. The present invention accordingly further provides a compound comprising one or more structures of the formula (I) and having a molecular weight of preferably not more than 10 000 g/mol, more preferably not more than 5000 g/mol, particularly preferably not more than 4000 g/mol, especially preferably not more than 3000 g/mol, specifically preferably not more than 2000 g/mol and most preferably not more than 1000 g/mol.

In addition, it is a feature of preferred compounds of the invention that they are sublimable. These compounds generally have a molar mass of less than about 1200 g/mol.

Additionally of particular interest are compounds of the invention which feature a high glass transition temperature. In this connection, preference is given especially to compounds of the invention comprising structures of the general formula (I) having a glass transition temperature of at least 70° C., more preferably of at least 110° C., even more preferably of at least 120° C. and especially preferably of at least 150° C., determined in accordance with DIN 51005. In addition, it should be emphasized that the compounds of the invention comprising at least one structure of the formula (I) already have an elevated glass transition temperature.

The present invention still further provides a formulation comprising a compound of the invention or an oligomer, polymer or dendrimer of the invention and at least one further compound. The further compound may preferably be a solvent. The further compound may alternatively be a further organic or inorganic compound which is likewise used in the electronic device, for example a matrix material. This further compound may also be polymeric.

Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (–)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention still further provides a composition comprising a compound of the invention and at least one further organic functional material. Functional materials are generally the organic or inorganic materials introduced between the anode and cathode. Preferably, the organic functional material is selected from the group consisting of fluorescent emitters, phosphorescent emitters, host materials, matrix materials, electron transport materials, electron injection materials, hole conductor materials, hole injection materials, n-dopants, wide band gap materials, electron blocker materials and hole blocker materials.

The present invention therefore also relates to a composition comprising at least one compound comprising structures of formula (I) and at least one further matrix material. According to a particular aspect of the present invention, the further matrix material has electron-transporting properties.

The present invention further provides a composition comprising at least one compound comprising at least one structure of formula (I) and at least one wide band gap material, a wide band gap material being understood to mean a material in the sense of the disclosure of U.S. Pat. No. 7,294,849. These systems exhibit particularly advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state $S_1$ of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

HOMO(eV)=((HEh*27.212)−0.9899)/1.1206

LUMO(eV)=((LEh*27.212)−2.0041)/1.385

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09 W" (Gaussian Inc.) and Q-Chem 4.1 (Q-Chem, Inc.).

The present invention also relates to a composition comprising at least one compound comprising structures of formula (I) and at least one phosphorescent emitter, the term "phosphorescent emitter" also being understood to mean phosphorescent dopants.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent dopants are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent dopants, compounds containing copper, molybdenum, tungsten, rhenium, ruthenium, osmium, rhodium, iridium, palladium, platinum, silver, gold or europium, especially compounds containing iridium, platinum or copper.

In the context of the present application, all luminescent iridium, platinum or copper complexes are considered to be phosphorescent compounds. Examples of phosphorescent dopants are adduced in a section which follows.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in mixed matrix systems are the preferred phosphorescent dopants specified hereinafter.

Examples of phosphorescent dopants can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the inventive devices.

Explicit examples of phosphorescent dopants are adduced in the following table:

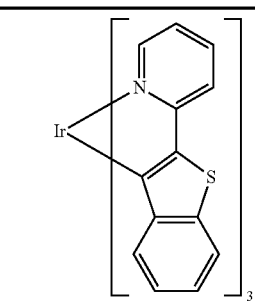

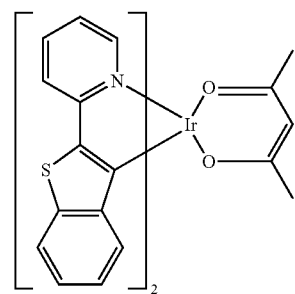

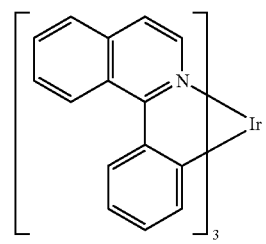

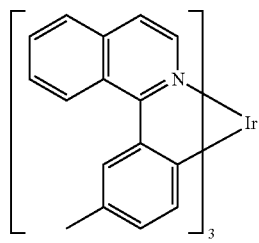

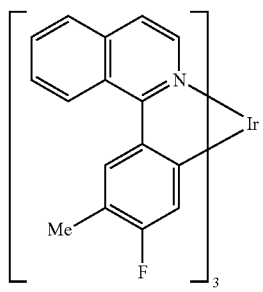

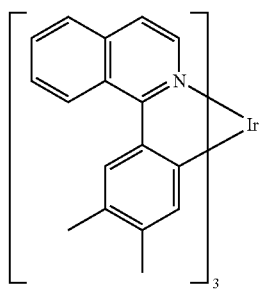

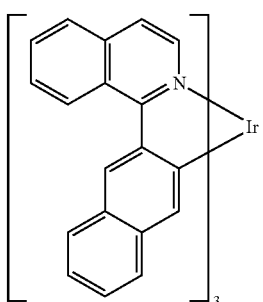

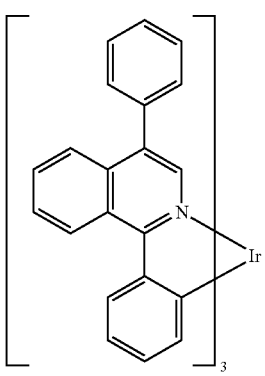

-continued
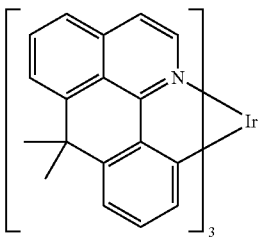
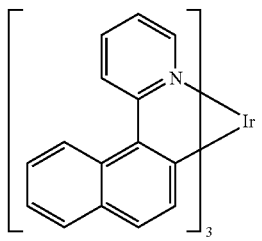
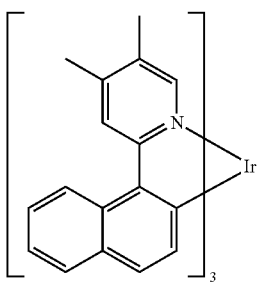
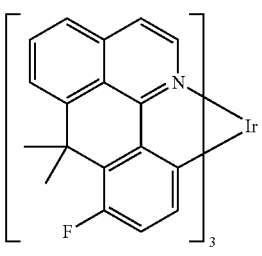
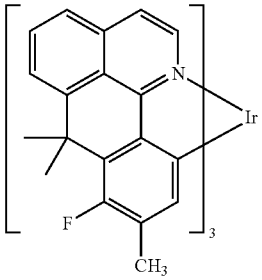
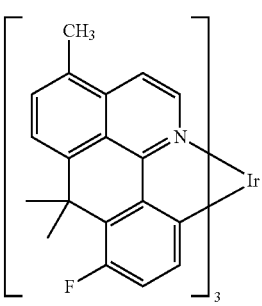
-continued
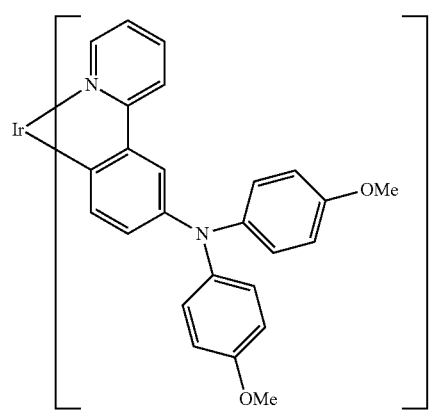
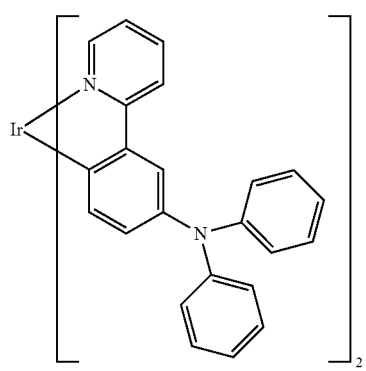
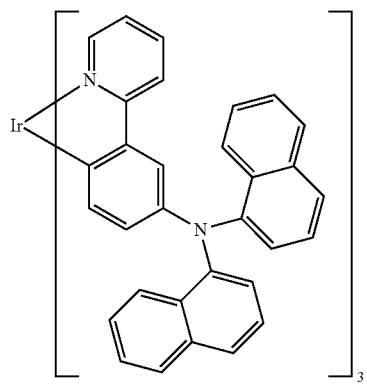
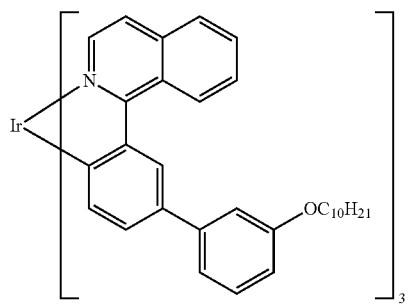

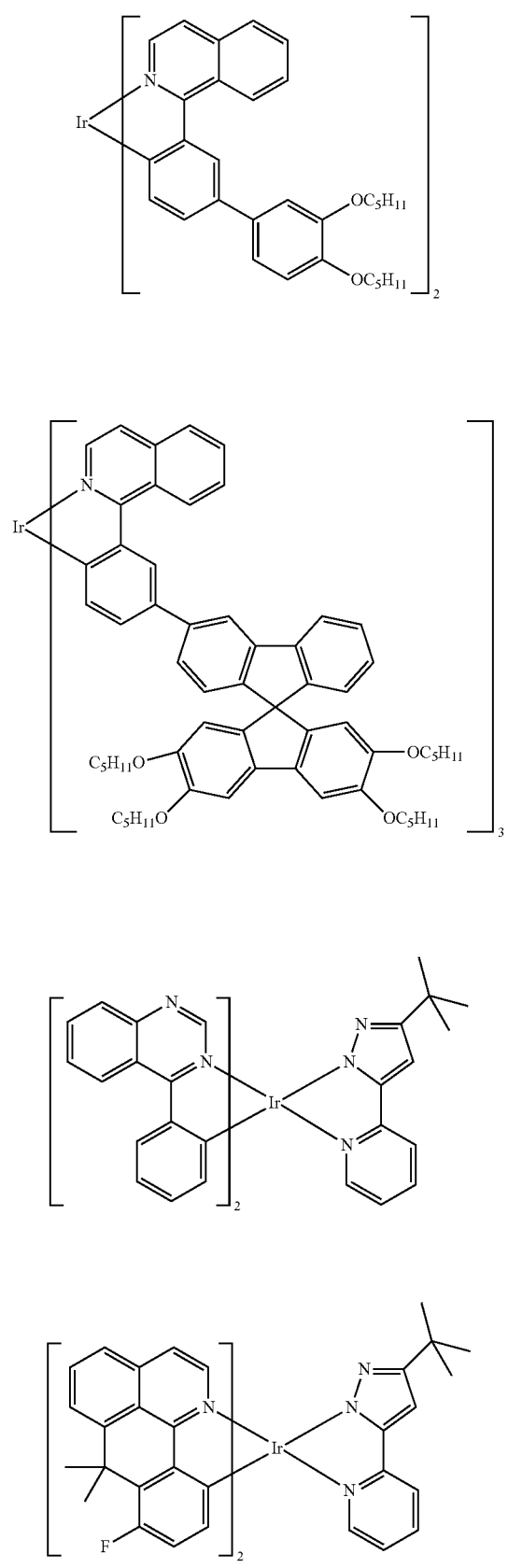
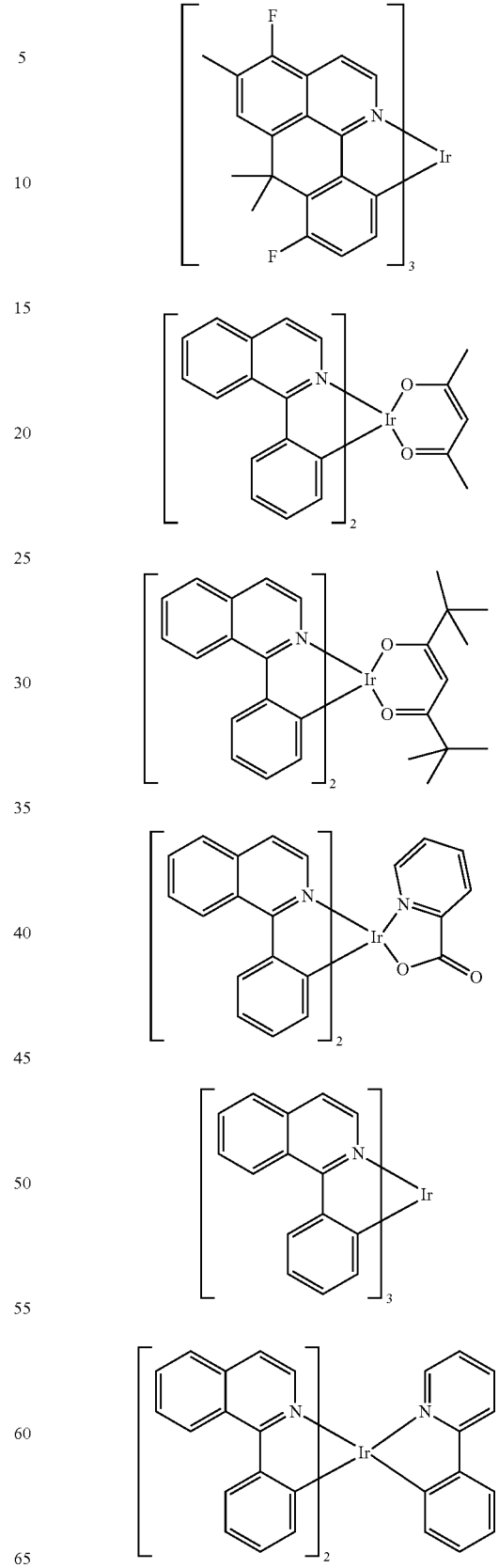

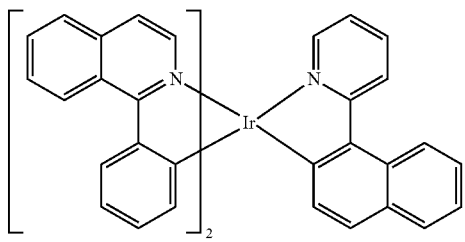
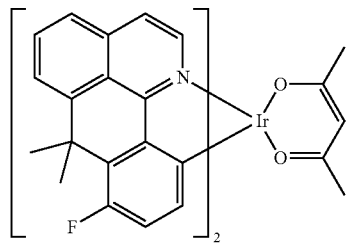
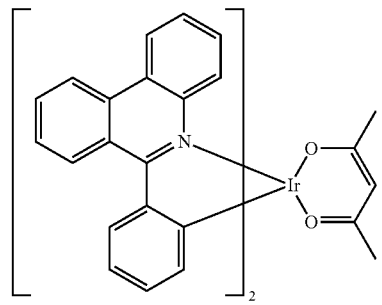
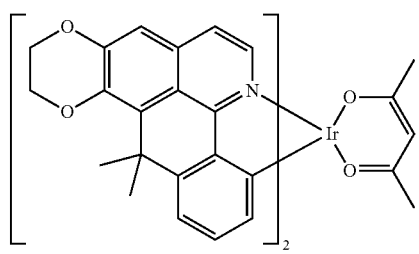
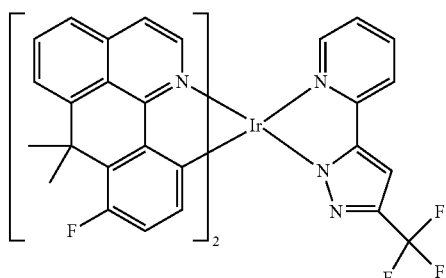
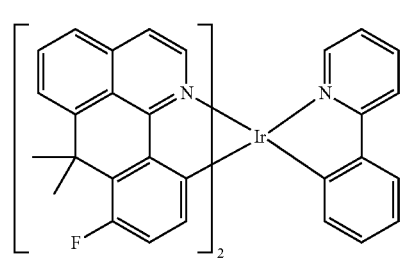
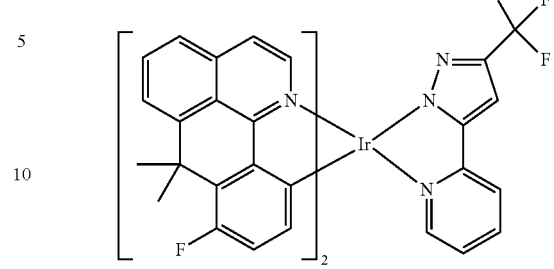
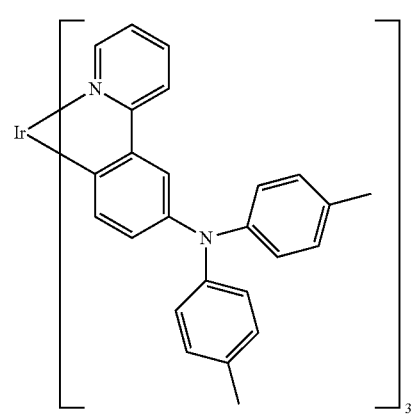
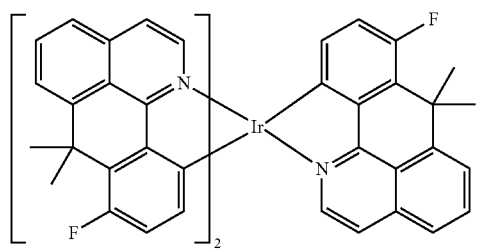
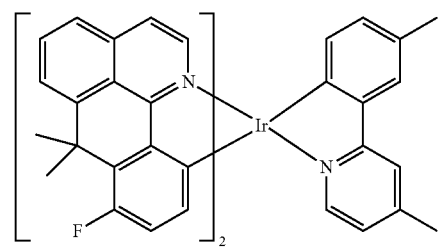
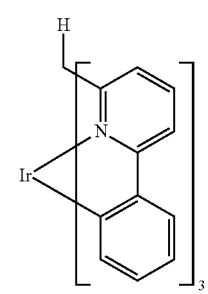

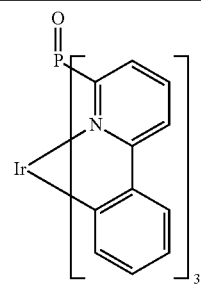
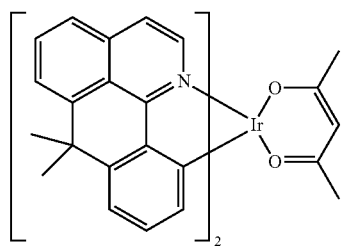
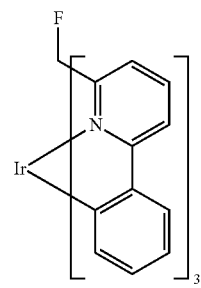
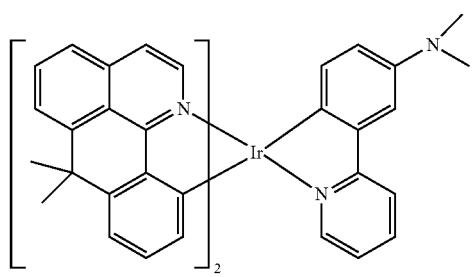
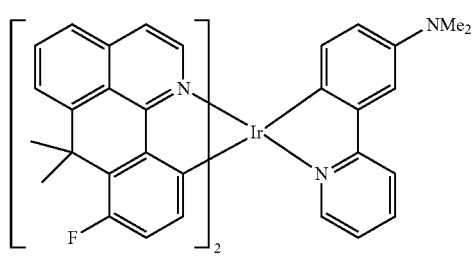
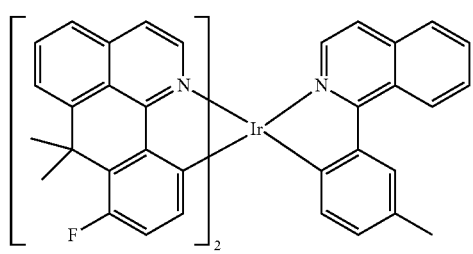
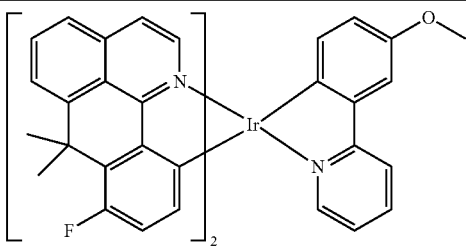
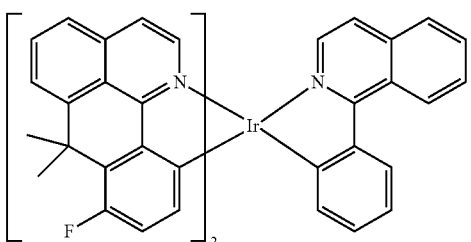
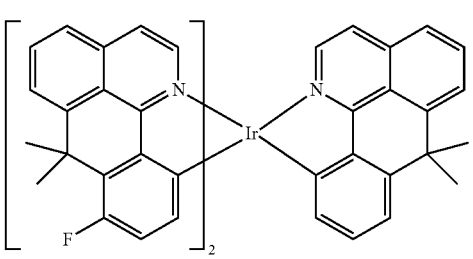
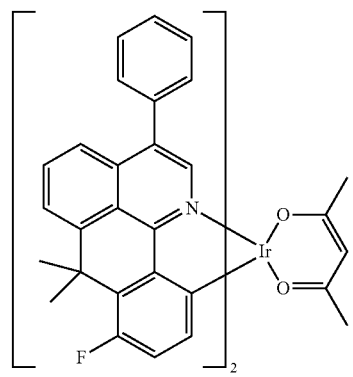
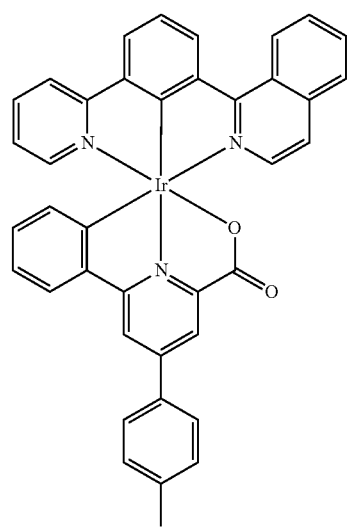

173
-continued
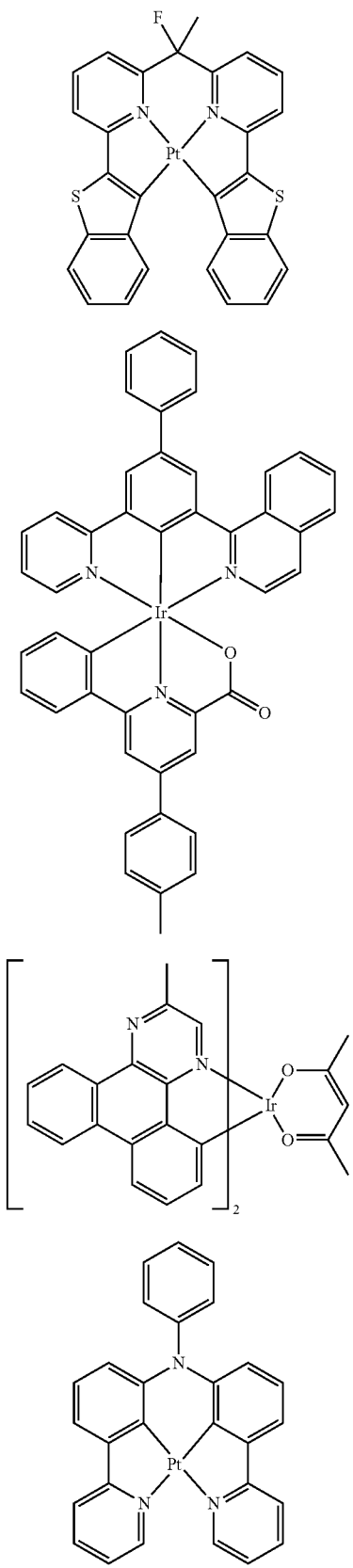
174
-continued
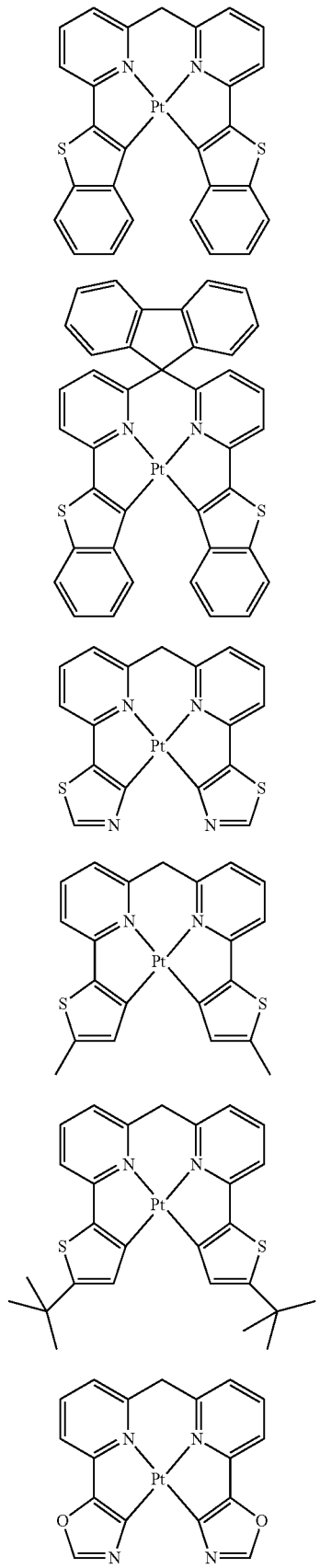

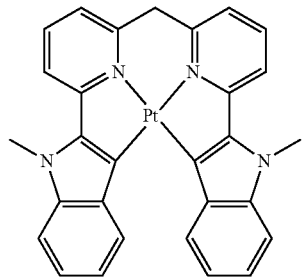
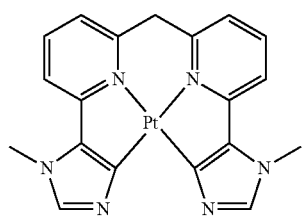
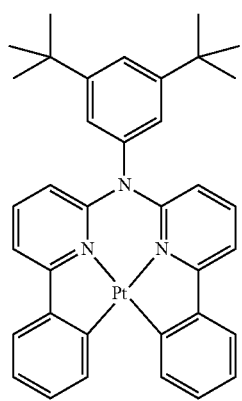
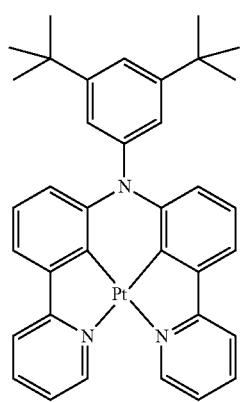
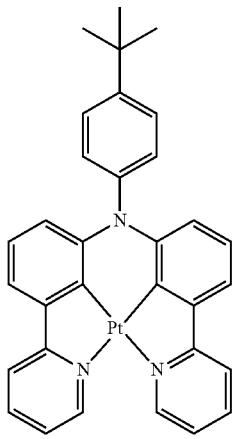
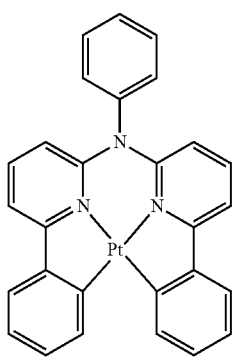
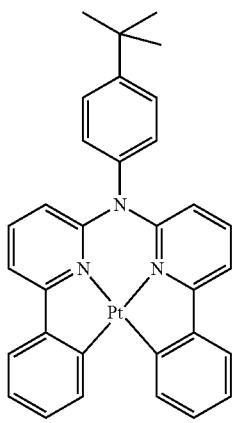
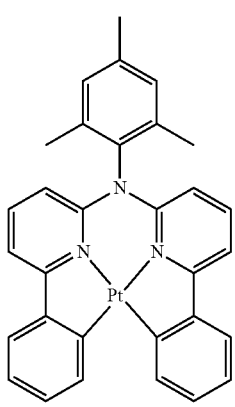

| 177 -continued | 178 -continued |
|---|---|
| 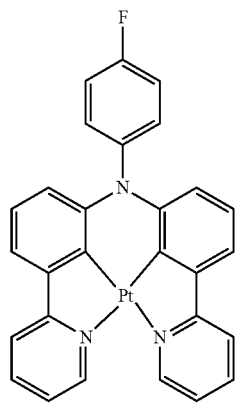 | 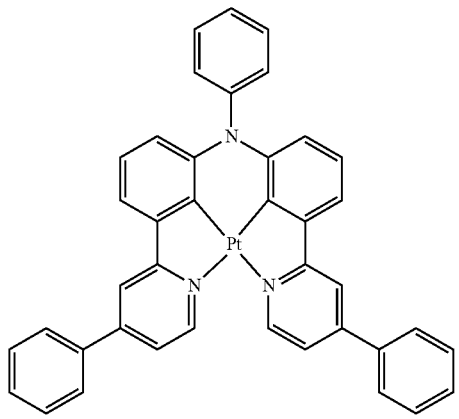 |
| 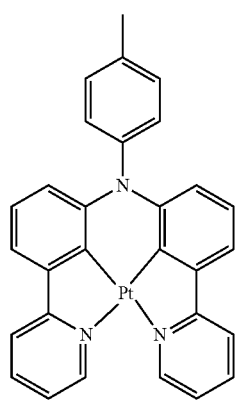 | 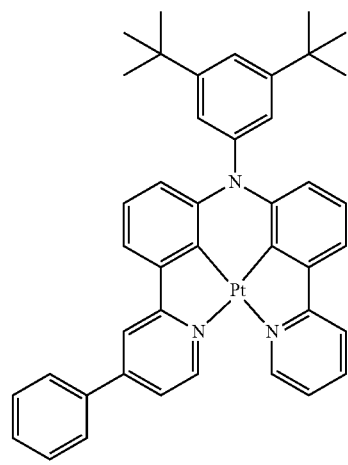 |
| 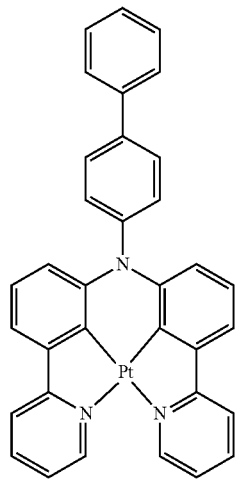 | 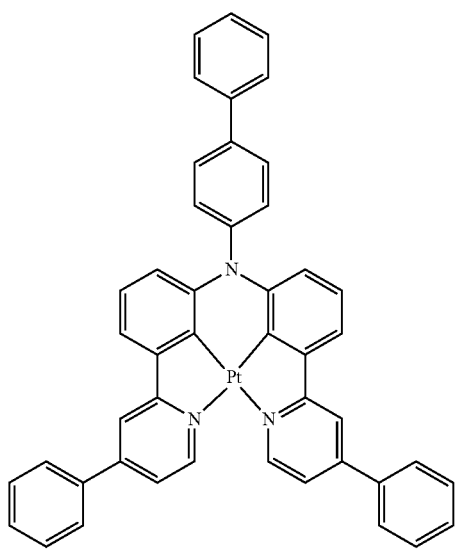 |

| 179 -continued | 180 -continued |
|---|---|
| 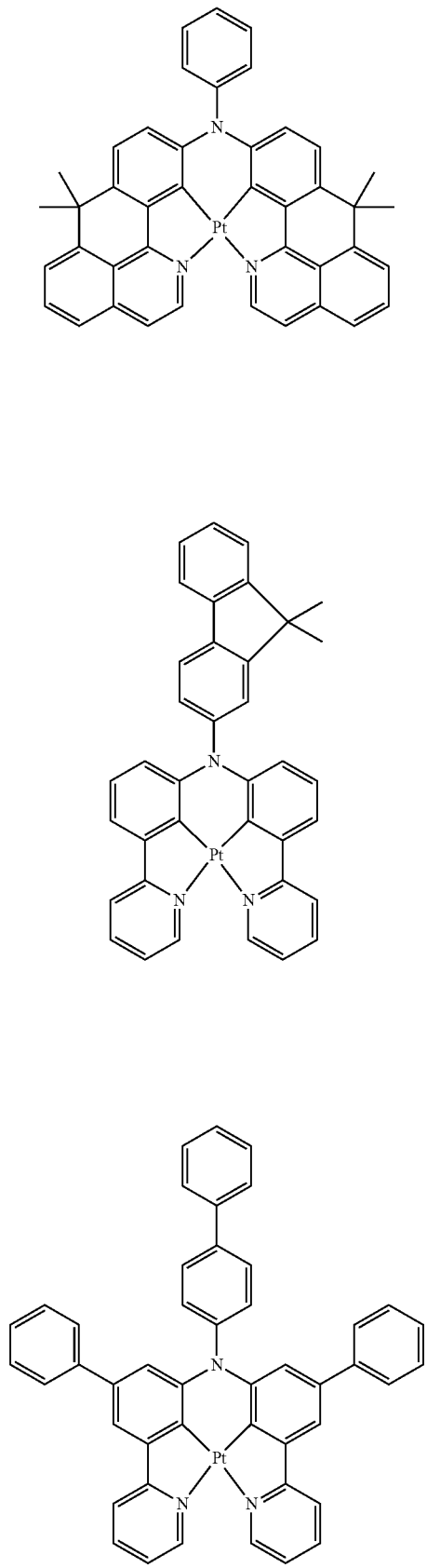 | 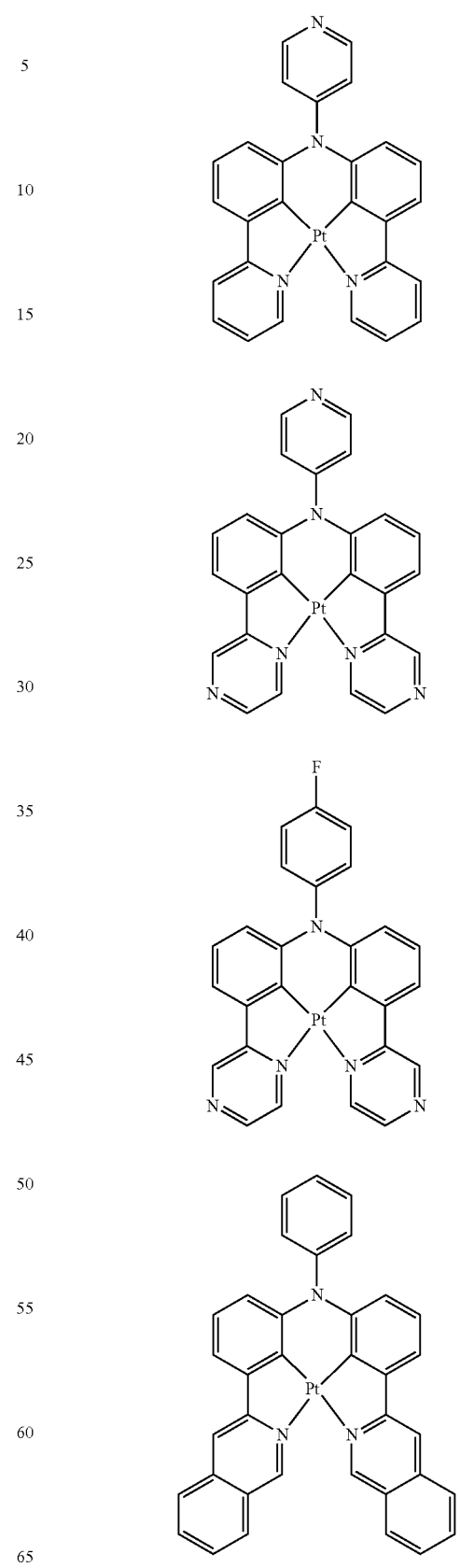 |

| 181 -continued | 182 -continued |
|---|---|
| 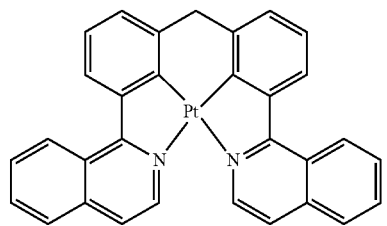 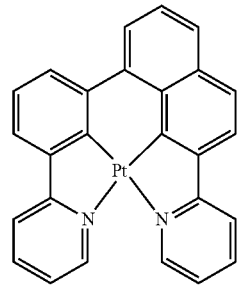 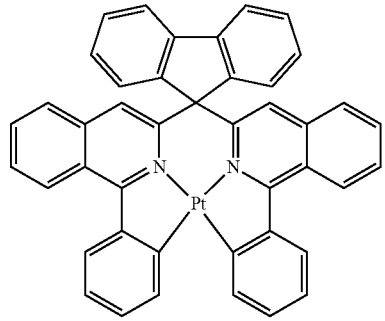 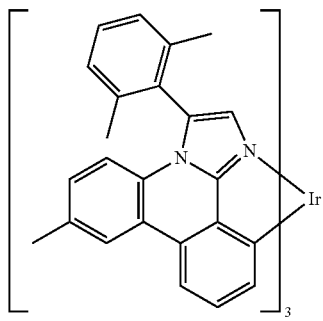 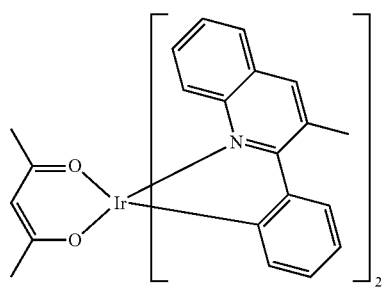 | 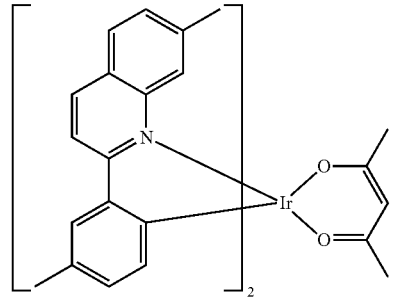 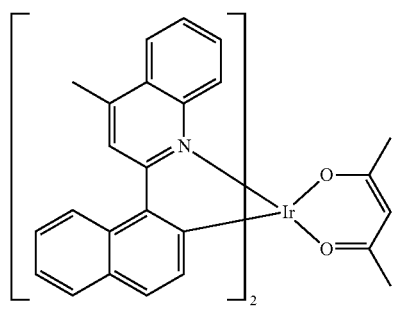 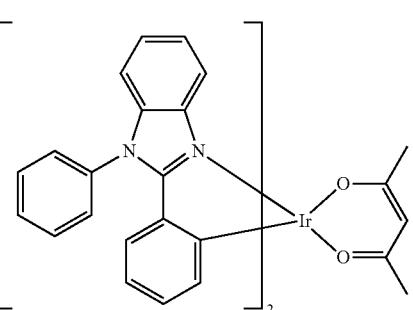 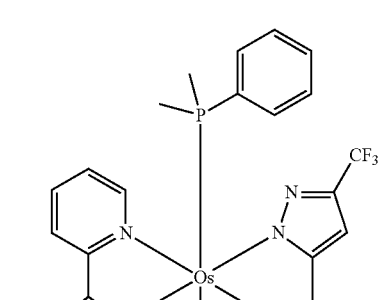 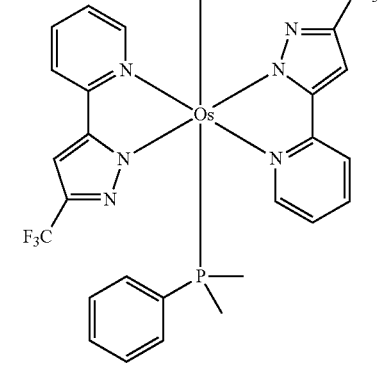 |

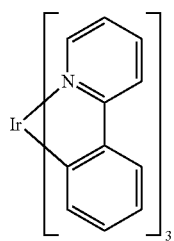
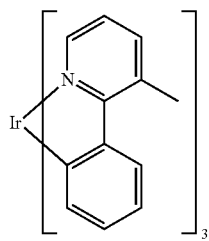
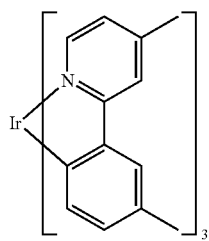
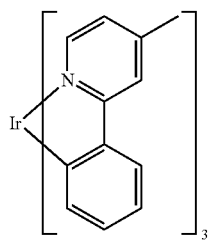
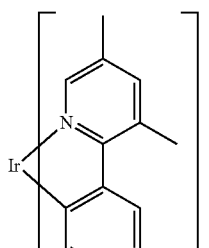
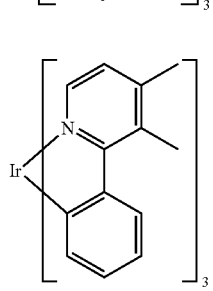
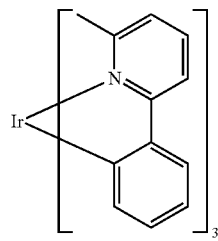
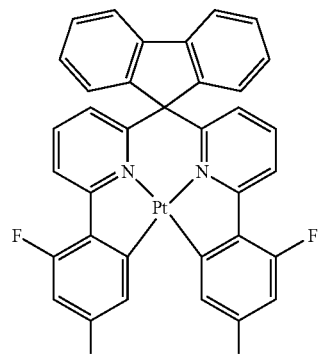
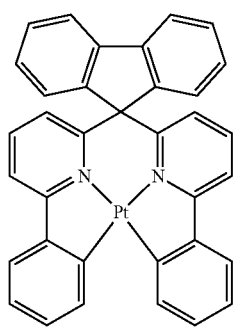
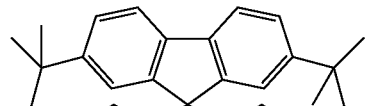
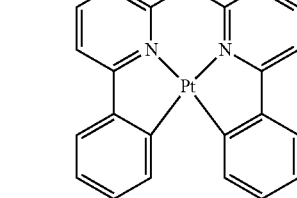
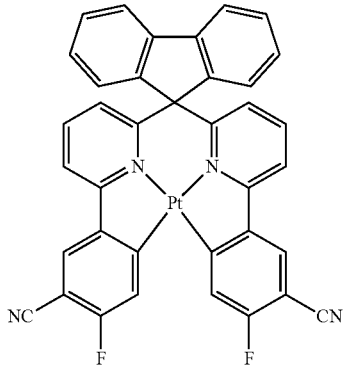

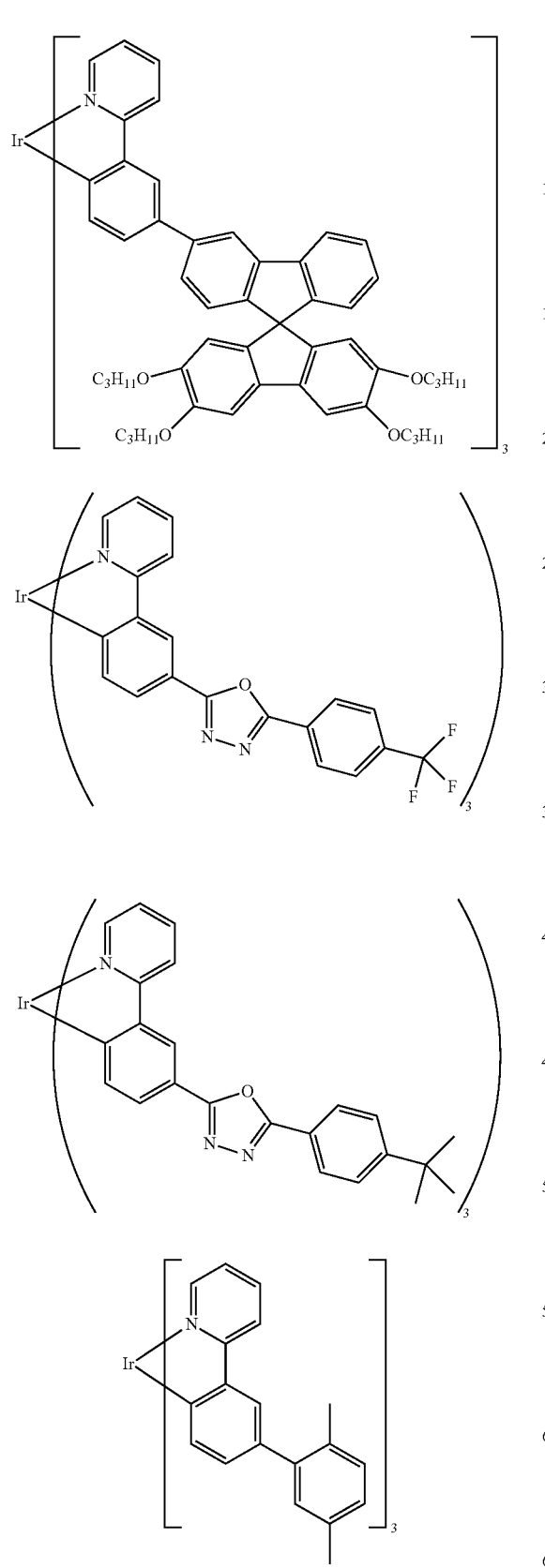
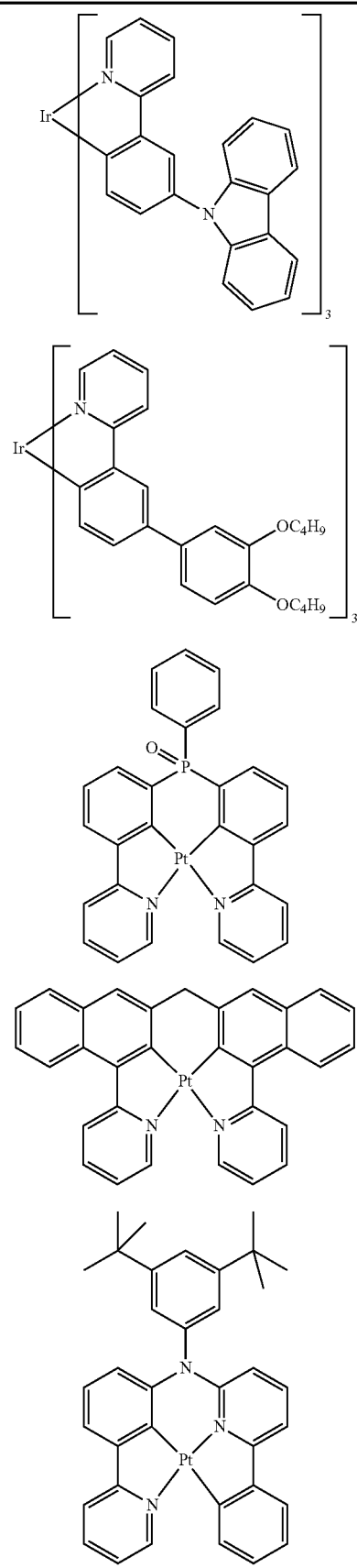

187
-continued
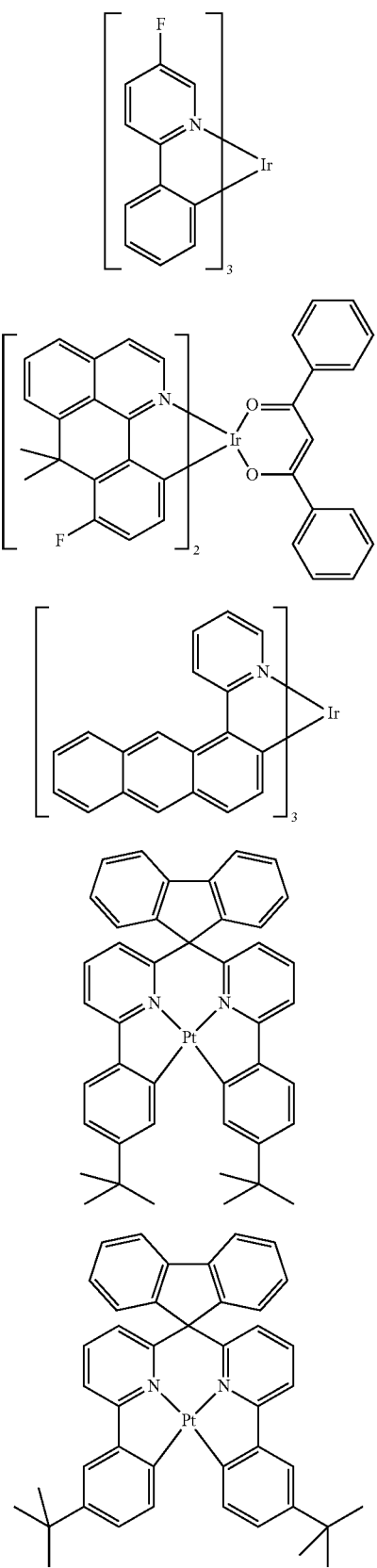
188
-continued
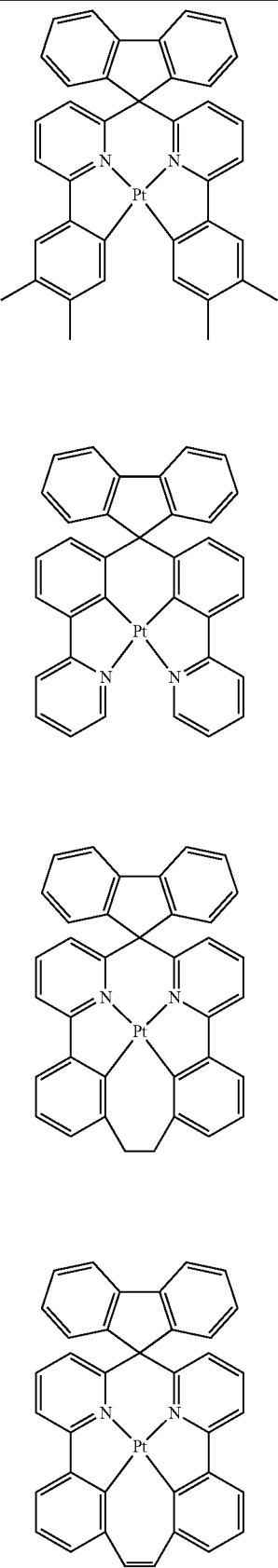

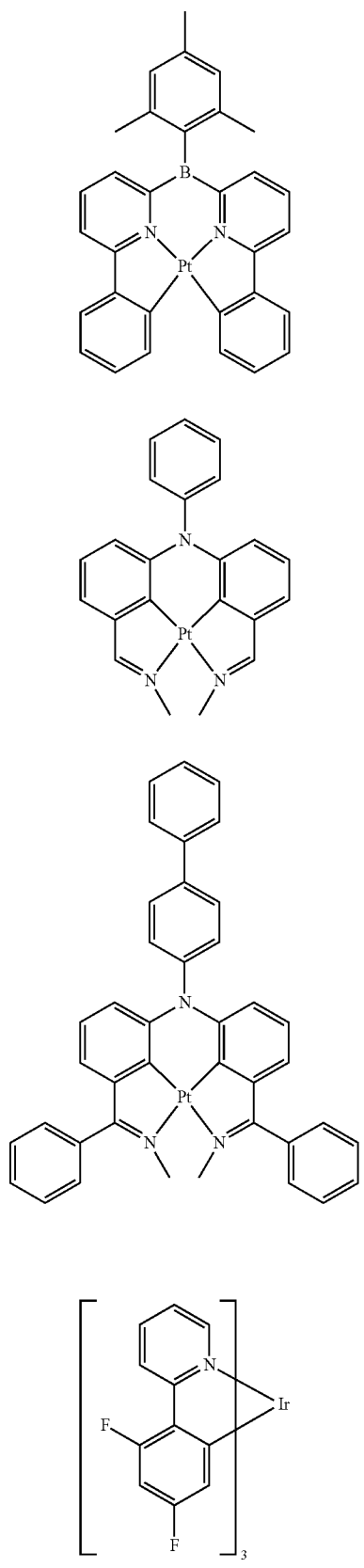
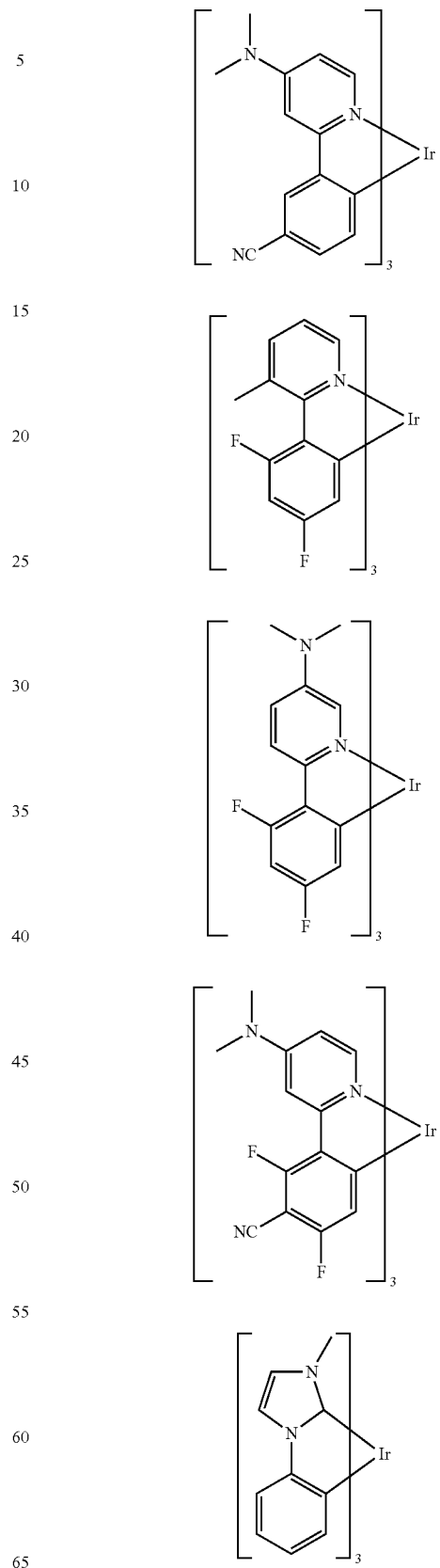

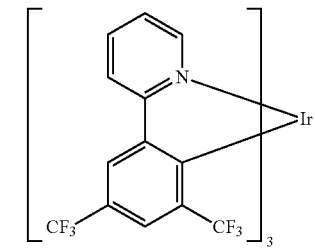
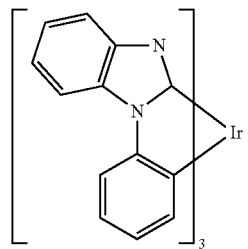
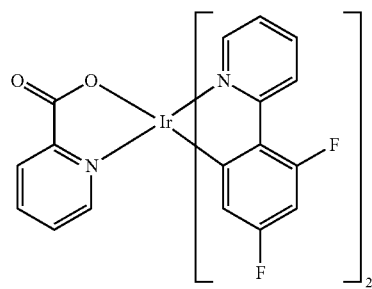
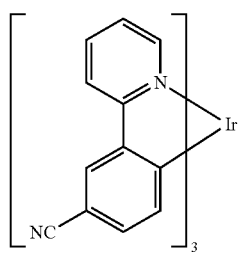
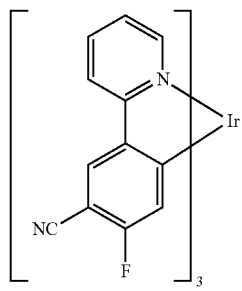
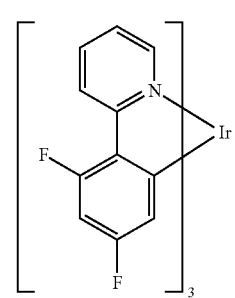
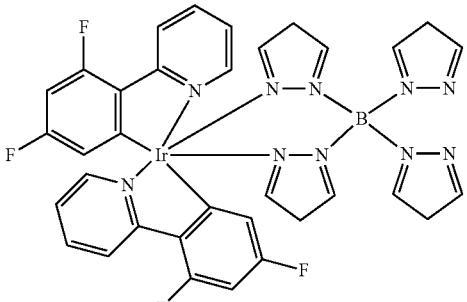
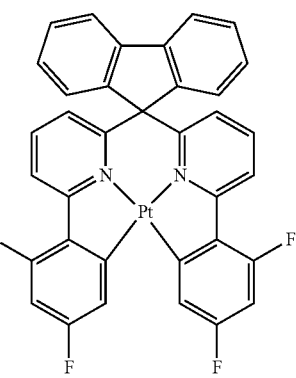
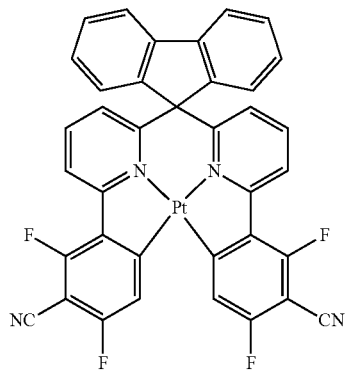
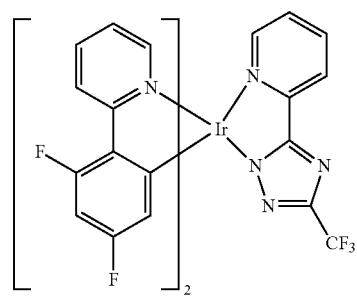

193
-continued
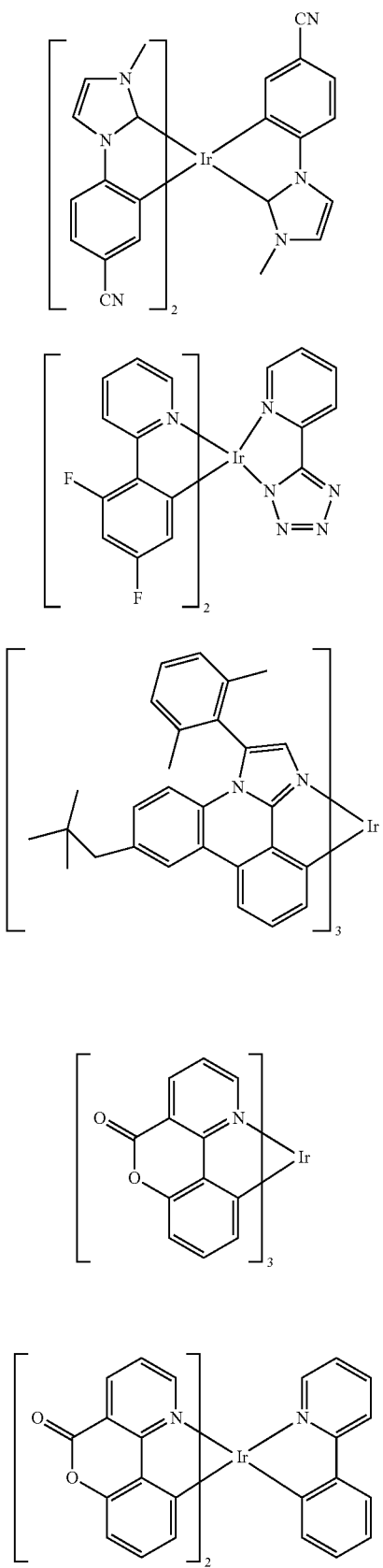
194
-continued
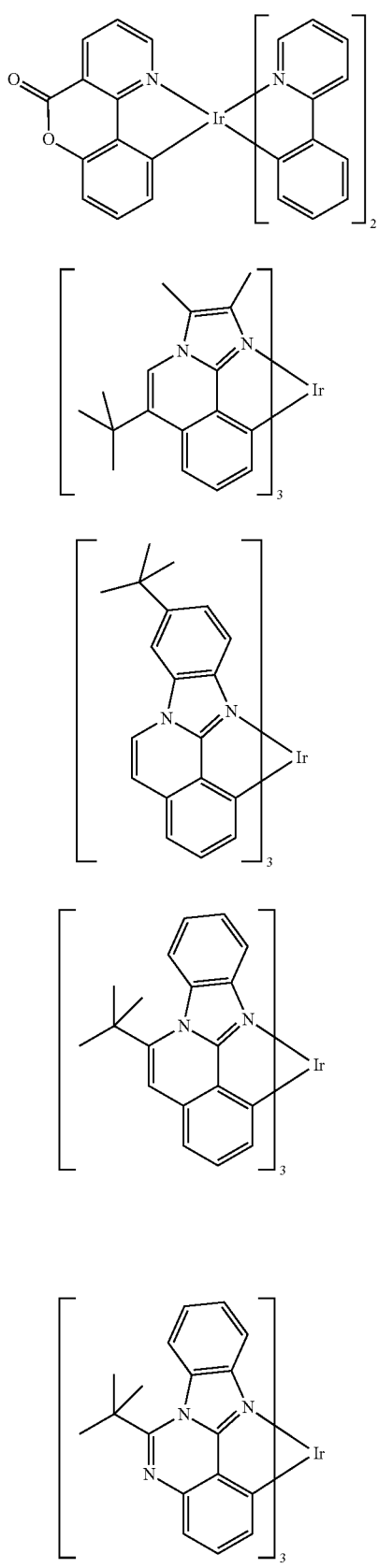

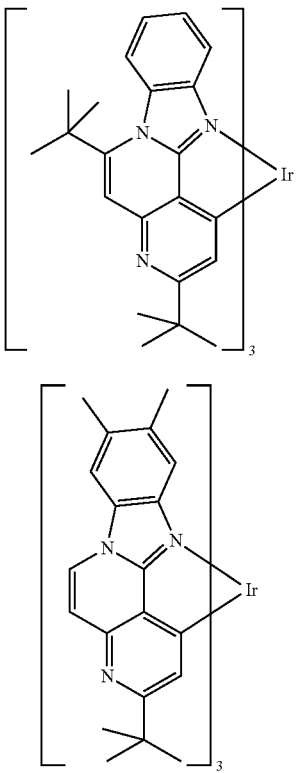

The above-described compound comprising structures of the formula (I) or the above-detailed preferred embodiments can preferably be used as active component in an electronic device. An electronic device is understood to mean any device comprising anode, cathode and at least one layer, said layer comprising at least one organic or organometallic compound. The electronic device of the invention thus comprises anode, cathode and at least one layer containing at least one compound comprising structures of the formula (I). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs) and organic laser diodes (O-lasers), containing at least one compound comprising structures of the formula (I) in at least one layer.

Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 mm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce.

In a preferred embodiment of the invention, the organic electroluminescent device contains the compound of the invention comprising structures of formula (I) or the above-detailed preferred embodiments as matrix material, preferably as hole-conducting matrix material, in one or more emitting layers, preferably in combination with a further matrix material, preferably an electron-conducting matrix material. An emitting layer comprises at least one emitting compound.

The matrix materials used may generally be any materials which are known for the purpose according to the prior art. The triplet level of the matrix material is preferably higher than the triplet level of the emitter.

Suitable matrix materials for the compounds of the invention are lactams, for example according to WO 2011/116865A1, WO 2013/064206A1, WO 2014/056567A1, WO 2014/094964A1, ketones, phosphine oxides, sulphoxides and sulphones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, dibenzofuran derivatives, for example according to WO 2009/148015, or bridged carbazole derivatives, for example according to US 2009/0136779, WO 2010/050778, WO 2011/042107 or WO 2011/088877.

It may also be preferable to use a plurality of different matrix materials as a mixture, especially of at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, it is possible to use a compound of the invention comprising structures of formula (I), in a preferred embodiment, as matrix material in an emission layer of an organic electronic device, especially in an organic electroluminescent device, for example in an OLED or OLEC. In this case, the matrix material containing compound comprising structures of formula (I) is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising structures of formula (I) is used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfil(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more hole-conducting layers (HTL), as hole-conducting compound. Preferably, one or more compounds of the invention and/or at least one oligomer, polymer or dendrimer of the invention can be used as hole injection material in a hole injection layer or as electron blocker material in an electron blocker layer (EBL). Preferably, it is possible to use compound of the invention comprising structures of formula (I) and/or at least one oligomer, polymer or dendrimer of the invention as matrix material, preferably as hole-conducting matrix material in one or more emitting layers (EML). In this context, particular preference is given to use in an HTL or EML.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/NiOx, Al/PtOx) may also be preferable. For some applications, at least one of the electrodes has to be transparent or partly transparent in order to enable the irradiation of the organic material (O-SC) or the emission of light (OLED/PLED, 0-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapour deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device can also be produced as a hybrid system by applying one or more layers from solution and applying one or more other layers by vapour deposition. For example, it is possible to apply an emitting layer comprising a compound of the invention comprising structures of formula (I) and a matrix material from solution, and to apply a hole blocker layer and/or an electron transport layer thereto by vapour deposition under reduced pressure.

These methods are known in general terms to those skilled in the art and can be applied without difficulty to electronic devices, especially organic electroluminescent devices comprising compounds of the invention comprising structures of formula (I) or the above-detailed preferred embodiments.

The electronic devices of the invention, especially organic electroluminescent devices, are notable for one or more of the following surprising advantages over the prior art:

1. Electronic devices, especially organic electroluminescent devices, comprising compounds, oligomers, polymers or dendrimers having structures of formula (I), especially as hole-conducting materials, have a very good lifetime.
2. Electronic devices, especially organic electroluminescent devices, comprising compounds, oligomers, polymers or dendrimers having structures of formula (I) as hole-conducting materials have excellent efficiency. More particularly, efficiency is much higher compared to analogous compounds containing no structural unit of formula (I).
3. The compounds, oligomers, polymers and dendrimers of the invention having structures of the formula (I) exhibit very high stability and lead to compounds having a very long lifetime.
4. With compounds, oligomers, polymers or dendrimers having structures of formula (I), it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
5. The use of compounds, oligomers, polymers or dendrimers having structures of formula (I) in layers of electronic devices, especially organic electroluminescent devices, leads to a high mobility of the electron conductor structures and/or the hole conductor structures.
6. Compounds, oligomers, polymers and dendrimers having structures of formula (I) feature excellent thermal stability, and compounds having a molar mass of less than about 1200 g/mol have good sublimability.
7. Compounds, oligomers, polymers and dendrimers having structures of formula (I) have excellent glass film formation.
8. Compounds, oligomers, polymers and dendrimers having structures of formula (I) form very good films from solutions
9. The compounds, oligomers, polymers and dendrimers comprising structures of formula (I) have a surprisingly high HOMO level, this being particularly true of compounds which are used as hole-conducting materials.

These abovementioned advantages are not accompanied by a deterioration in the further electronic properties.

The present invention further provides for the use of a compound of the invention and/or an oligomer, polymer or dendrimer of the invention in an electronic device as hole transport material, hole injection material, hole blocker material, electron injection material, electron blocker material and/or electron transport material, preferably as hole transport material, hole injection material, hole blocker material and/or matrix material, more preferably hole-conducting matrix material.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example from a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, are themselves inventive and should not be regarded merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature.

PREPARATION EXAMPLES

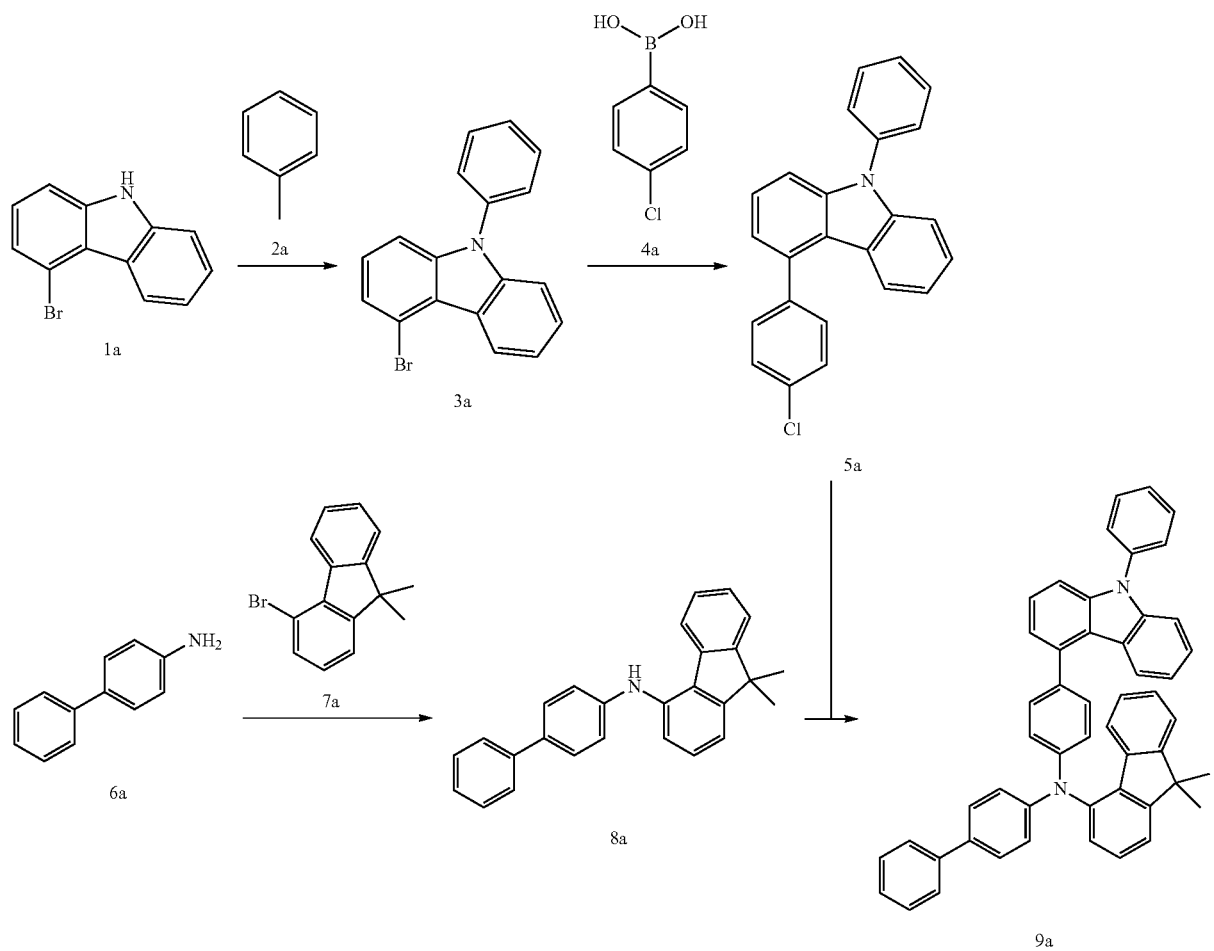

Preparation of 4-bromo-9-phenyl-9H-carbazole 3a

A 500 ml four-neck flask is initially charged with 15.0 g (61.0 mmol, 1.0 eq) of 4-bromo-9H-carbazole 1a (CAS 3652-89-9) together with 13.6 ml (122 mmol, 2.0 eq) of iodobenzene 2a and 16.8 g (122 mmol, 2.0 eq) of potassium carbonate, which are dissolved in 180 ml of dried DMF. After degassing by means of a nitrogen stream for 30 minutes, 1.38 g (6.10 mmol, 0.10 eq) of 1,3-di(2-pyridyl)-1,3-propanedione and 1.16 g (6.10 mmol, 0.10 eq) of copper(I) iodide are added. The mixture is stirred at 110° C. overnight and, after the reaction has ended, the solvent is removed on a rotary evaporator. The residue is taken up in 250 ml of DCM, conc. ammonium chloride solution is added and the mixture is filtered through Celite. Subsequently, the phases are separated, the aqueous phase is extracted twice with 100 ml each time of DCM and the combined organic phases are finally washed with water. After drying over sodium sulphate and removing the solvent under reduced pressure, the oily residue together with heptane is filtered through silica gel and the solvent is again removed on a rotary evaporator. 19.0 g(59.0 mmol, 97%) of a colourless oil 3a are obtained.

The following are prepared analogously:

| Compound | Reactant 1 | Reactant 2 | Product 3 | Yield [%] |
|---|---|---|---|---|
| 3b | 4-bromocarbazole | 3-iodobiphenyl | 9-(biphenyl-3-yl)-4-bromocarbazole | 92 |
| 3c | 4-bromocarbazole | 2-iodo-9,9-dimethylfluorene | 9-(9,9-dimethylfluoren-2-yl)-4-bromocarbazole | 89 |
| 3d | 4-bromocarbazole | 4-bromobiphenyl | 9-(biphenyl-4-yl)-4-bromocarbazole | 96 |
| 3e | 4-bromocarbazole | 3-bromo-9-phenylcarbazole | 4-bromo-9-(9-phenyl-9H-carbazol-3-yl)-9H-carbazole | 84 |

Preparation of 4-(4-chlorophenyl)-9-phenyl-9H-carbazole 5a

In a 500 ml four-neck flask, 18.9 g (58.7 mmol, 1.0 eq) of 4-bromo-9-phenyl-9H-carbazole 3, 9.17 g (58.7 mmol, 1.0 eq) of 4-chlorophenyl-boronic acid (CAS 1679-18-1) and 6.22 g (58.7 mmol, 1.0 eq) of sodium carbonate are dissolved in 150 ml of toluene, 36 ml of ethanol and 77 ml of water. After degassing by means of a nitrogen stream for 30 minutes, 678 mg (0.587 mmol, 0.01 eq) of tetrakis(triphenylphosphine)-palladium are added and the mixture is heated at reflux overnight. After the reaction has ended, the phases are separated, the aqueous phase is extracted three times with toluene and the combined organic phases are then washed with water. The organic phases are dried over sodium sulphate and the solution is concentrated on a rotary evaporator. The residue is introduced into 250 ml of ethanol and the solid formed is filtered off with suction. 19.9 g (56.4 mmol, 96%) of the desired product 5a are obtained.

The following are prepared analogously:

| Compound | Reactant 3 | Reactant 4 | Product 5 | Yield [%] |
|---|---|---|---|---|
| 5b | (structure: 4-bromo-9-(biphenyl-3-yl)-9H-carbazole) | (4-chlorophenyl boronic acid) [1679-18-1] | (structure: 9-(biphenyl-3-yl)-4-(4-chlorophenyl)-9H-carbazole) | 91 |
| 5c | (structure: 4-bromo-9-(9,9-dimethylfluoren-2-yl)-9H-carbazole) | (4-chlorophenyl boronic acid) [1679-18-1] | (structure: 4-(4-chlorophenyl)-9-(9,9-dimethylfluoren-2-yl)-9H-carbazole) | 87 |

-continued
| Compound | Reactant 3 | Reactant 4 | Product 5 | Yield [%] |
|---|---|---|---|---|
| 5d | 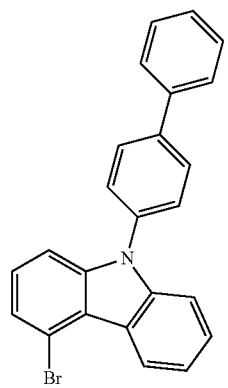 [SMILES: Brc1cccc2c1c1ccccc1n2-c1ccc(-c2ccccc2)cc1] | 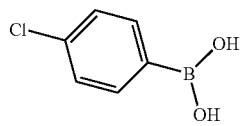<br>[1679-18-1] | 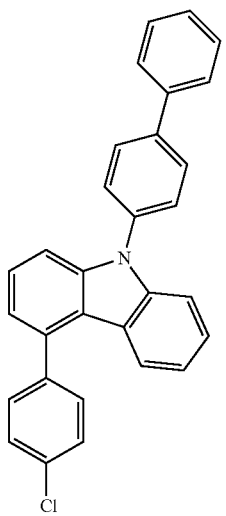 [SMILES: Clc1ccc(-c2cccc3c2c2ccccc2n3-c2ccc(-c3ccccc3)cc2)cc1] | 93 |
| 5e | 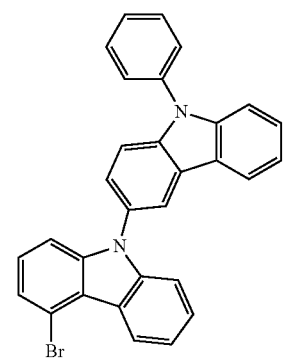 [SMILES: Brc1cccc2c1c1ccccc1n2-c1ccc2c(c1)c1ccccc1n2-c1ccccc1] | 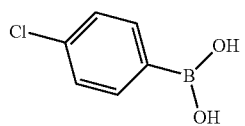<br>[1679-18-1] | 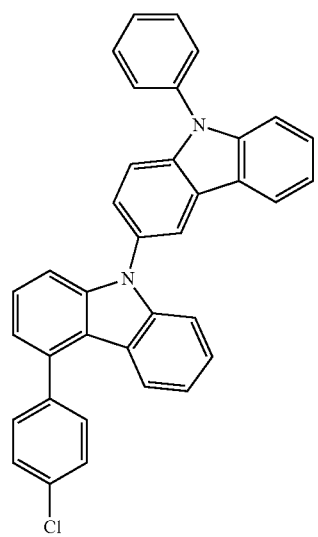 [SMILES: Clc1ccc(-c2cccc3c2c2ccccc2n3-c2ccc3c(c2)c2ccccc2n3-c2ccccc2)cc1] | 72 |
| 5f | 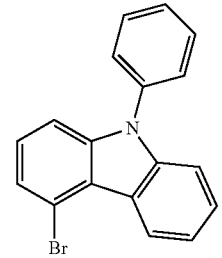 [SMILES: Brc1cccc2c1c1ccccc1n2-c1ccccc1] | 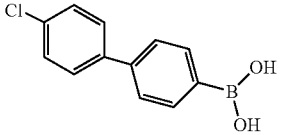<br>[364044-44-0] | 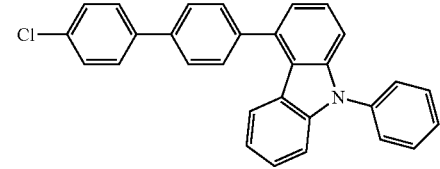 [SMILES: Clc1ccc(-c2ccc(-c3cccc4c3c3ccccc3n4-c3ccccc3)cc2)cc1] | 88 |

| Compound | Reactant 3 | Reactant 4 | Product 5 | Yield [%] |
|---|---|---|---|---|
| 5g | 4-bromo-5-phenyl-carbazole | 4-bromonaphthalen-1-yl boronic acid pinacol ester [1404070-40-1] | 4-(4-bromonaphthalen-1-yl)-9-phenylcarbazole | 91 |
| 5h | 4-bromo-9-phenyl-carbazole | (3'-chloro-[1,1'-biphenyl]-4-yl)boronic acid [1025496-32-5] | 4-(3'-chloro-[1,1'-biphenyl]-4-yl)-9-phenylcarbazole | 97 |
| 5i | 4-bromo-9-phenyl-carbazole | (7-bromo-9,9-dimethyl-9H-fluoren-2-yl)boronic acid [1213768-48-9] | 4-(7-bromo-9,9-dimethyl-9H-fluoren-2-yl)-9-phenylcarbazole | 87 |

Preparation of biphenyl-4-yl(9,9-dimethyl-9H-fluoren-4-yl)amine 8a (Variant A)

All 1 four-neck flask is initially charged with 14.0 g (51.4 mmol, 1.0 eq) of 4-bromo-9,9-dimethylfluorene 7a, and also 10.5 g (60.8 mmol, 1.2 eq) of biphenyl-4-amine 6a and 12.9 g (134 mmol, 2.6 eq) of sodium tert-butoxide, which are dissolved in 300 ml of dry p-xylene. Subsequently, the mixture is degassed for 45 minutes and 346 mg (1.54 mmol, 0.03 eq) of palladium(I) acetate and 1.71 g (3.09 mmol, 0.06 eq) of 1,1'-bis(diphenylphosphino)ferrocene are added and the mixture is stirred at 140° C. overnight. After the reaction has ended, the solvent is removed under reduced pressure, the residue is taken up in dichloromethane and heptane is added. The precipitated solid is filtered off with suction and dried in a vacuum drying cabinet. 11.0 g (30.5 mmol, 59%) of the desired product 8a are obtained.

The following are prepared analogously:

| Compound | Reactant 6 | Reactant 7 |
|---|---|---|
| 8b | [1,1'-biphenyl]-4-amine [92-67-1] | 4-bromo-9,9'-spirobifluorene [1161009-88-6] |

-continued
| | 211 | 212 |
|---|---|---|
| 8c | 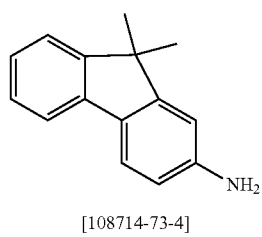 [SMILES: CC1(C)c2ccccc2-c2ccc(N)cc21]<br>[108714-73-4] | 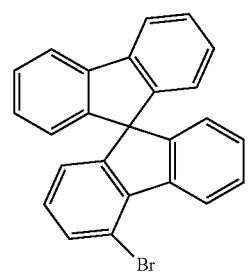<br>[1161009-88-6] |
| 8d | 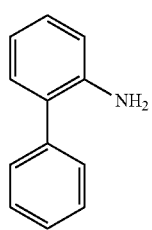<br>[90-41-5] | 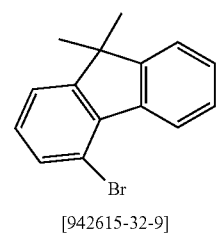 [SMILES: CC1(C)c2ccccc2-c2c(Br)cccc21]<br>[942615-32-9] |
| 8e | 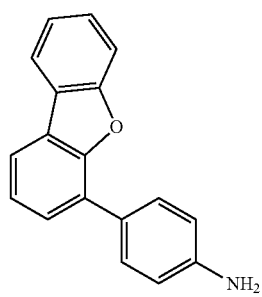<br>[578027-21-1] | 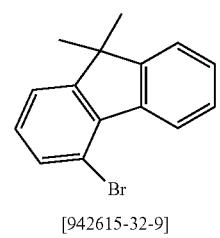 [SMILES: CC1(C)c2ccccc2-c2c(Br)cccc21]<br>[942615-32-9] |
| 8f | 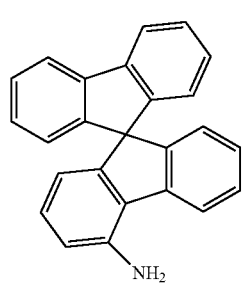<br>[1579281-06-3] | 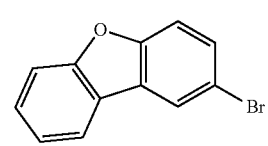<br>[86-76-0] |
| 8g | 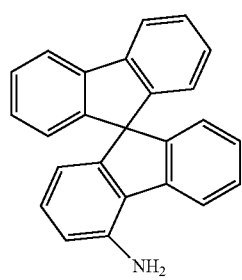<br>[1579281-06-3] | 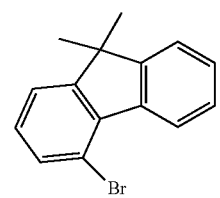<br>[942615-32-9] |

-continued
8h 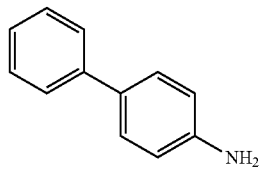
[92-67-1]
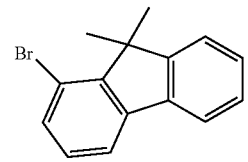
[1225053-54-2]
8i 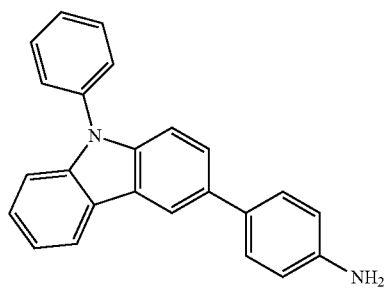
[1370037-59-5]
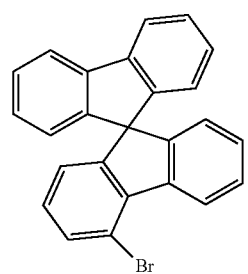
[1161009-88-6]
8j 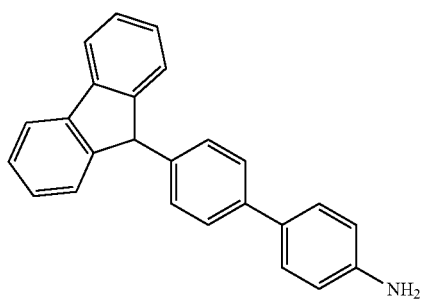
[207447-26-5]
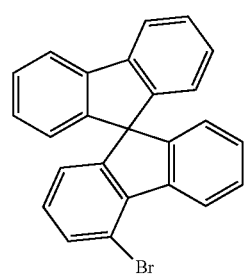
[1161009-88-6]
8k 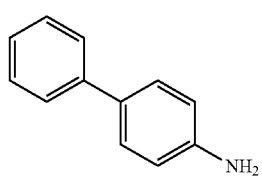
[92-67-1]
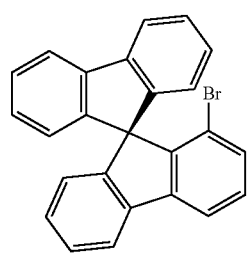
[1450933-18-2]
8l 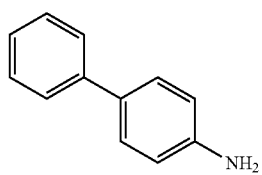
[92-67-1]
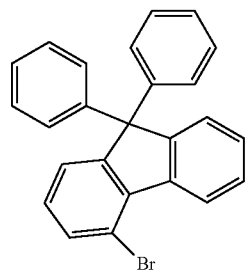
[713125-22-5]

| | | |
|---|---|---|
| 8m | 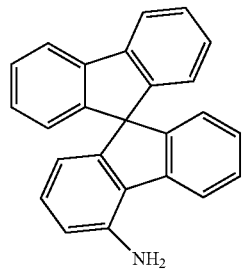 [1579281-06-3] | 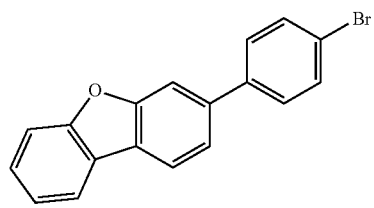 [86-76-0] |
| 8n | 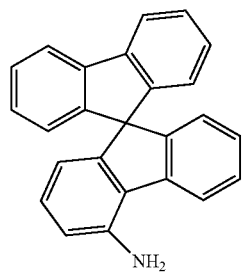 [1579281-06-3] | 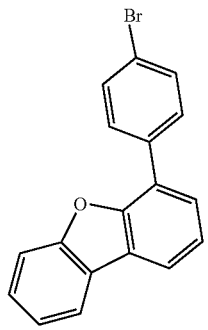 [955959-84-9] |
| 8o | 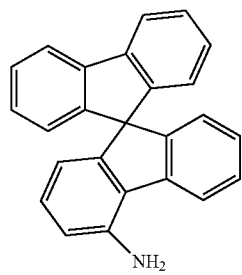 [1579281-06-3] | 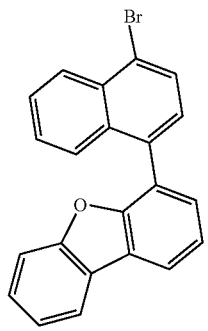 [1297532-85-4] |
| Compound | Product 8 | Yield [%] |
|---|---|---|
| 8b | 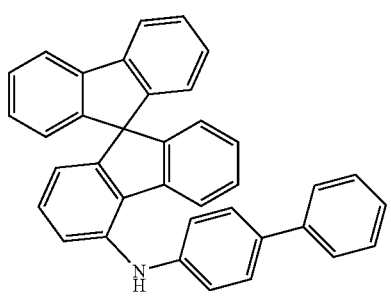 [SMILES: c1ccc(-c2ccc(Nc3cccc4c3-c3ccccc3C43c4ccccc4-c4ccccc43)cc2)cc1] | 73 |

-continued
| | | |
|---|---|---|
| 8c | 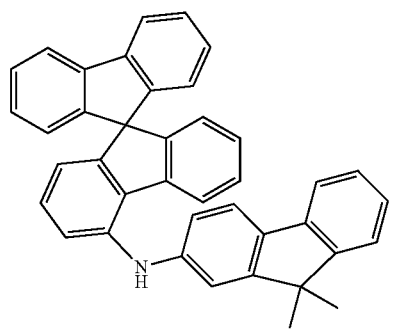 [SMILES: CC1(C)c2ccccc2-c2ccc(Nc3cccc4c3-c3ccccc3C43c4ccccc4-c4ccccc43)cc21] | 85 |
| 8d | 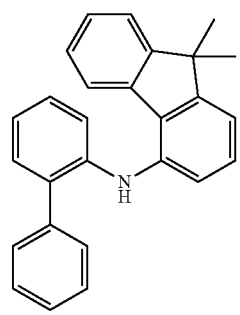 [SMILES: CC1(C)c2ccccc2-c2c(Nc3ccccc3-c3ccccc3)cccc21] | 69 |
| 8e | 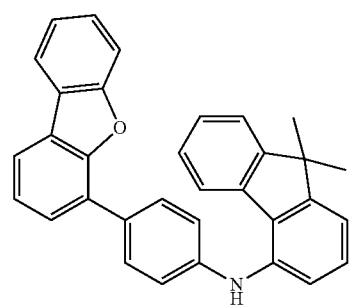 [SMILES: CC1(C)c2ccccc2-c2c(Nc3ccc(-c4cccc5c4oc4ccccc45)cc3)cccc21] | 37 |
| 8f | 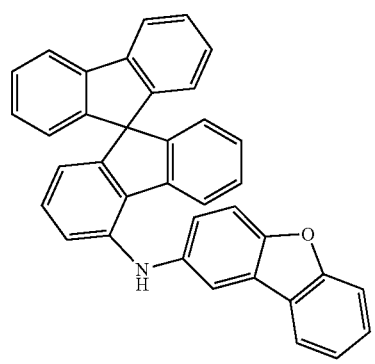 [SMILES: c1ccc2c(c1)-c1ccccc1C21c2ccccc2-c2c(Nc3ccc4oc5ccccc5c4c3)cccc21] | 88 |

-continued
| 8g | 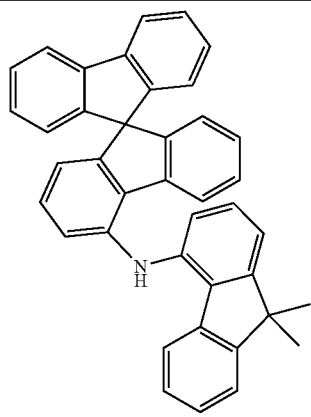 | 81 |
| 8h | 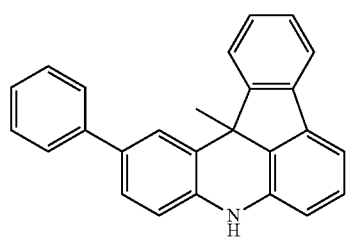 [SMILES: CC12c3cc(-c4ccccc4)ccc3Nc3cccc(c31)-c1ccccc12] | 77 |
| 8i | 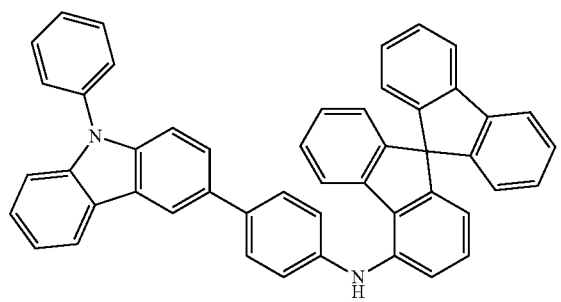 [SMILES: c1ccc(-n2c3ccccc3c3cc(-c4ccc(Nc5cccc6c5-c5ccccc5C65c6ccccc6-c6ccccc65)cc4)ccc32)cc1] | 89 |
| 8j | 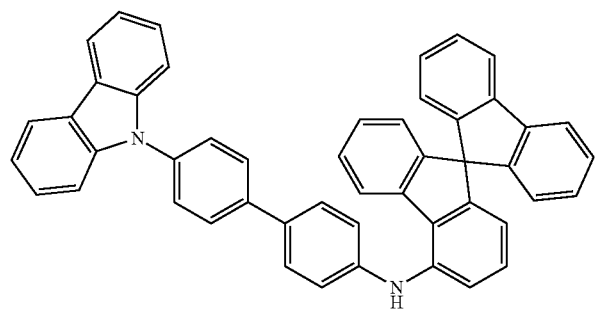 [SMILES: c1ccc2c(c1)-c1ccccc1C21c2ccccc2-c2c(Nc3ccc(-c4ccc(-n5c6ccccc6c6ccccc65)cc4)cc3)cccc21] | 93 |

| | |
|---|---|
| 8k | 21 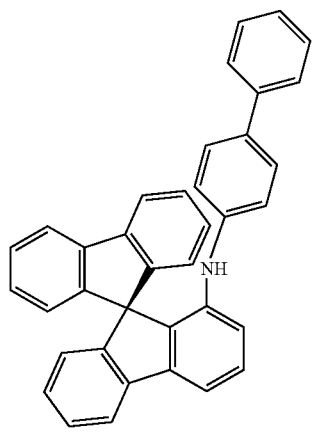 |
| 8l | 67 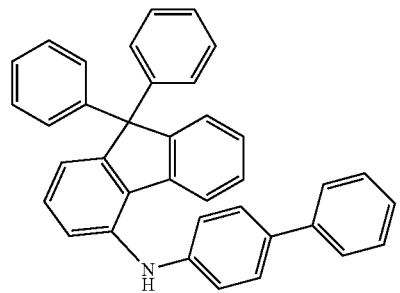 [SMILES: c1ccc(-c2ccc(Nc3cccc4c3-c3ccccc3C4(c3ccccc3)c3ccccc3)cc2)cc1] |
| 8m | 84 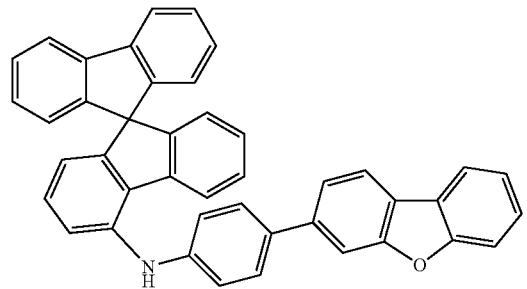 [SMILES: c1ccc2c(c1)-c1ccccc1C21c2ccccc2-c2c(Nc3ccc(-c4ccc5c(c4)oc4ccccc45)cc3)cccc21] |
| 8n | 91 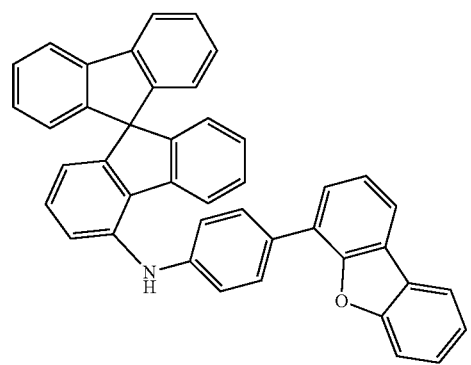 [SMILES: c1ccc2c(c1)-c1ccccc1C21c2ccccc2-c2c(Nc3ccc(-c4cccc5c4oc4ccccc45)cc3)cccc21] |

| | |
|---|---|
| 80 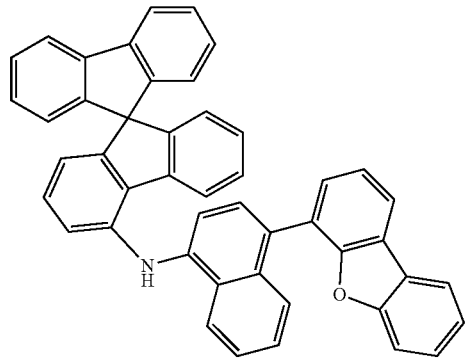 [SMILES: c1ccc2c(c1)-c1ccccc1C21c2ccccc2-c2c(Nc3ccc(-c4cccc5c4oc4ccccc45)c4ccccc34)cccc21] | 74 |

Preparation of biphenyl-4-yl(9,9-dimethyl-9H-fluoren-4-yl)[4-(9-phenyl-9H-carbazol-4-yl)phenyl]amine 9a (Variant A)

11.0 g (30.5 mmol, 1.0 eq) of the secondary amine 8a, and also 11.9 g (33.6 mmol, 1.1 eq) of 4-(4-chlorophenyl)-9-phenyl-9H-carbazole 5a, are dissolved in 250 ml of dry toluene and saturated with argon for about 30 minutes. Subsequently, 279 mg (0.305 mmol, 0.1 eq) of tris(dibenzylideneacetone)dipalladium and 250 mg (0.610 mmol, 0.02 eq) of 2-dicyclohexylphosphino-2',6'-methoxybiphenyl are added and the mixture is heated to reflux. After the reaction has ended, the mixture is transferred into a separating funnel and extracted twice with 300 ml of water. The aqueous phase is again extracted by shaking with toluene and the combined organic phases are dried over sodium sulphate. After the solvent has been removed on a rotary evaporator, a resinous solid is obtained, which is taken up in a little dichloromethane and introduced into ethanol. The solid obtained is purified by means of hot extraction and triple recrystallization from toluene/heptane and finally sublimed. 7.04 g (10.4 mmol, 34%) of the final stage 9a are obtained with an HPLC purity of >99.9%.

The following are prepared analogously:

| Compound | Reactant 6 | Reactant 7 |
|---|---|---|
| 9b | | |
| 9c | | |

-continued
| | | |
|---|---|---|
| 9d | 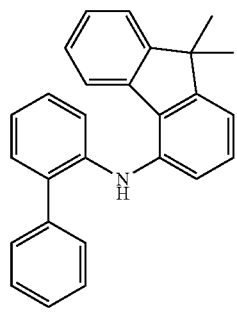 [SMILES: CC1(C)c2ccccc2-c2c(Nc3ccccc3-c3ccccc3)cccc21] | 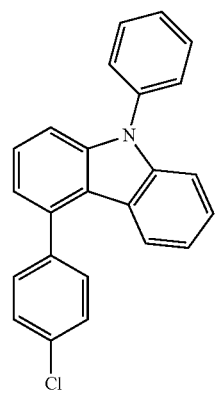 [SMILES: Clc1ccc(-c2cccc3c2c2ccccc2n3-c2ccccc2)cc1] |
| 9e | 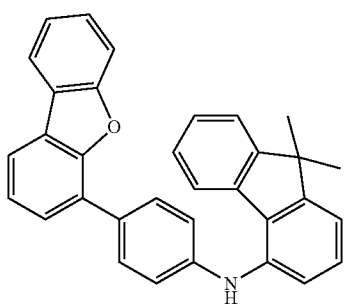 [SMILES: CC1(C)c2ccccc2-c2c(Nc3ccc(-c4cccc5c4oc4ccccc45)cc3)cccc21] | 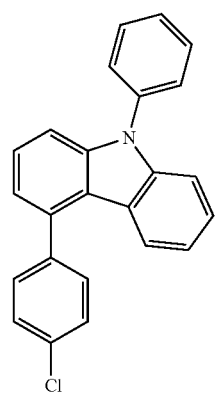 [SMILES: Clc1ccc(-c2cccc3c2c2ccccc2n3-c2ccccc2)cc1] |
| 9f | 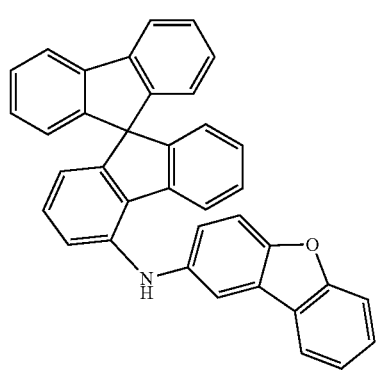 [SMILES: c1ccc2c(c1)-c1ccccc1C21c2ccccc2-c2c(Nc3ccc4oc5ccccc5c4c3)cccc21] | 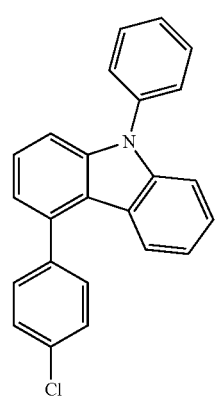 [SMILES: Clc1ccc(-c2cccc3c2c2ccccc2n3-c2ccccc2)cc1] |
| 9g | 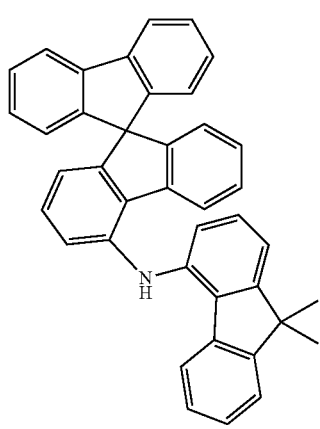 [SMILES: CC1(C)c2ccccc2-c2c(Nc3cccc4c3-c3ccccc3C43c4ccccc4-c4ccccc43)cccc21] | 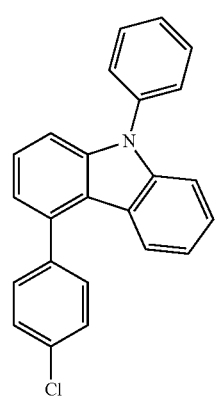 [SMILES: Clc1ccc(-c2cccc3c2c2ccccc2n3-c2ccccc2)cc1] |

| | | |
|---|---|---|
| 9h | 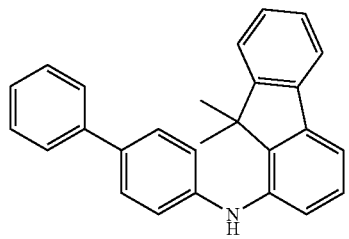 [SMILES: CC1(C)c2ccccc2-c2cccc(Nc3ccc(-c4ccccc4)cc3)c21] | 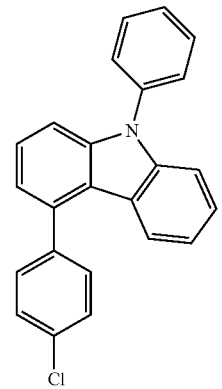 [SMILES: Clc1ccc(-c2cccc3c2c2ccccc2n3-c2ccccc2)cc1] |
| 9i | 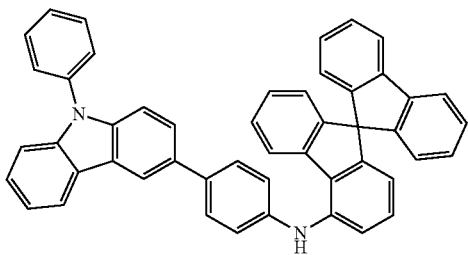 [SMILES: c1ccc(-n2c3ccccc3c3cc(-c4ccc(Nc5cccc6c5-c5ccccc5C65c6ccccc6-c6ccccc65)cc4)ccc32)cc1] | 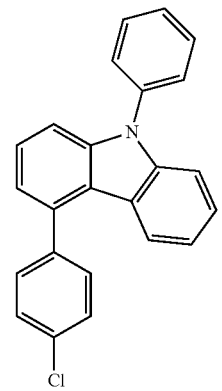 [SMILES: Clc1ccc(-c2cccc3c2c2ccccc2n3-c2ccccc2)cc1] |
| 9j | 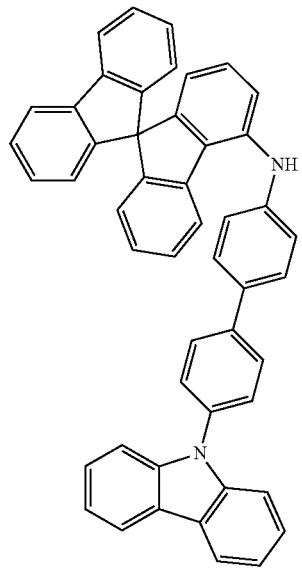 [SMILES: c1ccc2c(c1)-c1ccccc1C21c2ccccc2-c2c(Nc3ccc(-c4ccc(-n5c6ccccc6c6ccccc65)cc4)cc3)cccc21] | 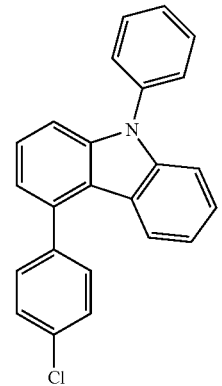 [SMILES: Clc1ccc(-c2cccc3c2c2ccccc2n3-c2ccccc2)cc1] |

| 9k | 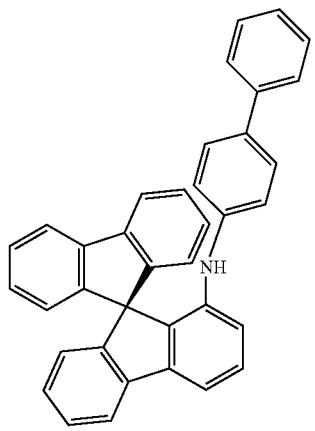 | 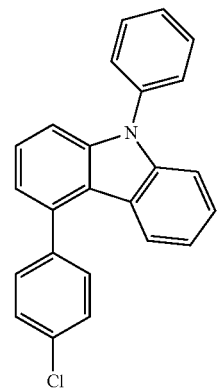 [SMILES: Clc1ccc(-c2cccc3c2c2ccccc2n3-c2ccccc2)cc1] |
| 9l | 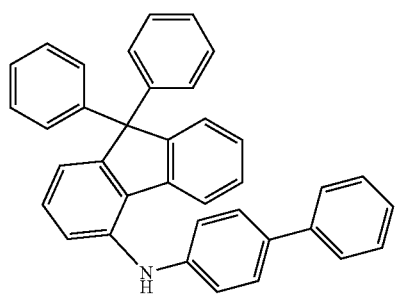 [SMILES: c1ccc(-c2ccc(Nc3cccc4c3-c3ccccc3C4(c3ccccc3)c3ccccc3)cc2)cc1] | 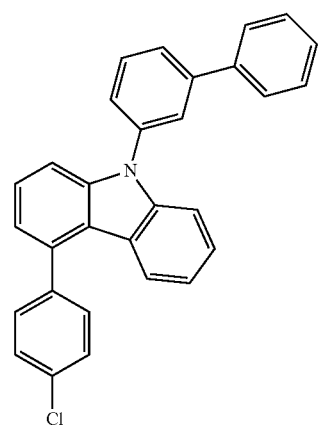 [SMILES: Clc1ccc(-c2cccc3c2c2ccccc2n3-c2cccc(-c3ccccc3)c2)cc1] |
| 9m | 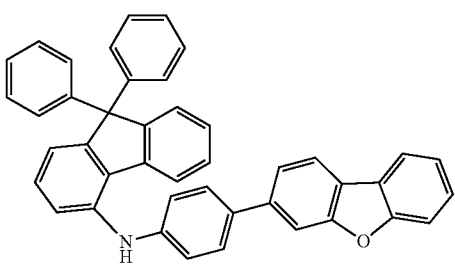 [SMILES: c1ccc(C2(c3ccccc3)c3ccccc3-c3c(Nc4ccc(-c5ccc6c(c5)oc5ccccc56)cc4)cccc32)cc1] | 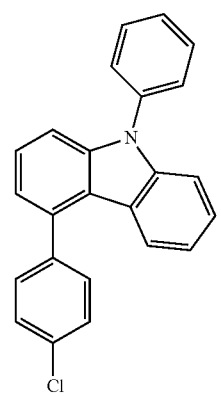 [SMILES: Clc1ccc(-c2cccc3c2c2ccccc2n3-c2ccccc2)cc1] |
| 9n | 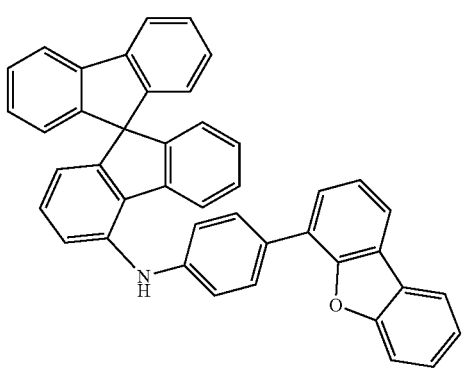 [SMILES: c1ccc2c(c1)-c1ccccc1C21c2ccccc2-c2c(Nc3ccc(-c4cccc5c4oc4ccccc45)cc3)cccc21] | 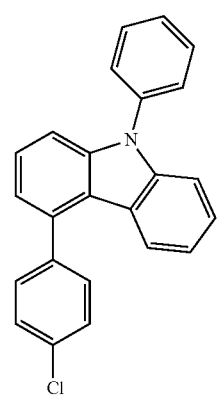 [SMILES: Clc1ccc(-c2cccc3c2c2ccccc2n3-c2ccccc2)cc1] |

| | | |
|---|---|---|
| 9o | 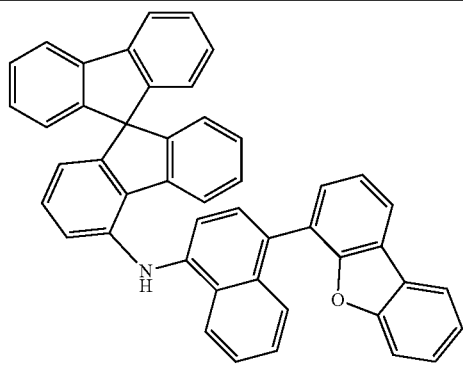 | 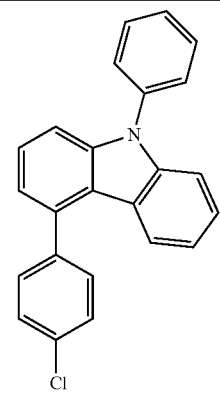 |
| 9p | 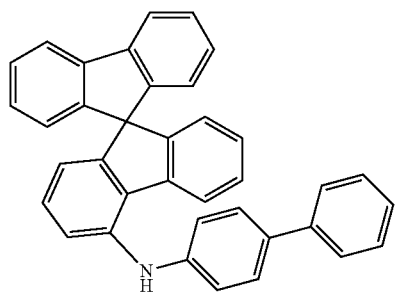 [SMILES: c1ccc(-c2ccc(Nc3cccc4c3-c3ccccc3C43c4ccccc4-c4ccccc43)cc2)cc1] | 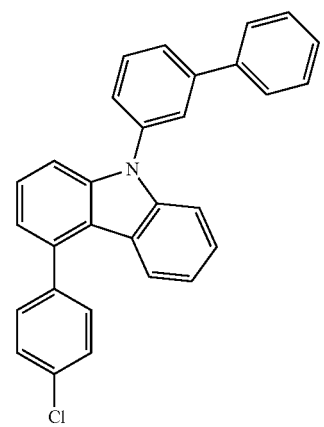 [SMILES: Clc1ccc(-c2cccc3c2c2ccccc2n3-c2cccc(-c3ccccc3)c2)cc1] |
| 9q | 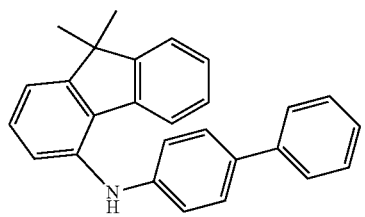 [SMILES: CC1(C)c2ccccc2-c2c(Nc3ccc(-c4ccccc4)cc3)cccc21] | 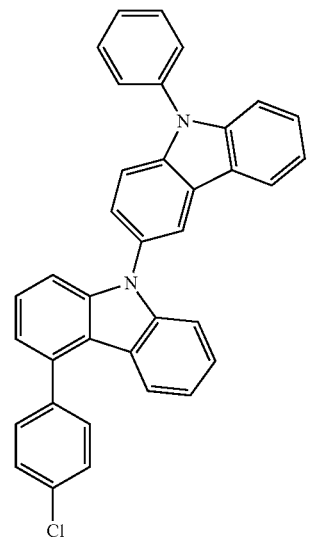 [SMILES: Clc1ccc(-c2cccc3c2c2ccccc2n3-c2ccc3c(c2)c2ccccc2n3-c2ccccc2)cc1] |

-continued
| | | |
|---|---|---|
| 9r | 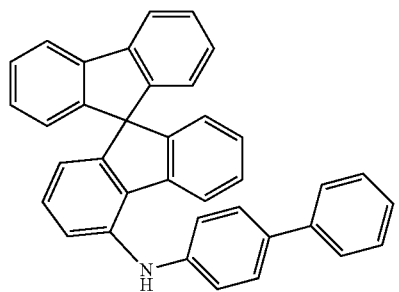 [SMILES: c1ccc(-c2ccc(Nc3cccc4c3-c3ccccc3C43c4ccccc4-c4ccccc43)cc2)cc1] | 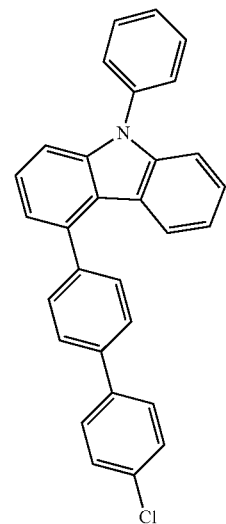 [SMILES: Clc1ccc(-c2ccc(-c3cccc4c3c3ccccc3n4-c3ccccc3)cc2)cc1] |
| 9s | 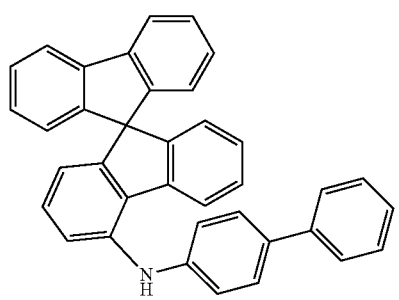 [SMILES: c1ccc(-c2ccc(Nc3cccc4c3-c3ccccc3C43c4ccccc4-c4ccccc43)cc2)cc1] | 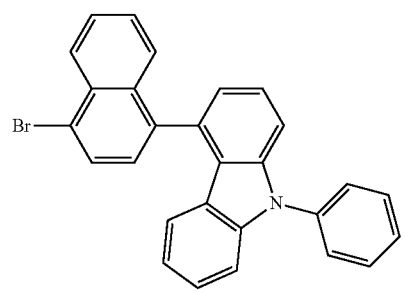 [SMILES: Brc1ccc(-c2cccc3c2c2ccccc2n3-c2ccccc2)c2ccccc12] |
| 9t | 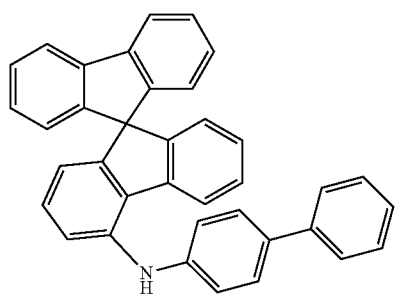 [SMILES: c1ccc(-c2ccc(Nc3cccc4c3-c3ccccc3C43c4ccccc4-c4ccccc43)cc2)cc1] | 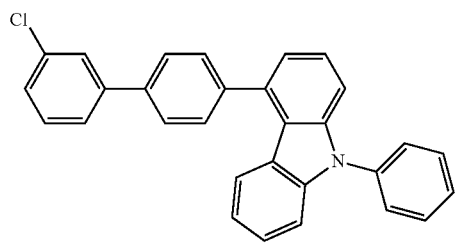 [SMILES: Clc1cccc(-c2ccc(-c3cccc4c3c3ccccc3n4-c3ccccc3)cc2)c1] |
| 9u | 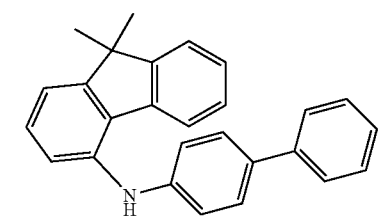 [SMILES: CC1(C)c2ccccc2-c2c(Nc3ccc(-c4ccccc4)cc3)cccc21] | 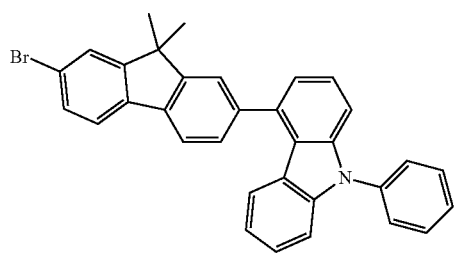 [SMILES: CC1(C)c2cc(Br)ccc2-c2ccc(-c3cccc4c3c3ccccc3n4-c3ccccc3)cc21] |

-continued
| Compound | Product 8 | Yield [%] |
|---|---|---|
| 9b | 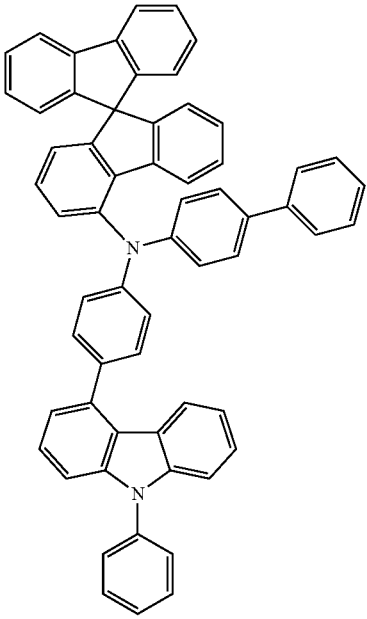 [SMILES: c1ccc(-c2ccc(N(c3ccc(-c4cccc5c4c4ccccc4n5-c4ccccc4)cc3)c3cccc4c3-c3ccccc3C43c4ccccc4-c4ccccc43)cc2)cc1] | 45 |
| 9c | 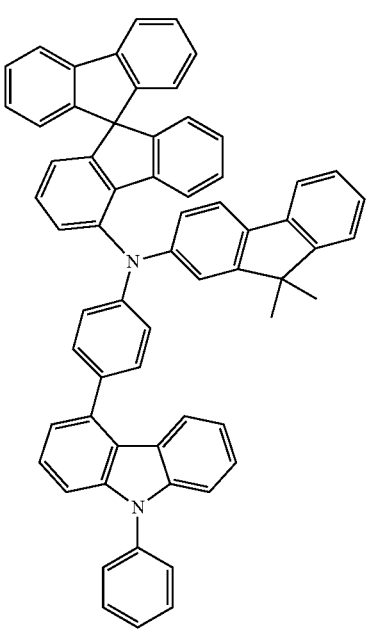 [SMILES: CC1(C)c2ccccc2-c2ccc(N(c3ccc(-c4cccc5c4c4ccccc4n5-c4ccccc4)cc3)c3cccc4c3-c3ccccc3C43c4ccccc4-c4ccccc43)cc21] | 51 |

9d 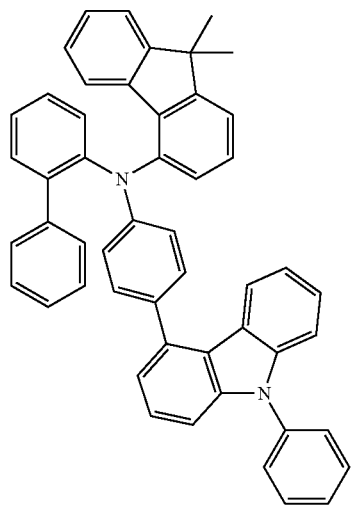 [SMILES: CC1(C)c2ccccc2-c2c(N(c3ccc(-c4cccc5c4c4ccccc4n5-c4ccccc4)cc3)c3ccccc3-c3ccccc3)cccc21] 47
9e 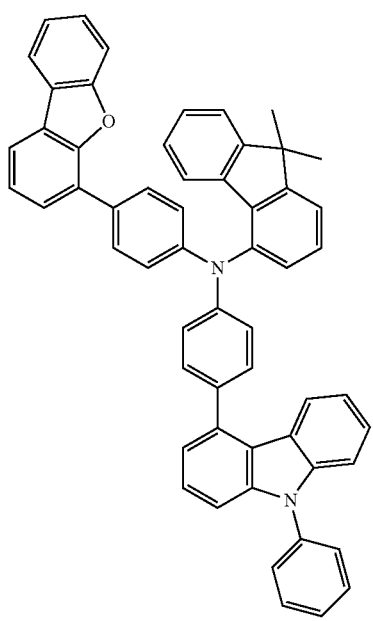 [SMILES: CC1(C)c2ccccc2-c2c(N(c3ccc(-c4cccc5c4oc4ccccc45)cc3)c3ccc(-c4cccc5c4c4ccccc4n5-c4ccccc4)cc3)cccc21] 21

9f
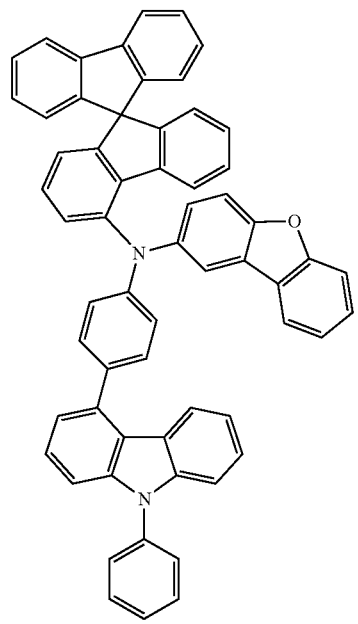 [SMILES: c1ccc(-n2c3ccccc3c3c(-c4ccc(N(c5ccc6oc7ccccc7c6c5)c5cccc6c5-c5ccccc5C65c6ccccc6-c6ccccc65)cc4)cccc32)cc1]
63
9g
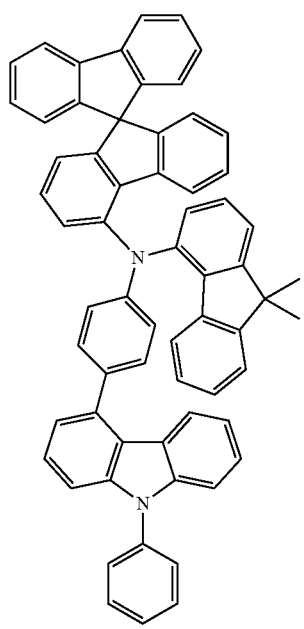 [SMILES: CC1(C)c2ccccc2-c2c(N(c3ccc(-c4cccc5c4c4ccccc4n5-c4ccccc4)cc3)c3cccc4c3-c3ccccc3C43c4ccccc4-c4ccccc43)cccc21]
44

41
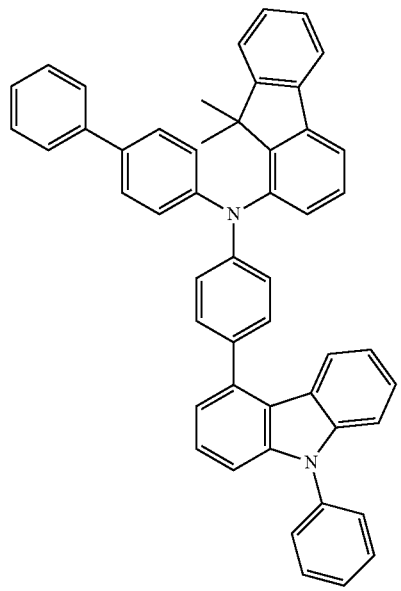 [SMILES: CC1(C)c2ccccc2-c2cccc(N(c3ccc(-c4ccccc4)cc3)c3ccc(-c4cccc5c4c4ccccc4n5-c4ccccc4)cc3)c21]
37
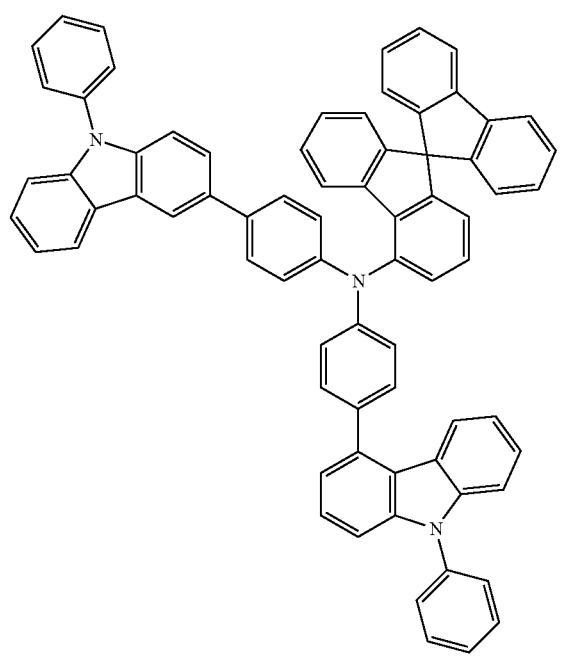 [SMILES: c1ccc(-n2c3ccccc3c3cc(-c4ccc(N(c5ccc(-c6cccc7c6c6ccccc6n7-c6ccccc6)cc5)c5cccc6c5-c5ccccc5C65c6ccccc6-c6ccccc65)cc4)ccc32)cc1]

-continued
9j 52
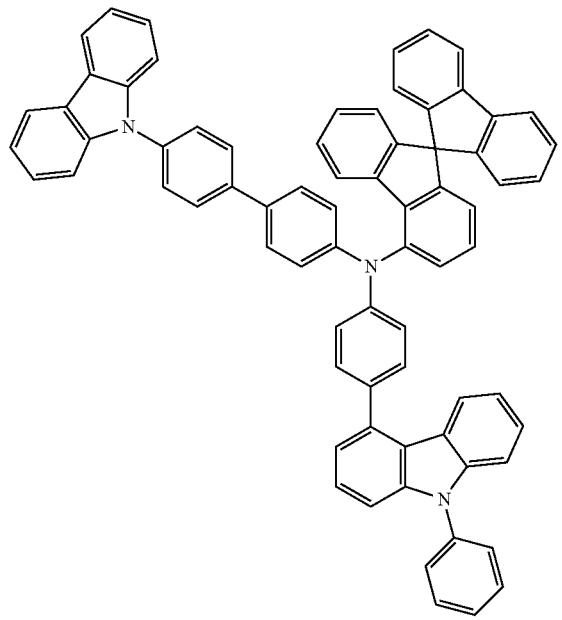 [SMILES: c1ccc(-n2c3ccccc3c3c(-c4ccc(N(c5ccc(-c6ccc(-n7c8ccccc8c8ccccc87)cc6)cc5)c5cccc6c5-c5ccccc5C65c6ccccc6-c6ccccc65)cc4)cccc32)cc1]
9k 28
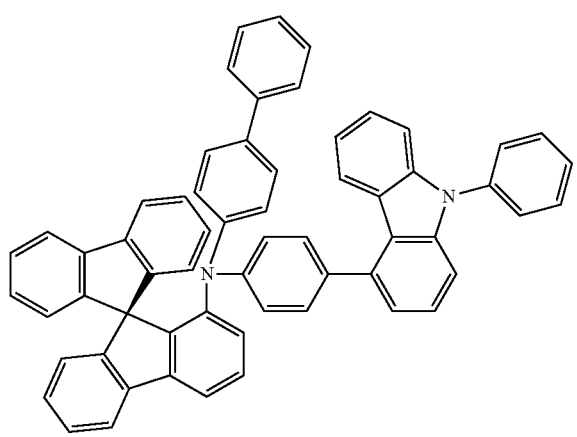

9l
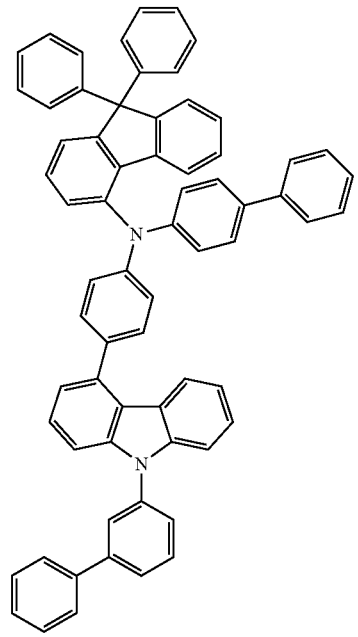 [SMILES: c1ccc(-c2ccc(N(c3ccc(-c4cccc5c4c4ccccc4n5-c4cccc(-c5ccccc5)c4)cc3)c3cccc4c3-c3ccccc3C4(c3ccccc3)c3ccccc3)cc2)cc1]
46
9m
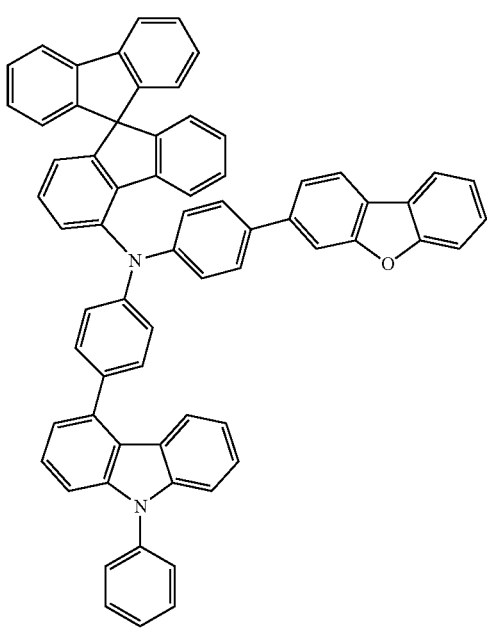 [SMILES: c1ccc(-n2c3ccccc3c3c(-c4ccc(N(c5ccc(-c6ccc7c(c6)oc6ccccc67)cc5)c5cccc6c5-c5ccccc5C65c6ccccc6-c6ccccc65)cc4)cccc32)cc1]
41

9n
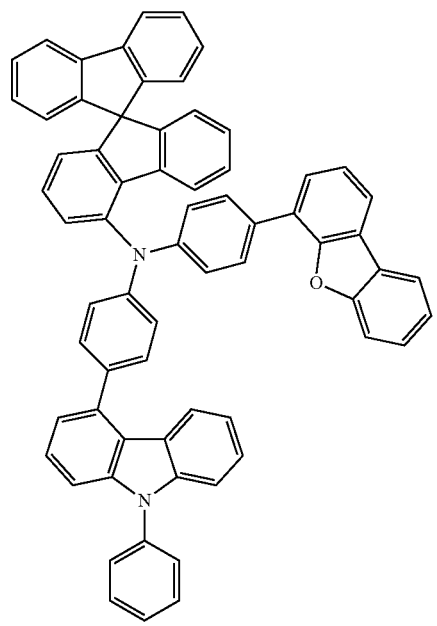 [SMILES: c1ccc(-n2c3ccccc3c3c(-c4ccc(N(c5ccc(-c6cccc7c6oc6ccccc67)cc5)c5cccc6c5-c5ccccc5C65c6ccccc6-c6ccccc65)cc4)cccc32)cc1]
39
9o
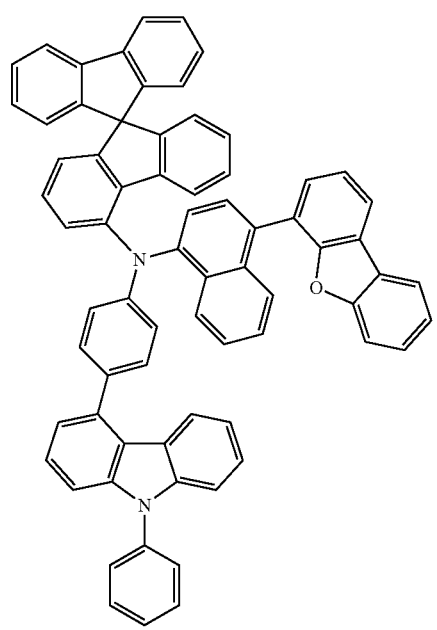 [SMILES: c1ccc(-n2c3ccccc3c3c(-c4ccc(N(c5cccc6c5-c5ccccc5C65c6ccccc6-c6ccccc65)c5ccc(-c6cccc7c6oc6ccccc67)c6ccccc56)cc4)cccc32)cc1]
36

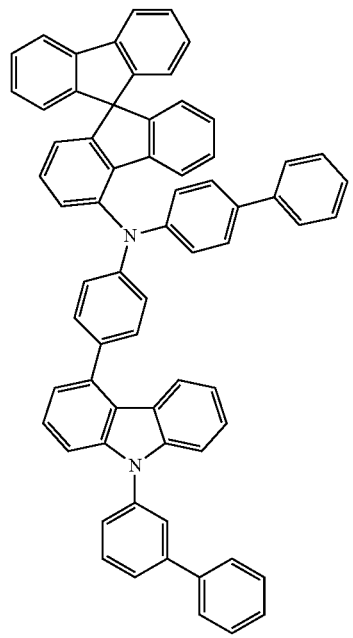 [SMILES: c1ccc(-c2ccc(N(c3ccc(-c4cccc5c4c4ccccc4n5-c4cccc(-c5ccccc5)c4)cc3)c3cccc4c3-c3ccccc3C43c4ccccc4-c4ccccc43)cc2)cc1]
9p
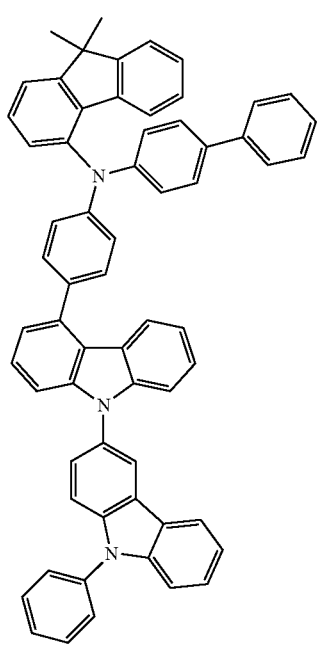 [SMILES: CC1(C)c2ccccc2-c2c(N(c3ccc(-c4ccccc4)cc3)c3ccc(-c4cccc5c4c4ccccc4n5-c4ccc5c(c4)c4ccccc4n5-c4ccccc4)cc3)cccc21]
9q

-continued
9r
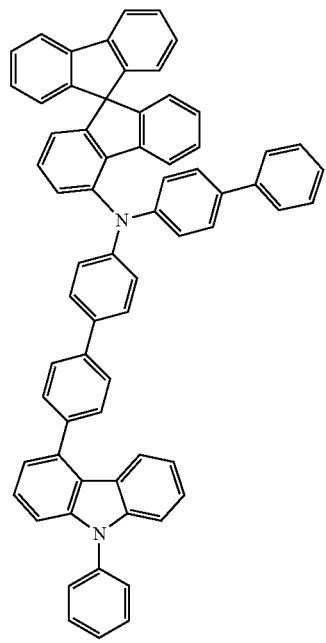 [SMILES: c1ccc(-c2ccc(N(c3ccc(-c4ccc(-c5cccc6c5c5ccccc5n6-c5ccccc5)cc4)cc3)c3cccc4c3-c3ccccc3C43c4ccccc4-c4ccccc43)cc2)cc1]
58
9s
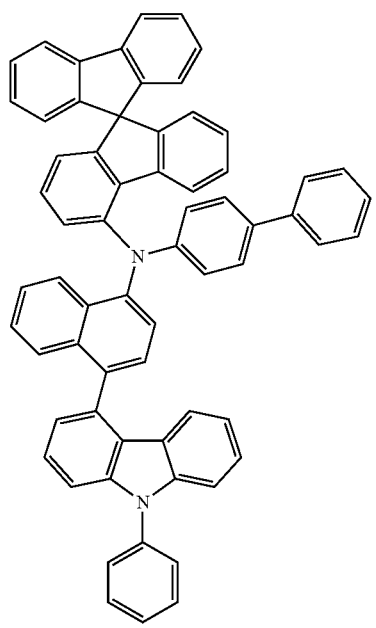 [SMILES: c1ccc(-c2ccc(N(c3cccc4c3-c3ccccc3C43c4ccccc4-c4ccccc43)c3ccc(-c4cccc5c4c4ccccc4n5-c4ccccc4)c4ccccc34)cc2)cc1]
45

9t

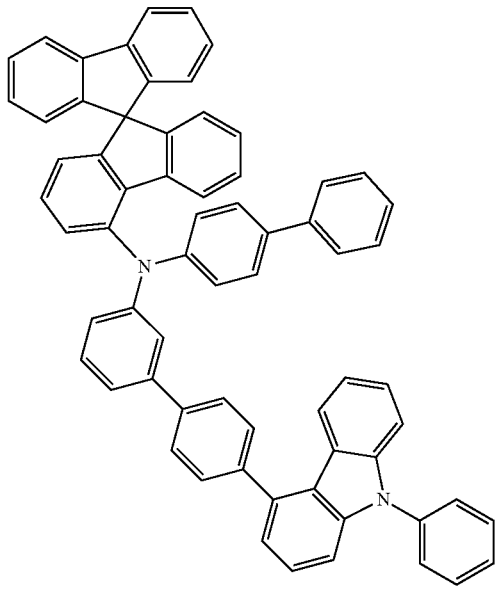 [SMILES: c1ccc(-c2ccc(N(c3cccc(-c4ccc(-c5cccc6c5c5ccccc5n6-c5ccccc5)cc4)c3)c3cccc4c3-c3ccccc3C43c4ccccc4-c4ccccc43)cc2)cc1]

44

9u

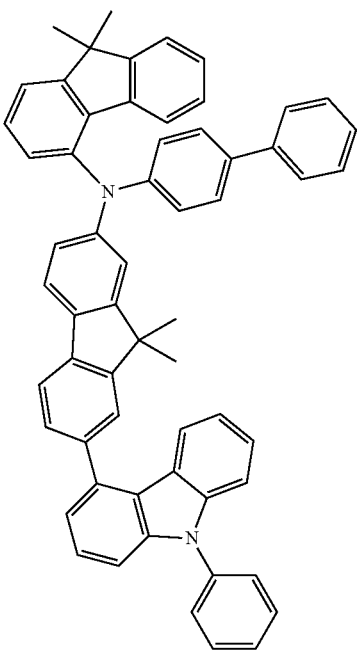 [SMILES: CC1(C)c2cc(-c3cccc4c3c3ccccc3n4-c3ccccc3)ccc2-c2ccc(N(c3ccc(-c4ccccc4)cc3)c3cccc4c3-c3ccccc3C4(C)C)cc21]

17

Production of the OLEDs

In Examples C1 to I14 which follow (see Tables 1 and 2), the data of various OLEDs are presented.

Pretreatment for Examples C1-I14: Glass plaques coated with structured ITO (indium tin oxide) of thickness 50 nm, for improved processing, are coated with 20 nm of PEDOT:PSS (poly(3,4-ethylenedioxythiophene) poly(styrenesulphonate), purchased as CLEVIOS™ P VP AI 4083 from Heraeus Precious Metals GmbH Deutschland, spun on from aqueous solution). These coated glass plaques form the substrates to which the OLEDs are applied.

The OLEDs basically have the following layer structure: substrate/hole transport layer (HTL)/optional interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm. The exact structure of the OLEDs can be found in Table 1. The materials required for production of the OLEDs are shown in Table 3.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:PA:TEG1 (55%:35%:10%) mean here that the material IC1 is present in the layer in a proportion by volume of 55%, PA in a proportion of 35% and TEG1 in a proportion of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian radiation characteristics, and also the lifetime are determined. The electroluminescence spectra are determined at a luminance of 1000 cd/m$^2$, and the CIE 1931 x and y colour coordinates are calculated therefrom. The parameter U1000 in Table 2 refers to the voltage which is required for a luminance of 1000 cd/m$^2$. CE1000 and PE1000 respectively refer to the current and power efficiencies which are achieved at 1000 cd/m$^2$. Finally, EQE1000 refers to the external quantum efficiency at an operating luminance of 1000 cd/m$^2$. The lifetime LT is defined as the time after which the luminance drops from the starting luminance to a certain proportion $L^1$ in the course of operation with constant current. A figure of $L_0;j_0$=4000 cd/m$^2$ and $L_1$=70% in Table 2 means that the lifetime reported in the LT column corresponds to the time after which the starting luminance falls from 4000 cd/m$^2$ to 2800 cd/m$^2$. Analogously, $L_0;j_0$=20 mA/cm$^2$, $L_1$=80% means that the luminance in the course of operation at 20 mA/cm$^2$ falls to 80% of its starting value after the time LT.

The data for the various OLEDs are collated in Table 2. Example C1 is a comparative example according to the prior art; Examples I1-I14 show data of OLEDs of the invention.

Some of the examples are elucidated in detail hereinafter, in order to illustrate the advantages of the OLEDs of the invention.

Use of Compounds of the Invention as Hole-Transporting Matrix Material of Phosphorescent OLEDs The materials of the invention, when used as hole-transporting matrix material in combination with an electron-conducting compound (for example compound IC1 in the examples adduced below) in the emission layer (EML) in phosphorescent OLEDs, resulting significant improvements over the prior art, particularly in relation to the lifetime of the OLEDs. Through use of compounds 9a and 9h of the invention, it is possible to observe an improvement in lifetime of more than 50% compared to the compound from the prior art PA (Examples 1, I1 and I2 or C2 and I15).

TABLE 1

Structure of the OLEDs

| Ex. | HIL thickness | IL thickness | HTL thickness | EBL thickness | EML thickness | HBL thickness | ETL thickness | EIL thickness |
|---|---|---|---|---|---|---|---|---|
| C1 | SpA1 70 nm | HATCN 5 nm | SpMA1 70 nm | — | IC1:PA:TEG1 (45%:45%:10%) 30 nm | IC1 10 nm | ST2:LiQ (50%:50%) 30 nm | — |
| C2 | SpA1 70 nm | HATCN 5 nm | SpMA1 70 nm | — | IC1:PA2:TEG1 (45%:45%:10%) 30 nm | IC1 10 nm | ST2:LiQ (50%:50%) 30 nm | — |
| I1 | SpA1 70 nm | HATCN 5 nm | SpMA1 70 nm | — | IC1:9a:TEG1 (45%:45%:10%) 30 nm | IC1 10 nm | ST2:LiQ (50%:50%) 30 nm | — |
| I2 | SpA1 70 nm | HATCN 5 nm | SpMA1 70 nm | — | IC1:9h:TEG1 (45%:45%:10%) 30 nm | IC1 10 nm | ST2:LiQ (50%:50%) 30 nm | — |
| I3 | SpA1 70 nm | HATCN 5 nm | SpMA1 80 nm | 9b 10 nm | IC1:IC3:TEG1 (65%:30%:5%) 30 nm | IC1 10 nm | ST2:LiQ (50%:50%) 30 nm | — |
| I4 | SpA1 70 nm | HATCN 5 nm | SpMA1 80 nm | 9c 10 nm | IC1:IC3:TEG1 (65%:30%:5%) 30 nm | IC1 10 nm | ST2:LiQ (50%:50%) 30 nm | — |
| I5 | SpA1 70 nm | HATCN 5 nm | SpMA1 90 nm | — | IC1:9f:TEG1 (65%:30%:5%) 30 nm | IC1 10 nm | ST2:LiQ (50%:50%) 30 nm | — |
| I6 | SpA1 90 nm | HATCN 5 nm | SpMA1 110 nm | 9g 20 nm | IC1:TER1 (92%:8%) 40 nm | — | ST2:LiQ (50%:50%) 40 nm | — |
| I7 | SpA1 90 nm | HATCN 5 nm | SpMA1 130 nm | — | IC1:9i:TEG1 (87%:5%:8%) 40 nm | — | ST2:LiQ (50%:50%) 40 nm | — |
| I8 | SpA1 90 nm | HATCN 5 nm | SpMA1 110 nm | 9j 20 nm | IC1:9j:TER1 (82%:10%:8%) 40 nm | — | ST2:LiQ (50%:50%) 40 nm | — |
| I9 | SpA1 90 nm | HATCN 5 nm | SpMA1 130 nm | — | IC1:9k:TEG1 (87%:5%:8%) 40 nm | — | ST2:LiQ (50%:50%) 40 nm | — |
| I10 | SpA1 70 nm | HATCN 5 nm | SpMA1 70 nm | — | IC1:9n:TEG1 (45%:45%:10%) 30 nm | IC1 10 nm | ST2:LiQ (50%:50%) 30 nm | — |
| I11 | SpA1 70 nm | HATCN 5 nm | SpMA1 70 nm | — | IC1:9p:TEG1 (60%:30%:10%) 30 nm | IC1 10 nm | ST2:LiQ (50%:50%) 30 nm | — |
| I12 | SpA1 70 nm | HATCN 5 nm | SpMA1 70 nm | — | IC1:9q:TEG1 (60%:30%:10%) 30 nm | IC1 10 nm | ST2:LiQ (50%:50%) 30 nm | — |
| I13 | SpA1 70 nm | HATCN 5 nm | SpMA1 80 nm | 9r 10 nm | IC1:IC3:TEG1 (55%:35%:10%) 30 nm | IC1 10 nm | ST2:LiQ (50%:50%) 30 nm | — |

TABLE 1-continued

Structure of the OLEDs

| Ex. | HIL thickness | IL thickness | HTL thickness | EBL thickness | EML thickness | HBL thickness | ETL thickness | EIL thickness |
|---|---|---|---|---|---|---|---|---|
| I14 | SpA1 70 nm | HATCN 5 nm | SpMA1 80 nm | 9u 10 nm | IC1:IC3:TEG1 (55%:35%:10%) 30 nm | IC1 10 nm | ST2:LiQ (50%:50%) 30 nm | — |
| I15 | SpA1 70 nm | HATCN 5 nm | SpMA1 70 nm | — | IC1:9h:TEG1 (45%:45%:10%) 30 nm | IC1 10 nm | ST2:LiQ (50%:50%) 30 nm | |

TABLE 2

Data of the OLEDs

| Ex. | U1000 (V) | CE1000 (cd/A) | PE1000 (lm/W) | EQE 1000 | CIE x/y at 1000 cd/m$^2$ | $L_0$; $j_0$ | $L_1$ % | LT (h) |
|---|---|---|---|---|---|---|---|---|
| C1 | 3.3 | 60 | 57 | 16.7% | 0.32/0.63 | 20 mA/cm$^2$ | 80 | 120 |
| C1 | 3.4 | 59 | 55 | 16.4% | 0.32/0.63 | 20 mA/cm$^2$ | 80 | 145 |
| I1 | 3.5 | 58 | 52 | 16.4% | 0.33/0.62 | 20 mA/cm$^2$ | 80 | 220 |
| I2 | 3.4 | 60 | 55 | 16.5% | 0.33/0.63 | 20 mA/cm$^2$ | 80 | 180 |
| I3 | 3.6 | 62 | 54 | 16.8% | 0.32/0.63 | 20 mA/cm$^2$ | 80 | 200 |
| I4 | 3.4 | 59 | 55 | 16.6% | 0.32/0.63 | 20 mA/cm$^2$ | 80 | 220 |
| I5 | 3.3 | 58 | 55 | 16.4% | 0.33/0.62 | 20 mA/cm$^2$ | 80 | 130 |
| I6 | 4.4 | 12 | 9 | 13.1% | 0.67/0.33 | 4000 cd/m$^2$ | 80 | 310 |
| I7 | 4.5 | 13 | 9 | 13.2% | 0.67/0.33 | 4000 cd/m$^2$ | 80 | 510 |
| I8 | 4.6 | 13 | 9 | 13.0% | 0.66/0.34 | 4000 cd/m$^2$ | 80 | 530 |
| I9 | 4.4 | 12 | 9 | 12.9% | 0.67/0.33 | 4000 cd/m$^2$ | 80 | 490 |
| I10 | 3.5 | 58 | 52 | 16.3% | 0.34/0.62 | 20 mA/cm$^2$ | 80 | 230 |
| I11 | 3.6 | 60 | 52 | 16.4% | 0.32/0.63 | 20 mA/cm$^2$ | 80 | 190 |
| I12 | 3.6 | 61 | 53 | 16.5% | 0.34/0.62 | 20 mA/cm$^2$ | 80 | 200 |
| I13 | 3.5 | 63 | 57 | 16.9% | 0.32/0.64 | 20 mA/cm$^2$ | 80 | 170 |
| I14 | 3.4 | 58 | 54 | 16.2% | 0.33/0.63 | 20 mA/cm$^2$ | 80 | 210 |
| I15 | 3.4 | 60 | 55 | 16.5% | 0.33/0.63 | 20 mA/cm$^2$ | 80 | 180 |

TABLE 3

Structural formulae of the materials for the OLEDs

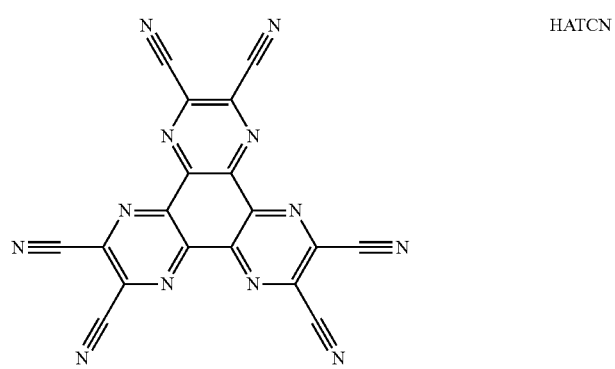

HATCN

TABLE 3-continued
Structural formulae of the materials for the OLEDs
SpA1
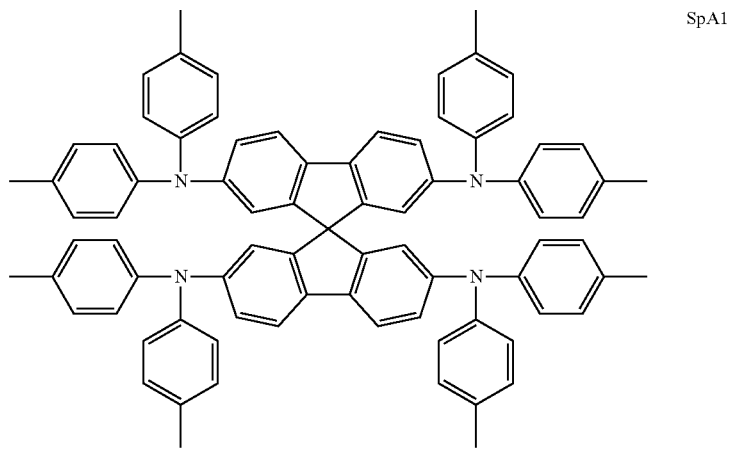
SpMA1
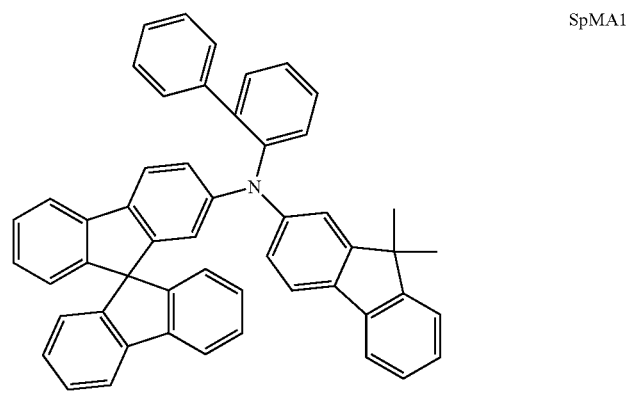
LiQ
SpMA2
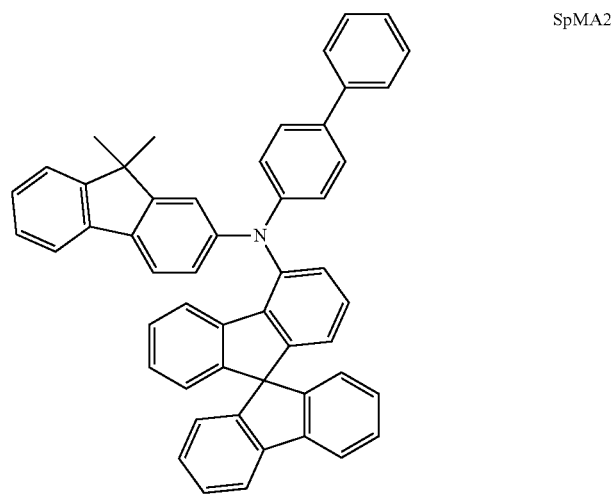

TABLE 3-continued
Structural formulae of the materials for the OLEDs
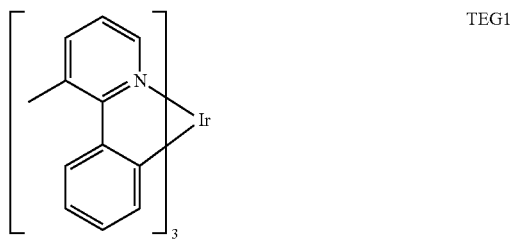
TEG1
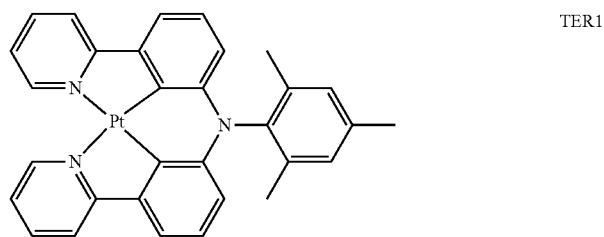
TER1
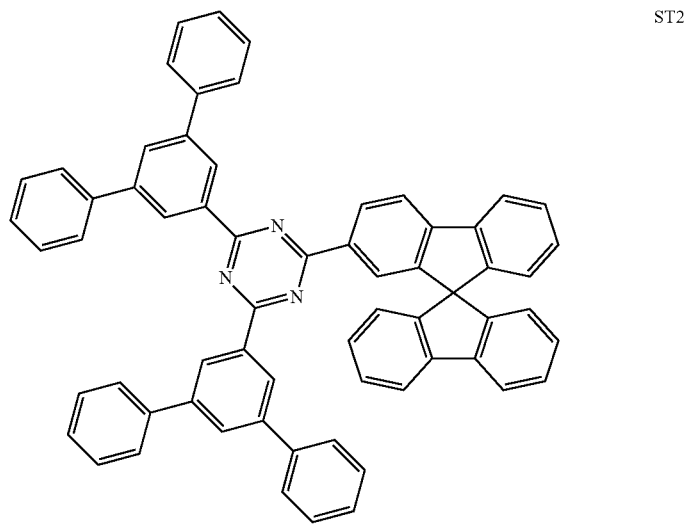
ST2
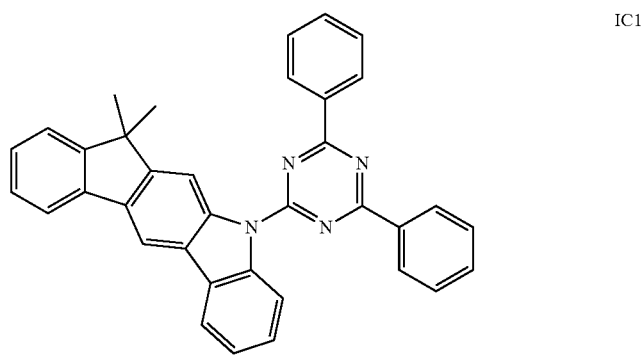
IC1

TABLE 3-continued
Structural formulae of the materials for the OLEDs
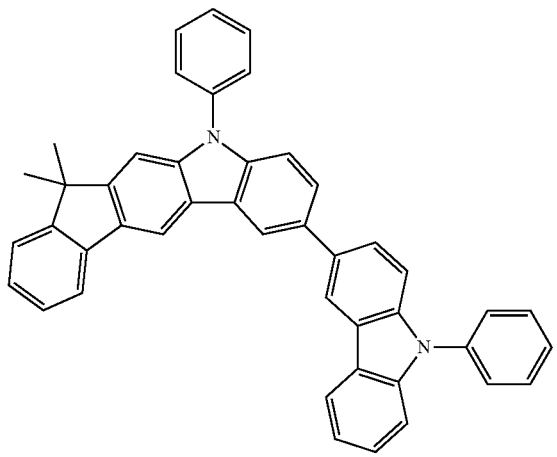 [SMILES: CC1(C)c2ccccc2-c2cc3c4cc(-c5ccc6c(c5)c5ccccc5n6-c5ccccc5)ccc4n(-c4ccccc4)c3cc21]
IC3
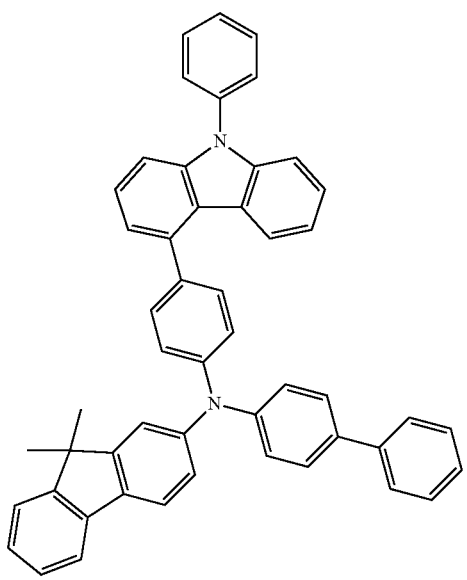 [SMILES: CC1(C)c2ccccc2-c2ccc(N(c3ccc(-c4ccccc4)cc3)c3ccc(-c4cccc5c4c4ccccc4n5-c4ccccc4)cc3)cc21]
PA
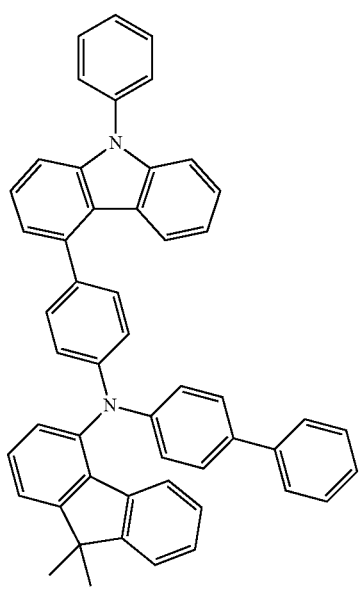 [SMILES: CC1(C)c2ccccc2-c2c(N(c3ccc(-c4ccccc4)cc3)c3ccc(-c4cccc5c4c4ccccc4n5-c4ccccc4)cc3)cccc21]
9a TABLE 3-continued
Structural formulae of the materials for the OLEDs
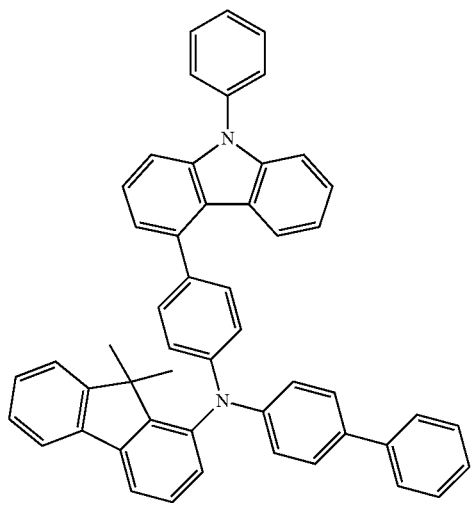 [SMILES: CC1(C)c2ccccc2-c2cccc(N(c3ccc(-c4ccccc4)cc3)c3ccc(-c4cccc5c4c4ccccc4n5-c4ccccc4)cc3)c21]
9h
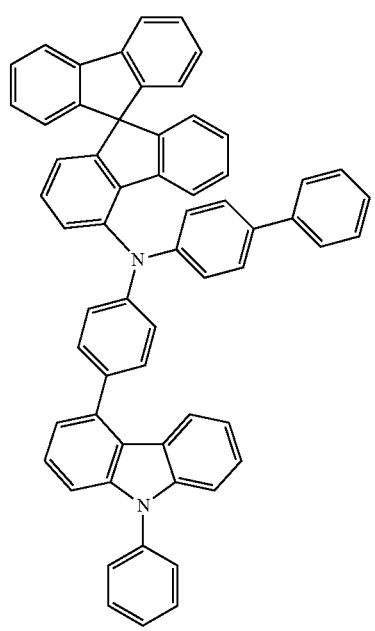 [SMILES: c1ccc(-c2ccc(N(c3ccc(-c4cccc5c4c4ccccc4n5-c4ccccc4)cc3)c3cccc4c3-c3ccccc3C43c4ccccc4-c4ccccc43)cc2)cc1]
9b TABLE 3-continued
Structural formulae of the materials for the OLEDs
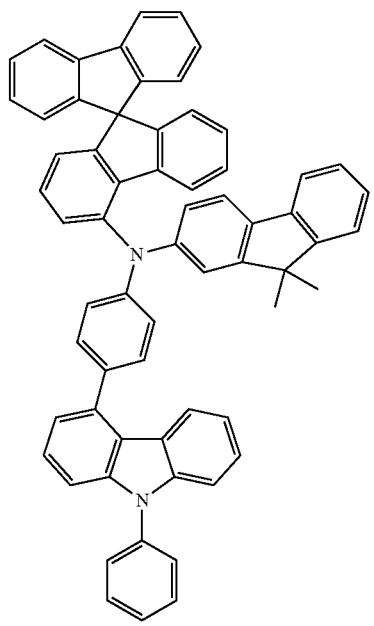 [SMILES: CC1(C)c2ccccc2-c2ccc(N(c3ccc(-c4cccc5c4c4ccccc4n5-c4ccccc4)cc3)c3cccc4c3-c3ccccc3C43c4ccccc4-c4ccccc43)cc21]
9c
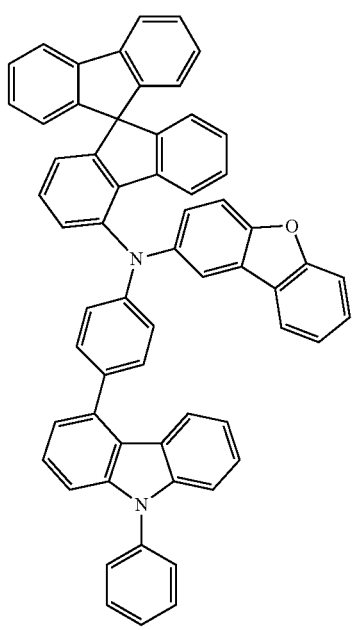 [SMILES: c1ccc(-n2c3ccccc3c3c(-c4ccc(N(c5ccc6oc7ccccc7c6c5)c5cccc6c5-c5ccccc5C65c6ccccc6-c6ccccc65)cc4)cccc32)cc1]
9f TABLE 3-continued
Structural formulae of the materials for the OLEDs
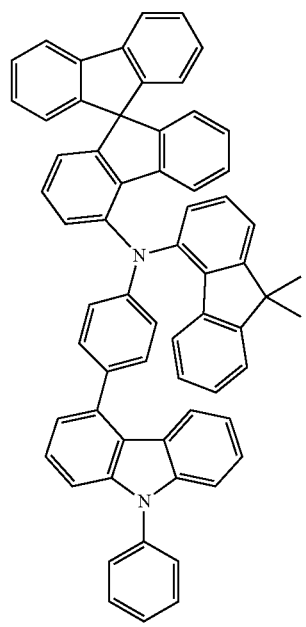 [SMILES: CC1(C)c2ccccc2-c2c(N(c3ccc(-c4cccc5c4c4ccccc4n5-c4ccccc4)cc3)c3cccc4c3-c3ccccc3C43c4ccccc4-c4ccccc43)cccc21]
9g
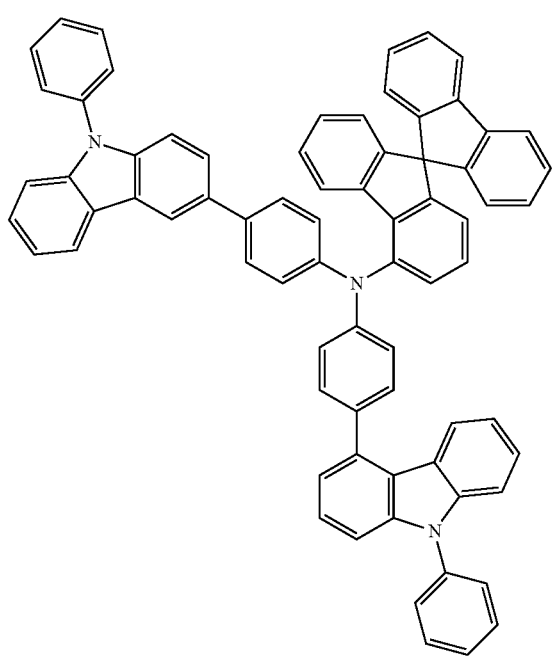 [SMILES: c1ccc(-n2c3ccccc3c3cc(-c4ccc(N(c5ccc(-c6cccc7c6c6ccccc6n7-c6ccccc6)cc5)c5cccc6c5-c5ccccc5C65c6ccccc6-c6ccccc65)cc4)ccc32)cc1]
9i TABLE 3-continued
Structural formulae of the materials for the OLEDs
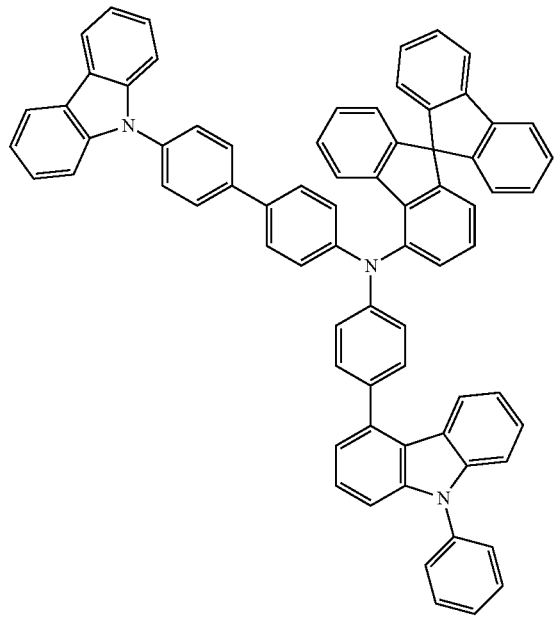 [SMILES: c1ccc(-n2c3ccccc3c3c(-c4ccc(N(c5ccc(-c6ccc(-n7c8ccccc8c8ccccc87)cc6)cc5)c5cccc6c5-c5ccccc5C65c6ccccc6-c6ccccc65)cc4)cccc32)cc1]
9j
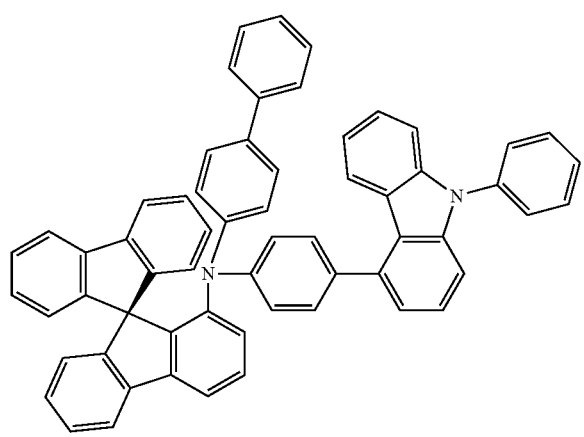
9k 273
TABLE 3-continued
Structural formulae of the materials for the OLEDs
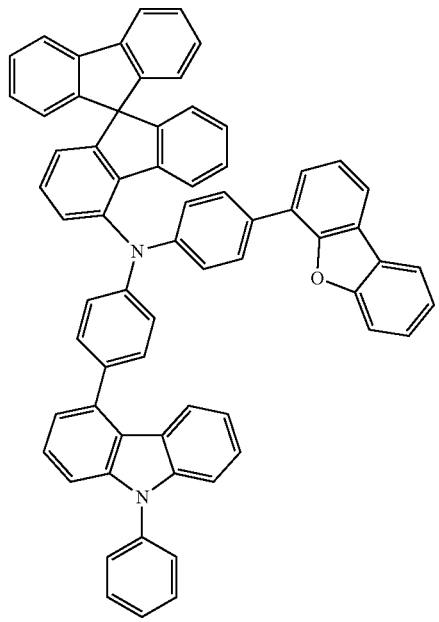 [SMILES: c1ccc(-n2c3ccccc3c3c(-c4ccc(N(c5ccc(-c6cccc7c6oc6ccccc67)cc5)c5cccc6c5-c5ccccc5C65c6ccccc6-c6ccccc65)cc4)cccc32)cc1]
9n
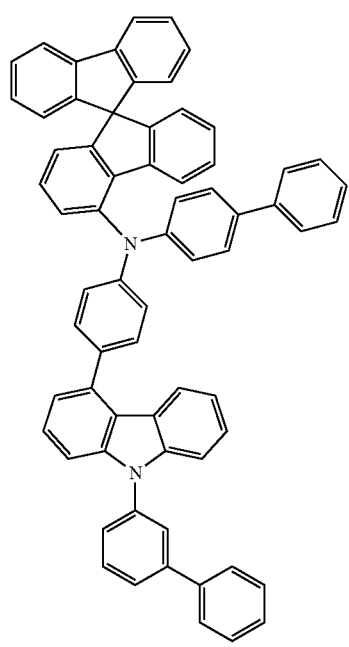 [SMILES: c1ccc(-c2ccc(N(c3ccc(-c4cccc5c4c4ccccc4n5-c4cccc(-c5ccccc5)c4)cc3)c3cccc4c3-c3ccccc3C43c4ccccc4-c4ccccc43)cc2)cc1]
9p TABLE 3-continued
Structural formulae of the materials for the OLEDs
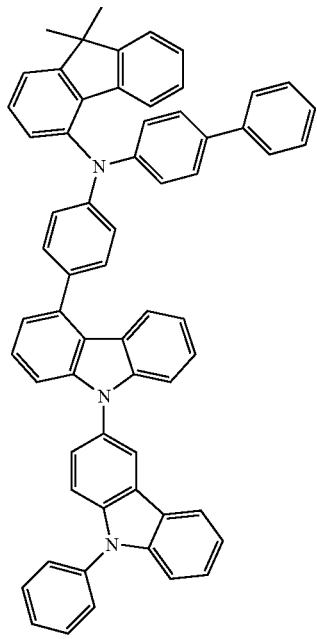 [SMILES: CC1(C)c2ccccc2-c2c(N(c3ccc(-c4ccccc4)cc3)c3ccc(-c4cccc5c4c4ccccc4n5-c4ccc5c(c4)c4ccccc4n5-c4ccccc4)cc3)cccc21]
9q
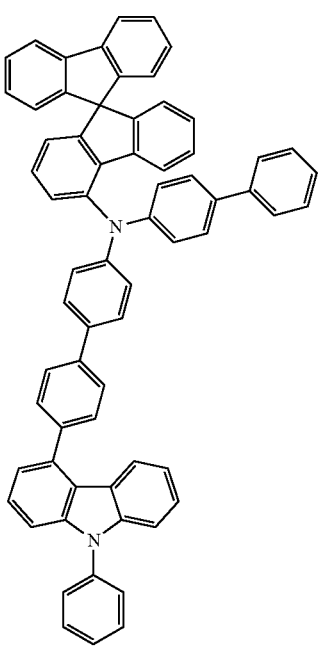 [SMILES: c1ccc(-c2ccc(N(c3ccc(-c4ccc(-c5cccc6c5c5ccccc5n6-c5ccccc5)cc4)cc3)c3cccc4c3-c3ccccc3C43c4ccccc4-c4ccccc43)cc2)cc1]
9r TABLE 3-continued Structural formulae of the materials for the OLEDs 9u

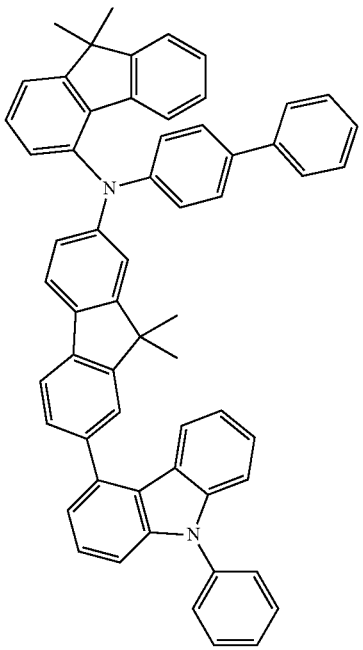 [SMILES: CC1(C)c2cc(-c3cccc4c3c3ccccc3n4-c3ccccc3)ccc2-c2ccc(N(c3ccc(-c4ccccc4)cc3)c3cccc4c3-c3ccccc3C4(C)C)cc21]

PA2

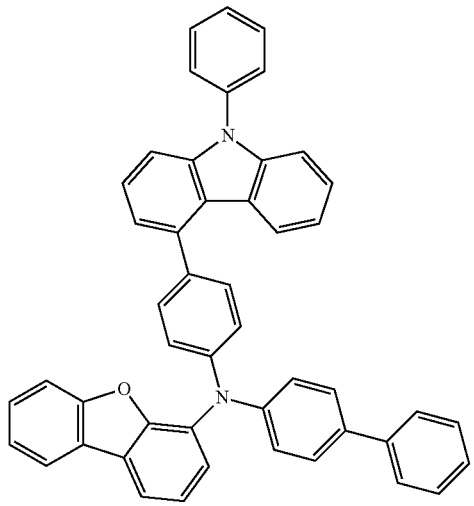 [SMILES: c1ccc(-c2ccc(N(c3ccc(-c4cccc5c4c4ccccc4n5-c4ccccc4)cc3)c3cccc4c3oc3ccccc34)cc2)cc1]

The invention claimed is:

1. A compound of formula (Ic)

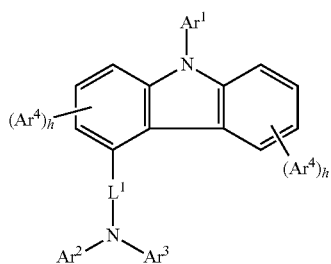

Formula (Ic)

wherein:

$L^1$ is an aromatic ring system having 6 to 20 carbon atoms or a heteroaromatic ring system having 3 to 20 carbon atoms, each of which may be substituted by one or more $R^1$ radicals;

$Ar^1$, $Ar^2$, $Ar^3$ is an aryl group having 6 to 40 carbon atoms or a heteroaryl group having 3 to 40 carbon atoms, each of which may be substituted by one or more $R^1$ radicals;

$R^1$ is the same or different at each instance and is H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent CH$_2$ groups may be replaced by —R$^2$C=CR$^2$—, —C≡C—, Si(R$^2$)$_2$, C=O, C=S, C=NR$^2$, —C(=O)O—, —C(=O)NR$^2$—, NR$^2$, P(=O)(R$^2$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^2$ radicals, or an aryloxy or heteroaryloxy group which has 5 to 40 aromatic ring atoms and may be substituted by one or more R$^2$ radicals, or a combination of these systems; at the same time, two or more adjacent R$^1$ substituents together may also form a mono- or polycyclic, aliphatic or aromatic ring system;

R$^2$ is the same or different at each instance and is H, D, F, Cl, Br, I, B(OR$^3$)$_2$, CHO, C(=O)R$^3$, CR$^3$=C(R$^3$)$_2$, CN, C(=O)OR$^3$, C(=O)N(R$^3$)$_2$, Si(R$^3$)$_3$, N(R$^3$)$_2$, NO$_2$, P(=O)(R$^3$)$_2$, OSO$_2$R$^3$, OR$^3$, S(=O)R$^3$, S(=O)$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^3$ radicals, where one or more nonadjacent CH$_2$ groups may be replaced by —R$^3$C=CR$^3$—, —C≡C—, Si(R$^3$)$_2$, C=O, C=S, C=NR$^3$, —C(=O)O—, —C(=O)NR$^3$—, NR$^3$, P(=O)(R$^3$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^3$ radicals, or an aryloxy or heteroaryloxy group which has 5 to 40 aromatic ring atoms and may be substituted by one or more R$^3$ radicals, or a combination of these systems; at the same time, two or more adjacent R$^2$ substituents together may also form a mono- or polycyclic, aliphatic or aromatic ring system;

R$^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more adjacent R$^3$ substituents together may also form a mono- or polycyclic, aliphatic or aromatic ring system;

h independently at each instance is 0, 1, 2, 3 or 4;

Ar$^4$ is an aryl group having 6 to 40 carbon atoms or a heteroaryl group having 3 to 40 carbon atoms, each of which may be substituted by one or more R$^1$ radicals;

with the proviso that at least one of the Ar$^2$ and Ar$^3$ radicals is a group of the formula (IIe), (IId), (IIe) or (IIf)

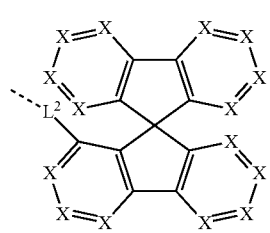

Formula (IIc)

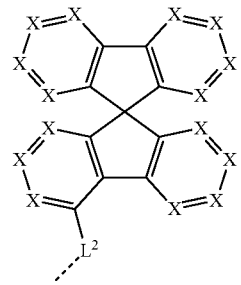

Formula (IId)

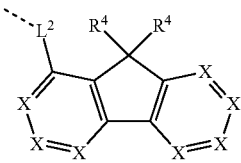

Formula (IIe)

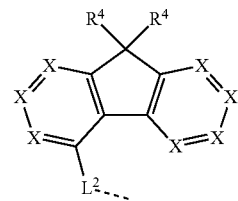

Formula (IIf)

in which all X are CR$^1$, where at most 4 of the CR groups that X represents are not the CH group, and R$^4$ is H, an aromatic ring system having 6 to 30 aromatic ring atoms, or an alkyl group having 1-20 carbon atoms, L$^2$ is a bond, an aromatic ring system having 6 to 60 carbon atoms or a heteroaromatic ring system having 3 to 60 carbon atoms, each of which may be substituted by one or more R$^1$ radicals;

and the dotted line represents the bonding site, such that L$^2$ binds to the same nitrogen atom as L$^1$.

2. An organic electroluminescent device comprising at least one compound according to formula (Ic)

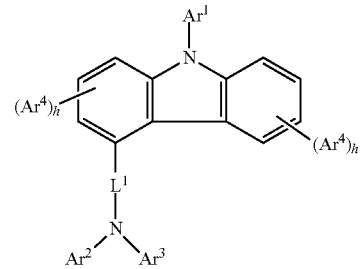

Formula (Ic)

wherein:

L$^1$ is an aromatic ring system having 6 to 20 carbon atoms or a heteroaromatic ring system having 3 to 20 carbon atoms, each of which may be substituted by one or more R$^1$ radicals;

Ar$^1$, Ar$^2$, Ar$^3$ is an aryl group having 6 to 40 carbon atoms or a heteroaryl group having 3 to 40 carbon atoms, each of which may be substituted by one or more R$^1$ radicals;

R¹ is the same or different at each instance and is H, D, F, Cl, Br, I, B(OR²)₂, CHO, C(=O)R², CR²=C(R²)₂, CN, C(=O)OR², C(=O)N(R²)₂, Si(R²)₃, N(R²)₂, NO₂, P(=O)(R²)₂, OSO₂R², OR², S(=O)R², S(=O)₂R², a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R² radicals, where one or more nonadjacent CH₂ groups may be replaced by —R²C=CR²—, —C≡C—, Si(R²)₂, C=O, C=S, C=NR², —C(=O)O—, —C(=O)NR²—, NR², P(=O)(R²), —O—, —S—, SO or SO₂ and where one or more hydrogen atoms may be replaced by D, F, Cl, Br, I, CN or NO₂, or an aromatic or heteroaromatic ring system which has 5 to 40 aromatic ring atoms and may be substituted in each case by one or more R² radicals, or an aryloxy or heteroaryloxy group which has 5 to 40 aromatic ring atoms and may be substituted by one or more R² radicals, or a combination of these systems; at the same time, two or more adjacent R¹ substituents together may also form a mono- or polycyclic, aliphatic or aromatic ring system;

R² is the same or different at each instance and is H, D, F, Cl, Br, I, B(OR³)₂, CHO, C(=O)R³, CR³=C(R³)₂, CN, C(=O)OR³, C(=O)N(R³)₂, Si(R³)₃, N(R³)₂, NO₂, P(=O)(R³)₂, OSO₂R³, OR³, S(=O)R³, S(=O)₂R³, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R³ radicals, where one or more nonadjacent CH₂ groups may be replaced by —R³C=CR³—, —C≡C—, Si(R³)₂, C=O, C=S, C=NR³, —C(=O)O—, —C(=O)NR³—, NR³, P(=O)(R³), —O—, —S—, SO or SO₂ and where one or more hydrogen atoms may be replaced by D, F, Cl, Br, I, CN or NO₂, or an aromatic or heteroaromatic ring system which has 5 to 40 aromatic ring atoms and may be substituted in each case by one or more R³ radicals, or an aryloxy or heteroaryloxy group which has 5 to 40 aromatic ring atoms and may be substituted by one or more R³ radicals, or a combination of these systems; at the same time, two or more adjacent R² substituents together may also form a mono- or polycyclic, aliphatic or aromatic ring system;

R³ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more adjacent R³ substituents together may also form a mono- or polycyclic, aliphatic or aromatic ring system;

h independently at each instance is 0, 1, 2, 3 or 4;

Ar⁴ is an aryl group having 6 to 18 carbon atoms or a heteroaryl group having 3 to 40 carbon atoms, wherein the heteroaryl group is optionally substituted by one or more R radicals;

with the proviso that
at least one of the Ar² and Ar³ radicals is a group of the formula (IIc), (IId), (IIe) or (IIf)

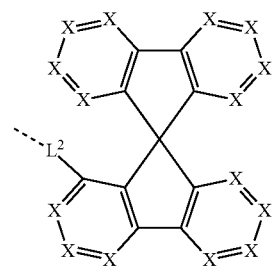

Formula (IIc)

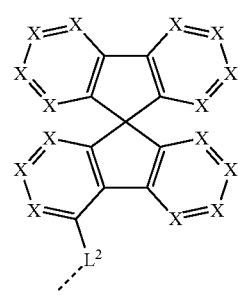

Formula (IId)

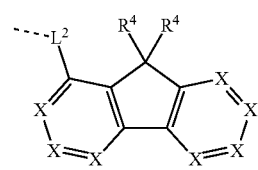

Formula (IIe)

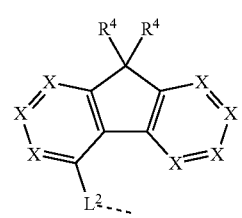

Formula (IIf)

in which all X are CR¹, where at most 4 of the CR¹ groups that X represents are not the CH group, and R⁴ is H, an aromatic ring system having 6 to 30 aromatic ring atoms, or an alkyl group having 1-20 carbon atoms L² is a bond, an aromatic ring system having 6 to 60 carbon atoms or a heteroaromatic ring system having 3 to 60 carbon atoms, each of which may be substituted by one or more R¹ radicals;

and the dotted line represents the bonding site, such that L² binds to the same nitrogen atom as L¹.

3. The compound according to claim 1, wherein R⁴ is methyl, ethyl, propyl or butyl.

4. The device according to claim 2, wherein an emission layer comprises the at least one compound of formula (Ic) as a matrix material and a phosphorescent emitter, and a further matrix material.

5. The device according to claim 4, wherein the at least one compound of formula (Ic) and the further matrix material are present in a ratio of from 1:50 to 1:1.

6. The device according to claim 2,

R⁴ is an alkyl group having 1-20 carbon atoms.

7. The device according to claim 2, wherein, at least one of Ar³ and Ar² has the structure of formulae (IIe) or (IIf),

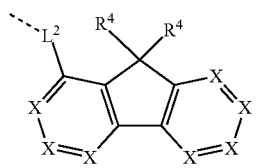

Formula (IIe)

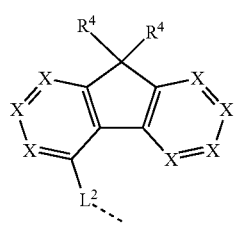

Formula (IIf)

R⁴ is an alkyl group having 1-20 carbon atoms, and at least one R¹, Ar¹, Ar², or Ar³ radical is a group selected from the formulae (R¹-1) to (R¹-72)

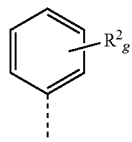

Formula (R¹-1)

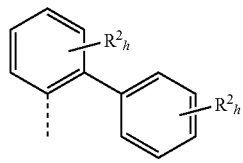

Formula (R¹-2)

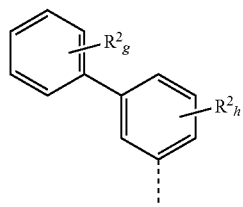

Formula (R¹-3)

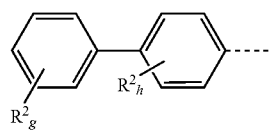

Formula (R¹-4)

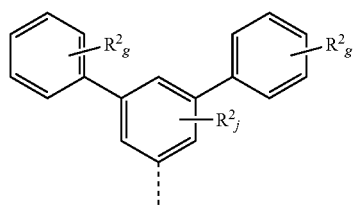

Formula (R¹-5)

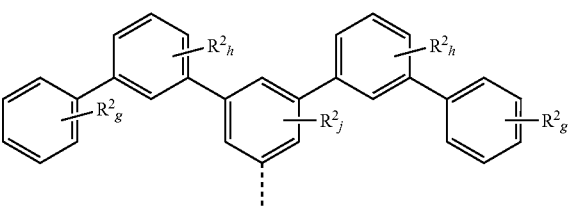

Formula (R¹-6)

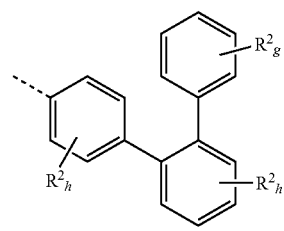

Formula (R¹-7)

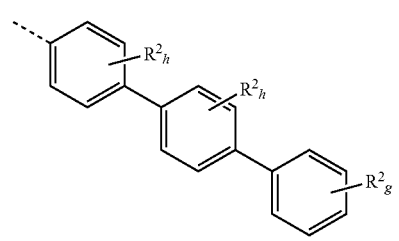

Formula (R¹-8)

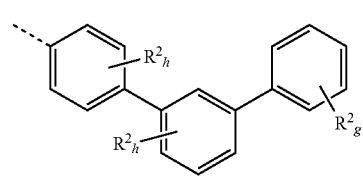

Formula (R¹-9)

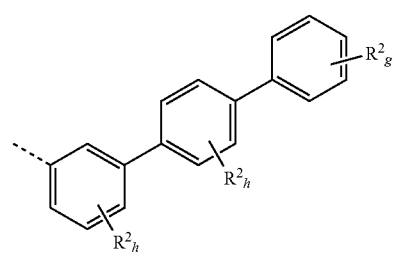

Formula (R¹-10)

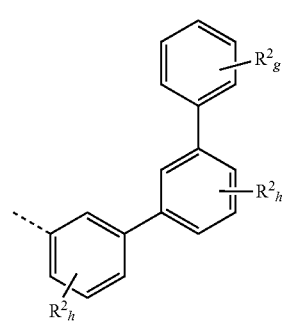

Formula (R¹-11)

Formula (R¹-12)
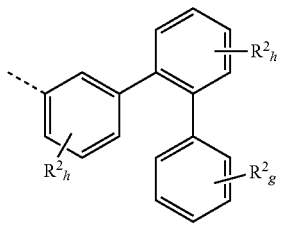
Formula (R¹-13)
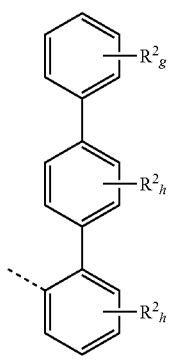
Formula (R¹-14)
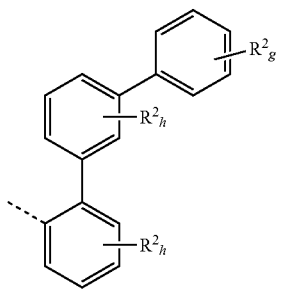
Formula (R¹-15)
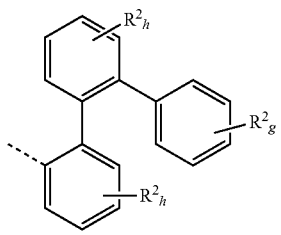
Formula (R¹-16)
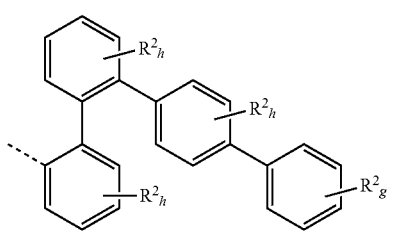
Formula (R¹-17)
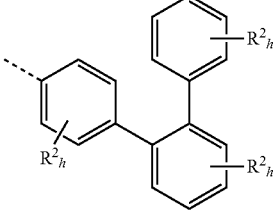
Formula (R¹-18)
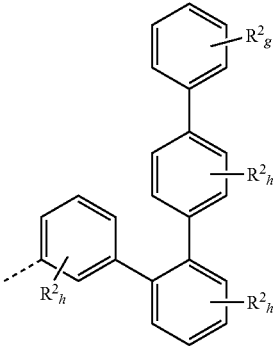
Formula (R¹-19)
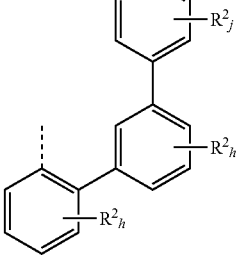
Formula (R¹-20)
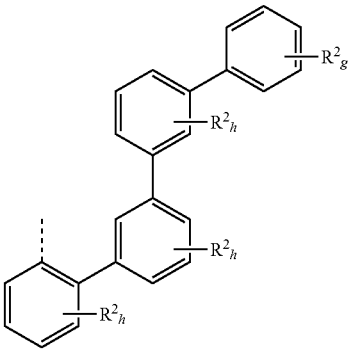

Formula (R¹-21)
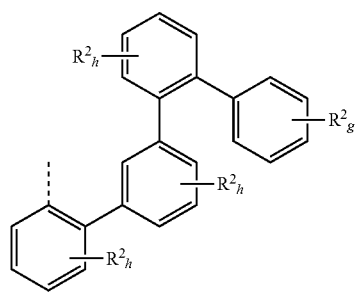
Formula (R¹-22)
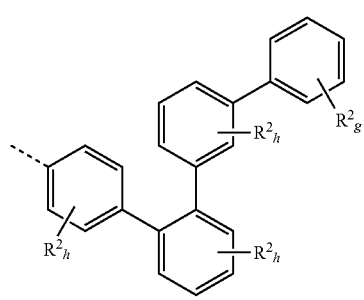
Formula (R¹-23)
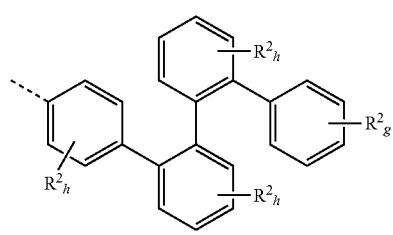
Formula (R¹-24)
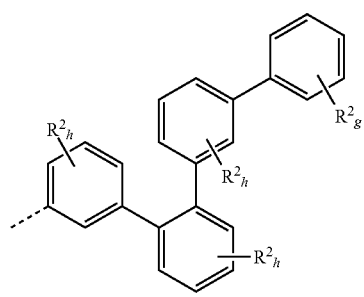
Formula (R¹-25)
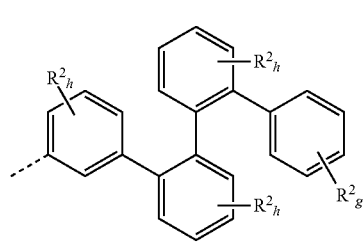
Formula (R¹-26)
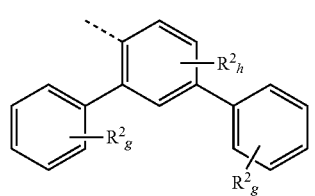
Formula (R¹-27)
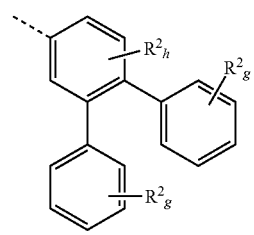
Formula (R¹-28)
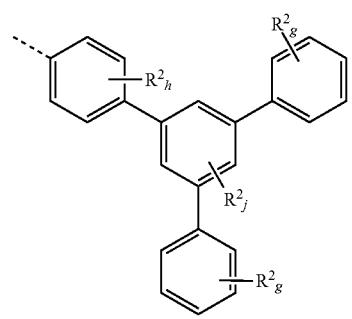
Formula (R¹-29)
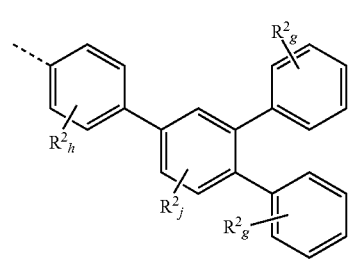
Formula (R¹-30)
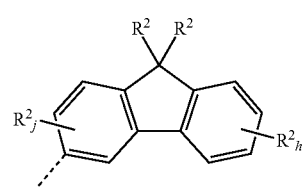
Formula (R¹-31)
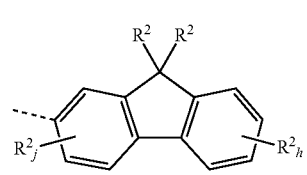
Formula (R¹-32)
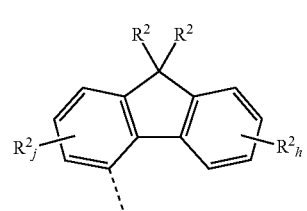
Formula (R¹-33)
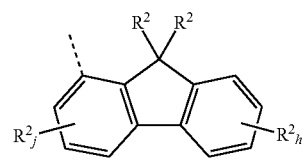

-continued
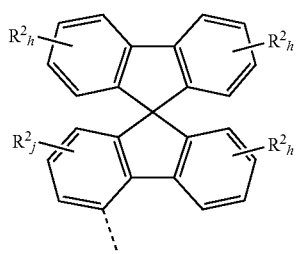
Formula (R¹-34)
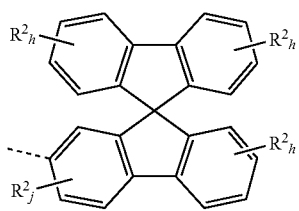
Formula (R¹-35)
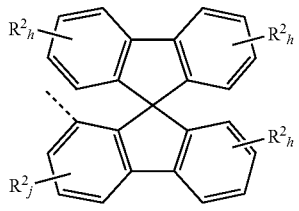
Formula (R¹-36)
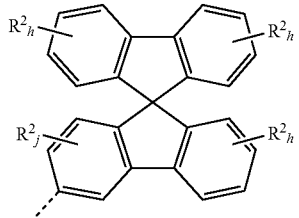
Formula (R¹-37)
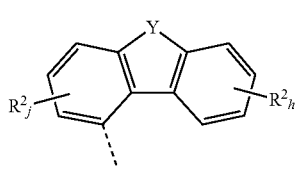
Formula (R¹-38)
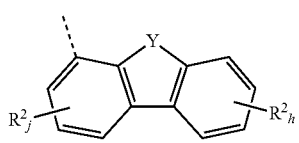
Formula (R¹-39)
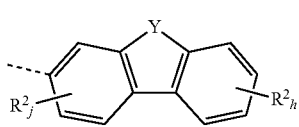
Formula (R¹-40)
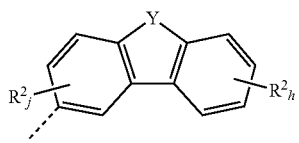
Formula (R¹-41)
-continued
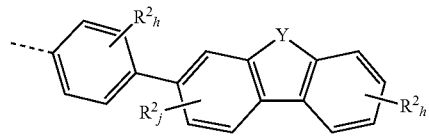
Formula (R¹-42)
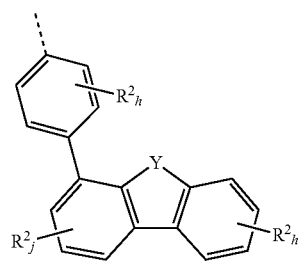
Formula (R¹-43)
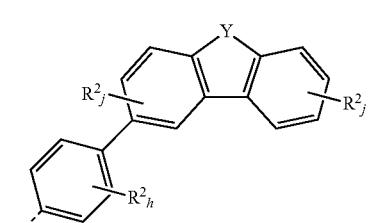
Formula (R¹-44)
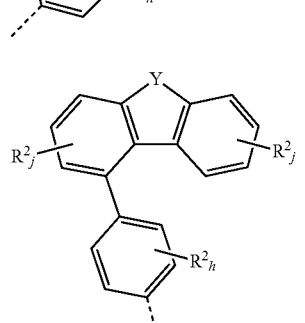
Formula (R¹-45)
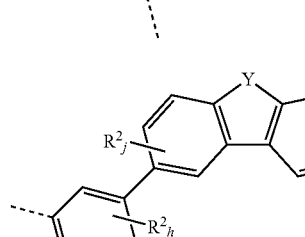
Formula (R¹-46)
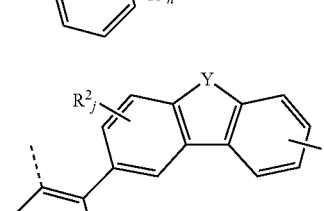
Formula (R¹-47)
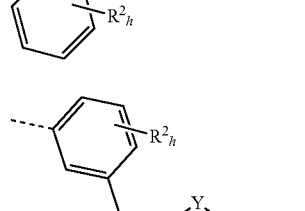
Formula (R¹-48)
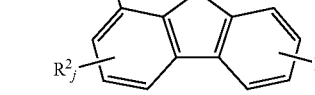

-continued
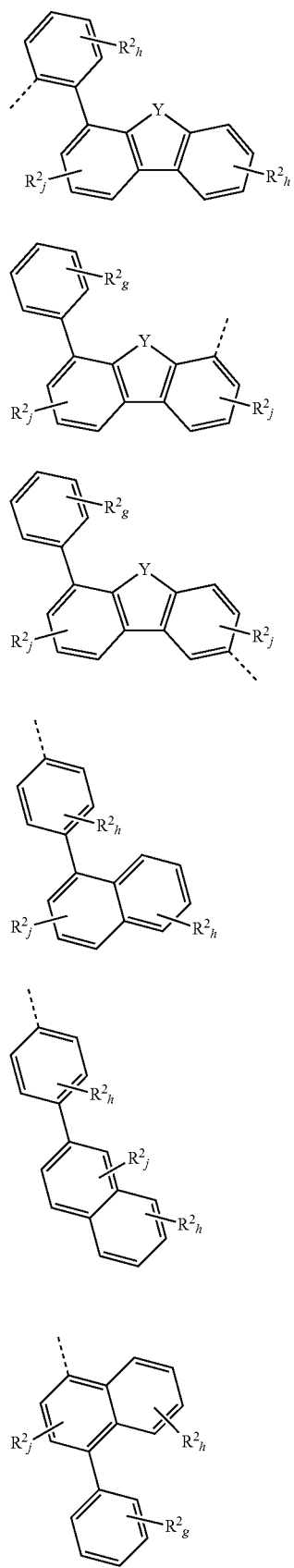
Formula (R¹-49)
Formula (R¹-50)
Formula (R¹-51)
Formula (R¹-52)
Formula (R¹-53)
Formula (R¹-54)
-continued
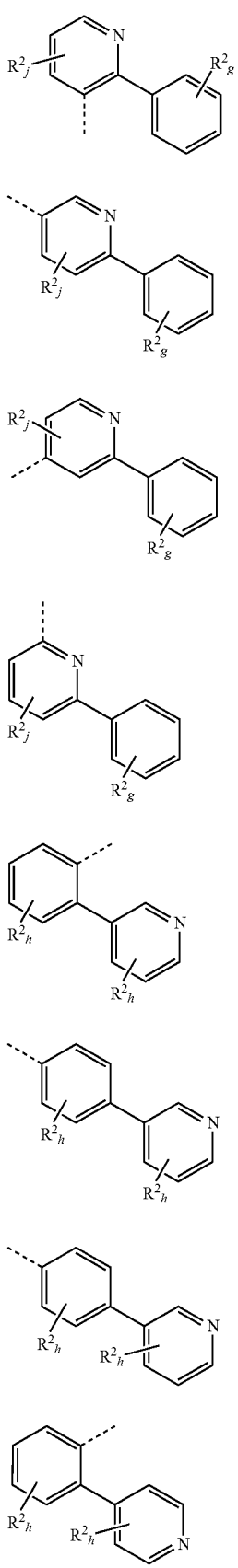
Formula (R¹-55)
Formula (R¹-56)
Formula (R¹-57)
Formula (R¹-58)
Formula (R¹-59)
Formula (R¹-60)
Formula (R¹-61)
Formula (R¹-62)

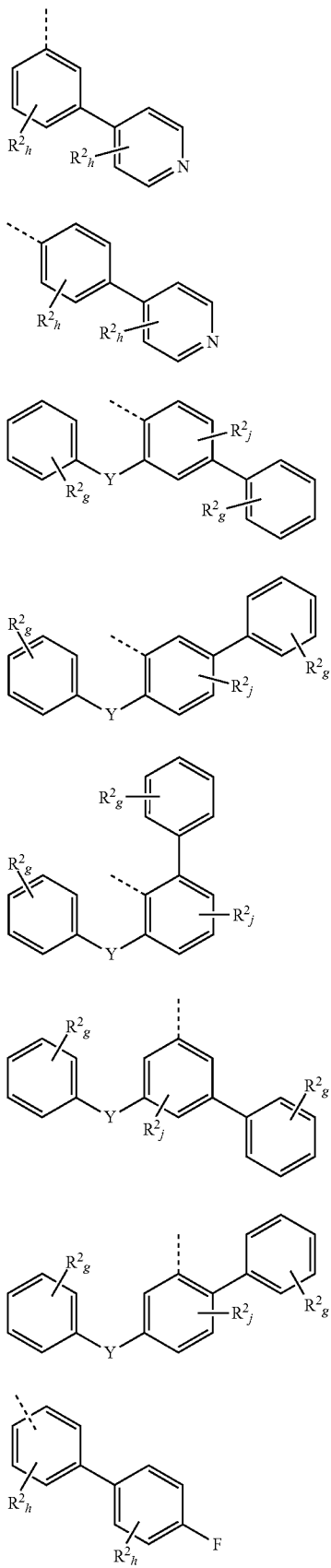

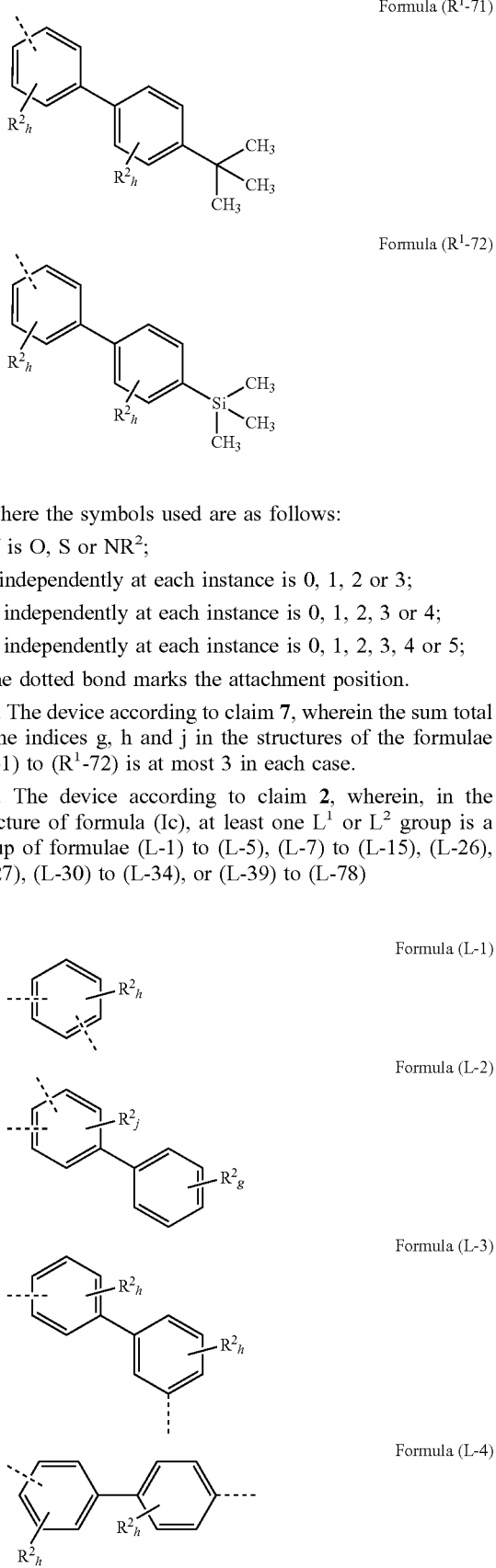

where the symbols used are as follows:

Y is O, S or NR²;

j independently at each instance is 0, 1, 2 or 3;

h independently at each instance is 0, 1, 2, 3 or 4;

g independently at each instance is 0, 1, 2, 3, 4 or 5;

the dotted bond marks the attachment position.

8. The device according to claim 7, wherein the sum total of the indices g, h and j in the structures of the formulae (R¹-1) to (R¹-72) is at most 3 in each case.

9. The device according to claim 2, wherein, in the structure of formula (Ic), at least one L¹ or L² group is a group of formulae (L-1) to (L-5), (L-7) to (L-15), (L-26), (L-27), (L-30) to (L-34), or (L-39) to (L-78)

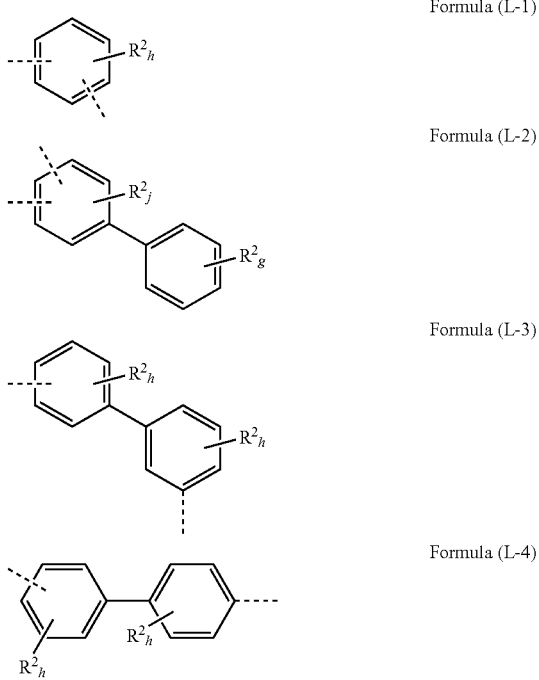

Formula (L-5)
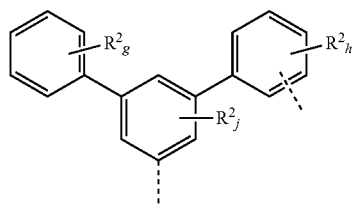
Formula (L-7)
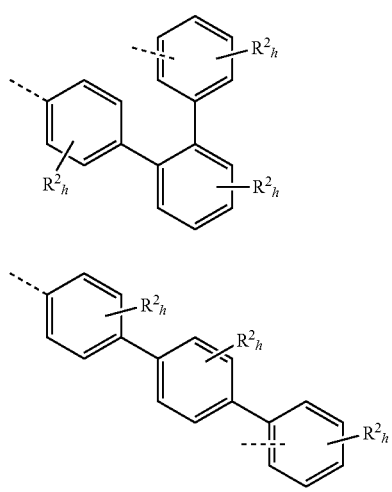
Formula (L-8)
Formula (L-9)
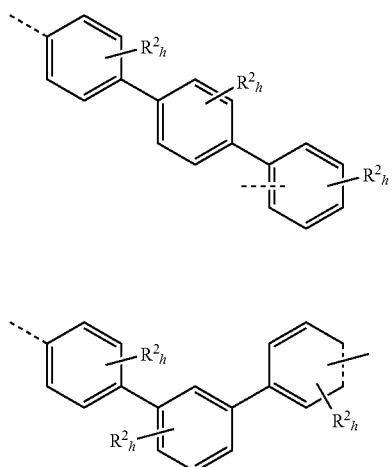
Formula (L-10)
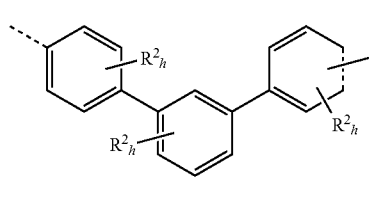
Formula (L-11)
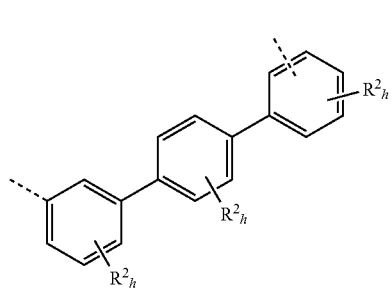
Formula (L-12)
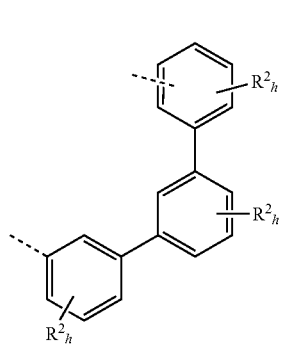
Formula (L-13)
Formula (L-14)
Formula (L-15)
Formula (L-26)
Formula (L-27)

Formula (L-30)
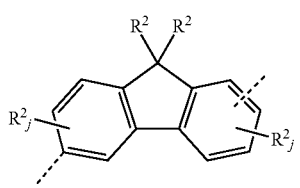
Formula (L-31)
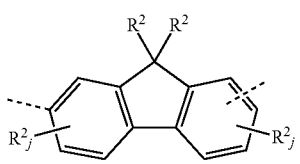
Formula (L-32)
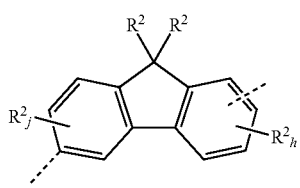
Formula (L-33)
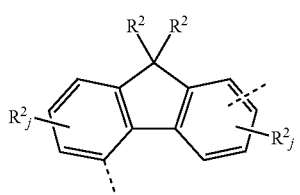
Formula (L-34)
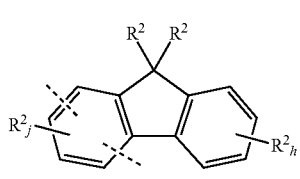
Formula (L-39)
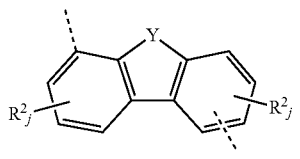
Formula (L-40)
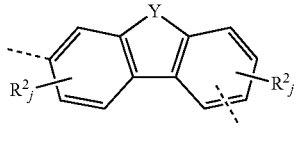
Formula (L-41)
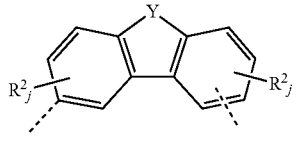
Formula (L-42)
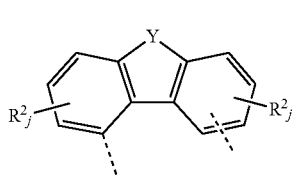
Formula (L-43)
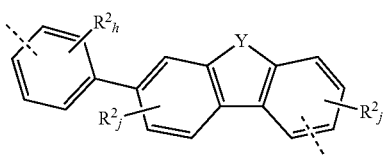
Formula (L-44)
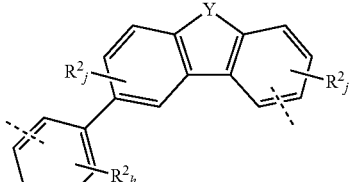
Formula (L-45)
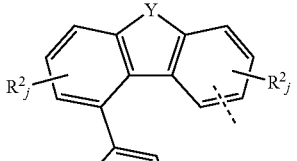
Formula (L-46)
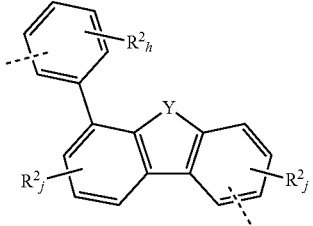
Formula (L-47)
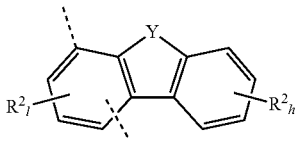
Formula (L-48)
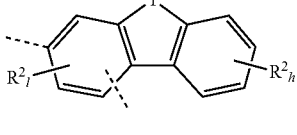
Formula (L-49)
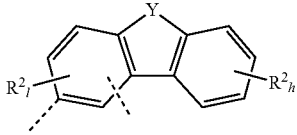
Formula (L-50)
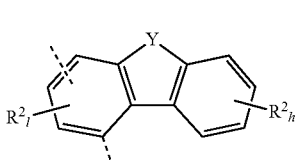
Formula (L-51)
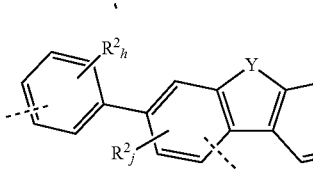

Formula (L-52)
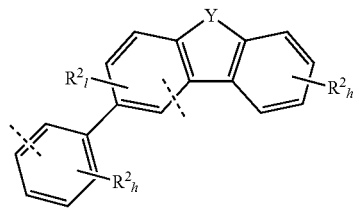
Formula (L-53)
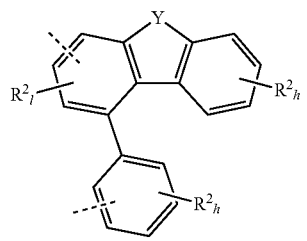
Formula (L-54)
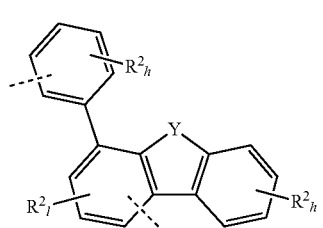
Formula (L-55)
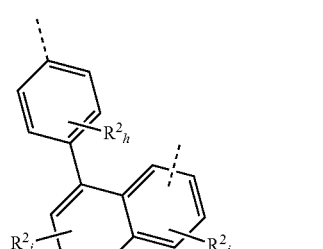
Formula (L-56)
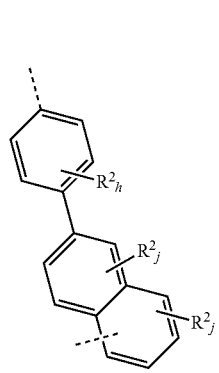
Formula (L-57)
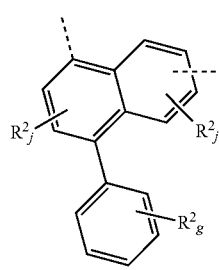
Formula (L-58)
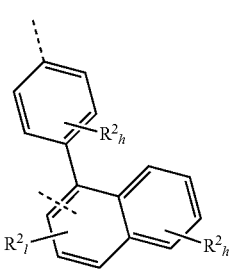
Formula (L-59)
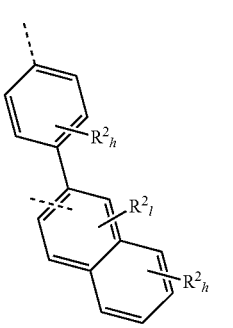
Formula (L-60)
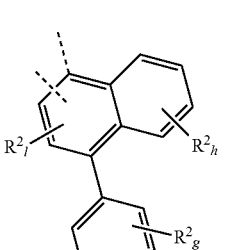
Formula (L-61)
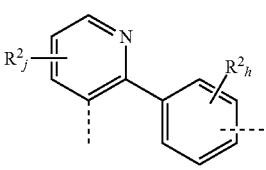
Formula (L-62)
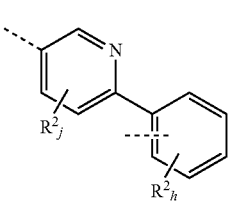
Formula (L-63)
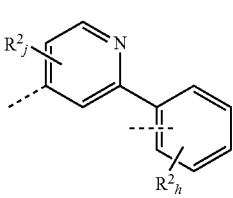
Formula (L-64)
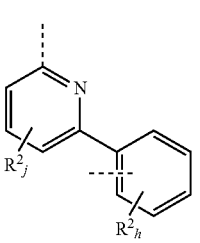

301
-continued

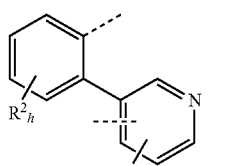
Formula (L-65)

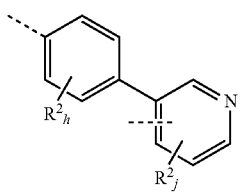
Formula (L-66)

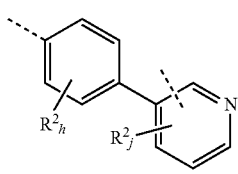
Formula (L-67)

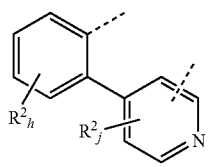
Formula (L-68)

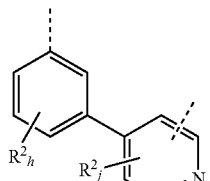
Formula (L-69)

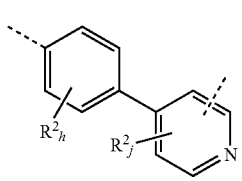
Formula (L-70)

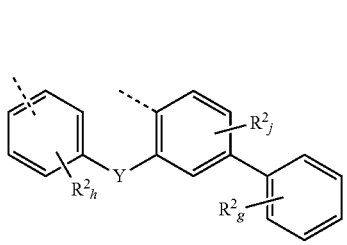
Formula (L-71)

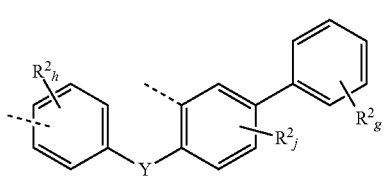
Formula (L-72)

302
-continued

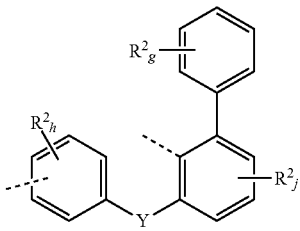
Formula (L-73)

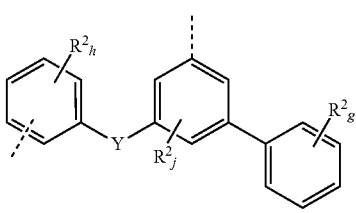
Formula (L-74)

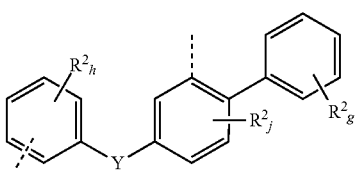
Formula (L-75)

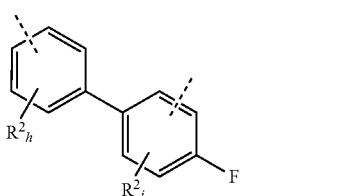
Formula (L-76)

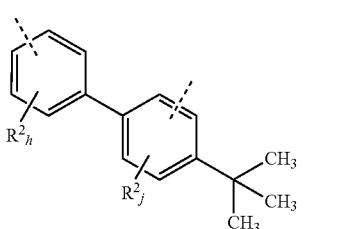
Formula (L-77)

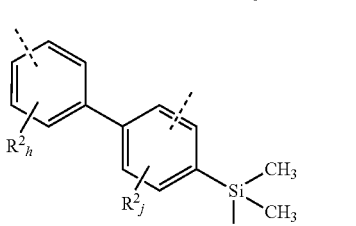
Formula (L-78)

where the dotted bonds in each case mark the attachment positions, the index l is 0, 1 or 2, the index g is 0, 1, 2, 3, 4 or 5, j independently at each instance is 0, 1, 2 or 3; h independently at each instance is 0, 1, 2, 3 or 4; Y is O, S or NR$^2$; and R$^2$ is as defined in claim 2.

10. The device according to claim 9, wherein the sum total of the indices l, g, h and j in the structures of the formulae (L-1) to (L-5), (L-7) to (L-15), (L-26), (L-27), (L-30) to (L-34), and (L-39) to (L-78) is at most 3 in each case.

11. The device according to claim 9, wherein, in the structure of formula (Ic), the L$^1$ group is a group of formulae (L-1) to (L-5), (L-7) to (L-15), (L-26), (L-27), (L-30) to (L-34), or (L-39) to (L-78).

12. The device according to claim 2, wherein $Ar^1$ and $Ar^3$ are an aryl group which has 6 to 20 carbon atoms.

13. The device according to claim 7, wherein $R^4$ is methyl, ethyl, propyl or butyl.

14. The device according to claim 7, wherein Y is O or S.

15. The device according to claim 11, wherein the $L^1$ group is a group selected from the formulae (L-1) to (L-5).

* * * * *

UNITED STATES PATENT AND TRADEMARK OFFICE
CERTIFICATE OF CORRECTION

PATENT NO. : 10,957,859 B2
APPLICATION NO. : 15/528310
DATED : March 23, 2021
INVENTOR(S) : Jatsch et al.

It is certified that error appears in the above-identified patent and that said Letters Patent is hereby corrected as shown below:

In the Claims

In Column 279, Claim 1, Line number 55, please correct the phrase:
"at least one of the $Ar^2$ and $Ar^3$ radicals is a group of the formula (IIe), (IId), (IIe) or (IIf)…"
Should be:
"at least one of the $Ar^2$ and $Ar^3$ radicals is a group of the formula (IIc), (IId), (IIe) or (IIf)…"

In Column 280, Claim 1, Line number 31, please correct the phrase:
"in which all X and $CR^1$, where at most 4 of the CR groups that X represents are not the CH group,…"
Should be:
"in which all X and $CR^1$, where at most 4 of the $CR^1$ groups that X represents are not the CH group,…"

In Column 281, Claim 2, Line number 64, please correct the phrase:
"Ar4 is an aryl group having 6 to 18 carbon atoms or a heteroaryl group having 3 to 40 carbon atoms, wherein 65 the heteroaryl group is optionally substituted by one or more R radicals;"
Should be:
"Ar4 is an aryl group having 6 to 18 carbon atoms or a heteroaryl group having 3 to 40 carbon atoms, wherein 65 the heteroaryl group is optionally substituted by one or more $R^1$ radicals;"

In Column 282, Claim 2, Line number 3, please correct the phrase:
"with the proviso that at least one of the Ar2 and Ar3 radicals is a group of the formula (IIe), (IId), (IIe) or (IIf)"
Should be:
"with the proviso that at least one of the $Ar^2$ and $Ar^3$ radicals is a group of the formula (IIc), (IId), (IIe) or (IIf)"

Signed and Sealed this
Sixth Day of July, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,957,859 B2

In Column 286, Claim 7, Lines 35-50, please correct the figure:

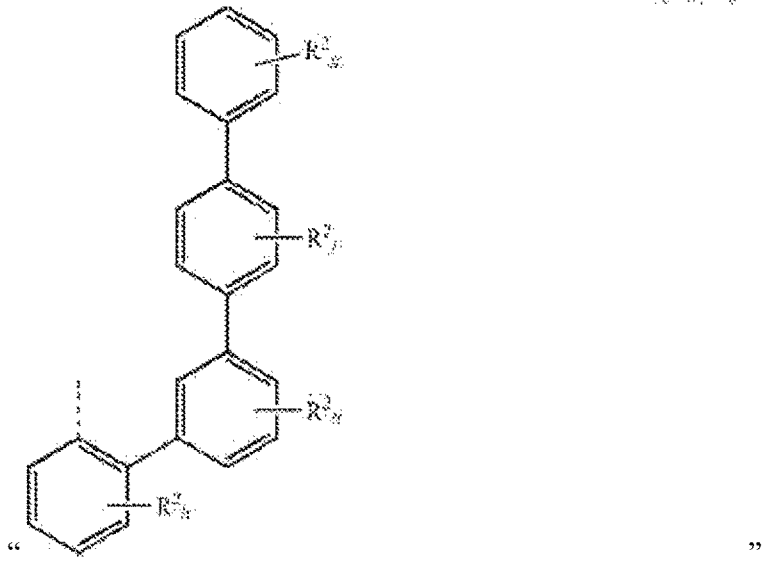

Should be:

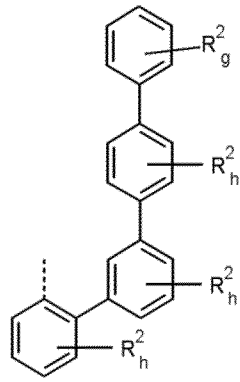

" Formula (R¹-19) "

In Column 290, Claim 7, Lines 30-40, please correct the figure:

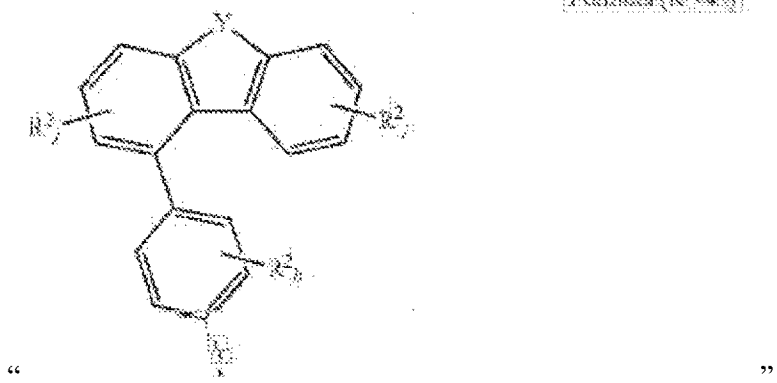

CERTIFICATE OF CORRECTION (continued)
U.S. Pat. No. 10,957,859 B2

Should be:

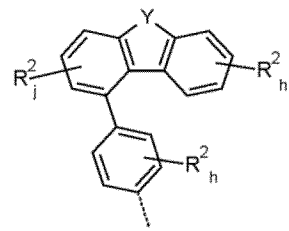

"                               Formula (R¹-45) ,,

In Column 298, Claim 9, Lines 60-65, please correct the figure:

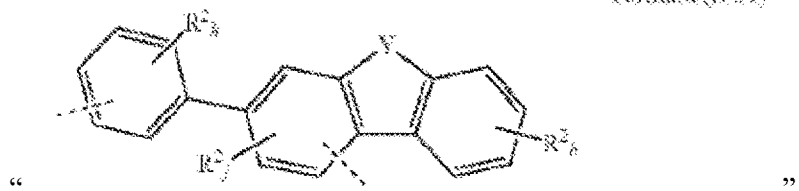

"                                                                                      "

Should be:

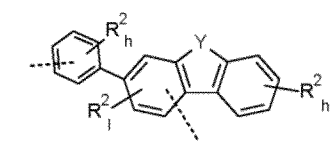

"                               Formula (L-51) "